(12) United States Patent
Bostrom et al.

(10) Patent No.: US 8,193,321 B2
(45) Date of Patent: Jun. 5, 2012

(54) MULTISPECIFIC ANTIBODIES

(75) Inventors: Jenny M. Bostrom, San Francisco, CA (US); Germaine Fuh, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/552,177

(22) Filed: Sep. 1, 2009

(65) Prior Publication Data

US 2010/0322946 A1    Dec. 23, 2010

Related U.S. Application Data

(60) Provisional application No. 61/190,856, filed on Sep. 3, 2008.

(51) Int. Cl.
*A61K 39/395* (2006.01)
*C07K 16/30* (2006.01)

(52) U.S. Cl. ............... 530/387.3; 530/388.2; 530/389.2

(58) Field of Classification Search ............... 530/387.3, 530/388.2, 389.2
See application file for complete search history.

(56) References Cited

U.S. PATENT DOCUMENTS

| | | | |
|---|---|---|---|
| 4,816,567 A | 3/1989 | Cabilly et al. |
| 5,491,074 A | 2/1996 | Aldwin et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,582,996 A | 12/1996 | Curtis |
| 5,591,669 A | 1/1997 | Krimpenfort et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,821,337 A | 10/1998 | Carter et al. |
| 5,932,448 A | 8/1999 | Tso et al. |
| 6,331,415 B1 | 12/2001 | Cabilly et al. |
| 6,833,441 B2 | 12/2004 | Wang et al. |
| 7,179,595 B2 | 2/2007 | Li |
| 2005/0186208 A1 | 8/2005 | Fyfe et al. |
| 2005/0282233 A1 | 12/2005 | Eriksson et al. |
| 2006/0088529 A1 | 4/2006 | Leung et al. |
| 2008/0050370 A1 | 2/2008 | Glaser et al. |
| 2008/0069820 A1 | 3/2008 | Fuh et al. |
| 2008/0181892 A1 | 7/2008 | Ledbetter et al. |
| 2009/0048122 A1 | 2/2009 | Glaser et al. |
| 2009/0148905 A1 | 6/2009 | Ashman et al. |
| 2009/0214541 A1 | 8/2009 | Gillies et al. |

FOREIGN PATENT DOCUMENTS

| | | |
|---|---|---|
| EP | 0 368 684 | 5/1990 |
| EP | 0 404 097 | 12/1990 |
| JP | 2002 355074 | 12/2002 |
| WO | WO 90/05144 | 5/1990 |
| WO | WO 91/10741 | 7/1991 |
| WO | WO 92/10209 | 6/1992 |
| WO | WO 93/11161 | 6/1993 |
| WO | WO 93/11162 | 6/1993 |
| WO | WO 93/15210 | 8/1993 |
| WO | WO 96/33735 | 10/1996 |
| WO | WO 96/34096 | 10/1996 |
| WO | WO 98/24893 | 6/1998 |
| WO | WO 02/02773 | 1/2002 |
| WO | WO 03/102157 | 12/2003 |
| WO | WO 2004/003019 | 1/2004 |
| WO | WO 2005/062967 | 7/2005 |
| WO | WO 2005/062972 | 7/2005 |
| WO | WO 2007/011363 | 1/2007 |
| WO | WO 2007/076923 | 7/2007 |
| WO | WO 2007/109254 | 9/2007 |
| WO | WO 2008/027236 | 3/2008 |
| WO | WO 2009/068649 | 6/2009 |
| WO | WO 2010/027981 | 3/2010 |

OTHER PUBLICATIONS

Rudikoff et al (Proc Natl Acad Sci USA 1982 vol. 79 p. 1979).*
Ward et al. (Nature 341:544-546 (1989).*
Agus et al., "Targeting ligand-activated ErbB2 signaling inhibits breast and prostate tumor growth," *Cancer Cell* 2: 127-137 (2002).
Arevalo et al., "Molecular basis of crossreactivity and the limits of antibody-antigen complementarity," *Nature* 365: 859-863 (1993).
Austin et al., "Endocytosis and sorting of ErbB2 and the site of action of cancer therapeutics trastuzumab and geldanamycin," *Mol Biol Cell* 15: 5268-5282 (2004).
Baselga et al., "Recombinant humanized anti-HER2 antibody (Herceptin) enhances the antitumor activity of paclitaxel and doxorubicin against HER2/neu overexpressing human breast cancer xenografts," *Cancer Res.* 58: 2825-2831 (1998).
Birk et al., "Current insights on the biology and clinical aspects of VEGF regulation," *Vasc Endovascular Surg.* 42: 517-530 (2008).
Boder et al., "Directed evolution of antibody fragments with monovalent femtomolar antigen-binding affinity," *Proc Natl Acad Sci USA* 97: 10701-10705 (2000).
Boder et al., "Yeast surface display for screening combinatorial polypeptide libraries," *Nat Biotechnol.* 15: 553-557 (1997).
Boniface et al., "Thermodynamics of T cell receptor binding to peptide-MHC: evidence for a general mechanism of molecular scanning," *Proc Natl Acad Sci USA* 96: 11446-11451 (1999).
Bostrom et al., "Design and construction of synthetic phage-displayed Fab libraries," *Methods Mol Biol.* 562: 17-35 (2009).
Bostrom et al., "Improving antibody binding affinity and specificity for therapeutic development," *Methods Mol Biol.* 525: 353-376 (2009).
Bostrom et al., "Variants of the antibody herceptin that interact with HER2 and VEGF at the antigen binding site," *Science* 323: 1610-1614 (2009) (including supplemental online material).
Boulanger et al., "Convergent mechanisms for recognition of divergent cytokines by the shared signaling receptor Gp130," *Mol Cell* 12: 577-589 (2003).
Brorson et al., "Mutational analysis of avidity and fine specificity of anti-levan antibodies," *J Immunol.* 163: 6694-6701 (1999).
Brüggemann et al., "Designer mice: the production of human antibody repertoires in transgenic animals," *Year Immunol.* 7: 33-40 (1993).
Brummell et al., "Probing the combining site of an anti-carbohydrate antibody by saturation-mutagenesis: role of the heavy-chain CDR3 residues," *Biochemistry* 32: 1180-1187 (1993).
Burks et al., "In vitro scanning saturation mutagenesis of an antibody binding pocket," *Proc Natl Acad Sci USA* 94: 412-417 (1997).

(Continued)

*Primary Examiner* — Lynn Bristol
(74) *Attorney, Agent, or Firm* — Clark & Elbing LLP

(57) ABSTRACT

The invention provides multispecific antibodies and methods of making and using such antibodies.

17 Claims, 74 Drawing Sheets

OTHER PUBLICATIONS

Capel et al., "Heterogeneity of human IgG Fc receptors," *Immunomethods* 4: 25-34 (1994).

Carter et al., "Potent antibody therapeutics by design," *Nat Rev Immunol.* 6: 343-357 (2006).

Casset et al., "A peptide mimetic of an anti-CD4 monoclonal antibody by rational design," *Biochem Biophys Res Commun.* 307: 198-205 (2003).

Chan et al., "Enhanced killing of primary ovarian cancer by retargeting autologous cytokine-induced killer cells with bispecific antibodies: a preclinical study," *Clin Cancer Res.* 12: 1859-1867 (2006).

Chen et al., "Selection and analysis of an optimized anti-VEGF antibody: crystal structure of an affinity-matured Fab in complex with antigen," *J Mol Biol.* 293: 865-881 (1999).

Cho et al., "Structure of the extracellular region of HER2 alone and in complex with the herceptin Fab," *Nature* 421: 756-760 (2003).

Chothia and Lesk, "Canonical structures for the hypervariable regions of immunoglobulins," *J Mol Biol.* 196: 901-917 (1987).

Christinger et al., "Crystallization of the receptor binding domain of vascular endothelial growth factor," *Proteins* 26: 353-357 (1996).

Clackson et al., "Making antibody fragments using phage display libraries," *Nature* 352: 624-628 (1991).

Clackson et al., "A hot spot of binding energy in a hormone-receptor interface," *Science* 267: 383-386 (1995).

Clynes et al., "Inhibitory Fc receptors modulate in vivo cytotoxicity against tumor targets," *Nat Med.* 6: 443-446 (2000).

Clynes et al., "Fc receptors are required in passive and active immunity to melanoma," *Proc Natl Acad Sci USA* 95: 652-656 (1998).

Colman et al., "Effects of amino acid sequence changes on antibody-antigen interactions," *Res Immunol.* 145: 33-36 (1994).

Collaborative Computational Project, No. 4, "The CCP4 suite: programs for protein crystallography," *Acta Crystallogr D* 50: 760-763 (1994).

Daëron, "Fc receptor biology," *Annu Rev Immunol.* 15: 203-234 (1997).

Dall'Acqua et al., "A mutational analysis of the binding of two different proteins to the same antibody," *Biochemistry* 35: 9667-9676 (1996).

Daugherty et al., "Development of an optimized expression system for the screening of antibody libraries displayed on the *Escherichia coli* surface," *Protein Eng.* 12: 613-621 (1999).

Davies et al., "Affinity improvement of single antibody VH domains: residues in all three hypervariable regions affect antigen binding," *Immunotechnology* 2: 169-179 (1996).

Davis et al., "Ligand recognition by alpha beta T cell receptors," *Annu Rev Immunol.* 16: 523-544 (1998).

de Haas et al., "Fcγ receptors of phagocytes," *J Lab Clin Med.* 126: 330-341 (1995).

de Kruif and Logtenberg, "Leucine zipper dimerized bivalent and bispecific scFv antibodies from a semi-synthetic antibody phage display library," *J Biol Chem.* 271: 7630-7634 (1996).

Delano et al., "Convergent solutions to binding at a protein-protein interface," *Science* 287: 1279-1283 (2000).

De Pascalis et al., "Grafting of 'abbreviated' complementarity-determining regions containing specificity-determining residues essential for ligand contact to engineer a less immunogenic humanized monoclonal antibody," *J Immunol.* 169: 3076-3084 (2002).

Dufner et al., "Harnessing phage and ribosome display for antibody optimization," *Trends Biotechnol.* 24: 523-529 (2006).

Eigenbrot et al., "X-ray structures of the antigen-binding domains from three variants of humanized anti-p185HER2 antibody 4D5 and comparison with molecular modeling," *J Mol Biol.* 229: 969-995 (1993).

Emsley and Cowtan, "Coot: model-building tools for molecular graphics," *Acta Crystallogr D* 60: 2126-2132 (2004).

Epstein et al., "HER-2/Neu-overexpressing human breast cancer xenografts exhibit increased angiogenic potential mediated by vascular endothelial growth factor (VEGF)," *Breast Cancer Res Treat.* (Abstract #570). (2002).

Fellouse et al., "Molecular recognition by a binary code," *J Mol Biol.* 348: 1153-1162 (2005).

Fellouse et al., "Synthetic antibodies from a four-amino-acid code: a dominant role for tyrosine in antigen recognition," *Proc Natl Aced Sci USA* 101: 12467-12472 (2004).

Ferrara et al., "Clinical applications of angiogenic growth factors and their inhibitors," -i Nat Med-l . 5: 1359-1364 (1999).

Ferrara et al., "The biology of VEGF and its receptors," *Nat Med.* 9: 669-676 (2003).

Fields et al., "Molecular basis of antigen mimicry by an anti-idiotope," *Nature* 374: 739-742 (1995).

Fishwild et al., "High-avidity human IgGκ monoclonal antibodies from a novel strain of minilocus transgenic mice," *Nat Biotechnol.* 14: 845-851 (1996).

Foote et al., "Antibody framework residues affecting the conformation of the hypervariable loops," *J Mol Biol.* 224: 487-499 (1992).

Foote et al., "Conformational isomerism and the diversity of antibodies," *Proc Natl Acad Sci USA* 91: 10370-10374 (1994).

Franklin et al., "Insights into ErbB signaling from the structure of the ErbB2-pertuzumab complex," *Cancer Cell* 5: 317-328 (2004).

Fuh et al., "Requirements for binding and signaling of the kinase domain receptor for vascular endothelial growth factor," *J Biol Chem.* 273: 11197-11204 (1998).

Fuh et al., "Structure-function studies of two synthetic anti-vascular endothelial growth factor Fabs and comparison with the Avastin™ Fab," *J Biol Chem.* 281: 6625-6631 (2006).

Gallop et al., "Applications of combinatorial technologies to drug discovery. 1. Background and peptide combinatorial libraries," *J Med Chem.* 37: 1233-1251 (1994).

Garcia et al., "The molecular basis of TCR germline bias for MHC is surprisingly simple," *Nat Immunol.* 10: 143-147 (2009).

Garrard and Henner, "Selection of an anti-IGF-1 Fab from a Fab phage library created by mutagenesis of multiple CDR loops," *Gene* 128: 103-109 (1993).

Gazzano-Santoro et al., "A non-radioactive complement-dependent cytotoxicity assay for anti-CD20 monoclonal antibody," *J Immunol Methods* 202: 163-171 (1997).

Gerber et al., "Complete inhibition of rhabdomyosarcoma xenograft growth and neovascularization requires blockade of both tumor and host vascular endothelial growth factor," *Cancer Res.* 60: 6253-6258 (2000).

Griffiths, "An antibody which behaves like a man with a wife and mistress," *Rev Med Virol.* 19: 181-183 (2009).

Grothey et al., "Targeting angiogenesis: progress with anti-VEGF treatment with large molecules," *Nat Rev Clin Oncol.* 6: 507-518 (2009).

Guo et al., "Breaking the one antibody-one target axiom," *Proc Natl Acad Sci USA* 103: 11009-11014 (2006).

Guyer et al., "Immunoglobulin binding by mouse intestinal epithelial cell receptors," *J Immunol.* 117: 587-593 (1976).

Hanes et al., "In vitro selection and evolution of functional proteins by using ribosome display," *Proc Natl Acad Sci USA* 94: 4937-4942 (1997).

Harvey et al., "Anchored periplasmic expression, a versatile technology for the isolation of high-affinity antibodies from *Escherichia coil*-expressed libraries," *Proc Natl Acad Sci USA* 101: 9193-9198 (2004).

Holliger et al., "'Diabodies': small bivalent and bispecific antibody fragments," *Proc Natl Acad Sci USA* 90: 6444-6448 (1993).

Holm et al., "Functional mapping and single chain construction of the anti-cytokeratin 8 monoclonal antibody TS1," *Mol Immunol.* 44: 1075-1084 (2007).

Holt et al., "Domain antibodies: proteins for therapy," *Trends Biotechnol.* 21: 484-490 (2003).

Hommelgaard et al., "Association with membrane protrusions makes ErbB2 an internalization-resistant receptor," *Mol Biol Cell* 15: 1557-1567 (2004).

Hoogenboom, "Mix and match: building manifold binding sites," *Nat Biotechnol.* 15: 125-126 (1997).

Hoogenboom, "Selecting and screening recombinant antibody libraries," *Nat Biotechnol.* 23: 1105-1116 (2005).

Hudziak and Ullrich, "Cell transformation potential of a HER2 transmembrane domain deletion mutant retained in the endoplasmic reticulum," *J Biol Chem.* 266: 24109-24115 (1991).

Hudziak et al., "P185HER2 monoclonal antibody has antiproliferative effects in vitro and sensitizes human breast tumor cells to tumor necrosis factor," *Mol Cell Biol*. 9: 1165-1172 (1989).

Hurwitz, "Integrating the anti-VEGF-A humanized monoclonal antibody bevacizumab with chemotherapy in advanced colorectal cancer," *Clin Colorectal Cancer* 4(Suppl. 2): S62-S68 (2004).

Huston et al., "Protein engineering of antibody binding sites: recovery of specific activity in an anti-digoxin single-chain Fv analogue produced in *Escherichia coli*," *Proc Natl Acad Sci USA* 85: 5879-5883 (1988).

International Preliminary Report on Patentability for PCT/US2007/018385, issued Mar. 3, 2009.

International Search Report for PCT/US2007/018385, mailed Nov. 5, 2008.

International Search Report for PCT/US2009/055625, mailed Jan. 5, 2010.

Jakobovits et al., "Germ-line transmission and expression of a human-derived yeast artificial chromosome," *Nature* 362: 255-258 (1993).

Jakobovits et al., "Analysis of homozygous mutant chimeric mice: deletion of the immunoglobulin heavy-chain joining region blocks B-cell development and antibody production," *Proc Natl Acad Sci USA* 90: 2551-2555 (1993).

James et al., "Antibody multispecificity mediated by conformational diversity," *Science* 299: 1362-1367 (2003).

Jang et al., "The structural basis for DNA binding by an anti-DNA autoantibody," *Mol Immunol*. 35: 1207-1217 (1998).

Jimenez et al., "Flexibility and molecular recognition in the immune system," *Proc Nat Acad Sci USA* 100: 92-97 (2003).

Johnson and Wu, "Kabat database and its applications: 30 years after the first variability plot," *Nucleic Acids Res*. 28: 214-218 (2000).

Jones et al., "Replacing the complementarity-determining regions in a human antibody with those from a mouse," *Nature* 321: 522-525 (1986).

Junttila et al., "Ligand-independent HER2/HER3/PI3K complex is disrupted by trastuzumab and is effectively inhibited by the PI3K inhibitor GDC-0941," *Cancer Cell* 15: 429-440 (2009).

Kabat et al., "Identical V region amino acid sequences and segments of sequences in antibodies of different specificities: relative contributions of VH and VL genes, minigenes, and complementarity-determining regions to binding of antibody-combining sites," *J Immunol*. 147: 1709-1719 (1991).

Keitel et al., "Crystallographic analysis of anti-P24 (HIV-1) monoclonal antibody crossreactivity and polyspecificity," *Cell* 91: 811-820 (1997).

Kelley and O'Connell, "Thermodynamic analysis of an antibody functional epitope," *Biochemistry* 32: 6828-6835 (1993).

Kelley et al., "Antigen binding thermodynamics and antiproliferative effects of chimeric and humanized anti-P185HER2 antibody Fab fragments," *Biochemistry* 31: 5434-5441 (1992).

Kiewe et al., "Phase I trial of the trifunctional anti-HER2 x anti-CD3 antibody ertumaxomab in metastatic breast cancer," *Clin Cancer Res*. 12: 3085-3091 (2006).

Kim et al., "Localization of the site of the murine IgG1 molecule that is involved in binding to the murine intestinal Fc receptor," *Eur J Immunol*. 24: 2429-2434 (1994).

Kim et al., "Inhibition of vascular endothelial growth factor-induced angiogenesis suppresses tumour growth in vivo," *Nature* 362: 841-844 (1993).

Klagsbrun and D'Amore, "Regulators of angiogenesis," *Annu Rev Physiol*. 53: 217-239 (1991).

Knappik et al., "Fully synthetic human combinatorial antibody libraries (HuCAL) based on modular consensus frameworks and CDRs randomized with trinucleotides," *J Mol Biol*. 296: 57-86 (2000).

Kobayashi et al., "Tryptophan H33 plays an important role in pyrimidine (6-4) pyrimidone photoproduct binding by a high-affinity antibody," *Protein Eng*. 12: 879-884 (1999).

Köhler and Milstein, "Continuous cultures of fused cells secreting antibody of predefined specificity," *Nature* 256: 495-497 (1975).

Konecny et al., "Association between HER-2/neu and vascular endothelial growth factor expression predicts clinical outcome in primary breast cancer patients," *Clin Cancer Res*. 10: 1706-1716 (2004).

Konner et al., "Use of soluble recombinant decoy receptor vascular endothelial growth factor trap (VEGF trap) to inhibit vascular endothelial growth factor activity," *Clin Colorectal Cancer* 4(Suppl. 2): S81-S85 (2004).

Kostelny et al., "Formation of a bispecific antibody by the use of leucine zippers," *J Immunol*. 148: 1547-1553 (1992).

Kramer et al., "Molecular basis for the binding promiscuity of an anti-P24 (HIV-1) monoclonal antibody," *Cell* 91: 799-809 (1997).

Kufer et al., "A revival of bispecific antibodies," *Trends Biotechnol*. 22: 238-244 (2004).

Kumar et al., "Molecular cloning and expression of the Fabs of human autoantibodies in *Escherichia coli*. Determination of the heavy or light chain contribution to the anti-DNA/-cardiolipin activity of the Fab," *J Biol Chem*. 275: 35129-35136 (2000).

Kunkel et al., "Rapid and efficient site-specific mutagenesis without phenotypic selection," *Methods Enzymol*. 154: 367-382 (1987).

Lane et al., "ErbB2 potentiates breast tumor proliferation through modulation of P27(Kip1)-Cdk2 complex formation: receptor overexpression does not determine growth dependency," *Mol Cell Biol*. 20: 3210-3223 (2000).

Lasky and Dowbenko, "DNA sequence analysis of the type-common glycoprotein-D genes of herpes simplex virus types 1 and 2," *DNA* 3: 23-29 (1984).

Lederman et al., "A single amino acid substitution in a common African allele of the CD4 molecule ablates binding of the monoclonal antibody, OKT4," *Mol Immunol*. 28: 1171-1181 (1991).

Lee et al., "Bivalent antibody phage display mimics natural immunoglobulin," *J Immunol Methods* 284: 119-132 (2004).

Lee et al., "High-affinity human antibodies from phage-displayed synthetic Fab libraries with a single framework scaffold," *J Mol Biol*. 340: 1073-1093 (2004).

Lee et al., "Synthetic anti-BR3 antibodies that mimic BAFF binding and target both human and murine B cells," *Blood* 108: 3103-3111 (2006).

Lewis et al., "Growth regulation of human breast and ovarian tumor cells by heregulin: evidence for the requirement of ErbB2 as a critical component in mediating heregulin responsiveness," *Cancer Res*. 56: 1457-1465 (1996).

Li et al., "β-endorphin omission analogs: dissociation of immunoreactivity from other biological activities," *Proc Natl Acad Sci USA* 77: 3211-3214 (1980).

Liang et al., "Cross-species vascular endothelial growth factor (VEGF)-blocking antibodies completely inhibit the growth of human tumor xenografts and measure the contribution of stromal VEGF," *J Biol Chem*. 281: 951-961 (2006).

Lipovsek et al., "In-vitro protein evolution by ribosome display and mRNA display," *J Immunol Methods* 290: 51-67 (2004).

Lonberg and Huszar, "Human antibodies from transgenic mice," *Intern Rev Immunol*. 13: 65-93 (1995).

Lonberg et al., "Antigen-specific human antibodies from mice comprising four distinct genetic modifications," *Nature* 368: 856-859 (1994).

Lovell et al., "Structure validation by Cα geometry: φ, Ψ and Cβ deviation," *Proteins* 50: 437-450 (2003).

Lowman et al., "Selecting high-affinity binding proteins by monovalent phage display," *Biochemistry* 30: 10832-10838 (1991).

Lum et al., "The new face of bispecific antibodies: targeting cancer and much more," *Exp Hematol*. 34: 1-6 (2006).

Ma et al., "Multiple diverse ligands binding at a single protein site: a matter of pre-existing populations," *Protein Sci*. 11: 184-197 (2002).

MacCallum et al., "Antibody-antigen interactions: contact analysis and binding site topography," *J Mol Biol*. 262: 732-745 (1996).

Manivel et al., "The primary antibody repertoire represents a linked network of degenerate antigen specificities," *J Immunol*. 169: 888-897 (2002).

Marks et al., "By-passing immunization: building high affinity human antibodies by chain shuffling," *Biotechnology* 10: 779-783 (1992).

Marks et al., "By-passing immunization. Human antibodies from V-gene libraries displayed on phage," *J Mol Biol.* 222: 581-597 (1991).
Marvin and Zhu, "Recombinant approaches to IgG-like bispecific antibodies," *ACTA Pharmacol Sin.* 26: 649-658 (2005).
Maynard and Georgiou, "Antibody engineering," *Annu Rev Biomed Eng.* 2: 339-376 (2000).
Merk et al., "Cell-free expression of two single-chain monoclonal antibodies against lysozyme: effect of domain arrangement on the expression," *J Biochem.* 125: 328-333 (1999).
Mohan et al., "Association energetics of cross-reactive and specific antibodies," *Biochemistry* 48: 1390-1398 (2009).
Mølhøj et al., "CD19-/CD3-bispecific antibody of the BiTE class is far superior to tandem diabody with respect to redirected tumor cell lysis," *Mol Immunol.* 44: 1935-1943 (2007).
Morrison, "Success in specification," *Nature* 368: 812-813 (1994).
Muller et al., "Vascular endothelial growth factor: crystal structure and functional mapping of the kinase domain receptor binding site," *Proc Natl Acad Sci USA* 94: 7192-7197 (1997).
Muller et al., "VEGF and the Fab fragment of a humanized neutralizing antibody: crystal structure of the complex at 2.4 Å resolution and mutational analysis of the interface," *Structure* 6: 1153-1167 (1998).
Mylvaganam et al., "Structural basis for the binding of an anti-cytochrome c antibody to its antigen: crystal structures of FabE8-cytochrome c complex to 1.8 Å resolution and FabE8 to 2.26 Å resolution," *J Mol Biol.* 281: 301-322 (1998).
Nagata et al., "PTEN activation contributes to tumor inhibition by trastuzumab, and loss of PTEN predicts trastuzumab resistance in patients," *Cancer Cell* 6: 117-127 (2004).
Nemazee, "Receptor editing in lymphocyte development and central tolerance," *Nat Rev Immunol.* 6: 728-740 (2006).
Neuberger, "Generating high-avidity human Mabs in mice," *Nat Biotechnol.* 14: 826 (1996).
Notkins et al., "Polyreactivity of antibody molecules," *Trends Immunol.* 25: 174-179 (2004).
Office Action for U.S. Appl. No. 11/893,693, mailed on Jul. 17, 2009.
Office Action for U.S. Appl. No. 11/893,693 mailed on Apr. 12, 2010.
Otwinowski and Minor, "Processing of X-ray diffraction data collected in oscillation mode," *Methods Enzymol.* 276: 307-326 (1997).
Parren and Burton, "Two-in-one designer antibodies," *Science* 323: 1567-1568 (2009).
Pini et al., "Design and use of a phage display library. Human antibodies with subnanomolar affinity against a marker of angiogenesis eluted from a two-dimensional gel," *J Biol Chem.* 273: 21769-21776 (1998).
Prabhakar et al., "Lymphocytes capable of making monoclonal autoantibodies that react with multiple organs are a common feature of the normal B cell repertoire," *J Immunol.* 133: 2815-2817 (1984).
Presta, "Antibody engineering," *Curr Op Struct Biol.* 2: 593-596 (1992).
Presta et al., "Humanization of an anti-vascular endothelial growth factor monoclonal antibody for the therapy of solid tumors and other disorders," *Cancer Res.* 57: 4593-4599 (1997).
Prewett et al., "Antivascular endothelial growth factor receptor (fetal liver kinase 1) monoclonal antibody inhibits tumor angiogenesis and growth of several mouse and human tumors," *Cancer Res.* 59: 5209-5218 (1999).
Ravetch and Kinet, "Fc receptors," *Annu Rev Immunol.* 9: 457-492 (1991).
Read, "Pushing the boundaries of molecular replacement with maximum likelihood," *Acta Crystallogr D* 57: 1373-1382 (2001).
Reese and Karnovsky, "Fine structural localization of a blood-brain barrier to exogenous peroxidase," *J Cell Biol.* 34: 207-217 (1967).
Reichert et al., "Monoclonal antibody successes in the clinic," *Nat Biotechnol.* 23: 1073-1078 (2005).
Riechmann et al., "Reshaping human antibodies for therapy," *Nature* 332: 323-327 (1988).
Sarup et al., "Characterization of an anti-P185HER2 monoclonal antibody that stimulates receptor function and inhibits tumor cell growth," *Growth Regul.* 1: 72-82 (1991).
Sato et al., "Molecular diagnosis of tumor angiogenesis and anti-angiogenic cancer therapy," *Int J Clin Oncol.* 8: 200-206 (2003).

Senn et al., "Combinatorial immunoglobulin light chain variability creates sufficient B cell diversity to mount protective antibody responses against pathogen infections," *Eur J Immunol.* 33: 950-961 (2003).
Sethi et al., "Differential epitope positioning within the germline antibody paratope enhances promiscuity in the primary immune response," *Immunity* 24: 429-438 (2006).
Shen et al., "Single variable domain-IgG fusion. A novel recombinant approach to Fc domain-containing bispecific antibodies," *J Biol Chem.* 281: 10706-10714 (2006).
Shen et al., "Single variable domain antibody as a versatile building block for the construction of IgG-like bispecific antibodies," *J Immunol Methods* 318: 65-74 (2007).
Sidhu et al., "Phage-displayed antibody libraries of synthetic heavy chain complementarity determining regions," *J Mol Biol.* 338: 299-310 (2004).
Sidhu et al., "Phage display for selection of novel binding peptides," *Methods Enzymol.* 328: 333-63 (2000).
Smith-Gill et al., "Contributions of immunoglobulin heavy and light chains to antibody specificity for lysozyme and two haptens," *J Immunol.* 139: 4135-4144 (1987).
Song et al., "Light chain of natural antibody plays a dominant role in protein antigen binding," *Biochem Biophys Res Commun.* 268: 390-394 (2000).
Stites, "Protein-protein interactions: interface structure, binding thermodynamics, and mutational analysis," *Chem Rev.* 97: 1233-1250 (1997).
Stone et al., "The assembly of single domain antibodies into bispecific decavalent molecules," *J Immunol Methods* 318: 88-94 (2007).
Storoni et al., "Likelihood-enhanced fast rotation functions," *Acta Crystallogr D* 60: 432-438 (2004).
Streit and Detmar, "Angiogenesis, lymphangiogenesis, and melanoma metastasis," *Oncogene* 22: 3172-3179 (2003).
Takagi et al., "C-terminal opening mimics 'inside-out' activation of integrin α5β1," *Nat Struct Biol.* 8: 412-416 (2001).
Tomlinson et al., "The imprint of somatic hypermutation on the repertoire of human germline V genes," *J Mol Biol.* 256: 813-817 (1996).
Tonegawa et al., "Somatic generation of antibody diversity," *Nature* 302: 575-581 (1983).
Tonini et al., "Molecular basis of angiogenesis and cancer," *Oncogene* 22: 6549-6556 (2003).
Trinh et al., "Antibody fragment Fv4155 bound to two closely related steroid hormones: the structural basis of fine specificity," *Structure* 5: 937-948 (1997).
Tsumoto et al., "Effect of the order of antibody variable regions on the expression of the single-chain HyHel10 Fv fragment in *E. coli* and the thermodynamic analysis of its antigen-binding properties," *Biochem Biophys Res Comm.* 201: 546-551 (1994).
Vajdos et al., "Comprehensive functional maps of the antigen-binding site of an anti-ErbB2 antibody obtained with shotgun scanning mutagenesis," *J Mol Biol.* 320: 415-428 (2002).
Valladares et al., "Designing Two-in-One Antibodies", *Immunotherapy* 1(5):749-751 (2009).
Wardemann et al., "Predominant autoantibody production by early human B cell precursors," *Science* 301: 1374-1377 (2003).
Wedemayer et al., "Structural insights into the evolution of an antibody combining site," *Science* 276: 1665-1669 (1997).
Weiss et al., "Rapid mapping of protein functional epitopes by combinatorial alanine scanning," *Proc Natl Acad Sci USA* 97: 8950-8954 (2000).
Wiesmann et al., "Crystal structure at 1.7 Å resolution of VEGF in complex with domain 2 of the Flt-1 receptor," *Cell* 91: 695-704 (1997).
Willcox et al., "TCR binding to peptide-MHC stabilizes a flexible recognition interface," *Immunity* 10: 357-365 (1999).
Winn et al., "Use of TLS parameters to model anisotropic displacements in macromolecular refinement," *Acta Crystallogr D Biol Crystallogr.* 57: 122-133 (2001).
Winter et al., "Making antibodies by phage display technology," *Annu Rev Immunol.* 12: 433-455 (1994).

Written Opinion of the International Searching Authority for PCT/US2007/018385, mailed Nov. 5, 2008.
Wu et al., "Humanization of a murine monoclonal antibody by simultaneous optimization of framework and CDR residues," *J Mol Biol.* 294: 151-162 (1999).
Xu et al., "Diversity in the CDR3 region of V(H) is sufficient for most antibody specificities," *Immunity* 13: 37-45 (2000).
Yang et al., "Mutational analysis of the affinity maturation of antibody 48G7," *J Mol Biol.* 294: 1191-1201 (1999).
Zapata et al., "Engineering linear F(ab')$_2$ fragments for efficient production in *Escherichia coli* and enhanced antiproliferative activity," *Protein Eng.* 8: 1057-1062 (1995).
Beck et al., "4$^{th}$ European Antibody Congress 2008: Dec. 1-3, 2008, Geneva, Switzerland," *MAbs* 1: 93-103 (2009).
Enever et al., "Next Generation Immunotherapeutics—Honing the Magic Bullet," *Curr. Opin. Biotechnol.* 20: 405-411 (2009).
Fellouse et al., "Tyrosine Plays a Dominant Functional Role in the Paratope of a Synthetic Antibody Derived from a Four Amino Acid Code," J. Mol. Biol. 357: 100-114 (2006).
Fukada et al., Enthalpy and Heat Capacity Changes for the Proton Dissociation of Various Buffer Components in 0.1 M Potassium Chloride. *Proteins* 33: 159-166 (1998).
Garber et al., "A Broad Range of Fab Stabilities Within a Host of Therapeutic IgGs," *Biochem. Biophys. Res. Commun.* 355: 751-757 (2007).
Holt et al., "Anti-Serum Albumin Domain Antibodies for Extending the Half-Lives of Short Lived Drugs," *Protein Eng. Des. Sel.* 21: 283-288 (2008).
Koenig and Fuh, "Two-in-One Antibodies," in *Bispecific Antibodies.* Ed. R. Kontermann. Springer-Verlag Berlin Heidelberg, pp. 187-198, (2011).
Kossiakoff et al., "Understanding Mechanisms Governing Protein-Protein Interactions from Synthetic Binding Interfaces," *Curr. Opin. Struct. Biol.* 18: 499-506 (2008).
Krogsgaard et al., "Evidence That Structural Rearrangements and/or Flexibility During TCR Binding Can Contribute to T Cell Activation," *Mol. Cell* 12: 1367-1378 (2003).
McFarland et al., "Thermodynamic Analysis of Degenerate Recognition by the NKG2D Immunoreceptor: Not Induced Fit but Rigid Adaptation," *Immunity* 19: 803-812 (2003).
Mietzner et al., "Autoreactive IgG Memory Antibodies in Patients with Systemic Lupus Erythematosus Arise from Nonreactive and Polyreactive Precursors," *Proc. Natl. Acad. Sci. USA* 105: 9727-9732 (2008).
Murphy et al., "Entropy in Biological Binding Processes: Estimation of Translational Entropy Loss," *Proteins* 18: 63-67 (1994).
Murphy et al., "Configurational Effects in Antibody-Antigen Interactions Studied by Microcalorimetry," *Proteins* 21: 83-90 (1995).
Petri et al., "Thermodynamic and Kinetic Characterization of the Binding of the TATA Binding Protein to the Adenovirus E4 Promoter," *Biochemistry* 34: 9977-9984 (1995).
Prabhu et al., "Heat Capacity in Proteins," *Annu. Rev. Phys. Chem.* 56: 521-548 (2005).
Reichmann et al., "The Modular Architecture of Protein-Protein Binding Interfaces," *Proc. Natl. Acad. Sci. USA* 102: 57-62 (2005).
Rudolph et al., "How TCRs bind MHCs, Peptides, and Coreceptors," *Annu. Rev. Immunol.* 24: 419-466 (2006).
Starovasnik et al., "Antibody Variable Region Binding by Staphylococcal Protein A: Thermodynamic Analysis and Location of the Fv Binding Site on E-Domain," *Protein Sci.* 8: 1423-1431 (1999).
Sundberg et al., "Molecular Recognition in Antibody-Antigen Complexes," *Adv. Protein Chem.* 61: 119-160 (2002).
Thielges et al., "Exploring the Energy Landscape of Antibody-Antigen Complexes: Protein Dynamics, Flexibility, and Molecular Recognition," *Biochemistry* 47: 7237-7247 (2008).
van der Merwe et al., "Analysis of Cell-Adhesion Molecule Interactions Using Surface Plasmon Resonance," Curr Opin Immunol 8: 257-261. (1996).
Walker et al., "Single Domain Antibodies Against the Collagen Signalling Receptor Glycoprotein VI Are Inhibitors of Collagen Induced Thrombus Formation," *Platelets* 20: 268-276 (2009).
Walker et al., "Anti-Serum Albumin Domain Antibodies in the Development of Highly Potent, Efficacious and Long-Acting Interferon," *Protein Eng. Des. Sel.* 23: 271-278 (2010).
Wells et al., "The Molecular Basis for Growth Hormone-Receptor Interactions," *Recent Prog. Horm. Res.* 48: 253-275 (1993).
Winzor et al., "Interpretation of the Temperature Dependence of Rate Constants in Biosensor Studies," *Anal. Biochem.* 337: 289-293 (2005).
Wurch et al., "Keystone Symposium on Antibodies as Drugs: Mar. 27-Apr. 1, 2009, Whistler, BC CA," *MAbs* 1: 318-325 (2009).
Office Action for U.S. Appl. No. 11/893,693, issued Sep. 27, 2011.
International Preliminary Report on Patentability (PCT/US2009/055625) issued Mar. 8, 2011.

* cited by examiner

| Library | 28 | 29 | 30 | 30a | 30b | 30c | 30d | 30e | 30f | 31 | 32 |
|---|---|---|---|---|---|---|---|---|---|---|---|
| | | | | | | CDR-L1 | | | | | |
| L1/L3 | Ss | | NNK | (NNK) | (NNK) | (NNK) | (NNK) | (NNK) | - | NNK | Ys |
| L1/L4 | Ss | | NNK | (NNK) | (NNK) | (NNK) | (NNK) | (NNK) | (NNK) | NNK | Ys |
| L1/L2/L3-A_1 | Ss | V/L | NNK | (NNK) | (NNK) | (NNK) | (NNK) | (NNK) | (NNK) | NNK | Ys |
| L1/L2/L3-A_2 | Ss | | NNK | (NNK) | (NNK) | (NNK) | (NNK) | (NNK) | (NNK) | NNK | Ys |
| L1/L2/L3-B_1 | NNK | NNK | NNK | - | - | - | - | - | - | NNK | NNK |
| L1/L2/L3-B_2 | NNK | NNK | NNK | (NNK) | - | - | - | - | - | NNK | NNK |
| L1/L2/L3-C | Ds | I/V | NNK | (NNK) | (NNK) | (NNK) | (NNK) | (NNK) | (NNK) | NNK | Y WRG YSPHNTDA |
| L1/L2/L3-D | Ds | I/V | NNK | (NNK) | (NNK) | (NNK) | (NNK) | (NNK) | (NNK) | NNK | Y WRG YSPHNTDA |

| | CDR-L2 | | | | Framework 3 | | | | | | CDR-L3 | | | | | | | |
|---|---|---|---|---|---|---|---|---|---|---|---|---|---|---|---|---|---|---|
| | 50 | 51 | 52 | 53 | 66 | 67 | 68 | 69 | 70 | | 91 | 92 | 93 | a | b | c | d | e | f | 94 |
| | NNK W | GAS | S | NNK | NNK NNK | Ss NNK | - Ss | T/Ts NNK | D/Ds NNK | | YADS H WRG | XYZ XYZ | XYZ XYZ | (XYZ) (XYZ) | (XYZ) | - | - | - | - | ATSG |
| | NNK W | GAS | S | NNK | | | | | | | | XYZ | XYZ | (XYZ) | (XYZ) | - | - | - | - | - |
| | NNK W | GAS | S | NNK | | | | | | | NNK | NNK | - | - | - | - | - | - | - | - |
| | NNK W WG | GA | S | YS NNK | | | | T Ts | D Ds | | NNK | NNK | - | - | - | - | - | - | - | - |
| | NNK W WG | GA | S | YS NNK | NNK | Ss | | | | | | XYZ | XYZ | - | - | - | - | - | - | ATSG |

| Library | L1/L3 | L1/L4 | L1/L2/L3-A | L1/L2/L3-B | L1/L2/L3-C, +L4-D |
|---|---|---|---|---|---|
| template<br>Format<br>Stop | 2C4<br>Fab-C<br>L1 | 2C4<br>Fab-C<br>L1 | 2C4<br>Fab-C<br>L1 | 4D5¹<br>ScFv<br>L1 | 4D5<br>ScFv<br>L1 |
| L1: 28<br>29<br>30<br>30a-e<br>31<br>32<br>33 | Ss<br>NNK<br>(NNK)0-4<br>NNK<br>Ys | Ss<br>NNK<br>(NNK)0-5<br>NNK<br>Ys | Ss<br>VL<br>NNK<br>(NNK)5<br>P<br>Y | G6-Av²<br>Fab-C<br>NNK<br>NNK<br>NNK<br>(NNK)2<br>NNK<br>NNK | Ds<br>I/V<br>NNK<br>(NNK)0-5<br>NNK<br>Y/WRG/YSPHSTDA |
| L2: 50<br>51<br>52<br>53 | | | NNK/W<br>GAS<br>NNK | NNK/W<br>GAS<br>NNK | NNK/W/WRG<br>GA<br>S<br>YS/NNK |
| L4: 66<br>67<br>68<br>69<br>70 | | NNK<br>Ss<br>NNK<br>NNK | | | NNK<br>Ss<br>T/Ts<br>D/Ds |
| L3: 91<br>92<br>93<br>93a<br>94 | XYZ<br>(XYZ)<br>(XYZ)0-2 | XYZ<br>(XYZ) | XYZ<br>XYZ<br>(XYZ)0-2<br>P<br>Y | NNK<br>NNK<br>XYZ | YADS/H/WRG XYZ<br>XYZ<br>(XYZ)0-2 ATSG<br>ATSG |
| Display | 5-7% | 5-7% | 5-7% | ~15-25% | ~17% |
| Target | VEGF<br>DR5<br>Albumin | VEGF<br>DR5 | VEGF<br>DR5 | VEGF | VEGF<br>DR5<br>IgG-Fc-fusion protein |

FIG. 3

Light chain CDRs:

| | CDR-L1 | | | | | | | CDR-L2 | | | | FR3(CDR-L4) | | | | | CDR-L3 | | | | | | |
|---|---|---|---|---|---|---|---|---|---|---|---|---|---|---|---|---|---|---|---|---|---|---|---|
| | 28 | 29 | 30 | 30a-f | 31 | 32 | 33 | 50 | 51 | 52 | 53 | 66 | 67 | 68 | 69 | 70 | 91 | 92 | 93 | 93a-e | 94 | 95 | 96 |
| hu4D5 | D | V | S | | T | A | V | S | A | S | F | G | S | G | T | D | H | Y | T | | T | P | P |
| 2C4 | D | V | S | | I | G | V | S | A | S | Y | G | S | G | T | D | Y | Y | I | | Y | P | Y |
| Fab12-G | D | V | S | | T | A | V | S | A | S | F | G | S | G | T | D | Y | S | T | | V | P | W |

Heavy chain CDRs:

| | CDR-H1 | | | | | | CDR-H2 | | | | | | | | | | | | CDR-H3 | | | | | | |
|---|---|---|---|---|---|---|---|---|---|---|---|---|---|---|---|---|---|---|---|---|---|---|---|---|---|
| | 29 | 30 | 31 | 32 | 33 | 34 | 49 | 50 | 51 | 52 | 52a | 53 | 54 | 55 | 56 | 57 | 58 | 59 | 94 | 95 | 96 | 97 | 98 | 99 | 100 | 100a |
| hu4D5 | I | K | D | T | Y | I | A | R | I | Y | P | T | N | G | Y | T | R | Y | R | W | G | G | D | G | F | Y |
| 2C4 | F | T | D | Y | T | M | A | D | V | N | P | N | S | G | S | I | | Y | R | N | L | G | P | S | F | |
| Fab12-G | I | S | D | G | | I | A | A | I | A | P | G | A | G | S | T | Y | Y | R | F | V | S | A | P | P | S |

| LC CDR | Position | Natural Diversity Prevalence (%) | | | | | | | | | | | | Design Diversity Prevalence (%) | | | | | | | | |
|---|---|---|---|---|---|---|---|---|---|---|---|---|---|---|---|---|---|---|---|---|---|---|
| CDR1 | 28 (D) | S 71 | G 12 | D 7 | N 4 | T 3 | R 2 | | | | | | | D 39 | E 10 | G 7 | A 7 | V 7 | N 6 | Y 6 | H 6 | X <2 |
| | 29 (V) | I 1 | V 12 | L | | | | | | | | | | I 1 | V 50 | | | | | | | |
| | 30 (N) | S 43 | L 42 | R 12 | G 6 | N 5 | V 4 | T 4 | D 2 | | | | | S 50 | L 9 | R 9 | G 6 | A 6 | V 6 | T 6 | P 6 | X 3 |
| | 30a-e (*) | S 55 | N 17 | Y 9 | G 8 | K 5 | H 4 | D 3 | | | | | | S 9 | L 9 | R 9 | G 6 | A 6 | V 6 | T 6 | P 6 | X 3 |
| | 31 (T) | S 34 | N 23 | T 10 | R 9 | D 8 | I 6 | K 5 | | | | | | S 9 | L 9 | R 9 | G 6 | A 6 | V 6 | T 6 | P 6 | X 3 |
| | 32 (A) | Y 44 | N 32 | W 11 | F 3 | S 2 | D 2 | R 2 | | | | | | Y 31 | W 8 | G 8 | R 8 | N 6 | S 6 | D 6 | T 6 | A 6 |
| | 33 (V) | L 68 | V 8 | F 6 | X 1 | | | | | | | | | V 50 | L | | | | | | | |
| | | 94 3 | | | | | | | | | | | | 50 | | | | | | | | |
| CDR2 | 50 (S) | G 25 | A 22 | D 19 | W 10 | K 8 | L 6 | E 3 | S 2 | | | | | W 16 | G 12 | S 7 | L 7 | R 7 | A 5 | V 5 | T 5 | P 5 | X 2 |
| | 51 (A) | A 79 | V 7 | G 6 | T 5 | | | | | | | | | A G 50 | | | | | | | | |
| | 52 (S) | S 95 | | | | | | | | | | | | S 50 | | | | | | | | |
| | 53 (F) | S 36 | N 28 | T 26 | K 3 | R 2 | I 2 | | | | | | | S 44 | Y 43 | Y X <2 | | | | | | |
| CDR3 | 91 (H) | Y 52 | S 12 | R 10 | A 7 | G 4 | H 4 | F 2 | L 2 | D 2 | | | | H 20 | Y 15 | S 15 | A 15 | D 7 | R 7 | V 7 | L 7 | C 5 | G W 7 |
| | 92 (Y) | G 22 | Y 22 | N 15 | S 12 | D 7 | L 6 | T 4 | H 3 | I 2 | | | | G 11 | S 9 | S 9 | D 8 | R 8 | V 7 | Y 6 | L 5 | N 5 | X <5 |
| | 93 (T) | S 46 | N 21 | Q 7 | T 6 | H 6 | G 4 | D 3 | R 2 | | | | | G 11 | G 9 | S 9 | D 8 | D 7 | V 6 | Y 6 | L 5 | C 5 | X <5 |
| | 93a-b (*) | W 28 | S 25 | T 17 | P 11 | L 6 | Y 4 | V 2 | A 2 | N 2 | | | | G 12 | D 10 | D 9 | Y 8 | R 7 | A 7 | V 6 | C 5 | N 5 | X <5 |
| | 94 (T) | T 19 | P 19 | S 18 | W 12 | Y 10 | L 7 | F 5 | A 3 | V 2 | G 1 | | | T 25 | S 25 | A 25 | G 25 | | | | | |

FIG. 4

|  | CDR-L1 | | | | | | | CDR-L2 | | | | | CDR-L3 | | | | | Mutations/ |
|  | 28 | 29 | 30 | 30a | 30b | 30c | 30d | 30e | 31 | 32 | 33 | 50 | 51 | 52 | 53 | 91 | 92 | 93 | 93a | 93b | 94 | Insertions |
|---|---|---|---|---|---|---|---|---|---|---|---|---|---|---|---|---|---|---|---|---|---|---|
| hu4D5 | D | V | N | | | | | | T | A | V | S | A | S | F | H | Y | T | | | T | - |
| anti-VEGF | D | I | G | G | | | | | G | S | V | W | G | S | F | H | Y | T | | | T | 7 |
|  | D | I | H | S | | | | | G | S | V | W | G | S | Y | H | Y | T | | | T | 8 |
|  | D | V | F | | | | | | T | S | V | D | A | S | Y | R | Y | I | W | | A | 8 |
|  | D | I | W | | | | | | R | A | V | P | A | S | N | G | Y | Y | I | | A | 9 |
|  | D | I | W | | | | | | R | W | V | A | A | S | H | A | G | | | | A | 9 |
|  | Y | V | W | | | | | | Q | Y | V | H | A | S | S | G | Y | W | V | | A | 10 |
|  | D | I | P | S | | | | | I | Y | V | G | A | S | Y | R | Y | W | V | | A | 11 |
|  | D | I | W | | | | | | R | W | L | A | G | S | S | H | D | Q | | | A | 11 |
|  | E | V | Y | | | | | | S | Y | V | P | A | S | S | G | F | W | I | | G | 11 |
|  | N | V | W | | | | | | D | W | V | P | A | S | S | G | W | Y | I | | A | 11 |
|  | N | V | W | | | | | | S | H | V | G | G | S | S | R | L | W | F | | T | 11 |
|  | W | V | P | S | | | | | H | T | V | L | G | S | Y | S | D | Y | | | T | 11 |
|  | Y | V | Y | S | | | | | T | T | V | N | G | S | S | A | S | | | | A | 11 |
|  | E | I | F | P | | | | | Y | Y | V | L | G | S | S | G | W | D | | | G | 13 |
|  | N | I | F | | | | | | S | H | V | P | G | S | Y | A | F | W | V | | S | 13 |
|  | Q | I | W | | | | | | R | H | L | T | G | S | S | S | Y | W | V | | A | 13 |
|  | Y | I | W | | | | | | N | Y | V | G | G | S | S | S | W | W | A | | G | 13 |
| anti-DR5 | S | V | S | | | | | | S | A | V | S | A | S | S | Y | S | S | | | S | 8 |
|  | V | V | S | | | | | | M | T | V | G | A | S | S | Y | G | S | Y | | S | 11 |
|  | N | V | G | | | | | | R | P | V | G | G | S | S | Y | G | S | F | | G | 12 |
|  | R | I | N | S | | | | | H | T | V | W | G | S | H | Y | S | N | R | | T | 12 |
|  | D | I | W | N | R | | | | R | A | L | E | G | S | S | G | G | S | Y | | S | 14 |
|  | D | I | W | N | R | | | | R | A | L | K | G | S | S | G | G | S | Y | | S | 14 |
| anti-Fc | E | V | L | | | | | | T | S | V | S | A | S | F | H | Y | T | | | T | 3 |
|  | K | I | Q | | | | | | A | Y | V | S | A | S | F | H | Y | T | | | T | 5 |
|  | N | I | V | V | R | | | | P | Y | V | S | A | S | F | H | Y | T | | | T | 7 |
|  | D | V | G | G | G | | | | S | G | V | G | G | S | H | Y | T | | | | T | 8 |
|  | D | I | G | | | | | | A | G | L | S | A | S | F | S | E | S | R | | T | 10 |
|  | D | I | S | | | | | | R | Y | L | S | A | S | F | Y | G | W | R | R | T | 10 |
|  | D | V | G | G | | | | | L | G | L | S | A | S | S | G | G | A | D | | T | 10 |
|  | D | V | N | | | | | | R | Y | V | A | G | S | Y | G | I | D | L | | A | 10 |
|  | D | V | S | R | | | | | Y | D | L | F | A | S | S | S | G | Y | H | | T | 11 |
|  | V | V | R | | | | | | Q | H | V | R | A | S | S | S | D | A | S | | A | 11 |
|  | D | V | H | R | | | | | D | S | V | W | G | S | Q | W | T | W | A | D | T | 12 |
|  | D | V | H | P | S | | | | P | R | V | L | G | S | S | A | N | V | D | | T | 12 |
|  | E | I | S | R | | | | | Y | A | V | W | A | S | S | G | V | Y | N | | A | 12 |
|  | N | V | P | R | | | | | W | S | L | W | A | S | S | W | V | T | H | E | T | 12 |
|  | P | V | F | R | | | | | R | G | L | S | A | S | S | G | L | R | H | | G | 12 |
|  | A | V | P | R | | | | | Y | G | V | W | G | S | D | S | G | W | S | | A | 13 |
|  | A | V | S | R | | | | | H | A | L | W | G | S | W | D | G | K | | | A | 13 |
|  | D | I | G | L | | | | | L | N | L | W | A | S | S | W | A | D | I | S | T | 13 |
|  | D | I | R | G | Q | | | | R | G | V | S | G | S | S | G | S | G | S | S | T | 13 |
|  | D | V | S | G | R | | | | R | G | L | D | A | S | S | G | A | A | Y | | A | 13 |
|  | E | I | V | | | | | | F | S | V | G | G | S | S | G | D | S | K | | S | 13 |
|  | N | V | P | L | | | | | N | D | V | H | G | S | S | W | A | H | Y | | G | 13 |
|  | V | I | A | R | | | | | Y | D | L | W | A | S | S | A | G | A | R | | A | 14 |
|  | D | I | P | E | H | | | | F | R | L | G | G | S | S | G | G | W | S | E | T | 15 |
|  | Y | I | P | R | | | | | D | A | L | W | G | S | Y | W | A | S | W | D | A | 15 |
|  | R | V | S | D | S | L | Q | | N | S | V | L | G | S | S | G | L | D | L | | A | 16 |
|  | N | V | S | R | V | S | W | F | E | T | L | G | G | S | Y | W | F | T | W | | G | 17 |

FIG.5A

|  | CDR-L1 | | | | | | | | | | CDR-L2 | | | | CDR-L3 | | | | | | Mutations/ |
| --- | 28 | 29 | 30 | 30a | 30b | 30c | 30d | 30e | 31 | 32 | 33 | 50 | 51 | 52 | 53 | 91 | 92 | 93 | 93a | 93b | 94 | Insertions |
| hu4D5 | D | V | N |  |  |  |  |  | T | A | V | S | A | S | F | H | Y | T |  |  | T | - |
| anti-HER2/VEGF | D | V | W |  |  |  |  |  |  |  |  | K | W | V | A | A | S | S | H | Y | T | 5 |
|  | D | I | K | N |  |  |  |  | G | S | V | W | A | S | F | H | Y | T |  |  | T | 6 |
|  | D | I | L | G |  |  |  |  | G | S | V | W | A | S | F | H | Y | T |  |  | T | 6 |
|  | D | I | M | S |  |  |  |  | G | S | V | W | A | S | F | H | Y | T |  |  | T | 6 |
|  | D | I | R | A |  |  |  |  | G | S | V | W | A | S | F | H | Y | T |  |  | T | 6 |
|  | D | I | R | G |  |  |  |  | G | S | V | W | A | S | F | H | Y | T |  |  | T | 6 |
|  | D | V | R | Q |  |  |  |  | G | S | V | W | G | S | F | H | Y | T |  |  | T | 6 |
|  | D | I | A | A |  |  |  |  | G | S | V | W | A | S | Y | H | Y | T |  |  | T | 7 |
|  | D | I | A | G |  |  |  |  | G | S | V | W | A | S | Y | H | Y | T |  |  | T | 7 |
|  | D | I | A | H |  |  |  |  | G | S | V | W | A | S | Y | H | Y | T |  |  | T | 7 |
|  | D | I | A | K |  |  |  |  | G | S | V | W | G | S | F | H | Y | T |  |  | T | 7 |
|  | D | I | G | A |  |  |  |  | G | S | V | W | G | S | F | H | Y | T |  |  | T | 7 |
|  | D | I | G | A |  |  |  |  | G | S | V | W | G | S | F | H | Y | T |  |  | T | 7 |
|  | D | I | G | G |  |  |  |  | G | S | V | W | G | S | F | H | Y | T |  |  | T | 7 |
|  | D | I | G | L |  |  |  |  | G | S | V | W | A | S | Y | H | Y | T |  |  | T | 7 |
|  | D | I | G | M |  |  |  |  | G | S | V | W | A | S | Y | H | Y | T |  |  | T | 7 |
|  | D | I | K | H |  |  |  |  | G | S | V | W | G | S | F | H | Y | T |  |  | T | 7 |
|  | D | I | L | A |  |  |  |  | G | S | V | W | G | S | F | H | Y | T |  |  | T | 7 |
|  | D | I | L | G |  |  |  |  | G | S | V | W | G | S | F | H | Y | T |  |  | T | 7 |
|  | D | I | L | I |  |  |  |  | G | S | V | W | G | S | F | H | Y | T |  |  | T | 7 |
|  | D | I | L | T |  |  |  |  | G | S | V | W | G | S | F | H | Y | T |  |  | T | 7 |
|  | D | I | M | L |  |  |  |  | G | S | V | W | G | S | F | H | Y | T |  |  | T | 7 |
|  | D | I | Q | S |  |  |  |  | G | S | V | W | G | S | F | H | Y | T |  |  | T | 7 |
|  | D | I | R | I |  |  |  |  | G | S | V | W | G | S | F | H | Y | T |  |  | T | 7 |
|  | D | I | R | M |  |  |  |  | G | S | V | W | G | S | F | H | Y | T |  |  | T | 7 |
|  | D | I | R | Q |  |  |  |  | G | S | V | W | A | S | Y | H | Y | T |  |  | T | 7 |
|  | D | I | R | T |  |  |  |  | G | S | V | W | G | S | F | H | Y | T |  |  | T | 7 |
|  | D | I | R | V |  |  |  |  | G | S | V | W | G | S | F | H | Y | T |  |  | T | 7 |
|  | D | I | S | M |  |  |  |  | G | S | V | W | G | S | F | H | Y | T |  |  | T | 7 |
|  | D | I | S | R |  |  |  |  | G | S | V | W | G | S | F | H | Y | T |  |  | T | 7 |
|  | D | I | S | V |  |  |  |  | G | S | V | W | G | S | F | H | Y | T |  |  | T | 7 |
|  | D | I | V | S |  |  |  |  | G | S | V | W | G | S | F | H | Y | T |  |  | T | 7 |
|  | D | I | W |  |  |  |  |  | H | W | V | A | G | S | S | H | Y | T |  |  | T | 7 |
|  | N | I | A | Q |  |  |  |  | G | S | V | W | A | S | F | H | Y | T |  |  | T | 7 |
|  | D | I | A | F |  |  |  |  | G | S | L | W | G | S | F | H | Y | T |  |  | T | 8 |
|  | D | I | A | M |  |  |  |  | G | S | V | W | G | S | Y | H | Y | T |  |  | T | 8 |
|  | D | I | A | R |  |  |  |  | G | S | V | W | G | S | M | H | Y | T |  |  | T | 8 |
|  | D | I | A | S |  |  |  |  | G | S | V | W | G | S | L | H | Y | T |  |  | T | 8 |
|  | D | I | A | S |  |  |  |  | G | S | V | W | G | S | S | H | Y | T |  |  | T | 8 |
|  | D | I | G | S |  |  |  |  | G | S | V | W | G | S | Y | H | Y | T |  |  | T | 8 |
|  | D | I | I | G |  |  |  |  | G | S | V | W | G | S | Y | H | Y | T |  |  | T | 8 |
|  | D | I | K | A |  |  |  |  | G | S | V | W | G | S | Y | H | Y | T |  |  | T | 8 |
|  | D | I | K | F |  |  |  |  | G | S | V | W | G | S | S | H | Y | T |  |  | T | 8 |
|  | D | I | K | L |  |  |  |  | G | S | V | W | G | S | L | H | Y | T |  |  | T | 8 |
|  | D | I | K | L |  |  |  |  | G | S | V | W | G | S | M | H | Y | T |  |  | T | 8 |
|  | D | I | K | S |  |  |  |  | G | S | V | W | G | S | T | H | Y | T |  |  | T | 8 |

FIG.5B-1

|  | 28 | 29 | 30 | CDR-L1 30a 30b 30c 30d 30e | 31 | 32 | 33 | 50 | CDR-L2 51 52 | 53 | 91 | CDR-L3 92 93 93a 93b | 94 | Mutations/Insertions |
|---|---|---|---|---|---|---|---|---|---|---|---|---|---|---|
| hu4D5 | D | V | N |  | T | A | V | S | A S | F | H | Y T | T | - |
|  | D | I | K | V | G | S | V | W | G S | Y | H | Y T | T | 8 |
|  | D | I | K | W | G | S | V | W | G S | T | H | Y T | T | 8 |
|  | D | I | L | K | G | S | V | W | G S | Y | H | Y T | T | 8 |
|  | D | I | L | S | G | S | V | W | G S | W | H | Y T | T | 8 |
|  | D | I | Q | R | G | S | V | W | G S | C | H | Y T | T | 8 |
|  | D | I | Q | S | G | S | V | W | G S | Y | H | Y T | T | 8 |
|  | D | I | Q | T | G | S | V | W | G S | Y | H | Y T | T | 8 |
|  | D | I | R | E | G | S | V | W | G S | S | H | Y T | T | 8 |
|  | D | I | R | F | G | S | V | W | G S | Y | H | Y T | T | 8 |
|  | D | I | R | G | G | S | V | W | G S | Y | H | Y T | T | 8 |
|  | D | I | R | L | G | S | V | W | G S | Y | H | Y T | T | 8 |
|  | D | I | R | M | G | S | V | W | G S | S | H | Y T | T | 8 |
|  | D | I | R | R | G | S | V | W | G S | Y | H | Y T | T | 8 |
|  | D | I | R | R | G | S | V | W | G S | A | H | Y T | T | 8 |
|  | D | I | R | S | G | S | V | W | G S | Y | H | Y T | T | 8 |
|  | D | I | R | S | G | S | V | W | G S | T | H | Y T | T | 8 |
|  | D | I | R | S | G | S | V | W | G S | N | H | Y T | T | 8 |
|  | D | I | R | S | G | S | V | W | G S | E | H | Y T | T | 8 |
|  | D | I | R | S | G | S | V | W | G S | S | H | Y T | T | 8 |
|  | D | I | R | V | G | S | V | W | G S | Y | H | Y T | T | 8 |
|  | D | I | S | S | G | S | V | W | G S | Y | H | Y T | T | 8 |
|  | D | I | T | M | G | S | V | W | G S | L | H | Y T | T | 8 |
|  | D | I | Y | M | G | S | V | W | G S | Y | H | Y T | T | 8 |
|  | D | I | A | T | G | S | L | W | G S | Y | H | Y T | T | 9 |
|  | D | I | K | S | G | S | L | W | G S | Y | H | Y T | T | 9 |
|  | D | I | R | G | G | S | V | G | G S | Y | Y | Y T | T | 9 |
|  | G | I | R | T | G | S | V | W | G S | Y | H | Y T | T | 9 |
|  | N | I | A | M | G | S | V | W | G S | Y | H | Y T | T | 9 |
|  | N | I | R | S | G | S | V | W | G S | V | H | Y T | T | 9 |
|  | N | I | R | T | G | S | V | W | G S | Y | H | Y T | T | 9 |
|  | D | I | R | A | G | S | V | W | G S | Y | H | F N | A | 11 |
|  | N | I | Y | A | G | S | L | W | G S | Y | H | Y T | T | 10 |
|  | N | I | Y | S | G | S | L | W | G S | Y | H | Y T | T | 10 |
|  | D | I | P | R S I S | G | Y | V | W | G S | Y | H | Y T | T | 11 |
| anti-HER2/DR5 | N | I | R | N G | G | G | L | S | A S | F | H | Y T | T | 8 |
|  | N | V | S |  | K | H | V | W | G S | Y | S | Y S | G | 10 |
| anti-HER2/Fc | Q | V | S | K | Y | D | V | W | G S | S | S | G F R | S | 13 |

FIG.5B-2

| Sorting Round | Binding condition | Protein | Titer | Enrichment | OD/mL |
|---|---|---|---|---|---|
| 1 | bind 4 hrs. wash 4X BSA | Human Fc fusion hVEGF hDR5 - long L - 3 (short L1's) L - 4 (long L1's) | $1.8 \times 10^6$ $1.5 \times 10^6$ $8 \times 10^5$ $4.8 \times 10^6$ $1 \times 10^6$ | | 21 18.3 20.9 |
| 2 | bind 3 hrs. wash 5X BSA/ovalbumin | Human Fc fusion hVEGF hDR5 - long | $5.2 \times 10^5$ $3.6 \times 10^5$ $4.2 \times 10^5$ | 1.86 1.33 1.05 | 26.6 18.2 15.4 |
| 3 | bind 3 hrs. wash 10X BSA/milk | Human Fc fusion hVEGF hDR5 - long | $9 \times 10^3$ $8 \times 10^3$ $1.4 \times 10^4$ | 1.5 0.75 2.8 | 16.2 8.17 17.3 |
| 4 | bind 2 hrs. wash 12X casein | Human Fc fusion hVEGF hDR5 - long | $5.5 \times 10^5$ $7.4 \times 10^6$ $4.5 \times 10^7$ | 22.9 96.1 818.2 | 25.3 14.8 9.7 |
| 5 | bind 1.75 hrs. wash 12X BSA | Human Fc fusion hVEGF hDR5 - long | $1.4 \times 10^6$ $2.2 \times 10^7$ $6.5 \times 10^7$ | 14 110 325 | |

FIG. 7

| 28 | 29 | 30 | 30a | 31 | 32 | 33 | 50 | 51 | 52 | | 91 | 92 | 93 |
|---|---|---|---|---|---|---|---|---|---|---|---|---|---|
| Dsoft | IV | NWK | | NWK | | LV | | G/A | | | | | XYZ |
| D | I | R | S | G | S | V | W | G | S | Y | | | |
| D | I | R | T | G | S | V | W | G | S | F | | | |
| D | I | R | V | G | S | V | W | G | S | F | | | |
| D | I | A | G | G | S | V | W | A | S | Y | | | |
| D | I | R | F | G | S | V | W | G | S | F | | | |
| D | V | K | S | G | S | V | W | G | S | Y | | | |
| W | I | A | R | H | T | V | L | G | S | Y | S | D | Y |
| D | I | P | S | G | S | V | W | A | S | F | | | |
| D | I | N | G | G | S | V | W | G | S | Y | | | |
| D | V | L | Q | G | S | V | W | G | S | Y | | | |
| D | I | R | M | G | S | V | W | G | S | F | | | |
| D | I | R | T | G | S | V | W | G | S | Y | | | |
| D | I | K | H | G | S | L | W | A | S | F | | | |
| D | V | A | S | G | S | V | P | G | S | S | G | W | Y |
| N | I | K | | D | W | V | W | A | S | V | | | |
| D | I | K | H | G | S | V | W | G | S | W | | | |
| D | V | R | M | R | H | L | T | G | S | F | S | Y | W |
| Q | I | W | | G | S | V | W | G | S | Y | | | |
| N | I | K | H | G | Y | V | P | A | S | S | G | W | W |
| E | V | S | M | S | P | L | W | A | S | Y | Y | F | A |
| V | I | A | | Q | H | V | P | A | S | S | G | Y | R |
| D | I | Y | K | G | Y | V | G | G | S | F | | | |
| D | I | R | K A/F/G | G | W | L | W | G | S | Y | A | F | W |
| D | I | K | | S | P | V | P | A | S | S | G | A | A |
| D | I | F | T | G | H | V | A | G | S | F | | | |
| D | I | R | F | R | S | V | W | G | S | S | | | |
| D | I | L | M | G | W | L | W | G | S | Y | H | D | Q |
| D | I | W | | G | S | V | W | G | S | Y | | | |
| D | I | Y | M | G | S | V | W | G | S | F | | | |
| D | I | S | M | G | S | V | W | G | S | Y | | | |
| N | I | A | Q | G | S | V | W | A | S | F | | | T |

FIG.8 hVEGF Binders-Combined plate and solution selection

| | L1 | | | | | | | | | | L2 | | | | L3 | | | | | Phage IC50(nM) | |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 94 | hVEGF | HER2 |
| 4D5 | D | V | S | | | | | T | A | V | S | A | S | F | H | Y | T | T | T | | |
| H6 | Y | I | W | | | | | N | Y | V | G | G | S | S | S | W | W | A | G | 87 | ND |
| H7 | N | V | W | | | | | D | W | V | P | A | S | S | G | W | Y | I | A | 60 | ND |
| H8 | E | I | F | P | | | | Y | Y | V | L | G | S | S | G | W | D | | G | 226 | ND |
| H9 | Y | V | W | | | | | Q | Y | V | H | A | S | S | G | Y | W | V | A | 41 | ND |
| H10 | D | V | F | | | | | T | S | V | D | A | S | Y | R | Y | I | W | A | 170 | ND |

| | ELISA Affinity screen | | | | L1 | | | | | | L2 | | | L3 | | | | |
|---|---|---|---|---|---|---|---|---|---|---|---|---|---|---|---|---|---|---|---|
| | SSC +/- 50 or 100nM VEGF | | SSC +/- 20nM HER2 | | 28 | 29 | 30 | 31 | 32 | 33 | 50 | 53 | | 91 | 92 | 93 | 94 | 94a |
| 6 | 2.12 | 1.81 | 85.6 | 0.04 | 0.04 | 103.3 | D | I | W | R | A | V | P | A | N | G | Y | Y | I | A |
| 8 | 2.48 | 1.88 | 76.1 | 0.05 | 0.06 | 126.5 | Y | – | W | N | Y | V | G | G | S | S | W | Y | – | G |
| 12 | 2.23 | 1.81 | 81.3 | 0.04 | 0.04 | 97.9 | D | – | G | G | W | V | W | S | F | H | Y | W | A | A |
| 18 | 2.88 | 2.56 | 88.8 | 0.04 | 0.04 | 96.7 | W | V | G | H | S | V | L | G | Y | S | D | T | T | – |
| 20 | 2.46 | 2.21 | 90.0 | 0.04 | 0.04 | 91.5 | Q | – | P | R | T | L | T | S | S | S | Y | Y | T | – |
| 43 | 1.96 | 1.76 | 89.5 | 0.04 | 0.04 | 96.1 | D | – | S | R | H | V | A | S | S | H | W | W | V | A |
| 5 | 2.47 | 0.41 | 16.6 | 0.04 | 0.04 | 99.7 | N | V | W | D | W | V | P | A | S | G | A | G | A | – |
| 26 | 2.68 | 2.11 | 78.5 | 0.04 | 0.04 | 110.8 | N | – | F | S | H | V | P | G | S | A | F | S | V | A |
| 27 | 2.82 | 2.70 | 95.7 | 0.04 | 0.04 | 98.5 | Y | V | Y | T | T | V | N | S | S | A | S | D | A | S |
| 28 | 2.58 | 1.83 | 71.2 | 0.04 | 0.04 | 47.3 | E | – | F | Y | Y | V | L | A | S | G | W | W | D | – |
| 38 | 3.09 | 0.69 | 22.2 | 0.04 | 0.04 | 105.5 | Y | V | W | Q | Y | Y | H | G | Y | H | Y | W | V | A' |
| 45 | 3.08 | 2.72 | 88.2 | 0.04 | 0.04 | 93.6 | D | – | H | G | S | V | D | S | S | R | Y | T | T | A |
| 67 | 2.08 | 1.02 | 49.0 | 0.04 | 0.04 | 103.1 | D | V | F | T | V | V | G | S | Y | R | L | – | W | A |
| 75 | 2.90 | 2.47 | 85.1 | 0.07 | 0.07 | 102.3 | D | – | P | – | Y | V | G | A | S | S | D | W | V | T |
| 86 | 3.25 | 2.57 | 79.0 | 0.06 | 0.07 | 104.6 | N | V | W | S | H | L | L | S | Y | G | W | Y | F | A |
| 19 | 2.13 | 1.86 | 87.6 | 0.05 | | | W | V | P | H | T | V | P | S | S | S | Y | W | – | A |
| 37 | 1.36 | 0.26 | 18.8 | 0.05 | | | N | V | V | D | W | V | T | S | S | S | F | Y | V | A |
| 41 | 1.36 | 0.72 | 53.3 | 0.05 | | | Q | – | W | R | R | L | P | S | S | G | W | V | A | G |
| 46 | 1.22 | 0.24 | 20.1 | 0.05 | | | E | V | Y | S | S | V | P | A | S | A | F | W | V | S |
| 51 | 1.05 | 0.59 | 58.5 | 0.05 | | | N | – | F | S | Y | V | P | G | S | T | W | V | V | A |
| 67 | 1.05 | 0.90 | 85.8 | 0.05 | | | D | – | W | R | R | V | A | A | S | H | D | Q | T | – |
| 70 | 1.84 | 0.43 | 23.3 | 0.05 | | | Y | V | W | Q | W | L | H | S | Y | G | Y | W | A | A |
| 84 | 1.37 | 0.33 | 23.9 | 0.05 | | | W | V | P | H | Y | V | L | G | Y | S | D | Y | V | S |
| 88 | 2.00 | 1.56 | 77.8 | 0.05 | | | N | V | W | S | H | V | G | G | S | R | L | W | T | A |
| 90 | 1.30 | 0.68 | 52.3 | 0.05 | | | D | – | W | R | R | W | A | S | S | H | A | G | A | T |
| 92 | 1.39 | 1.02 | 72.3 | 0.05 | | | – | I | W | R | Y | V | W | S | S | G | L | W | Y | S |
| c3-1 | | | | | | | | | | | | | | | | | | | | |
| c3-3 | | | | | | | | | | | | | | | | | | | | |
| c3-4 | | | | | | | | | | | | | | | | | | | | |
| c3-6 | | | | | | | | | | | | | | | | | | | | |
| c3-7 | | | | | | | | | | | | | | | | | | | | |
| c3-8 | | | | | | | | | | | | | | | | | | | | |

FIG. 11

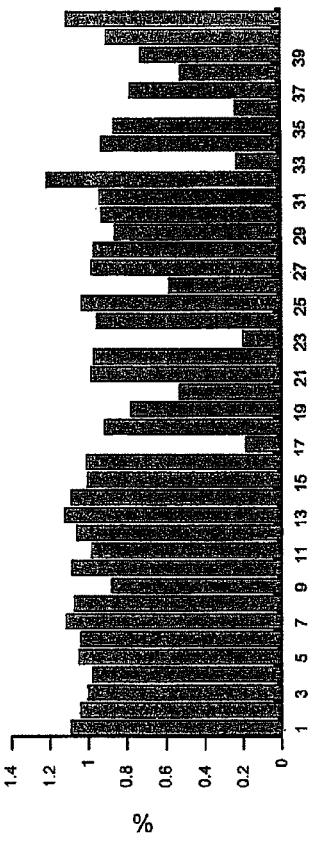
FIG.12
FIG13-A
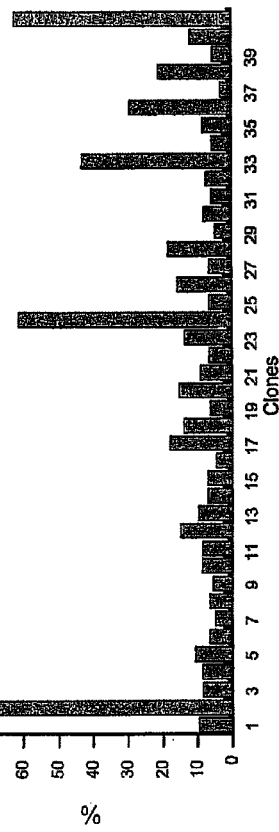
FIG13-B hVEGF Binders Plate-Sorted Directly on HER2

| | L1 | | | | | | | | | | | L2 | | | | L3 | | | | Phage IC50(nM) | |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 94 | hVEGF | HER2 |
| 4D5 | D | V | S | | | | | T | A | V | S | A | S | F | H | Y | T | | T | | |
| H1 | D | I | P | R | S | I | S | G | Y | V | W | G | S | Y | H | Y | T | T | T | 77 | 10 |
| H3 | D | I | G | L | | | | G | S | V | W | A | S | Y | H | Y | T | T | T | 232 | 2.6 |
| H4 | N | I | R | T | | | | G | S | V | W | G | S | Y | H | Y | T | T | T | 115 | 0.54 |
| H5 | D | I | R | M | | | | G | S | V | W | G | S | F | H | Y | T | T | T | 242 | 721 |

FIG.15

| | L1 | | | | | | | | | | L2 | | | | L3 | | | | | | Single/Dual Specificity |
|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 93b | 94 | |
| 4D5 | D | V | S | | | | | T | A | V | S | A | S | F | H | Y | T | | | T | |
| 3-1 | N | V | W | | | | | D | W | V | P | A | S | S | G | W | Y | I | | A | hVEGF |
| 3-6 | Y | V | W | R | | | | Q | Y | V | H | A | S | S | G | Y | W | V | | A | hVEGF |
| 3-7 | Y | I | W | L | | | | R | Y | V | W | G | S | S | G | L | W | Y | | S | hVEGF |
| H1 | D | I | P | R | | I | | G | Y | V | W | G | S | Y | H | Y | T | | | T | hVEGF/Her2 |
| H3 | D | I | G | | S | | | G | S | V | W | A | S | Y | H | Y | T | | | T | |
| H4_N | N | I | R | | | | | G | S | V | W | A | S | Y | H | Y | T | | | T | |
| H4_D | D | I | R | | | | | G | S | V | W | G | S | Y | H | Y | T | | | T | |
| 4-1 | D | I | W | N | R | | | R | A | L | E | G | S | S | G | G | S | Y | S | S | DR5 |
| 4-5 | N | V | G | | | | | R | P | V | G | G | S | S | Y | G | S | F | G | T | |
| 4-6 | S | V | S | | | | | S | A | V | S | A | S | S | Y | S | S | | | S | |
| D1 | N | V | S | | | | | K | H | V | W | G | S | Y | S | Y | S | | | G | DR5/Her2 |
| D2 | N | I | R | | G | | | G | G | L | S | A | S | F | H | Y | T | | | T | |

FIG.16

| Clone | Specificity | Yield | | | Aggregation (%) | |
|---|---|---|---|---|---|---|
| | | Fab/E. Coli Small Scale | Fab/E. Coli Fermentor Run | hIgG/L 293 | Fab | hIgG |
| 3_1 | hVEGF | 8.5 mg ** | / | 60 mg | 3 | 2 |
| H1 | hVEGF/Her2 | 0.8 mg* | 66.8 mg | 40 mg | 4 | 5 |
| H3 | hVEGF/Her2 | 9.2 mg** | / | 40 mg | / | 4 |
| H4_N | hVEGF/Her2 | 0.8 mg* | / | 37 mg | / | / |
| H4_D | hVEGF/Her2 | / | / | 43 mg | / | / |
| 4_1 | DR5 | 15.2 mg** | / | 10 mg | / | / |
| 4_5 | DR5 | ND | / | 6.7 mg | / | / |
| D1 | DR5/Her2 | ND | / | 10 mg | / | / |
| D2 | DR5/Her2 | ND | / | 6.7 mg | / | / |

\* Based on 1 L Culture
\*\* Based on 4 L Culture
/ Not Determined
ND=No Fab detected in soluble fraction

| Clone | Format | Specificity | Her2-ECD | | | hVEGF$_{109}$ | | | mVEGF$_{108}$ | | |
|---|---|---|---|---|---|---|---|---|---|---|---|
| | | | $k_{on}$(1/Ms) | $k_{off}$(1/s) | $K_D$(nM) | $k_{on}$(1/Ms) | $k_{off}$(1/s) | $k_D$(nM) | $k_{on}$(1/Ms) | $k_{off}$(1/s) | $K_D$(nM) |
| 3_1 | Fab | hVEGF | | NB | | 1.4E+05 | 2.2E-03 | 15 | 3.5E+04 | 3.6E-03 | 105 |
| | IgG | | | NB | | 8.0E+04 | 9.6E-04 | 12 | 3.6E+05 | 1.6E-02 | 44 |
| 3_6 | Fab | hVEGF | | NB | | 4.5E+05 | 1.1E-03 | 3 | 8.3E+04 | 4.5E-03 | 54 |
| | IgG | | | NB | | 2.0E+05 | 9.7E-04 | 5 | 1.8E+05 | 1.4E-02 | 78 |
| 3_7 | Fab | hVEGF | | NB | | 8.0E+05 | 2.5E-03 | 3 | 7.2E+04 | 5.6E-03 | 78 |
| | IgG | | | NB | | 5.8E+05 | 4.2E-03 | 7 | 5.0E+05 | 1.5E-02 | 30 |
| H1 | Fab | hVEGF/Her2 | | | 59.1 | 2.7E+04 | 9.3E-03 | 350 | / | / | |
| | IgG | | 170000 | 0.0017 | 9.8 | 3.4E+04 | 4.6E-03 | 140 | | | |
| H3 | Fab | hVEGF/Her2 | | | 8 | 1.5E+03 | 5.9E-03 | 3930 | | NB | |
| | IgG | | 1.0E+05 | 2.1E-03 | 20 | * | * | ** | | NB | |
| H4_N | Fab | hVEGF/Her2 | 140000 | 0.0013 | 9.87 | * | * | 550 | | NB | |
| | IgG | | 230000 | 0.0013 | 6 | * | * | ** | | NB | |
| H4_D | Fab | hVEGF/Her2 | / | / | | * | * | / | | NB | |
| | IgG | | 1.0E+05 | 1.2E-03 | 11 | * | * | 2300 | | NB | |

*Accurate kinetic analysis not possible, use steady state binding analysis
**repeat experiment with higher analyte concentration to enable SS binding analysis
NB=No Binding detected

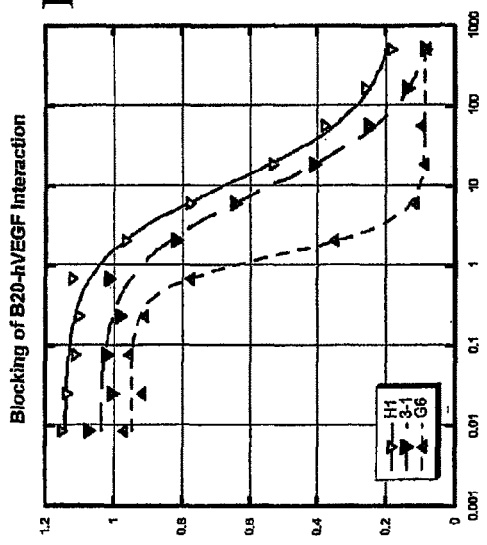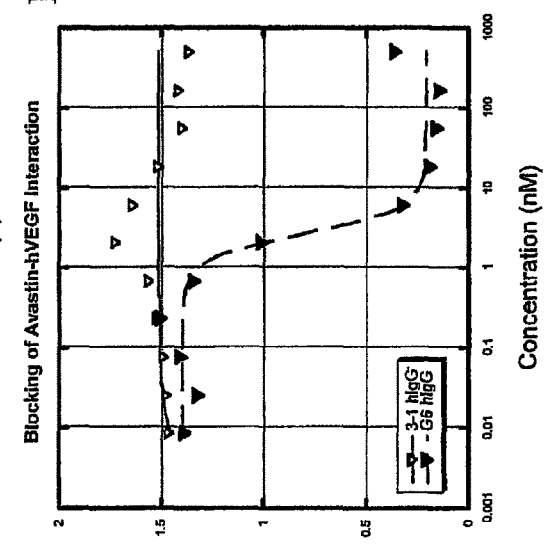

FIG. 26
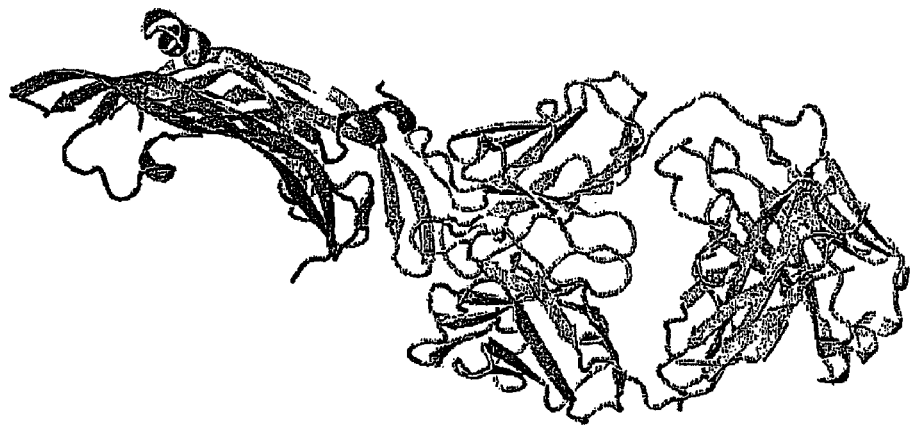
bH1 Fab/VEGF
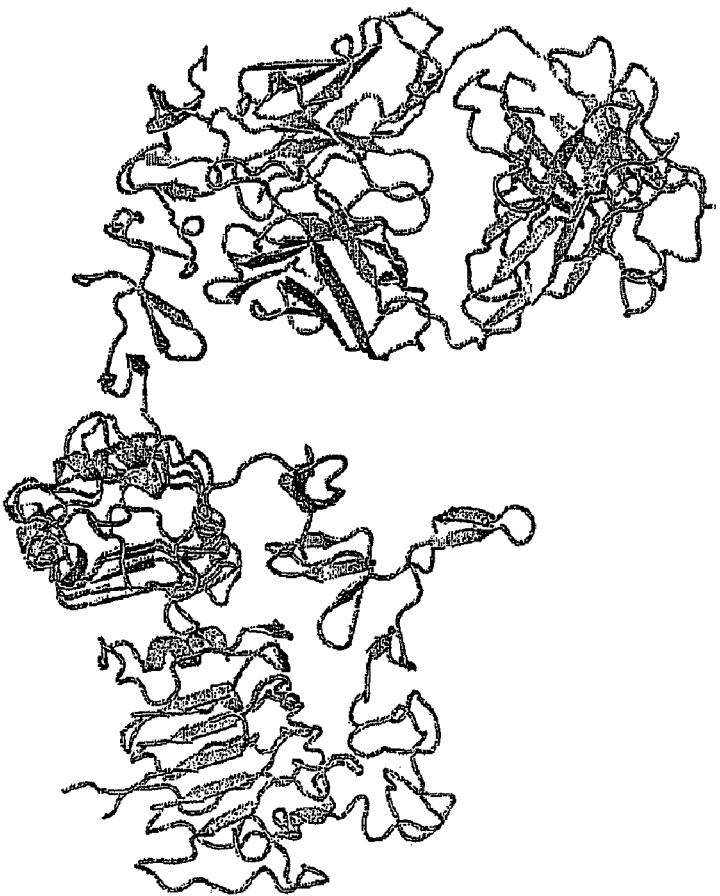
bH1 Fab/HER2

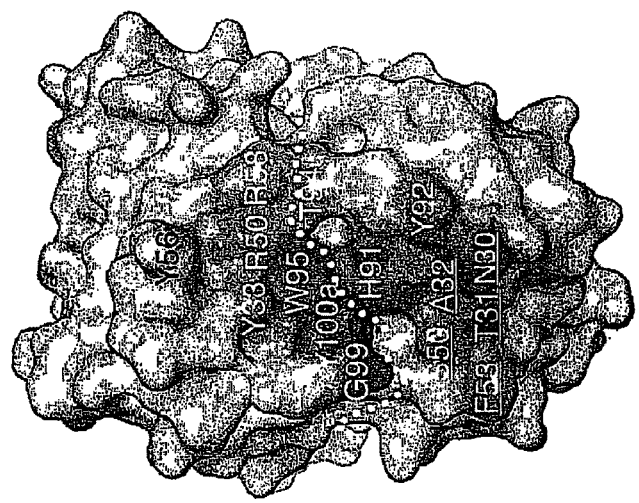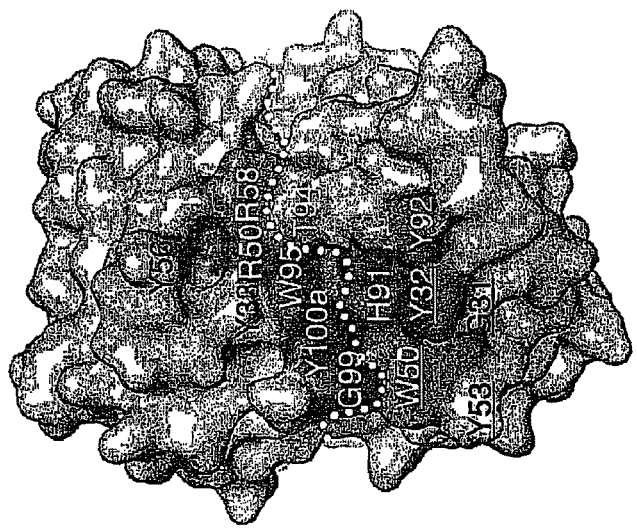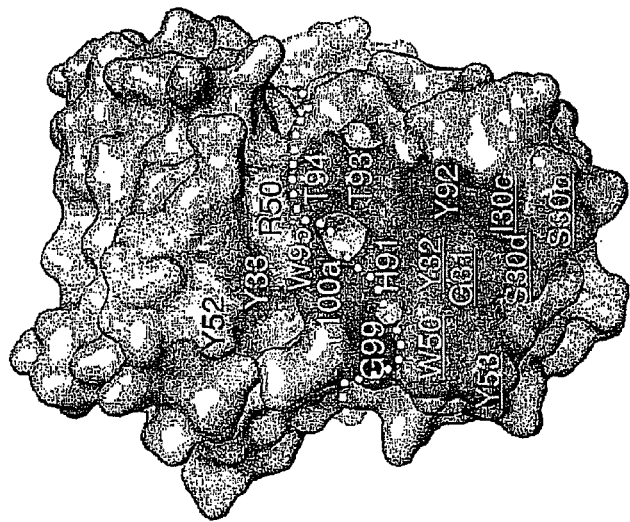
FIG. 28

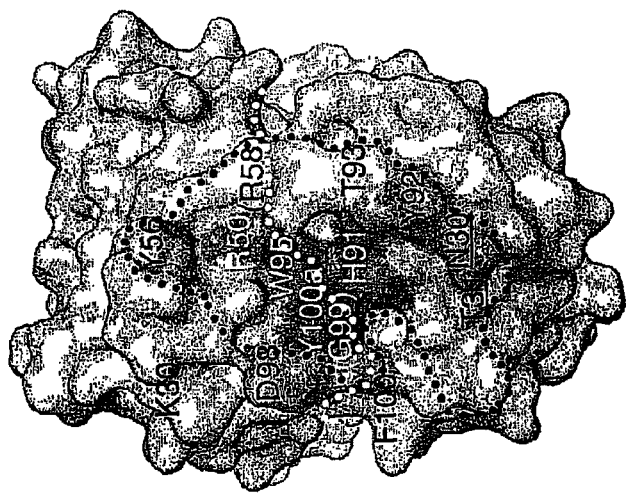
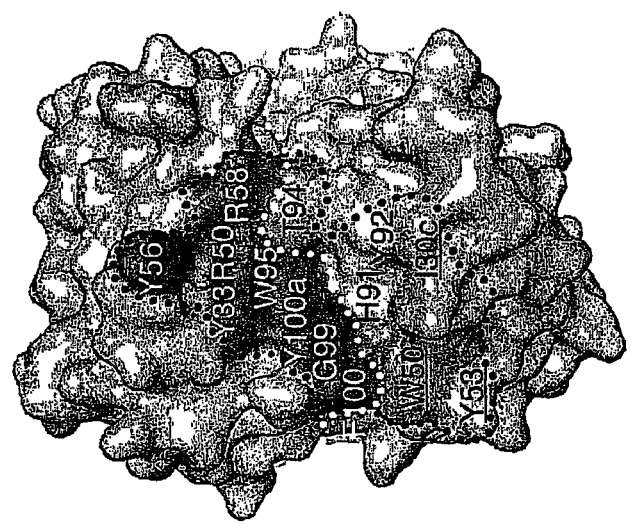
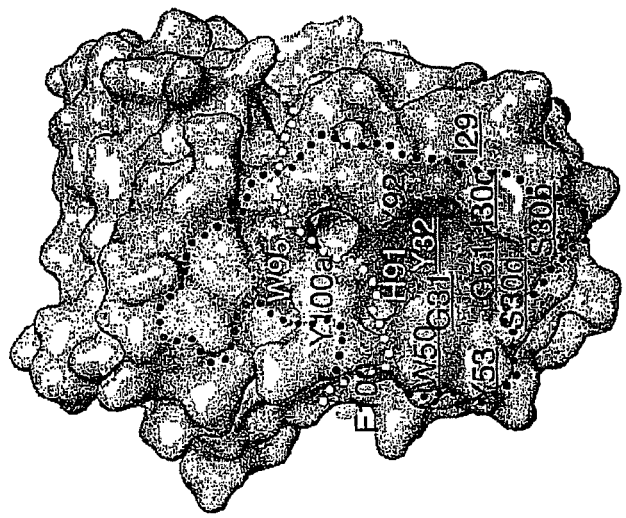
FIG. 32

| CDR | Wild Type Codon | Alanine-scan m1 | m2 | m3 |
|---|---|---|---|---|
| CDR-L1 | D28 | GMT | A | |
| | I29 | RYT | A | T | V |
| | P30 | SCA | A | | |
| | R30a | SST | A | G | P |
| | S30b | KCC | A | | |
| | I30c | RYT | A | T | V |
| | S30d | KCC | A | | |
| | G31 | GST | A | | |
| | Y32 | KMT | A | D | S |
| CDR-L2 | W50 | KSG | A | G | S |
| | G51 | GST | A | | |
| | S52 | KCC | A | D | S |
| | Y53 | KMT | A | D | P |
| CDR-L3 | H91 | SMT | A | D | S |
| | Y92 | KMT | A | | |
| | T93 | RCT | A | | |
| | T94 | RCT | A | | |
| CDR-H1 | K30 | RMA | A | E | T |
| | D31 | GMT | A | | |
| | T32 | RCT | A | D | S |
| | Y33 | KMT | A | G | P |
| | R50 | SST | A | D | S |
| CDR-H2 | Y52 | KMT | A | | |
| | T53 | RCT | A | | |
| | N54 | RMC | A | D | T |
| | Y56 | KMT | A | D | S |
| | R58 | SST | A | G | P |
| CDR-H3 | W95 | KSG | A | G | S |
| | G96 | GST | A | | |
| | G97 | GST | A | | |
| | D98 | GMT | A | | |
| | G99 | GST | A | | |
| | F100 | KYT | A | S | V |
| | Y100a | KMT | A | D | S |

| CDR | Wild Type Codon | Homolog-scan m1 (Hom Res) | m2 | m3 | m4 | m5 |
|---|---|---|---|---|---|---|
| CDR-L1 | Q27 | SAA | E | | | | |
| | D28 | RAM | E | N | | | |
| | I29 | VTY | V | L | K | | |
| | P30 | SCA | A | | | | |
| | R30a | ARG | K | | | | |
| | S30b | RST | A | G | T | | |
| | I30c | VTY | V | L | | | |
| | S30d | RST | A | G | T | | |
| | G31 | RST | A | S | T | | |
| | Y32 | THY | F | S | | | |
| CDR-L2 | W50 | TKG | L | | | | |
| | G51 | GST | A | | | | |
| | S52 | KCC | A | | | | |
| | Y53 | TWC | F | | | | |
| CDR-L3 | H91 | HWT | N | F | Y | | |
| | Y92 | TWC | F | | | | |
| | T93 | ASC | S | | | | |
| | T94 | RST | S | A | G | | |
| CDR-H1 | K30 | ARG | R | | | | |
| | D31 | GAM | E | | | | |
| | T32 | ASC | S | | | | |
| | Y33 | TWC | F | | | | |
| CDR-H2 | R50 | ARG | K | | | | |
| | Y52 | TWC | F | | | | |
| | T53 | ASC | S | | | | |
| | N54 | RAC | D | | | | |
| | Y56 | TWC | F | | | | |
| | R58 | ARG | K | | | | |
| CDR-H3 | W95 | TKG | L | | | | |
| | G96 | GST | A | | | | |
| | G97 | GST | A | | | | |
| | D98 | GAM | E | | | | |
| | G99 | GST | A | | | | |
| | F100 | TWC | Y | | L | | |
| | Y100a | TWC | F | | | | I |

FIG. 33

Library Construction

| Library | CDRs | Residues | Shotgun Codons | Oligonucleotides | Theoretical Diversity |
|---|---|---|---|---|---|
| LC-Ala | L1 | D28, I29, P30, R30a, S30b, I30c, S30d, G31, Y32 | Alanine | L1-ALA | 3.3 e7 |
| | L2 | W50, G51, S52, Y53 | | L2-ALA | |
| | L3 | H91, Y92, T93, T94 | | L3-ALA | |
| LC-Hom | L1 | Q27, D28, I29, P30, R30a, S30b, I30c, S30d, G31, Y32 | Homolog | L1-HOM | 1.4 e7 |
| | L2 | W50, G51, S52, Y53 | | L2-HOM | |
| | L3 | H91, Y92, T93, T94 | | L3-HOM | |
| HC-Ala | H1 | K30 D31 T32 Y33 | Alanine | H1-ALA | 1.3 e8 |
| | H2 | R50 Y52 T53 N54 Y56 R58 | | H2-ALA | |
| | H3 | W95 G96 G97 D98 G99 F100 Y100a | | H3-ALA | |
| HC-Hom | H1 | K30 D31 T32 Y33 | Homolog | H1-HOM | 1.3 e5 |
| | H2 | R50 Y52 T53 N54 Y56 R58 | | H2-HOM | |
| | H3 | W95 G96 G97 D98 G99 F100 Y100a | | H3-HOM | |

FIG. 34

| | | Antigen selection (VEGF) | | | Display Selection (anti-gD) | | | | Fwd/mut values | | | |
|---|---|---|---|---|---|---|---|---|---|---|---|---|
| | | wt/m1 | wt/m2 | wt/m3 | wt/m4 | wt/m1 | wt/m2 | wt/m3 | wt/m4 | | Fwd/m1 | Fwd/m2 | Fwd/m3 | Fwd/m4 |
| CDR-L1 | Q27 | 2.38 | | | 1.39 | 1.73 | | | 0.97 | Q27 | 1.38 | | | 1.44 |
| | D28 | 8.33 | 8.33 | | (6.0)$^E$ | 1.95 | 3.00 | 0.98 | (1.29)$^E$ | D28 | 4.27 | 2.78 | | (4.66)$^E$ |
| | I29 | 1.83 | | 1.32 | (0.94)$^L$ | 1.18 | | | (1.15)$^L$ | I29 | 1.56 | | 1.35 | (0.81)$^L$ |
| | P30 | 1.91 | 3.50 | 2.63 | 4.27 | 2.38 | 0.91 | 0.94 | 1.33 | P30 | 0.80 | 3.84 | 2.79 | 3.22 |
| | R30a | 4.75 | | | 0.90 | 1.06 | | | 1.93 | R30a | 4.49 | | | 0.47 |
| | S30b | 7.67 | 7.67 | 1.05 | (0.85)$^T$ | 3.23 | 2.80 | 1.00 | (1.1)$^T$ | S30b | 2.37 | 2.74 | 1.05 | (0.80)$^T$ |
| | I30c | 8.80 | | | 48.00 | 1.44 | | | 1.03 | I30c | 6.09 | | | 46.8$^L$ |
| | S30d | 9.20 | | | (12.2)$^T$ | 2.00 | | | (1.3)$^T$ | S30d | 4.60 | | | 9.36$^T$ |
| | G31 | 14.00 | 42.00 | 14.00 | (38.5)$^A$ | 1.44 | 1.89 | 1.13 | (2.90)$^A$ | G31 | 9.72 | 22.17 | 12.44 | (13.3)$^A$ |
| | Y32 | | | | (38.5)$^F$ | | | | (0.62)$^F$ | Y32 | | | | (47.0)$^F$ |
| CDR-L2 | W50 | 22.0 | 14.7 | 46.0 | 78.0 | 4.20 | 1.20 | 1.68 | 1.77 | W50 | 5.24 | 12.22 | 27.38 | 44.13 |
| | G51 | 9.2 | | | 78.0 | 3.00 | | | 2.00 | G51 | 3.07 | | | 39.00 |
| | S52 | 1.8 | 32.0 | 5.3 | 7.8 | 1.60 | 2.00 | 1.08 | 1.61 | S52 | 1.14 | 16.00 | 4.93 | 4.83 |
| | Y53 | 5.3 | | | 0.1 | 2.67 | | | 0.83 | Y53 | 2.00 | | | 0.06 |
| CDR-L3 | H91 | 46.0 | 46.0 | 23.0 | (>79)$^N$ | 2.67 | 2.09 | 2.09 | (1.86)$^N$ | H91 | 17.25 | 22.04 | 11.02 | (>42.5)$^N$ |
| | Y92 | 41.0 | 8.2 | 41.0 | 1.2 | 2.36 | 1.74 | 0.72 | 0.50 | Y92 | 17.39 | 4.72 | 57.15 | 2.33 |
| | T93 | 0.9 | | | 1.1 | 1.02 | | | 1.50 | T93 | 0.86 | | | 0.74 |
| | T94 | 0.8 | | | (0.58)$^S$ | 0.65 | | | (1.28)$^S$ | T94 | 1.16 | | | (0.45)$^S$ |
| CDR-H1 | K30 | 4.36 | 1.92 | 3.00 | 1.50 | 3.31 | 1.65 | 1.87 | 1.14 | K30 | 1.32 | 1.16 | 1.60 | 1.31 |
| | D31 | 2.19 | | | 0.63 | 1.63 | | | 0.93 | D31 | 1.35 | | | 0.68 |
| | T32 | 0.82 | 0.26 | 0.21 | 2.10 | 1.50 | 1.31 | 0.64 | 0.64 | T32 | 0.55 | 0.20 | 0.14 | 3.27 |
| | Y33 | 2.50 | | | 5.86 | 1.48 | | | 2.47 | Y33 | 1.69 | | | 2.37 |
| CDR-H2 | R50 | 0.63 | 0.55 | 11.00 | 1.57 | 1.13 | 0.53 | 9.00 | 0.98 | R50 | 0.56 | 1.04 | 1.22 | 1.60 |
| | Y62 | 4.35 | 74.00 | 9.25 | 1.18 | 2.17 | 1.63 | 1.63 | 0.91 | Y52 | 2.01 | 45.54 | 5.69 | 1.30 |
| | T53 | 0.39 | | | 0.68 | 0.93 | | | 0.58 | T53 | 0.42 | | | 1.19 |
| | N54 | 0.65 | 0.20 | 0.61 | 0.68 | 0.97 | 1.07 | 1.88 | 1.02 | N54 | 0.67 | 0.19 | 0.33 | 0.67 |
| | Y56 | 5.33 | 6.40 | 4.92 | 0.83 | 3.85 | 3.13 | 1.92 | 0.76 | Y56 | 1.39 | 2.05 | 2.56 | 1.08 |
| | R58 | 0.83 | 0.55 | 24.00 | 1.19 | 1.12 | 0.76 | 2.42 | 2.09 | R58 | 0.74 | 0.71 | 9.53 | 0.57 |
| CDR-H3 | W95 | >102 | >102 | 1.56 | >96 | 3.63 | 1.12 | 0.69 | 0.46 | W95 | >28.1 | >91.4 | 2.27 | >209 |
| | G96 | 1.86 | | | 5.27 | 1.33 | | | 1.39 | G96 | 1.39 | | | 3.80 |
| | G97 | 1.38 | | | 4.88 | 1.69 | | | 1.23 | G97 | 0.82 | | | 3.95 |
| | D98 | 0.96 | | | 1.64 | 1.00 | | | 0.94 | D98 | 0.96 | | | 1.74 |
| | G99 | 0.30 | | | 0.52 | 1.17 | | | 1.89 | G99 | 0.26 | | | 0.28 |
| | F100 | 11.50 | 23.00 | 0.86 | 8.60 | 3.36 | 2.20 | 1.63 | 2.50 | F100 | 3.40 | 10.45 | 0.59 | 3.44 |
| | Y100a | 4.75 | 57.00 | 1.90 | 0.27 | 2.11 | 2.35 | 1.43 | 0.46 | Y100a | 2.26 | 24.23 | 1.33 | 0.59 |

FIG. 35

| | | Antigen Selection (Her2) | | | Display Selection (anti-gD) | | | | | Fwd/mut values | | | |
|---|---|---|---|---|---|---|---|---|---|---|---|---|---|
| CDR | | wt/m1 | wt/m2 | wt/m3 | wt/m4 | wt/m1 | wt/m2 | wt/m3 | wt/m4 | | Fwd/m1 | Fwd/m2 | Fwd/m3 | Fwd/m4 |
| CDR-L1 | Q27 | 1.82 | | | 2.85 | 1.73 | | | 0.97 | Q27 | 1.05 | | | 2.94 |
| | D28 | 1.47 | 2.00 | 0.78 | (2.0)$^E$ | 1.95 | 3.00 | 0.98 | (1.29)$^E$ | D28 | 0.76 | 0.67 | 0.80 | (1.55)$^E$ |
| | I29 | 1.31 | | | (1.13)$^L$ | 1.18 | | | (1.15)$^L$ | I29 | 1.11 | | | (0.98)$^L$ |
| | P30 | | | | 1.22 | | | | 1.33 | P30 | | | | 0.92 |
| | R30a | 1.67 | 1.75 | 1.67 | 2.31 | 2.38 | 0.91 | 0.94 | 1.93 | R30a | 0.70 | 1.92 | 1.77 | 1.20 |
| | S30b | 1.74 | | | (4.25)$^T$ | 1.06 | | | (1.1)$^T$ | S30b | 1.64 | | | (3.86)$^T$ |
| | I30c | 14.75 | 11.80 | 2.03 | (1.41)$^L$ | 3.23 | 2.80 | 1.00 | (1.02)$^L$ | I30c | 4.57 | 4.21 | 2.03 | (1.38)$^L$ |
| | S30d | 1.00 | | | (1.0)$^T$ | 1.44 | | | (1.3)$^T$ | S30d | 0.69 | | | (0.769)$^T$ |
| | G31 | 3.36 | 12.00 | 0.24 | (4.17)$^A$ | 2.00 | 1.89 | 1.13 | (2.9)$^A$ | G31 | 1.68 | 6.33 | 0.21 | (1.43)$^A$ |
| | Y32 | 0.36 | | | (1.8)$^F$ | 1.44 | | | (0.82)$^F$ | Y32 | 0.25 | | | (2.20)$^F$ |
| CDR-L2 | W50 | 45.50 | 22.75 | >98 | 16.00 | 4.20 | 1.20 | 1.68 | 1.77 | W50 | 10.83 | 18.96 | >58.3 | 9.05 |
| | G51 | 1.94 | | | 2.57 | 3.00 | | | 2.00 | G51 | 0.65 | | | 1.29 |
| | S52 | 2.88 | | | 4.67 | 1.60 | | | 1.61 | S52 | 1.79 | | | 2.90 |
| | Y53 | 11.29 | 39.50 | 8.78 | 0.65 | 2.67 | 2.00 | 1.08 | 0.83 | Y53 | 4.23 | 19.75 | 8.12 | 0.78 |
| CDR-L3 | H91 | 12.43 | 0.98 | >98 | (3.0)$^N$ | 2.67 | 2.09 | 2.09 | (1.86)$^N$ | H91 | 4.66 | 0.47 | >47.0 | (1.61)$^N$ |
| | Y92 | 5.50 | 38.50 | 81.00 | 1.83 | 2.36 | 1.74 | 0.72 | 0.60 | Y92 | 2.33 | 22.17 | 112.91 | 3.67 |
| | T93 | 0.54 | | | 31.00 | 1.02 | | | 1.50 | T93 | 0.53 | | | 20.67 |
| | T94 | 6.46 | | | (4.3)$^S$ | 0.65 | | | (1.28)$^S$ | T94 | 9.99 | | | (3.36)$^S$ |
| CDR-H1 | K30 | 2.13 | 1.68 | 2.13 | 1.13 | 3.31 | 1.65 | 1.87 | 1.14 | K30 | 0.64 | 1.02 | 1.14 | 0.99 |
| | D31 | 3.05 | | | 0.66 | 1.63 | | | 0.93 | D31 | 1.88 | | | 0.71 |
| | T32 | 0.76 | | | 0.75 | 1.50 | | | 0.64 | T32 | 0.51 | | | 1.16 |
| | Y33 | >81 | >81 | >81 | 47.00 | 1.48 | 1.31 | 1.55 | 2.47 | Y33 | >54.8 | >61.9 | >52.4 | 19.05 |
| CDR-H2 | R50 | >81 | >81 | >81 | 95.00 | 1.13 | 0.53 | 9.00 | 0.98 | R50 | >72 | >153 | >9.0 | 96.83 |
| | Y52 | 0.55 | 2.67 | 0.53 | 0.60 | 2.17 | 1.63 | 1.63 | 0.91 | Y52 | 0.25 | 1.64 | 0.33 | 0.66 |
| | T53 | 1.03 | | | 0.70 | 0.93 | | | 0.58 | T53 | 1.11 | | | 1.22 |
| | N54 | 0.26 | 0.50 | 0.45 | 1.04 | 0.97 | 1.07 | 1.88 | 1.02 | N54 | 0.27 | 0.47 | 0.24 | 1.02 |
| | Y56 | >81 | >81 | >81 | 1.21 | 3.85 | 3.13 | 1.92 | 0.76 | Y56 | >21.1 | >25.9 | >42.1 | 1.59 |
| | R58 | >81 | 80.00 | >81 | >96 | 1.12 | 0.76 | 2.42 | 2.09 | R58 | >72.6 | 104.83 | >33.5 | >46.0 |
| CDR-H3 | W95 | >81 | >81 | >81 | >96 | 3.63 | 1.12 | 0.69 | 0.46 | W95 | >22.3 | >72.6 | >117 | >209 |
| | G96 | 1.53 | | | 0.61 | 1.33 | | | 1.39 | G96 | 1.15 | | | 0.44 |
| | G97 | 3.05 | | | 3.75 | 1.69 | | | 1.23 | G97 | 1.80 | | | 3.04 |
| | D98 | 0.80 | | | 0.40 | 1.00 | | | 0.94 | D98 | 0.80 | | | 0.42 |
| | G99 | 26.00 | | | 18.00 | 1.17 | | | 1.89 | G99 | 22.29 | | | 9.53 |
| | F100 | >81 | >81 | 39.50 | 95.00 | 3.38 | 2.20 | 1.63 | 2.50 | F100 | >23.9 | >36.8 | 24.24 | 38.00 |
| | Y100a | 80.00 | >81 | >81 | 6.31 | 2.11 | 2.35 | 1.43 | 0.46 | Y100a | 38.00 | >34.4 | >56.7 | 13.76 |

FIG. 36

|  |  | Antigen Selection (VEGF) | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
|  |  | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L1 | Q27 |  |  |  | 1.4 |  |  |  | 1.0 |  |  |  | 1.4$^E$ |  |  |  | 0.6$^E$ |
|  | D28 | 1.8 | 17.0 |  | 3.5 | 1.7 |  |  | 1.3 | 1.1$^A$ |  |  | 2.7$^E$ | 0$^A$ | 0.2$^E$ |  | 0.1$^L$ |
|  | I29 | 12.8 | 17.0 | 1.9 | 1.4 | 2.0 | 3.0 | 1.0 | 1.2 | 6.5$^A$ | 5.7$^T$ | 1.9$^V$ | 1.2$^L$ | 1.1$^A$ | 1.0$^T$ | 0.4$^V$ | 0.6$^A$ |
|  | P30 | 1.7 |  |  | 3.8 | 1.2 |  |  | 1.3 | 1.5$^A$ |  |  | 2.9$^A$ | 0.2$^A$ |  |  | 0.6$^A$ |
|  | R30a | 1.9 | 4.1 | 1.9 | 0.8 | 2.4 | 0.9 | 0.9 | 1.9 | 0.8$^A$ | 4.5$^G$ | 2.1$^P$ | 0.4$^K$ | -0.2$^A$ | 0.9$^G$ | 0.4$^P$ | -0.5$^K$ |
|  | S30b** | 5.5 |  |  | 0.7 | 1.1 |  |  | 1.1 | 5.2$^A$ |  |  | 0.6$^T$ | 1.0$^A$ |  |  | -0.3$^T$ |
|  | I30c*** | 12.7 | 7.6 | 1.0 | 23.8 | 3.2 | 2.8 | 1.0 | 1.0 | 3.9$^A$ | 2.7$^T$ | 1.0$^V$ | 23.2$^L$ | 0.8$^A$ | 0.6$^T$ | 0$^V$ | 1.9$^L$ |
|  | S30d** | 13.2 |  |  | 16.9 | 1.4 |  |  | 1.3 | 9.1$^A$ |  |  | 13.0$^T$ | 1.3$^A$ |  |  | 1.5$^T$ |
|  | G31* | 16.0 |  |  | 35.5 | 2.0 |  |  | 2.9 | 8.0$^A$ |  |  | 12.2$^A$ | 1.2$^A$ |  |  | 1.5$^A$ |
|  | Y32*** | 26.0 | 78.0 | 16.0 | 23.0 | 1.4 | 1.9 | 1.1 | 0.8 | 18.1$^A$ | 41.2$^D$ | 23.1$^S$ | >28$^F$ | 1.7$^A$ | 2.2$^D$ | 1.9$^S$ | >2.0$^F$ |
| CDR-L2 | W50** | 39.0 | 26.0 | 39.0 | 20.4 | 4.2 | 1.2 | 1.7 | 1.8 | 9.3$^A$ | 21.7$^G$ | 23.2$^S$ | 11.6$^L$ | 1.3$^A$ | 1.8$^G$ | 1.9$^S$ | 1.5$^L$ |
|  | G51 | 16.0 |  |  | 20.4 | 3.0 |  |  | 2.0 | 5.3$^A$ |  |  | 10.2$^A$ | 1.0$^A$ |  |  | 1.4$^A$ |
|  | S52 | 2.0 |  |  | 6.5 | 1.6 |  |  | 1.6 | 1.3$^A$ |  |  | 4.0$^A$ | 0.1$^A$ |  |  | 0.8$^A$ |
|  | Y53** | 9.0 | 63.0 | 4.5 | 0.1 | 2.7 | 2.0 | 1.1 | 0.8 | 3.4$^A$ | 31.5$^D$ | 4.2$^S$ | 0.1$^F$ | 0.7$^A$ | 2.0$^D$ | 0.8$^S$ | -1.4$^F$ |

FIG.39A-1

| | | Antigen Selection (VEGF) | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L3 | H91*** | 80.0 | 40.0 | 40.0 | >150 | 2.7 | 2.1 | 2.1 | 1.9 | 30$^A$ | 19.2$^D$ | 19.2$^P$ | >80$^N$ | 2.0$^A$ | 1.7$^D$ | 1.7$^P$ | >2.6$^N$ |
| | Y92*** | 25.0 | 12.5 | 75.0 | 1.0 | 2.4 | 1.7 | 0.7 | 0.5 | 10.6$^A$ | 7.2$^D$ | 104.5$^S$ | 2.0$^F$ | 1.4$^A$ | 1.2$^D$ | 2.8$^S$ | 0.4$^F$ |
| | T93** | 0.7 | | | 0.9 | 1.0 | | | 1.5 | 0.7$^A$ | | | 0.6$^S$ | -0.3$^A$ | | | -0.3$^S$ |
| | T94** | 0.7 | | | 0.6 | 0.6 | | | 1.3 | 1.1$^A$ | | | 0.4$^S$ | 0$^A$ | | | -0.5$^S$ |
| CDR-H1 | K30 | 4.4 | 1.9 | | 1.5 | 3.3 | 1.7 | 1.9 | 1.1 | 1.3$^A$ | 1.2$^E$ | 1.6$^T$ | 1.3$^R$ | 0.2$^A$ | 0.1$^E$ | 0.3$^T$ | 0.2$^R$ |
| | D31 | 2.2 | | | 0.6 | 1.6 | | | 0.9 | 1.3$^A$ | | | 0.7$^E$ | 0.2$^A$ | | | -0.2$^E$ |
| | T32 | 0.8 | | | 2.1 | 1.5 | | | 0.6 | 0.5$^A$ | | | 3.3$^S$ | -0.4$^A$ | | | 0.7$^S$ |
| | Y33*** | 2.5 | 0.3 | 0.2 | 5.9 | 1.5 | 1.3 | 1.5 | 2.5 | 1.7$^A$ | 0.2$^D$ | 0.1$^S$ | 2.4$^F$ | 0.3$^A$ | -1.0$^D$ | -1.2$^S$ | 0.5$^F$ |

FIG. 39A-2

|  |  | Antigen Selection (VEGF) | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
|  |  | wt/m1 | wt/m2 | wt/m3 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-H2 | R50* | 0.6 | 0.6 | 11.0 | 1.6 | 1.1 | 0.5 | 9.0 | 1.0 | 0.6$^A$ | 1.0$^G$ | 1.2$^P$ | 1.6$^K$ | -0.3$^A$ | 0$^G$ | 0.1$^P$ | 0.3$^K$ |
| | Y52* | 4.4 | 74.0 | 9.3 | 1.2 | 2.2 | 1.6 | 1.6 | 0.9 | 2.0$^A$ | 45.5$^D$ | 5.7$^S$ | 1.3$^F$ | 0.4$^A$ | 2.3$^D$ | 1.0$^S$ | 0.2$^F$ |
| | T53 | 0.4 | | | 0.9 | | | | 0.6 | 0.4$^A$ | | | 1.2$^S$ | -0.5$^A$ | | | 0.1$^S$ |
| | N54 | 0.6 | 0.2 | 0.7 | 1.0 | 1.1 | 1.1 | 1.9 | 1.0 | 0.7$^A$ | 0.2$^D$ | 0.3$^T$ | 0.7$^D$ | -0.2$^A$ | -1.0$^D$ | -0.7$^T$ | -0.2$^D$ |
| | Y56 | 5.3 | 6.4 | 4.9 | 0.8 | 3.8 | 3.1 | 1.9 | 0.8 | 1.4$^A$ | 2.0$^D$ | 2.6$^S$ | 1.1$^F$ | 0.2$^A$ | 0.4$^D$ | 0.6$^S$ | 0$^F$ |
| | R58 | 0.8 | 0.5 | 24.0 | 1.2 | 1.1 | 0.8 | 2.4 | 2.1 | 0.7$^A$ | 0.7$^G$ | 9.9$^P$ | 0.6$^K$ | -0.2$^A$ | -0.2$^G$ | 1.4$^P$ | -0.3$^K$ |
| CDR-H3 | W95** | >102 | >102 | 1.6 | >96 | 3.6 | 1.1 | 0.7 | 0.5 | >28$^A$ | >91$^G$ | 2.3$^S$ | >209$^L$ | >2.0$^A$ | >2.7$^G$ | 0.5$^S$ | >3.2$^L$ |
| | G96 | 1.9 | | | 5.3 | 1.3 | | 1.4 | | 1.4$^A$ | | | 3.8$^A$ | 0.2$^A$ | | | 0.8$^A$ |
| | G97 | 1.4 | | | 4.9 | 1.7 | | 1.2 | | 0.8$^A$ | | | 4.0$^A$ | -0.1$^A$ | | | 0.8$^A$ |
| | D98 | 1.0 | | | 1.6 | 1.0 | | 0.9 | | 1.0$^A$ | | | 1.7$^E$ | 0$^A$ | | | 0.3$^E$ |
| | G99*** | 0.3 | | | 0.5 | 1.2 | | 1.9 | | 0.3$^A$ | | | 0.3$^A$ | -0.8$^A$ | | | -0.8$^A$ |
| | F100 | 11.5 | 23.0 | 1.0 | 8.6 | 3.4 | 2.2 | 1.6 | 2.5 | 3.4$^A$ | 10.5$^S$ | 0.6$^V$ | 3.4$^Y$ | 0.7$^A$ | 1.4$^S$ | -0.3$^V$ | 0.7$^Y$ |
| | Y100a*** | 4.8 | 57.0 | 1.9 | 0.3 | 2.1 | 2.4 | 1.4 | 0.5 | 2.3$^A$ | 24.2$^D$ | 1.3$^S$ | 0.6$^F$ | 0.5$^A$ | 1.9$^D$ | 0.2$^S$ | -0.3$^F$ |

FIG. 39A-3

| | Antigen Selection (Her2) | | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
| | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L1 | | | | | | | | | | | | | | | | |
| Q27 | | | | | | | | 1.0 | | | | 1.6$^E$ | | | | 0.3$^E$ |
| D28 | 1.8 | | | | 1.7 | | | 1.3 | 1.1$^A$ | | | 1.3$^E$ | 0$^A$ | | | 0.2$^E$ |
| I29 | 1.5 | 2.0 | 0.8 | | 2.0 | 3.0 | 1.0 | 1.2 | 0.8$^A$ | 0.7$^T$ | 0.8$^V$ | 1.1$^L$ | -0.2$^A$ | -0.2$^T$ | -0.1$^V$ | 0.1$^L$ |
| P30 | 1.3 | | | | 1.2 | | | 1.3 | 1.1$^A$ | | | 0.6$^A$ | 0.1$^A$ | | | -0.3$^A$ |
| R30a | 1.7 | 1.8 | 1.7 | | 2.4 | 0.9 | 0.9 | 1.9 | 0.7$^A$ | 1.9$^G$ | 1.8$^P$ | 0.7$^K$ | -0.2$^A$ | 0.4$^G$ | 0.3$^P$ | -0.2$^K$ |
| S30b | 1.7 | | | | 1.1 | | | 1.1 | 1.6$^A$ | | | 1.6$^T$ | 0.3$^A$ | | | 0.3$^T$ |
| I30c | 14.8 | 11.8 | 2.0 | | 3.2 | 2.8 | 1.0 | 1.0 | 4.6$^A$ | 4.2$^T$ | 2.0$^V$ | 1.2$^L$ | 0.9$^A$ | 0.9$^T$ | 0.4$^V$ | 0.1$^L$ |
| S30d | 1.0 | | | | 1.4 | | | 1.3 | 0.7$^A$ | | | 1.7$^T$ | -0.2$^A$ | | | 0.3$^T$ |
| G31* | 3.4 | | | | 2.0 | | | 2.9 | 1.7$^A$ | | | 1.8$^A$ | 0.3$^A$ | | | 0.3$^A$ |
| Y32*** | 0.4 | 12.0 | 0.2 | | 1.4 | 1.9 | 1.1 | 0.8 | 0.3$^A$ | 6.3$^D$ | 0.2$^S$ | 2.1$^F$ | -0.8$^A$ | 1.1$^D$ | -1.0$^S$ | 0.4$^F$ |
| CDR-L2 | | | | | | | | | | | | | | | | |
| W50** | 45.5 | 22.8 | >98 | 17.0 | 4.2 | 1.2 | 1.7 | 1.8 | 10.8$^A$ | 19$^G$ | >58$^S$ | 9.6$^L$ | 1.4$^A$ | 1.7$^G$ | >2.4$^S$ | 1.3$^L$ |
| G51 | 1.9 | | | 1.7 | 3.0 | | | 2.0 | 0.6$^A$ | | | 0.9$^A$ | -0.3$^A$ | | | -0.1$^A$ |
| S52 | 2.9 | | | 3.0 | 1.6 | | | 1.6 | 1.8$^A$ | | | 1.9$^A$ | 0.3$^A$ | | | 0.4$^A$ |
| Y53* | 11.3 | 39.5 | 8.8 | 0.6 | 2.7 | 2.0 | 1.1 | 0.8 | 4.2$^A$ | 19.8$^D$ | 8.1$^S$ | 0.8$^F$ | 0.9$^A$ | 1.8$^D$ | 1.2$^S$ | -0.1$^F$ |

FIG. 39B-1

| | | Antigen Selection (Her2) | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L3 | H91*** | 12.4 | 1.0 | >98 | 2.8 | 2.7 | 2.1 | 2.1 | 1.9 | 4.7$^A$ | 0.5$^D$ | >47$^P$ | 1.5$^N$ | 0.9$^A$ | -0.4$^D$ | >2.3$^P$ | 0.2$^N$ |
| | Y92** | 5.5 | 38.5 | 81.0 | 1.8 | 2.4 | 1.7 | 0.7 | 0.5 | 2.3$^A$ | 22.2$^D$ | 112.9$^S$ | 3.5$^F$ | 0.5$^A$ | 1.8$^D$ | 2.8$^S$ | 0.7$^F$ |
| | T93 | 0.5 | | | 0.7 | 1.0 | | | 1.5 | 0.5$^A$ | | | 0.5$^S$ | -0.4$^A$ | | | -0.4$^S$ |
| | T94** | 6.5 | | | 1.4 | 0.6 | | | 1.3 | 10$^A$ | | | 1.1$^S$ | 1.4$^A$ | | | 0.1$^S$ |
| CDR-H1 | K30 | 2.1 | 1.7 | 2.1 | 1.1 | 3.3 | 1.7 | 1.9 | 1.1 | 0.6$^A$ | 1.0$^E$ | 1.1$^T$ | 1.0$^R$ | -0.3$^A$ | 0$^E$ | 0.1$^T$ | 0$^R$ |
| | D31 | 3.1 | | | 0.7 | 1.6 | | | 0.9 | 1.9$^A$ | | | 0.7$^E$ | 0.4$^A$ | | | -0.2$^E$ |
| | T32 | 0.8 | | | 0.7 | 1.5 | | | 0.6 | 0.5$^A$ | | | 1.2$^S$ | -0.4$^A$ | | | 0.1$^S$ |
| | Y33* | >81 | >81 | >81 | 47.0 | 1.5 | 1.3 | 1.5 | 2.5 | >55$^A$ | >62$^D$ | >52$^S$ | 19.1$^F$ | >2.4$^A$ | >2.4$^D$ | >2.3$^S$ | 1.7$^F$ |

FIG.39B-2

| | | Antigen Selection (Her2) | | | | Display Selection (anti-gD) | | | | $F_{wt/mut}$ values | | | | $\Delta\Delta G_{wt/mut}$ (kcal/mol) | | | |
|---|---|---|---|---|---|---|---|---|---|---|---|---|---|---|---|---|---|
| | | wt/m1 | wt/m2 | wt/m3 | wt/m4 | wt/m1 | wt/m2 | wt/m3 | wt/m4 | $F_{wt/m1}$ | $F_{wt/m2}$ | $F_{wt/m3}$ | $F_{wt/m4}$ | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-H2 | R50*** | >81 | >81 | >81 | 95.0 | 1.1 | 0.5 | 9.0 | 1.0 | >72$^A$ | >153$^G$ | >9$^P$ | 96.8$^K$ | >2.5$^A$ | >3.0$^G$ | >1.3$^P$ | 2.7$^K$ |
| | Y52 | 0.6 | 2.7 | 0.5 | 0.6 | 2.2 | 1.6 | 1.6 | 0.9 | 0.3$^A$ | 1.6$^D$ | 0.3$^S$ | 0.7$^F$ | -0.8$^A$ | 0.3$^D$ | -0.7$^S$ | -0.2$^F$ |
| | T53 | 1.0 | | | 0.7 | 0.9 | | | 0.6 | 1.1$^A$ | | | 1.2$^S$ | 0.1$^A$ | | | 0.1$^S$ |
| | N54 | 0.3 | 0.5 | 0.5 | 1.0 | 1.0 | 1.1 | 1.9 | 1.0 | 0.3$^A$ | 0.5$^D$ | 0.2$^T$ | 1.0$^D$ | -0.8$^A$ | -0.5$^D$ | -0.9$^T$ | 0$^D$ |
| | Y56* | >81 | >81 | >81 | 1.2 | 3.8 | 3.1 | 1.9 | 0.8 | >21$^A$ | >26$^D$ | >42$^S$ | 1.6$^F$ | >1.8$^A$ | >1.9$^D$ | >2.2$^S$ | 0.3$^F$ |
| | R58** | >81 | 80.0 | >81 | >96 | 1.1 | 0.8 | 2.4 | 2.1 | >73$^A$ | 104.8$^G$ | >33$^P$ | >46$^K$ | >2.5$^A$ | 2.8$^G$ | >2.1$^P$ | >2.3$^K$ |
| CDR-H3 | W95*** | >81 | >81 | >81 | >96 | 3.6 | 1.1 | 0.7 | 0.5 | >22$^A$ | >73$^G$ | >117$^S$ | >209$^L$ | >1.8$^A$ | >2.5$^G$ | >2.8$^S$ | >3.2$^L$ |
| | G96 | 1.5 | | | 0.6 | 1.3 | | | 1.4 | 1.1$^A$ | | | 0.4$^A$ | 0.1$^A$ | | | -0.5$^A$ |
| | G97 | 3.1 | | | 3.8 | 1.7 | | | 1.2 | 1.8$^A$ | | | 3.0$^A$ | 0.3$^A$ | | | 0.7$^A$ |
| | D98 | 0.8 | | | 0.4 | 1.0 | | | 0.9 | 0.8$^A$ | | | 0.4$^E$ | -0.1$^A$ | | | -0.5$^E$ |
| | G99*** | 26.0 | | | 18.0 | 1.2 | | | 1.9 | 22.3$^A$ | | | 9.5$^A$ | 1.8$^A$ | | | 1.3$^A$ |
| | F100 | >81 | >81 | 39.5 | 95.0 | 3.4 | 2.2 | 1.6 | 2.5 | >24$^A$ | >37$^S$ | 24.2$^V$ | 38.0$^Y$ | >1.9$^A$ | >2.1$^S$ | 1.9$^V$ | 2.2$^Y$ |
| | Y100a*** | 80.0 | >81 | >81 | 6.3 | 2.1 | 2.4 | 1.4 | 0.5 | 38$^A$ | >34$^D$ | >56.7$^S$ | 13.8$^F$ | 2.2$^A$ | >2.1$^D$ | >2.4$^S$ | -1.6$^F$ |

I
| | FR1 | | FR2 | |
|---|---|---|---|---|
| A | QVQLVQSGAEVKKPGASVKVSCKASGYTFT | -H1- | WVRQAPGQGLEWMG | -H2- |
| B | QVQLVQSGAEVKKPGASVKVSCKAS | -H1- | WVRQAPGQGLEWM | -H2- |
| C | QVQLVQSGAEVKKPGASVKVSCKAS | -H1- | WVRQAPGQGLEWM | -H2- |
| D | QVQLVQSGAEVKKPGASVKVSCKAS | -H1- | WVRQAPGQGLEWM | -H2- |

II
| | | | | |
|---|---|---|---|---|
| A | QVQLQESGPGLVKPSQTLSLTCTVSGGSVS | -H1- | WIRQPPGKGLEWIG | -H2- |
| B | QVQLQESGPGLVKPSQTLSLTCTVS | -H1- | WIRQPPGKGLEWI | -H2- |
| C | QVQLQESGPGLVKPSQTLSLTCTVS | -H1- | WIRQPPGKGLEWI | -H2- |
| D | QVQLQESGPGLVKPSQTLSLTCTVS | -H1- | WIRQPPGKGLEWI | -H2- |

III
| | | | | |
|---|---|---|---|---|
| A | EVQLVESGGGLVQPGGSLRLSCAASGFTFS | -H1- | WVRQAPGKGLEWVS | -H2- |
| B | EVQLVESGGGLVQPGGSLRLSCAAS | -H1- | WVRQAPGKGLEWV | -H2- |
| C | EVQLVESGGGLVQPGGSLRLSCAAS | -H1- | WVRQAPGKGLEWV | -H2- |
| D | EVQLVESGGGLVQPGGSLRLSCAAS | -H1- | WVRQAPGKGLEWV | -H2- |

Acceptor
| | | | | |
|---|---|---|---|---|
| A | EVQLVESGGGLVQPGGSLRLSCAASGFNIK | -H1- | WVRQAPGKGLEWVS | -H2- |
| B | EVQLVESGGGLVQPGGSLRLSCAAS | -H1- | WVRQAPGKGLEWV | -H2- |
| C | EVQLVESGGGLVQPGGSLRLSCAAS | -H1- | WVRQAPGKGLEWV | -H2- |

Second Acceptor
| | | | | |
|---|---|---|---|---|
| A | EVQLVESGGGLVQPGGSLRLSCAASGFNIK | -H1- | WVRQAPGKGLEWVS | -H2- |
| B | EVQLVESGGGLVQPGGSLRLSCAAS | -H1- | WVRQAPGKGLEWV | -H2- |
| C | EVQLVESGGGLVQPGGSLRLSCAAS | -H1- | WVRQAPGKGLEWV | -H2- |
| D | EVQLVESGGGLVQPGGSLRLSCAAS | -H1- | WVRQAPGKGLEWV | -H2- |

FIG. 52B

I
```
                FR3                              FR4
RVTITADTSTSTAYMELSSLRSEDTAVYYCAR    -H3-    WGQGTLVTVSS
RVTITADTSTSTAYMELSSLRSEDTAVYYCAR    -H3-    WGQGTLVTVSS
RVTITADTSTSTAYMELSSLRSEDTAVYYCAR    -H3-    WGQGTLVTVSS
RVTITADTSTSTAYMELSSLRSEDTAVYYCA     -H3-    WGQGTLVTVSS
RVTITADTSTSTAYMELSSLRSEDTAVYYC      -H3-    WGQGTLVTVSS
```

II
```
RVTISVDTSKNQFSLKLSSVTAADTAVYYCAR    -H3-    WGQGTLVTVSS
RVTISVDTSKNQFSLKLSSVTAADTAVYYCAR    -H3-    WGQGTLVTVSS
RVTISVDTSKNQFSLKLSSVTAADTAVYYCAR    -H3-    WGQGTLVTVSS
RVTISVDTSKNQFSLKLSSVTAADTAVYYCA     -H3-    WGQGTLVTVSS
RVTISVDTSKNQFSLKLSSVTAADTAVYYC      -H3-    WGQGTLVTVSS
```

III
```
RFTISRDNSKNTLYLQMNSLRAEDTAVYYCAR    -H3-    WGQGTLVTVSS
RFTISRDNSKNTLYLQMNSLRAEDTAVYYCAR    -H3-    WGQGTLVTVSS
RFTISRDNSKNTLYLQMNSLRAEDTAVYYCAR    -H3-    WGQGTLVTVSS
RFTISRDNSKNTLYLQMNSLRAEDTAVYYCA     -H3-    WGQGTLVTVSS
RFTISRDNSKNTLYLQMNSLRAEDTAVYYC      -H3-    WGQGTLVTVSS
```

Acceptor
```
RFTISADTSKNTAYLQMNSLRAEDTAVYYCSR    -H3-    WGQGTLVTVSS
RFTISADTSKNTAYLQMNSLRAEDTAVYYCSR    -H3-    WGQGTLVTVSS
RFTISADTSKNTAYLQMNSLRAEDTAVYYCS     -H3-    WGQGTLVTVSS
```

Second Acceptor
```
RFTISADTSKNTAYLQMNSLRAEDTAVYYCAR    -H3-    WGQGTLVTVSS
RFTISADTSKNTAYLQMNSLRAEDTAVYYCAR    -H3-    WGQGTLVTVSS
RFTISADTSKNTAYLQMNSLRAEDTAVYYCAR    -H3-    WGQGTLVTVSS
RFTISADTSKNTAYLQMNSLRAEDTAVYYCA     -H3-    WGQGTLVTVSS
RFTISADTSKNTAYLQMNSLRAEDTAVYYC      -H3-    WGQGTLVTVSS
```

FIG. 53

```
         FR1                              FR2
kv1  DIQMTQSPSSLSASVGDRVTITC -L1- WYQQKPGKAPKLLIY
kv2  DIVMTQSPLSLPVTPGEPASISC -L1- WYLQKPGQSPQLLIY
kv3  EIVLTQSPGTLSLSPGERATLSC -L1- WYQQKPGQAPRLLIY
kv4  DIVMTQSPDSLAVSLGERATINC -L1- WYQQKPGQPPKLLIY

FR3                                          FR4
kv1  -L2- GVPSRFSGSGSGTDFTLTISSLQPEDFATYYC -L3- FGQGTKVEIK
kv2  -L2- GVPDRFSGSGSGTDFTLKISRVEAEDVGVYYC -L3- FGQGTKVEIK
kv3  -L2- GIPDRFSGSGSGTDFTLTISRLEPEDFAVYYC -L3- FGQGTKVEIK
kv4  -L2- GVPDRFSGSGSGTDFTLTISSLQAEDVAVYYC -L3- FGQGTKVEIK
```

FIG. 58
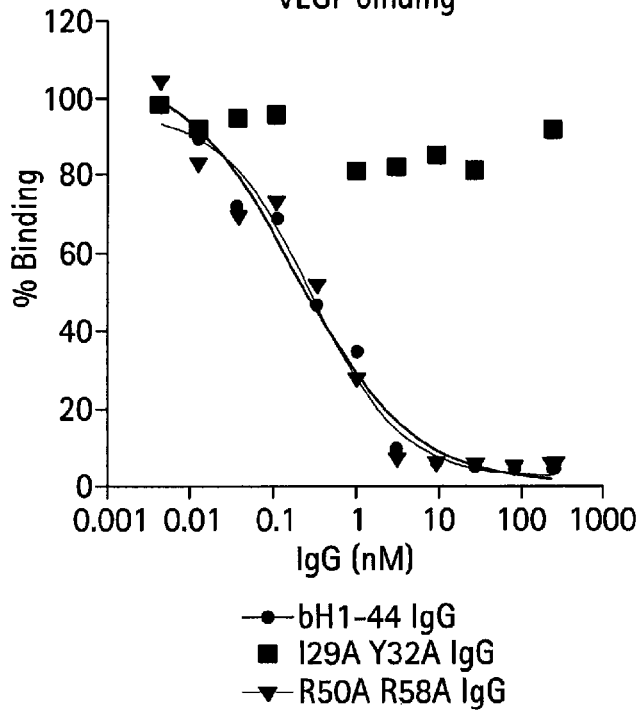
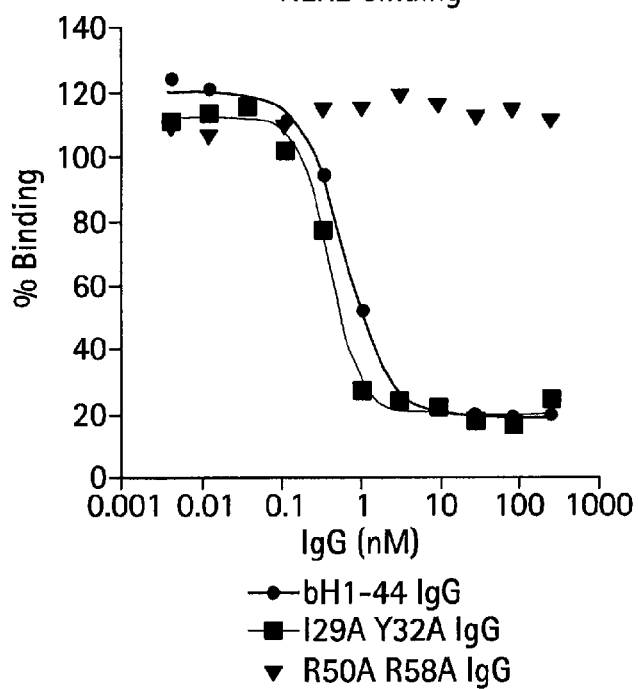

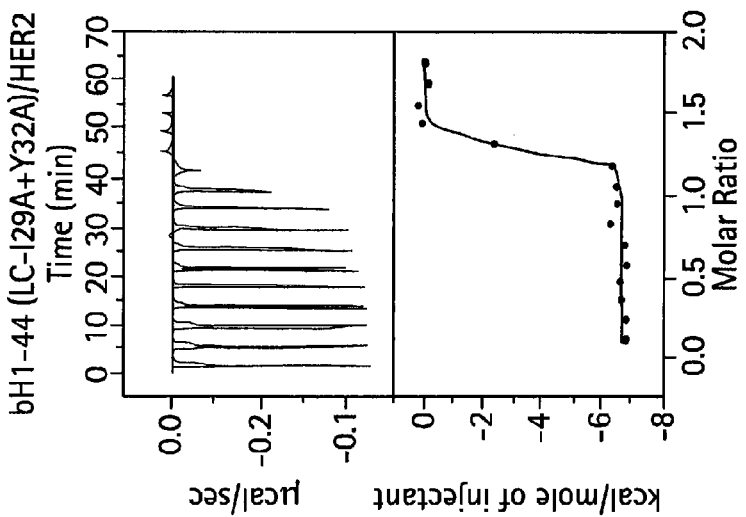
FIG. 59F
FIG. 59E
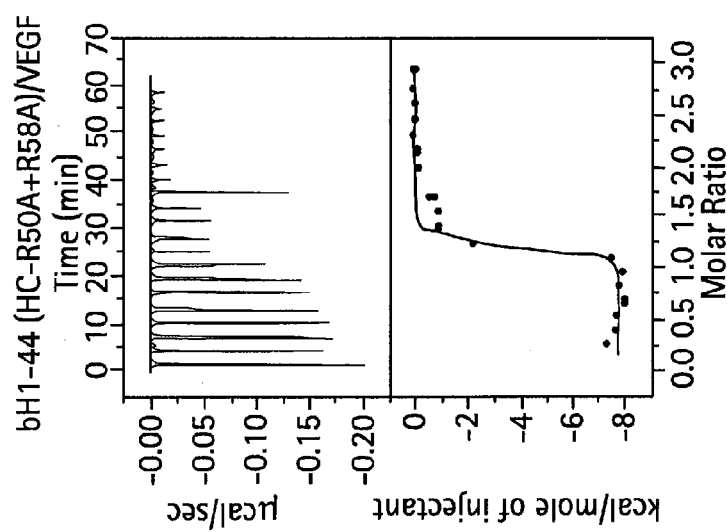
FIG. 59D
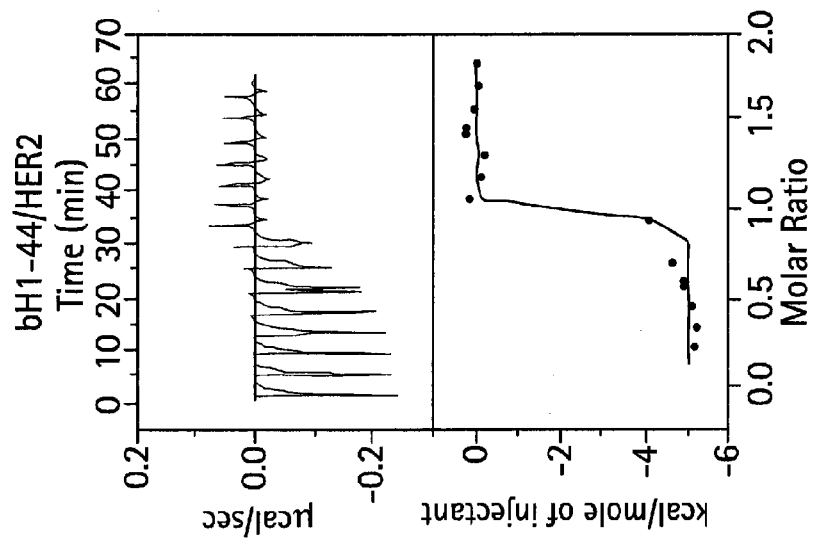

MULTISPECIFIC ANTIBODIES

CROSS-REFERENCE TO RELATED APPLICATIONS

This application claims the benefit of the filing date of U.S. provisional patent application 61/190,856, filed Sep. 3, 2008, the disclosure of which is hereby incorporated by reference.

FIELD OF THE INVENTION

The present invention relates to multispecific antibodies, and methods of making and using such antibodies.

BACKGROUND OF THE INVENTION

Antibodies are specific immunoglobulin polypeptides produced by the vertebrate immune system in response to challenge by foreign proteins, glycoproteins, cells, or other antigenic foreign substances. An important part of this process is the generation of antibodies that bind specifically to a particular foreign substance. The binding specificity of such polypeptides to a particular antigen is highly refined, and the multitude of specificities capable of being generated by the individual vertebrate is remarkable in its complexity and variability. Thousands of antigens are capable of eliciting responses, each almost exclusively directed to the particular antigen which elicited it.

Specific antigen recognition is essential for antibodies to function in the adaptive immune response. The combinatorial association of heavy chain (HC) and light chain (LC) is conserved in all vertebrates in the generation of the antibody repertoire. There is, however, asymmetry of diversity in the two chains. The variable domain of HC ($V_H$) contains significantly higher sequence diversity and contributes the determinants of antigen recognition more often than the variable domain of the LC ($V_L$). The role of the LC in determining antigen-specificity is indicated by a process called receptor editing. Ongoing recombination of the $V_L$ genes to edit the B cell receptor is the main mechanism to correct self reactive antibody precursors, which appear to constitute a significant portion of the initial repertoire (~75%). Altering of the light chain is demonstrated to extinguish unwanted binding specificity or multi-specificity.

The specificity of antibodies and antibody fragments for a particular antigen or antigens makes antibodies desirable therapeutic agents. Antibodies and antibody fragments can be used to target particular tissues, for example, a tumor, and thereby minimize the potential side effects of non-specific targeting. As such, there is a current and continuing need to identify and characterize therapeutic antibodies, especially antibodies, fragments, and derivatives thereof, useful in the treatment of cancer and other proliferative disorders.

SUMMARY OF THE INVENTION

The present invention provides an isolated antibody comprising a hypervariable region (HVR) L1 sequence comprising the sequence NIAKTISGY (SEQ ID NO:1), where the antibody specifically binds human epidermal growth factor receptor 2 (HER2) and vascular endothelial growth factor (VEGF). In one embodiment, the antibody further comprises an HVR-L2 comprising the sequence WGSFLY (SEQ ID NO: 2) and/or an HVR-L3 comprising the sequence HYSSPP (SEQ ID NO: 3). In another embodiment, the antibody further comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In another embodiment, the antibody further comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9).

In another aspect, the invention features an isolated antibody comprising an HVR-L1 sequence comprising the sequence $X_1IX_3X_4X_5X_6X_7X_8X_9Y$ (SEQ ID NO: 83), wherein $X_1$ is any amino acid except aspartic acid, $X_3$ is any amino acid except proline, $X_4$ is any amino acid except arginine, and $X_5$ is any amino acid except serine, where the antibody specifically binds HER2 and VEGF. In one embodiment, an antibody comprising the sequence $X_1IX_3X_4X_5X_6X_7X_8X_9Y$ (SEQ ID NO: 83) has an asparagine at $X_1$, an alanine at $X_3$, a lysine at $X_4$, a threonine at $X_5$, a serine at $X_7$, and/or a glycine at $X_5$, or any combination thereof. In various embodiments of this aspect of the invention, any of the HVR-L1 residues shown in FIG. 57 to have an F value of greater than 1, 5, or 10 are residues that are preferably maintained as the same residue found in the same position of the HVR-L1 of bH1-44 or bH1-81 (SEQ ID NO: 1). In additional embodiments, any of the HVR-L1 residues shown in Table 14 to have ΔΔG values greater than 1 are residues that are preferably maintained as the same residue found in the same position of the HVR-L1 of bH1-44 or bH1-81 (SEQ ID NO: 1). In one embodiment, the antibody comprises an HVR-H2 sequence comprising the sequence $RX_2X_3X_4X_5X_6X_7X_8X_9R$ (SEQ ID NO: 84). In one embodiment, the antibody further comprises an HVR-L2 comprising the sequence WGSFLY (SEQ ID NO: 2) and/or an HVR-L3 comprising the sequence HYSSPP (SEQ ID NO: 3). In another embodiment, the antibody further comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In another embodiment, the antibody further comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9).

In another aspect, the invention features an isolated antibody comprising an HVR-H2 sequence comprising the sequence $RX_2X_3X_4X_5X_6X_7X_8X_9R$ (SEQ ID NO: 85), wherein $X_5$ is any amino acid except threonine and $X_6$ is any amino acid except asparagine and where the antibody specifically binds HER2 and VEGF. In another embodiment, an antibody comprising the sequence $RX_2X_3X_4X_5X_6X_7X_8X_9R$ (SEQ ID NO: 84) has a tyrosine at $X_8$. In one embodiment, an antibody comprising the sequence $RX_2X_3X_4X_5X_6X_7X_8X_9R$ (SEQ ID NO: 84) has a serine at $X_5$ and/or a glutamic acid at $X_6$. In another embodiment of this aspect, the antibodies further comprise one, two, or three HVR sequences selected from the group of a HVR-L1 comprising the sequence NIAKTISGY (SEQ ID NO: 1), a HVR-L2 comprising the sequence WGSFLY (SEQ ID NO: 2), and/or a HVR-L3 comprising the sequence HYSSPP (SEQ ID NO: 3). In any of the embodiments described herein, the antibodies further comprise, one or two HVR sequences selected from (i) HVR-H1 comprising the sequence NIKDTY (SEQ ID NO:4) and (ii) HVR-H3 comprising the sequence WGGDGFYAMD (SEQ ID NO:6).

In an additional embodiment, the antibodies further comprise, one or two HVR sequences selected from (i) HVR-H1 comprising the sequence NISGTY (SEQ ID NO:7) and (ii) HVR-H3 comprising the sequence WVGVGFYAMD (SEQ ID NO:9).

In various embodiments of this aspect of the invention, any of the HVR-H2 residues shown in FIG. 57 to have an F value of greater than 1, 5, or 10 are residues that are preferably maintained as the same residue found in the same position of the HVR-H2 of bH1-44 or bH1-81 (SEQ ID NOS: 8 and 5, respectively). In additional embodiments, any of the HVR-H2 residues shown in Table 14 to have ΔΔG values greater than 1 are residues that are preferably maintained as the same residue found in the same position of the HVR-H2 of bH1-44 or bH1-81 (SEQ ID NOS: 8 and 5, respectively).

In particular embodiments, the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6) or comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NISGTY (SEQ ID NO:7); an HVR-H2 sequence comprising RIYPSEGYTR (SEQ ID NO:8); and/or an HVR-H3 sequence comprising WVGVGFYAMD (SEQ ID NO:9).

In a further particular embodiment the isolated antibody comprises HVR-L1, HVR-L2, HVR-L3, HVR-H1, HVR-H2, and HVR-H3, wherein each, in order, comprises the sequence NIAKTISGY (SEQ ID NO:1); WGSFLY (SEQ ID NO:2); HYSSPP (SEQ ID NO:3); NIKDTY (SEQ ID NO:4); RIYPTNGYTR (SEQ ID NO:5); and WGGDGFYAMD (SEQ ID NO:6) and specifically binds HER2 and VEGF. In another particular embodiment, the antibody comprises HVR-L1, HVR-L2, HVR-L3, HVR-H1, HVR-H2, and HVR-H3, wherein each, in order, comprises the sequence NIAKTISGY (SEQ ID NO:1); WGSFLY (SEQ ID NO:2); HYSSPP (SEQ ID NO:3); NISGTY (SEQ ID NO:7); RIYPSEGYTR (SEQ ID NO:8); and WVGVGFYAMD (SEQ ID NO:9) and specifically binds HER2 and VEGF.

In various embodiments of any of the aspects described herein, the antibody binds human and murine VEGF with a Kd of 150 nM or stronger and HER2 with a Kd of 7 nM or stronger. In additional embodiments, the antibody inhibits VEGF-induced cell proliferation and proliferation of a HER2 expressing cell relative to a control. In a particular embodiment, the antibody binds human and murine VEGF with a Kd of 36 nM or stronger and HER2 with a Kd of 1 nM or stronger. In an additional embodiment, the antibody inhibits VEGF binding to VEGFR2.

In another aspect, the invention features an isolated antibody that binds human and murine VEGF with a Kd of 150 nM or stronger and HER2 with a Kd of 7 nM or stronger and wherein the antibody inhibits VEGF-induced cell proliferation and proliferation of a HER2 expressing cell relative to a control. In one embodiment, the antibody binds human and murine VEGF with a Kd of 36 nM or stronger and HER2 with a Kd of 1 nM or stronger.

In yet another aspect the invention provides an isolated antibody fragment that binds human VEGF with a Kd of 58 nM or stronger and HER2 with a Kd of 6 nM or stronger, and/or inhibits VEGF-induced cell proliferation and proliferation of a HER2 expressing cell relative to a control. In a particular embodiment, the antibody fragment binds human and murine VEGF with a Kd of 33 nM or stronger and HER2 with a Kd of 0.7 nM or stronger. In another particular embodiment, the fragment is a Fab fragment or a single chain variable fragment (scFv).

In any of the above-described aspects, the antibody may be a monoclonal antibody. In another embodiment of all the above aspects, the antibody may be an IgG antibody. In additional embodiments of all the above aspects, at least a portion of the framework sequence of the antibody may be a human consensus framework sequence.

In another aspect, the invention features a fragment of an antibody any of the antibodies described herein. One embodiment of an antibody fragment is a fragment comprising a HVR-L1 sequence comprising the sequence NIAKTISGY (SEQ ID NO:1) that specifically binds HER2 and VEGF. In another embodiment, the antibody fragment further comprises one or two HVR sequences selected from (i) HVR-L2 comprising the sequence WGSFLY (SEQ ID NO:2); and (ii) HVR-L3 comprising the sequence HYSSPP (SEQ ID NO:3). In another embodiment, the antibody fragment further comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In an additional embodiment, the antibody fragment further comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9). In particular embodiments, the antibody fragment comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6) or comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NISGTY (SEQ ID NO:7); an HVR-H2 sequence comprising RIYPSEGYTR (SEQ ID NO:8); and an HVR-H3 sequence comprising WVGVGFYAMD (SEQ ID NO:9). In one embodiment, the fragment is a Fab fragment or a single chain variable fragment (scFv). In additional embodiments of all the above aspects, at least a portion of the framework sequence of the antibody may be a human consensus framework sequence.

In further aspects, the invention features polynucleotides encoding any antibody or antibody fragment described herein, as well as a vector comprising such a polynucleotide. In particular embodiments, the encoded antibody comprises an HVR-L1 sequence comprising NIAKTISGY (SEQ ID NO:1). Optionally or additionally, the polynucleotide encodes an antibody that also comprises an HVR-L2 sequence comprising WGSFLY (SEQ ID NO:2); and/or an HVR-L3 sequence comprising HYSSPP (SEQ ID NO:3), or any combination thereof. In an additional aspect, the polynucleotide may further encode an antibody comprising one, two, or three of an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6); or an antibody comprising one, two, or three of an HVR-H1 comprising NISGTY (SEQ ID NO:7); an HVR-H2 comprising RIYPSE- GYTR (SEQ ID NO:8); and/or an HVR-H3 sequence comprising WVGVGFYAMD (SEQ ID NO:9).

In additional aspects of the invention, the polynucleotide encodes an HVR-H1 sequence comprising the sequence of NISGTY (SEQ ID NO: 7), an HVR-H2 comprises the sequence of RIYPSEGYTR (SEQ ID NO: 8), or an HVR-H3 comprises the sequence of WVGVGFYAMD (SEQ ID NO: 9), or any combination thereof.

In other aspects, the invention features an isolated polynucleotide encoding an HVR-L1 sequence comprising the sequence NIAKTISGY (SEQ ID NO:1) and, optionally, the polynucleotide further encodes one, two, or three HVR sequences selected from (i) an HVR-H1 comprising the sequence NIKDTY (SEQ ID NO:4); (ii) an HVR-H2 comprising the sequence RIYPTNGYTR (SEQ ID NO:5); and (iii) an HVR-H3 comprising the sequence WGGDGFYAMD (SEQ ID NO:6). In additional aspects, the invention features an isolated polynucleotide encoding an HVR-L1 sequence comprising the sequence NIAKTISGY (SEQ ID NO:1); and (i) an HVR-L2 sequence comprising the sequence WGSFLY (SEQ ID NO:2) or (ii) an HVR-L3 sequence comprising the sequence HYSSPP (SEQ ID NO:3), or both, and, optionally, the polynucleotide further encodes one, two, or three HVR sequences selected from (i) an HVR-H1 comprising the sequence NIKDTY (SEQ ID NO:4); (ii) an HVR-H2 comprising the sequence RIYPTNGYTR (SEQ ID NO:5); and (iii) an HVR-H3 comprising the sequence WGGDGFYAMD (SEQ ID NO:6).

In a further aspect, the invention features an isolated polynucleotide encoding an HVR-L1 sequence comprising the sequence NIAKTISGY (SEQ ID NO:1); an HVR-H1 comprising the sequence NISGTY (SEQ ID NO:7); an HVR-H2 comprising the sequence RIYPSEGYTR (SEQ ID NO:8); and an HVR-H3 comprising the sequence WVGVGFYAMD (SEQ ID NO:9). In yet another aspect, the invention features an isolated polynucleotide encoding an HVR-L1 sequence comprising the sequence NIAKTISGY (SEQ ID NO:1); an HVR-L2 sequence comprising the sequence WGSFLY (SEQ ID NO:2); an HVR-L3 sequence comprising the sequence HYSSPP (SEQ ID NO:3); an HVR-H1 comprising the sequence NISGTY (SEQ ID NO:7); an HVR-H2 comprising the sequence RIYPSEGYTR (SEQ ID NO:8); and an HVR-H3 comprising the sequence WVGVGFYAMD (SEQ ID NO:9).

In other aspects, the invention features an isolated polynucleotide encoding an HVR-H1 sequence comprising the sequence NISGTY (SEQ ID NO:7), an isolated polynucleotide encoding an HVR-H2 sequence comprising the sequence RIYPSEGYTR (SEQ ID NO:8), and an isolated polynucleotide encoding an HVR-H3 sequence comprising the sequence WVGVGFYAMD (SEQ ID NO:9). In another aspect, the invention features an isolated polynucleotide encoding an polypeptide comprising an HVR-H1 sequence comprising the sequence NISGTY (SEQ ID NO:7); an HVR-H2 sequence comprising the sequence RIYPSEGYTR (SEQ ID NO:8); and an HVR-H3 sequence comprising the sequence WVGVGFYAMD (SEQ ID NO:9).

In an additional embodiment of the invention, the isolated polynucleotide encodes an HVR-L1 sequence comprising the sequence $X_1IX_3X_4X_5X_6X_7X_8X_9Y$ (SEQ ID NO: 83), wherein $X_1$ is any amino acid except aspartic acid, $X_3$ is any amino acid except proline, $X_4$ is any amino acid except arginine, and $X_5$ is any amino acid except serine. In another embodiment of the invention, the polynucleotide encodes an HVR-L1 sequence comprising the sequence $X_1IX_3X_4X_5X_6X_7X_8X_9Y$ (SEQ ID NO: 83), wherein $X_1$ is any amino acid except Asp, $X_3$ is any amino acid except proline, $X_4$ is any amino acid except arginine, and $X_5$ is any amino acid except serine; and a HVR-L2 sequence comprising the sequence WGSFLY (SEQ ID NO: 2) and/or an HVR-L3 sequence comprising the sequence HYSSPP (SEQ ID NO: 3). In additional embodiments of this aspect of the invention, the polynucleotide encodes an antibody comprising the sequence $X_1IX_3X_4X_5X_6X_7X_8X_9Y$ (SEQ ID NO: 83) that has an asparagine at $X_1$, an alanine at $X_3$, a lysine at $X_4$, a threonine at $X_5$, a serine at $X_7$, and/or a glycine at $X_8$, or any combination thereof. In various embodiments of this aspect of the invention, any of the HVR-L1 residues shown in FIG. 57 to have an F value of greater than 1, 5, or 10 are residues that are preferably maintained as the same residue found in the same position of the HVR-L1 of bH1-44 or bH1-81 (SEQ ID NO: 1). In additional embodiments, any of the HVR-L1 residues shown in Table 14 to have 6AG values greater than 1 are residues that are preferably maintained as the same residue found in the same position of the HVR-L1 of bH1-44 or bH1-81 (SEQ ID NO: 1). In an additional embodiment of the invention, the polynucleotide encodes an HVR-H2 sequence comprising the sequence $RX_2X_3X_4X_5X_6X_7X_8X_9R$ (SEQ ID NO: 85), wherein $X_5$ is any amino acid except threonine and $X_6$ is any amino acid except asparagine. In another aspect, the invention provides a polynucleotide encoding an HVR-H1 sequence comprising the sequence NISGTY (SEQ ID NO: 7); an HVR-H2 sequence comprising the sequence $RX_2X_3X_4X_5X_6X_7X_8X_9R$ (SEQ ID NO: 85), wherein $X_5$ is any amino acid except threonine and $X_6$ is any amino acid except asparagine; and an HVR-H3 sequence comprising the sequence WVGVGFYAMD (SEQ ID NO: 9). In an additional embodiments of the invention, the polynucleotide encodes an HVR-H2 sequence comprising the sequence $RX_2X_3X_4X_5X_6X_7X_8X_9R$ (SEQ ID NO: 84) that has a serine at $X_5$, a glutamic acid at $X_6$, and/or a tyrosine at $X_8$, or any combination thereof. In various embodiments of this aspect of the invention, any of the HVR-H2 residues shown in FIG. 57 to have an F value of greater than 1, 5, or 10 are residues that are preferably maintained as the same residue found in the same position of the HVR-H2 of bH1-44 or bH1-81 (SEQ ID NOS: 8 and 5, respectively). In additional embodiments, any of the HVR-H2 residues shown in Table 14 to have DLG values greater than 1 are residues that are preferably maintained as the same residue found in the same position of the HVR-H2 of bH1-44 or bH1-81 (SEQ ID NOS: 8 and 5, respectively).

In further aspects, the invention features an isolated polypeptide comprising an HVR-L1 sequence comprising the sequence NIAKTISGY (SEQ ID NO:1) or an isolated polypeptide comprising an HVR-L1 sequence comprising the sequence NIAKTISGY (SEQ ID NO:1); an HVR-L2 sequence comprising the sequence WGSFLY (SEQ ID NO:2); and/or an HVR-L3 sequence comprising the sequence HYSSPP (SEQ ID NO:3). In another aspect, the invention provides a polypeptide comprising an HVR-L1 sequence comprising the sequence $X_1IX_3X_4X_5X_6X_7X_8X_9Y$ (SEQ ID NO: 83), wherein $X_1$ is any amino acid except aspartic acid, $X_3$ is any amino acid except proline, $X_4$ is any amino acid except arginine, and $X_5$ is any amino acid except serine. In another embodiment of this aspect, the polypeptide comprises the HVR-L1 sequence $X_1IX_3X_4X_5X_6X_7X_8X_9Y$ (SEQ ID NO: 83), wherein $X_1$ is any amino acid except aspartic acid, $X_3$ is any amino acid except proline, $X_4$ is any amino acid except arginine, and $X_5$ is any amino acid except serine. Optionally, the polypeptide further comprises an HVR-L2 sequence comprising the sequence WGSFLY (SEQ ID NO: 2) and/or an HVR-L3 sequence comprising the sequence HYSSPP (SEQ ID NO: 3). In particular embodiments of any of the above aspects that comprise a polypeptide that comprises the sequence $X_1 X_3 X_4 X_5 X_6 X_7 X_8 X_9 Y$ (SEQ ID NO: 83), there is an asparagine at $X_L$, an alanine at $X_3$, a lysine at $X_4$, a threonine at $X_5$, a serine at $X_7$, and/or a glycine at $X_8$, or any combination thereof. In various embodiments of this aspect of the invention, any of the HVR-L1 residues shown in FIG. 57 to have an F value of greater than 1, 5, or 10 are residues that are preferably maintained as the same residue found in the same position of the HVR-L1 of bH1-44 or bH1-81 (SEQ ID NO: 1). In additional embodiments, any of the HVR-L1 residues shown in Table 14 to have ΔΔG values greater than 1 are residues that are preferably maintained as the same residue found in the same position of the HVR-L1 of bH1-44 or bH1-81 (SEQ ID NO: 1).

The invention also provides a polypeptide comprising an HVR-H2 sequence comprising the sequence $RX_2 X_3 X_4 X_5 X_6 X_7 X_8 X_9 R$ (SEQ ID NO: 85), wherein $X_5$ is any amino acid except threonine and $X_6$ is any amino acid except asparagine. In another aspect of the invention, the polypeptide comprises the HVR-H2 sequence $RX_2 X_3 X_4 X_5 X_6 X_7 X_5 X_9 R$ (SEQ ID NO: 85), wherein $X_5$ is any amino acid except threonine and $X_6$ is any amino acid except asparagine, a HVR-H1 sequence comprising the sequence NISGTY (SEQ ID NO: 7), and an HVR-H3 sequence comprising the sequence WVGVGFYAMD (SEQ ID NO: 9). In different embodiments of the above aspects, the polypeptide comprising the HVR-H2 sequence comprising the sequence $RX_2 X_3 X_4 X_5 X_6 X_7 X_8 X_9 R$ (SEQ ID NO: 84) has a serine at $X_5$, a glutamic acid at $X_6$, and/or a tyrosine at $X_8$, or any combination thereof. In various embodiments of this aspect of the invention, any of the HVR-H2 residues shown in FIG. 57 to have an F value of greater than 1, 5, or 10 are residues that are preferably maintained as the same residue found in the same position of the HVR-H2 of bH1-44 or bH1-81 (SEQ ID NOS: 8 and 5, respectively). In additional embodiments, any of the HVR-H2 residues shown in Table 14 to have ΔΔG values greater than 1 are residues that are preferably maintained as the same residue found in the same position of the HVR-H2 of bH1-44 or bH1-81 (SEQ ID NOS: 8 and 5, respectively).

The invention also provides a polypeptide comprising one, two, or three of an HVR-H1 sequence comprising the sequence NISGTY (SEQ ID NO: 7), a HVR-H2 sequence comprising the sequence RIYPSEGYTR (SEQ ID NO: 8), and/or an HVR-H3 sequence comprising the sequence WVGVGFYAMD (SEQ ID NO: 9), or any combination thereof. In any of the above aspects, the isolated polypeptide may further comprise one, two, or three of an HVR-L 1 sequence comprising the sequence NIAKTISGY (SEQ ID NO:1); an HVR-H1 comprising the sequence NIKDTY (SEQ ID NO:4); an HVR-H2 comprising the sequence RIYPTNGYTR (SEQ ID NO:5); and/or an HVR-H3 comprising the sequence WGGDGFYAMD (SEQ ID NO:6), or any combination thereof.

In any of the above aspects, the isolated polypeptide may further comprise one, two, or three of an HVR-L1 sequence comprising the sequence NIAKTISGY (SEQ ID NO:1); an HVR-L2 sequence comprising the sequence WGSFLY (SEQ ID NO:2); and/or an HVR-L3 sequence comprising the sequence HYSSPP (SEQ ID NO:3), or any combination thereof.

In any of the above aspects, the isolated polypeptide may further comprise an HVR-H1 comprising the sequence NIKDTY (SEQ ID NO:4); an HVR-H2 comprising the sequence RIYPTNGYTR (SEQ ID NO:5); and/or an HVR-H3 comprising the sequence WGGDGFYAMD (SEQ ID NO:6), or any combination thereof.

In any of the above aspects, the isolated polypeptide may further comprise one, two, or three HVR sequences selected from an HVR-H1 comprising the sequence NISGTY (SEQ ID NO: 7); an HVR-H2 sequence comprising the sequence RIYPSEGYTR (SEQ ID NO: 8); and/or an HVR-H3 comprising the sequence WVGVGFYAMD (SEQ ID NO: 9), or any combination thereof.

In additional aspects, the invention features an isolated polypeptide comprising an HVR-L1 sequence comprising the sequence NIAKTISGY (SEQ ID NO:1) and (i) an HVR-L2 sequence comprising the sequence WGSFLY (SEQ ID NO:2) or (ii) an HVR-L3 sequence comprising the sequence HYSSPP (SEQ ID NO:3), or both; and one, two, of three HVR sequences selected from (i) an HVR-H1 comprising the sequence NISGTY (SEQ ID NO:7); (ii) an HVR-H2 comprising the sequence RIYPSEGYTR (SEQ ID NO:8); and/or (iii) an HVR-H3 comprising the sequence WVGVGFYAMD (SEQ ID NO:9), or any combination thereof.

In additional aspects, the invention features an isolated polypeptide comprising an HVR-L1 sequence comprising the sequence NIAKTISGY (SEQ ID NO:1) and (i) an HVR-L2 sequence comprising the sequence WGSFLY (SEQ ID NO:2) or (ii) an HVR-L3 sequence comprising the sequence HYSSPP (SEQ ID NO:3), or both; and one, two, of three HVR sequences selected from (i) an HVR-H1 comprising the sequence NIKDTY (SEQ ID NO:4); (ii) an HVR-H2 comprising the sequence RIYPTNGYTR (SEQ ID NO:5); and/or (iii) an HVR-H3 comprising the sequence WGGDGFYAMD (SEQ ID NO:6), or any combination thereof.

In further aspects, the invention features an isolated polypeptide comprising an HVR-H1 sequence comprising the sequence NISGTY (SEQ ID NO:7), an isolated polypeptide comprising an HVR-H2 sequence comprising the sequence RIYPSEGYTR (SEQ ID NO:8), and an isolated polypeptide comprising an HVR-H3 sequence comprising the sequence WVGVGFYAMD (SEQ ID NO:9). In yet a further aspect, the invention features an isolated polypeptide comprising an HVR-H1 sequence comprising the sequence NISGTY (SEQ ID NO:7); an HVR-H2 sequence comprising the sequence RIYPSEGYTR (SEQ ID NO:8); and an HVR-H3 sequence comprising the sequence WVGVGFYAMD (SEQ ID NO:9).

In one embodiment, the invention provides a vector comprising any of the above described polynucleotides of the invention. In another aspect, the invention features a host cell comprising any of the vectors of the invention. In one embodiment, the host cell is prokaryotic. In another embodiment, the host cell is eukaryotic, for example, a mammalian cell.

In another aspect, the invention features a method of producing any of the antibodies or antibody fragments described above. This method comprises culturing a host cell that comprises a vector comprising a polynucleotide encoding the antibody and recovering the antibody. In certain embodiments, the polynucleotide encodes an HVR-L1 sequence comprising the sequence NIAKTISGY (SEQ ID NO:1) and, optionally, the polynucleotide further encodes an HVR-H1 comprising the sequence NIKDTY (SEQ ID NO:4); an HVR-H2 comprising the sequence RIYPTNGYTR (SEQ ID NO:5); and an HVR-H3 comprising the sequence WGGDGFYAMD (SEQ ID NO:6). In other embodiments, the polynucleotide encodes an HVR-L1 sequence comprising the sequence NIAKTISGY (SEQ ID NO:1); an HVR-L2 sequence comprising the sequence WGSFLY (SEQ ID NO:2); and an HVR-L3 sequence comprising the sequence HYSSPP (SEQ ID NO:3) and, optionally, the polynucleotide further encodes an HVR-H1 comprising the sequence NIKDTY (SEQ ID NO:4); an HVR-H2 comprising the sequence RIYPTNGYTR (SEQ ID NO:5); and an HVR-H3 comprising the sequence WGGDGFYAMD (SEQ ID NO:6). In another embodiment, the polynucleotide encodes an HVR-L1 sequence comprising the sequence NIAKTISGY (SEQ ID NO:1); an HVR-H1 comprising the sequence NISGTY (SEQ ID NO:7); an HVR-1-12 comprising the sequence RIYPSEGYTR (SEQ ID NO:8); and an HVR-H3 comprising the sequence WVGVGFYAMD (SEQ ID NO:9). In yet another embodiment, the polynucleotide encodes an HVR-L1 sequence comprising the sequence NIAKTISGY (SEQ ID NO:1); an HVR-L2 sequence comprising the sequence WGSFLY (SEQ ID NO:2); an HVR-L3 sequence comprising the sequence HYSSPP (SEQ ID NO:3); an HVR-H1 comprising the sequence NISGTY (SEQ ID NO:7); an HVR-H2 comprising the sequence RIYPSEGYTR (SEQ ID NO:8); and an HVR-H3 comprising the sequence WVGVGFYAMD (SEQ ID NO:9).

In further embodiments, the polynucleotide encodes an HVR-H1 sequence comprising the sequence NISGTY (SEQ ID NO:7), an HVR-H2 sequence comprising the sequence RIYPSEGYTR (SEQ ID NO:8), or an HVR-H3 sequence comprising the sequence WVGVGFYAMD (SEQ ID NO:9). In yet a further embodiment, the polynucleotide encodes a polypeptide comprising an HVR-H1 sequence comprising the sequence NISGTY (SEQ ID NO:7); an HVR-H2 sequence comprising the sequence RIYPSEGYTR (SEQ ID NO:8); and an HVR-H3 sequence comprising the sequence WVGVGFYAMD (SEQ ID NO:9).

In one embodiment, the host cell is prokaryotic and in another embodiment, the host cell is eukaryotic, such as a mammalian cell.

In a further aspect, the invention features a method of treating a tumor in a subject. This method comprises administering to the subject an antibody or antibody fragment described herein, where the administering is for a time and in an amount sufficient to treat or prevent the tumor in the subject. In one embodiment, the tumor is a colorectal tumor, a breast cancer, a lung cancer, a renal cell carcinoma, a glioma, a glioblastoma, or an ovarian cancer. In another embodiment, the antibody comprises an HVR-L1 sequence comprising the sequence NIAKTISGY (SEQ ID NO:1) and specifically binds HER2 and VEGF. According to one embodiment, the antibody further comprises one or two HVR sequences selected from (i) HVR-L2 comprising the sequence WGSFLY (SEQ ID NO:2); and (ii) HVR-L3 comprising the sequence HYSSPP (SEQ ID NO:3). In another embodiment, the antibody comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In an additional embodiment, the antibody comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9). In particular embodiments, the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6) and specifically binds HER2 and VEGF. In another embodiment, the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NISGTY (SEQ ID NO:7); an HVR-H2 sequence comprising RIYPSEGYTR (SEQ ID NO:8); and an HVR-H3 sequence comprising WVGVGFYAMD (SEQ ID NO:9) and specifically binds HER2 and VEGF.

In an embodiment, the method further comprises administering to the subject an additional anti-cancer therapy. In another embodiment, the additional anti-cancer therapy comprises another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, or a growth-inhibitory agent.

In an additional embodiment, the additional anti-cancer therapy is administered prior to or subsequent to the administration of an antibody. In a further embodiment, the additional anti-cancer therapy is administered concurrently with an antibody.

In a further aspect, the invention features a method of treating an autoimmune disease in a subject. This method comprises administering to the subject an antibody or antibody fragment described herein, where the administering is for a time and in an amount sufficient to treat or prevent the autoimmune disease in the subject. In one embodiment, the antibody comprises an HVR-L1 sequence comprising the sequence NIAKTISGY (SEQ ID NO:1) and specifically binds HER2 and VEGF. According to one embodiment, the antibody comprises one or two HVR sequences selected from (i) HVR-L2 comprising the sequence WGSFLY (SEQ ID NO:2); and (ii) HVR-L3 comprising the sequence HYSSPP (SEQ ID NO:3). In another embodiment, the antibody comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In an additional embodiment, the antibody comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9). In particular embodiments, the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6) and specifically binds HER2 and VEGF or the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NISGTY (SEQ ID NO:7); an HVR-H2 sequence comprising RIYPSEGYTR (SEQ ID NO:8); and an HVR-H3 sequence comprising WVGVGFYAMD (SEQ ID NO:9) and specifically binds HER2 and VEGF.

In yet another aspect, the invention features a method of treating a non-malignant disease involving abnormal activation of HER2 in a subject. This method comprises administering to the subject an antibody or antibody fragment described herein, where the administering is for a time and in an amount sufficient to treat or prevent the non-malignant disease in the subject. In one embodiment, the antibody comprises an HVR-L1 sequence comprising the sequence NIAK- TISGY (SEQ ID NO:1) and specifically binds HER2 and VEGF. According to one embodiment, the antibody comprises one or two HVR sequences selected from (i) HVR-L2 comprising the sequence WGSFLY (SEQ ID NO:2); and (ii) HVR-L3 comprising the sequence HYSSPP (SEQ ID NO:3). In another embodiment, the antibody further comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In an additional embodiment, the antibody comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9). In particular embodiments, the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6) and specifically binds HER2 and VEGF or the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NISGTY (SEQ ID NO:7); an HVR-H2 sequence comprising RIYPSEGYTR (SEQ ID NO:8); and an HVR-H3 sequence comprising WVGVGFYAMD (SEQ ID NO:9) and specifically binds HER2 and VEGF.

Additional aspects of the invention feature the use of the antibodies and antibody fragments described herein in the treatment of a tumor, an autoimmune disease, or a non-malignant disease involving abnormal activation of HER2 in a subject, as well as use in the manufacture of a medicament for the treatment of a tumor, an autoimmune disease, or a non-malignant disease involving abnormal activation of HER2 in a subject. In one embodiment of these uses, the antibody comprises an HVR-L1 sequence comprising the sequence NIAKTISGY (SEQ ID NO:1) and specifically binds HER2 and VEGF. According to one embodiment, the antibody further comprises one or two HVR sequences selected from (i) HVR-L2 comprising the sequence WGSFLY (SEQ ID NO:2); and (ii) HVR-L3 comprising the sequence HYSSPP (SEQ ID NO:3). In another embodiment, the antibody comprises, one, two, or three HVR sequences selected from (i) HVR-H1 comprising the sequence NIKDTY (SEQ ID NO:4); (ii) HVR-H2 comprising the sequence RIYPTNGYTR (SEQ ID NO:5); and (iii) HVR-H3 comprising the sequence WGGDGFYAMD (SEQ ID NO:6). In an additional embodiment, the antibody comprises, one, two, or three HVR sequences selected from (i) HVR-H1 comprising the sequence NISGTY (SEQ ID NO:7); (ii) HVR-H2 comprising the sequence RIYPSEGYTR (SEQ ID NO:8); and (iii) HVR-H3 comprising the sequence WVGVGFYAMD (SEQ ID NO:9). In particular embodiments, the antibody comprises an HVR-L1 sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NIKDTY (SEQ ID NO:4); an HVR-H2 sequence comprising RIYPTNGYTR (SEQ ID NO:5); and an HVR-H3 sequence comprising WGGDGFYAMD (SEQ ID NO:6) and specifically binds HER2 and VEGF or the antibody comprises an HVR-L I sequence comprising NIAKTISGY (SEQ ID NO:1); an HVR-L2 sequence comprising WGSFLY (SEQ ID NO:2); an HVR-L3 sequence comprising HYSSPP (SEQ ID NO:3); an HVR-H1 sequence comprising NISGTY (SEQ ID NO:7); an HVR-H2 sequence comprising RIYPSEGYTR (SEQ ID NO:8); and an HVR-H3 sequence comprising WVGVG-FYAMD (SEQ ID NO:9) and specifically binds HER2 and VEGF.

In an embodiment of the methods of treating a tumor, an autoimmune disease, or a non-malignant disease involving abnormal activation of HER2 described herein, the subject is a human.

Also, contemplated are kits, compositions, and articles of manufacture comprising the antibodies and antibody fragments described herein.

BRIEF DESCRIPTION OF THE DRAWINGS

FIG. 1 shows the designed diversity in various LC libraries.

FIG. 2 shows a summary of four light chain libraries used to alter anti-VEGF antibodies or anti-Her2 antibodies to bind to an additional target. The italicized NNK and XYZ refer to codon sets. Ys, Ds, Ts and Ss refer to soft randomizations by having tyrosine, aspartic acid, threonine and serine, respectively, occurring 50% of the time and any one of the 20 amino acids occurring the other 50% of the time. D/Ds and T/Ts refer to a soft randomization having D or T, respectively, occurring 75% of the time and any one of the 20 amino acids occurring the other 25% of the time.

FIG. 3 shows sequences of HC, LC CDR residues of light chain templates.

FIG. 4 shows the natural and designed diversity of light chain CDRs. At each position, the Herceptin® antibody sequence is shown in parenthesis. An "*" denotes an insertion not present in the Herceptin® antibody.

FIGS. 5A and 5B1-5B2 show the sequences of specific antigen-binding clones isolated from the light chain (LC) library. FIG. 5A shows the LC CDR sequences of monospecific phage clones biding to VEGF, DR5, and Fc, and FIG. 5B shows bispecific Fabs binding to VEGF/HER2, DR5/HER2, and Fc/HER2. The light chain framework and heavy chain sequences correspond to that of the Herceptin® antibody with the exception of LC framework substitution R66G.

FIG. 7 shows sorting conditions and enrichment of Library C and D.

FIG. 8 shows VEGF binders. Residues 28, 30, 30a, 31, 92, 93, and 93a were fully diverse. Residues 32, 50, 53, 91 and 94 were restricted. Residues 29, 33, and 51 were limited (<3).

FIG. 9 shows human VEGF binders, combined plate and solution selection.

FIGS. 10A and 10B show clones that bind both VEGF and HER2.

FIG. 11 shows clones that only bind VEGF and lost the binding activity with HER2.

FIG. 12 shows clones binding to VEGF.

FIGS. 13A and 13B show clones that block VEGF binding to VEGFR1-D2 or D1.

FIG. 15 shows clones that can bind both hVEGF and HER2.

FIG. 16 shows the LC library binders used in scFv'2 formation and displayed on phage.

FIG. 17 shows the expression of various clones in Fab or hIgG form.

FIG. 21 shows a Biacore Analysis of binding to VEGF or HER2.

FIG. 24 shows antibodies blocking B20-4.1 and VEGF binding.

FIG. 25 shows antibodies blocking Avastin® antibody and VEGF binding.

FIG. 26 shows crystal structures of the bispecific bH1 Fab bound to HER2 or VEGF.

FIG. 28 shows crystal structures of the bispecific bH1 Fab bound to HER2 or VEGF.

FIG. 32 shows the energetically important binding sites of bH1 for VEGF and HER2 binding.

FIG. 33 shows codons of bH1 that were shotgun scanned.

FIG. 34 shows the library construction.

FIG. 35 shows an antibody clone with shotgun scan mutations screened by binding to VEGF.

FIG. 36 shows an antibody clone with shotgun scan mutations screened by binding to HER2.

FIGS. 37A and 37B show the results of an alanine scan of bH1 for (FIG. 37A) VEGF binding or (FIG. 37B) HER2 binding and the results of a homolog scan of bH1 for (FIG. 37C) VEGF binding or (FIG. 37D) HER2 binding.

FIGS. 39A1-39A3 and 39B1-39B3 show shotgun alanine- and homolog scanning of bH1 Fab for binding to VEGF and HER2.

FIG. 41 shows bH1 VEGF-affinity matured clone sequences and binding affinity for VEGF or HER2.

FIG. 47A shows human VEGF binding and FIG. 47B shows murineVEGF binding.

FIG. 49B), but not to HER2 negative NR6 cells (FIG. 49A).

FIGS. 52A, 52B, and 53 depict exemplary acceptor human consensus framework sequences for use in practicing the instant invention with sequence identifiers as follows:

Variable heavy (VH) consensus frameworks (FIGS. 52A and 52B)

human VH subgroup I consensus framework regions FR1, FR2, FR3, and FR4 minus Kabat CDRs (IA: SEQ ID NOS: 42-45, respectively)

human VH subgroup I consensus framework regions FR1, FR2, FR3, and FR4 minus extended hypervariable regions (IB: SEQ ID NOS: 46, 47, 44, and 45, respectively; IC: SEQ ID NOS: 46-48 and 45, respectively; ID: SEQ ID NOS: 42, 47, 49, and 45, respectively)

human VH subgroup II consensus framework regions FR1, FR2, FR3, and FR4 minus Kabat CDRs (IIA: SEQ ID NOS: 50-52 and 45, respectively)

human VH subgroup II consensus framework regions FR1, FR2, FR3, and FR4 minus extended hypervariable regions (IIB: SEQ ID NOS: 53, 54, 52, and 45, respectively; IIC: SEQ ID NOS: 53-55 and 45, respectively; IID: SEQ ID NOS: 53, 54, 56, and 45, respectively)

human VH subgroup III consensus framework regions FR1, FR2, FR3, and FR4 minus Kabat CDRs (IIIA: SEQ ID NOS: 57-59 and 45, respectively)

human VH subgroup III consensus framework regions FR1, FR2, FR3, and FR4 minus extended hypervariable regions (IIIB: SEQ ID NOS: 60, 61, 59, and 45, respectively; IIIC: SEQ ID NOS: 60-62 and 45, respectively; IIID: SEQ ID NOS: 60, 61, 63, and 45, respectively)

human VH acceptor framework regions FR1, FR2, FR3, and FR4 minus Kabat CDRs (Acceptor A: SEQ ID NOS: 64, 58, 65, and 45, respectively)

human VH acceptor framework regions FR1, FR2, FR3, and FR4 minus extended hypervariable regions (Acceptor B: SEQ ID NOS: 60, 61, 65, and 45, respectively; Acceptor C: SEQ ID NOS: 60, 61, 66, and 45, respectively)

human VH acceptor 2 framework regions FR1, FR2, FR3, and FR4 minus Kabat CDRs (Second Acceptor A: SEQ ID NOS: 64, 58, 67, and 45, respectively)

human VH acceptor 2 framework regions FR1, FR2, FR3, and FR4 minus extended hypervariable regions (Second Acceptor B: SEQ ID NOS: 60, 61, 67, and 45, respectively; Second Acceptor C: SEQ ID NOS: 60, 61, 68, and 45, respectively; Second Acceptor D: SEQ ID NOS: 60, 61, 69, and 45, respectively)

Variable light (VL) consensus frameworks (FIG. 53)

human VL kappa subgroup I consensus framework regions FR1, FR2, FR3, and FR4 (kv1: SEQ ID NOS: 70-73, respectively)

human VL kappa subgroup II consensus framework regions FR1, FR2, FR3, and FR4 (kv2: SEQ ID NOS: 74-76 and 73, respectively)

human VL kappa subgroup III consensus framework regions FR1, FR2, and FR3 (kv3: SEQ ID NOS: 77-79 and 73, respectively)

human VL kappa subgroup IV consensus framework regions FR1, FR2, and FR3 (kv4: SEQ ID NOS: 80-82 and 73, respectively)

Figure 54:
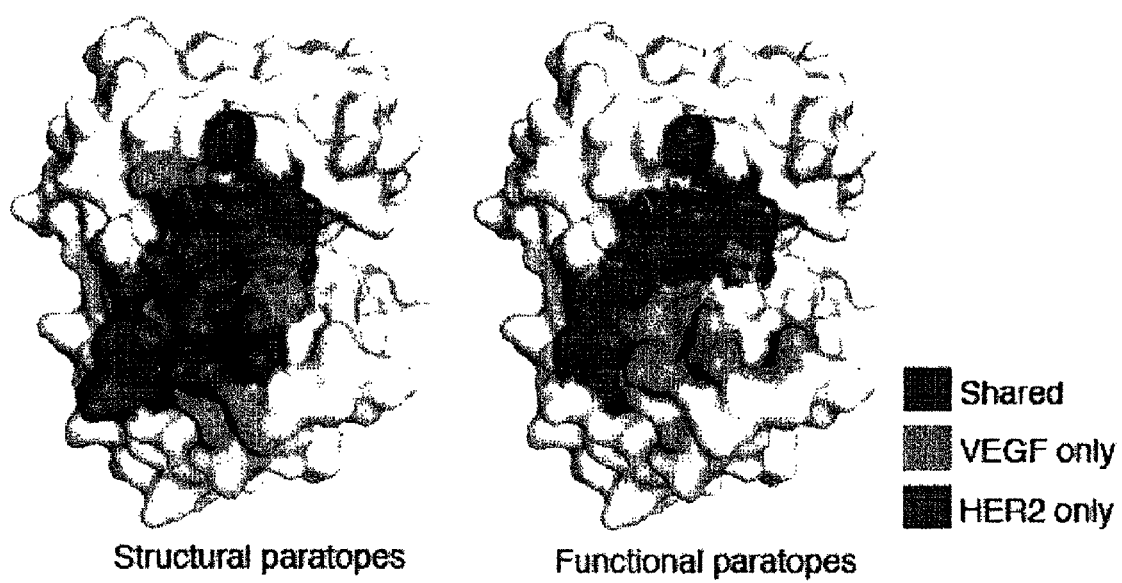

FIG. 54 shows the residues that make structural contacts or an energetic interaction with HER2, VEGF, or both. The residues that make structural contacts (>25% buried) or an energetic interaction (MG>10% total binding energy) with HER2 (light grey), VEGF (grey), or both (shared, black) are mapped on the surface of HER2-bound bH1.

Figure 55:
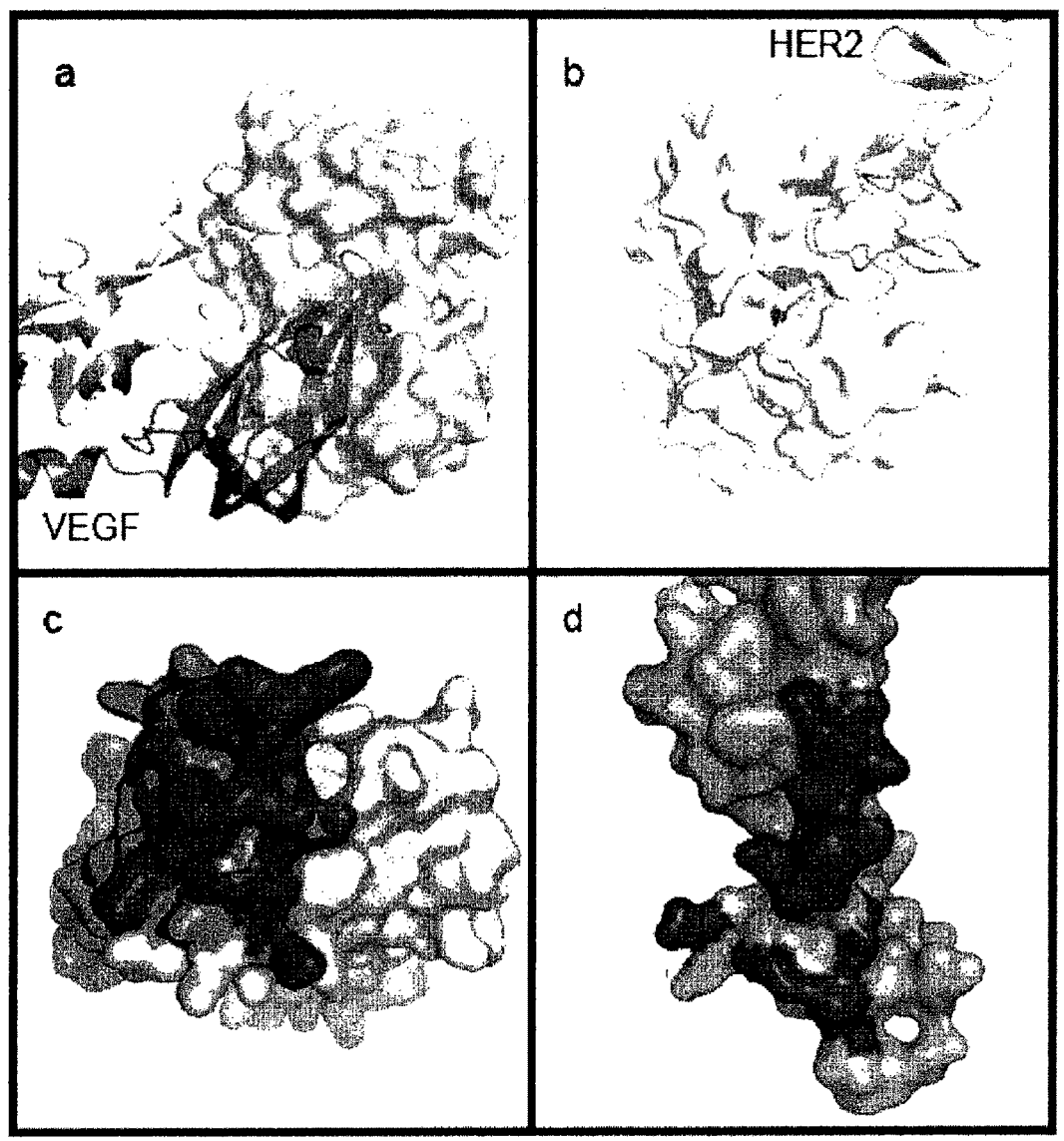

FIG. 55 shows the bH1/VEGF and bH1/HER2 binding interfaces. A close-up of the bH1/VEGF (A) and the bH1/HER2 (B) binding interface illustrates the structural differences between VEGF and HER2 in the regions of antibody binding. Surface representations of VEGF (C) and HER2-ECD (D) are shown in the same orientation relative to bH1 Fab. The residues in contact with bH1 Fab (closer than 4.5 Å) are highlighted. There is no apparent similarity between the two epitopes for bH1 in terms of chemical composition or topology.

Figure 56:
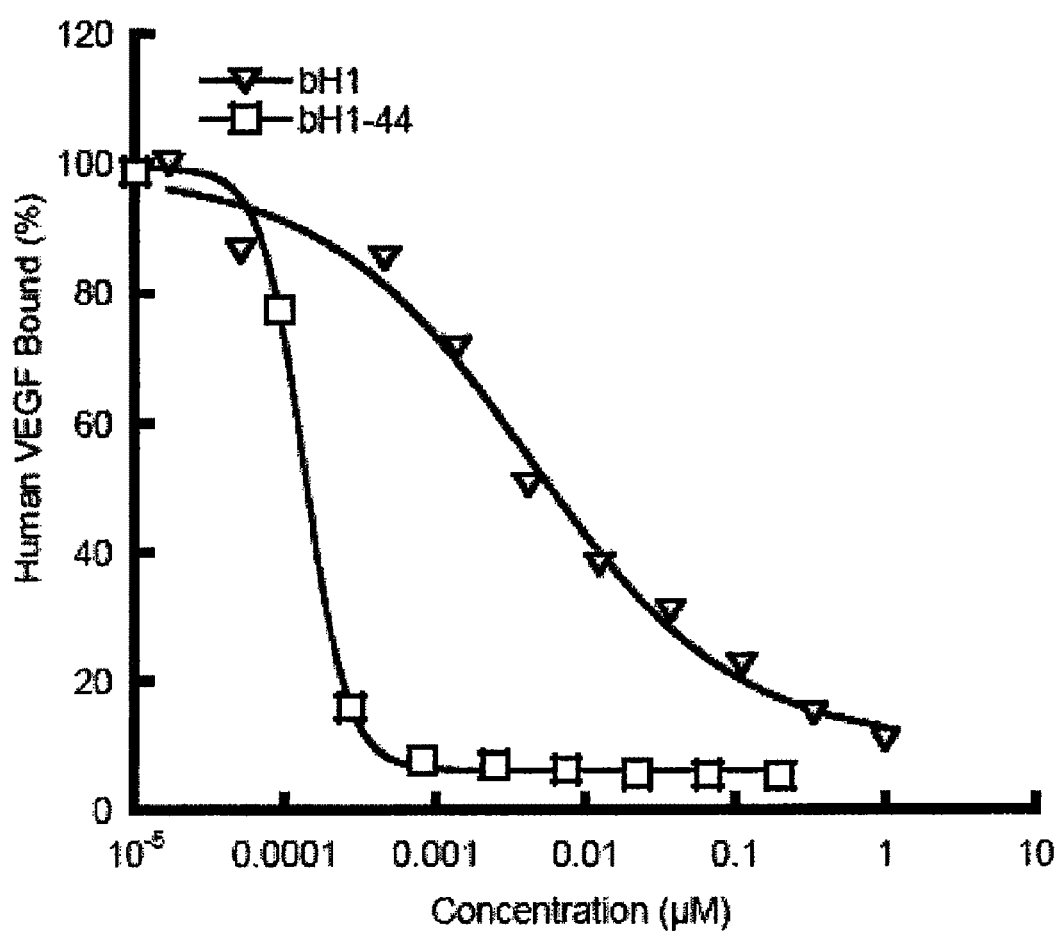

FIG. 56 shows that bH1 and bH1-44 antibodies block human VEGF binding to VEGFR1. Biotinylated human $VEGF_{165}$ was incubated with increasing concentrations of IgG α-axis), then captured on immobilized human VEGFR1-Fc, and detected with horseradish peroxidase-conjugated streptavidin with added substrate (normalized % $OD_{450}$, y-axis).

Figure 57:
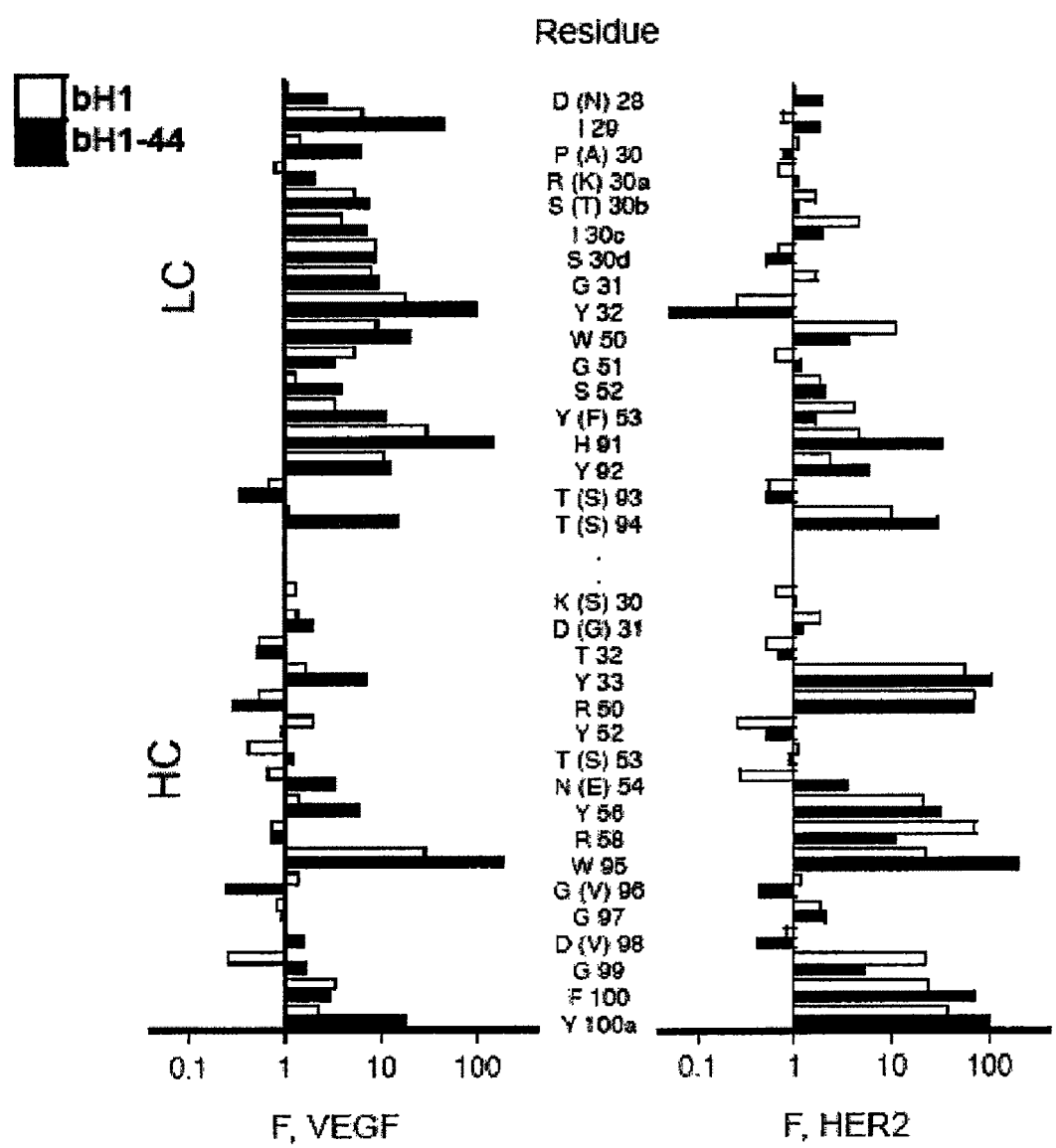

FIG. 57 shows alanine scanning results of bH1 and bH1-44 mutants. Alanine scanning mutagenesis identified the functionally important residues for VEGF and/or HER2 binding. F values represent the relative contribution of each scanned residue to antigen binding. F values were determined for bH1-44 binding to VEGF and HER2 (black bars), and compared to the F values of bH1 (white bars). The amino acids in parenthesis denote bH1-44 residues that differ from bH1. This graph was adapted from FIG. 56.

FIG. 58 shows the binding of bH1-44 129A Y32A bH1-44 and R50A R58A bH1-44 antibodies to VEGF and HER2. The ELISA binding assays show the ability of bH1-44 IgG and the two double mutants to bind to biotinylated $VEGF_{109}$ (left) or HER2-ECD (right), and compete with the immobilized anti-VEGF antibody or Herceptin, respectively. The 129A/Y32A LC mutant has lost binding of VEGF, while maintaining similar affinity for HER2 as bH1-44. The R50A/R58A HC mutant has lost affinity for HER2, but retains VEGF binding.

Figure 59A:
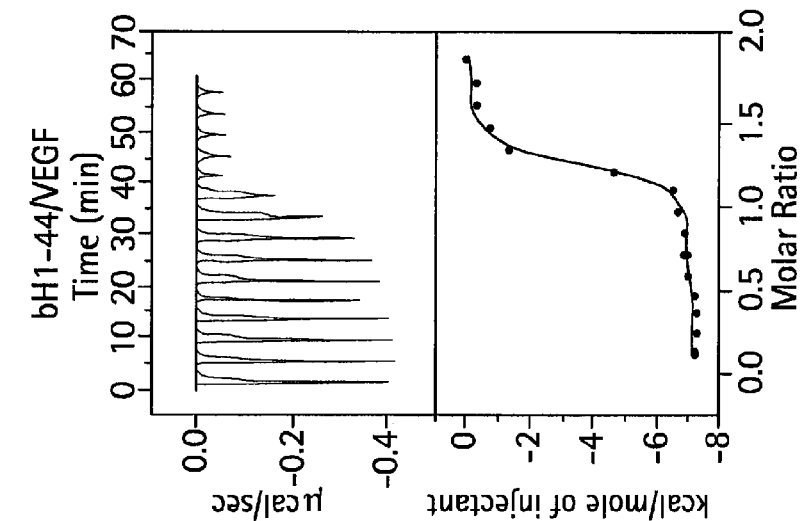
Figure 59B:
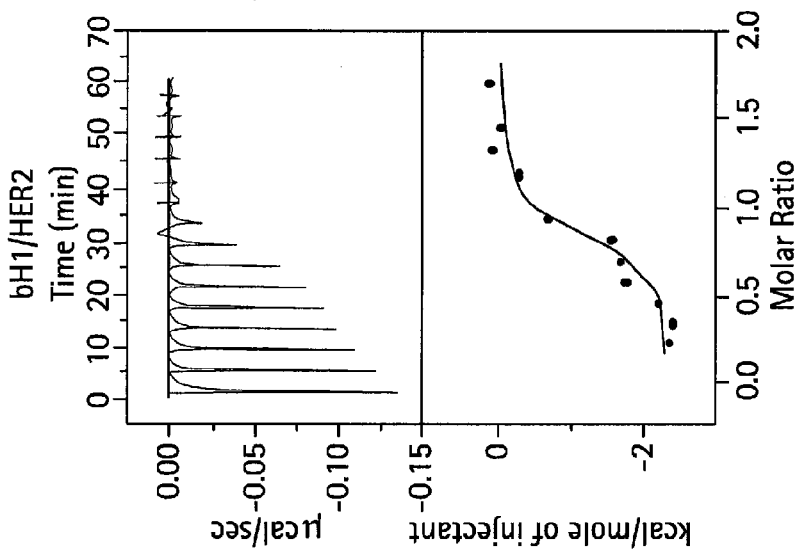
Figure 59C:
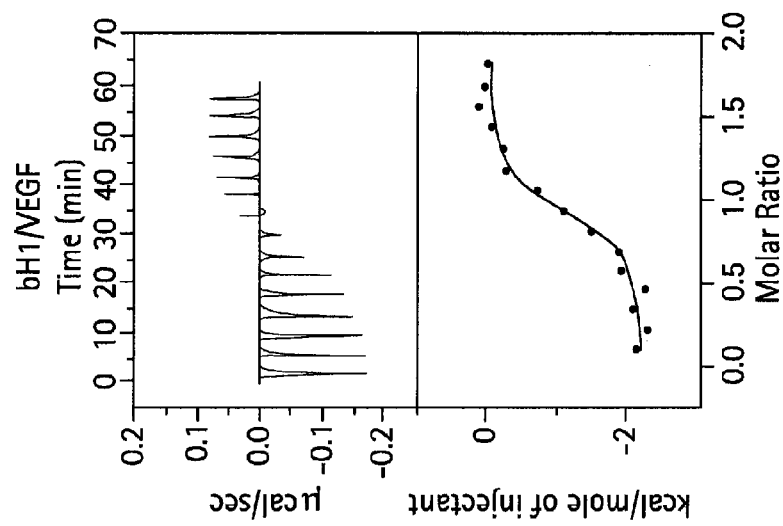

FIG. 59 shows the calorimetric measurements of the enthalpy changes associated with antigen binding. FIGS. 59A-F show the data for bH1 binding to VEGF, bH1 binding to HER2, bH1-44 binding to VEGF, bH1-44 binding to HER2, bH1-44 HC-R50A+R58A binding to VEGF, bH1-44 LC-129A+Y32A binding to HER2, respectively. The figures show the individual heat pulses (top) and the heats of reaction (bottom), which are calculated by integration of each pulse, plotted as a function of the antibody to antigen ratio at the end of the injections. The small magnitude of the enthalpy changes required relatively high protein concentrations, which precluded accurate estimation of $K_D$ when the affinity was high.

FIGS. 59A-D: Solutions of $VEGF_{109}$ of HER2-ECD at concentrations ranging from 10-20 μM were titrated by 15 injections of bH1 or bH1-44 Fab at concentrations from 100 to 200 μM. FIGS. 59E-F: Solutions of $VEGF_{109}$ or HER2-ECD at concentrations of 10 to 20 μM were titrated by 20 injections of bH1-44 LC-129A+Y32A Fab or bH1-44 HC-R50A+R58A Fab at concentrations of 150 and 250 μM. Titrations number 1 and 13 in (FIG. 59E) were excluded from the analysis due to instrument noise.

Figure 60:
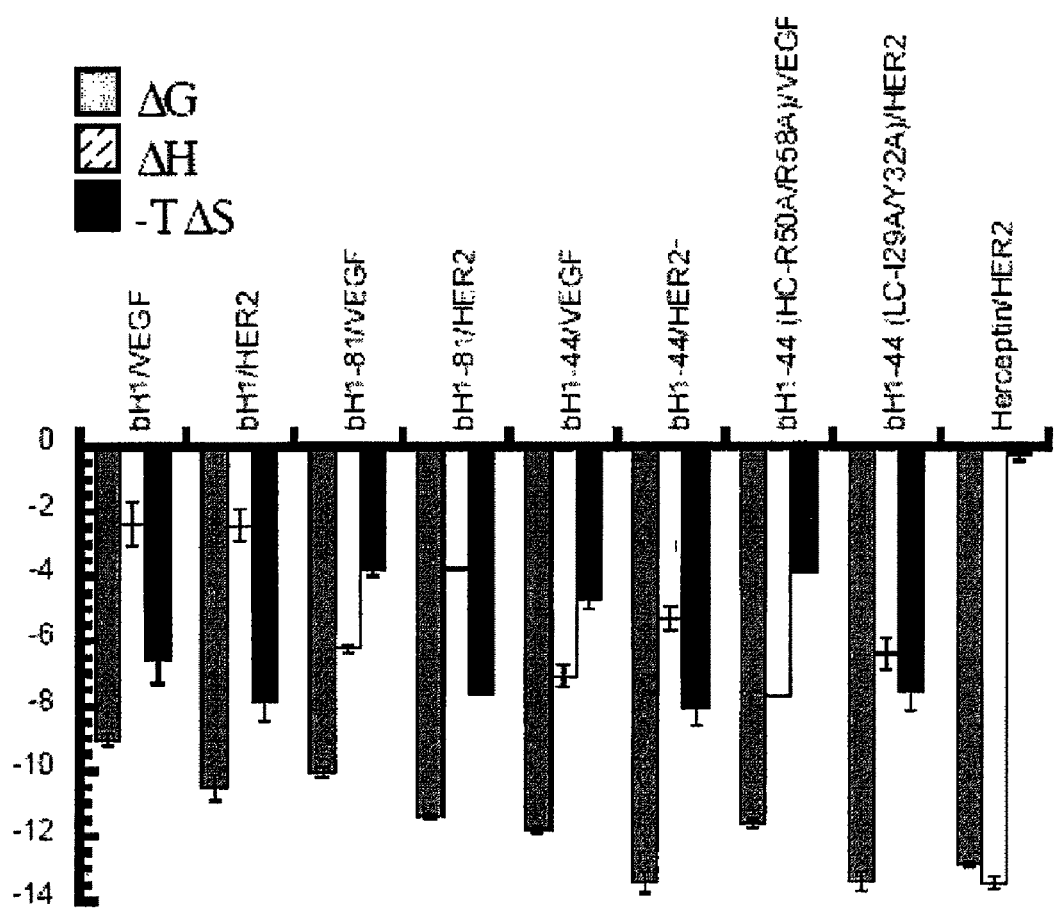

FIG. 60 shows the thermodynamic profiles of the bH1 variants and the Herceptin® antibody. Each dual specific variant (bH1, bH1-81, and bH1-44) has thermodynamic profiles characterized by favorable enthalpy and entropy for both VEGF and HER2 binding. The variants HC-R50A+R58A and LC-129A+Y32A that have lost affinity for HER2 or VEGF respectively, display similar thermodynamic profiles as bH1-44. The thermodynamic profiles of the bH1-44/HER2 interaction are distinct from Herceptin/HER2.

Figure 61:
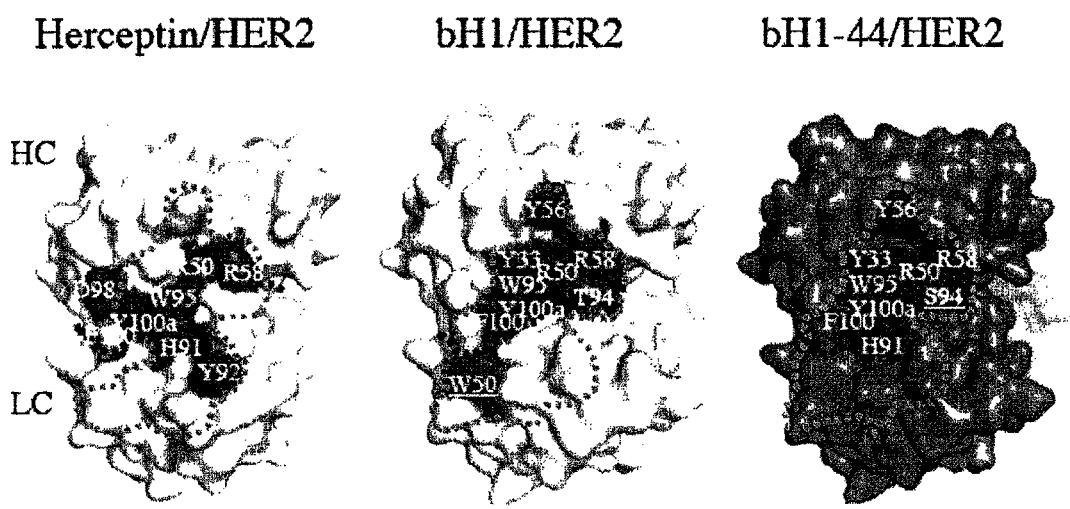

FIG. 61 shows the comparison of the bH1, bH1-44, and the Herceptin® antibody hotspots for HER2 binding based on the alanine scanning mutagenesis data. Hotspot residues are highlighted in grey mapped onto the Herceptin® (Herceptin) structure or bH1 Fab structures (bH1, bH1-44). Hotspots are defined as ΔΔG greater than or equal to 10% of the total binding free energy (AG). The structural contact sites (within 4.5 Å of the antigens in the structures) are outlined by light dotted lines. The HC and LC are separated by a black dotted line. The underlined residues differ in sequence from Herceptin®.

Figure 62:
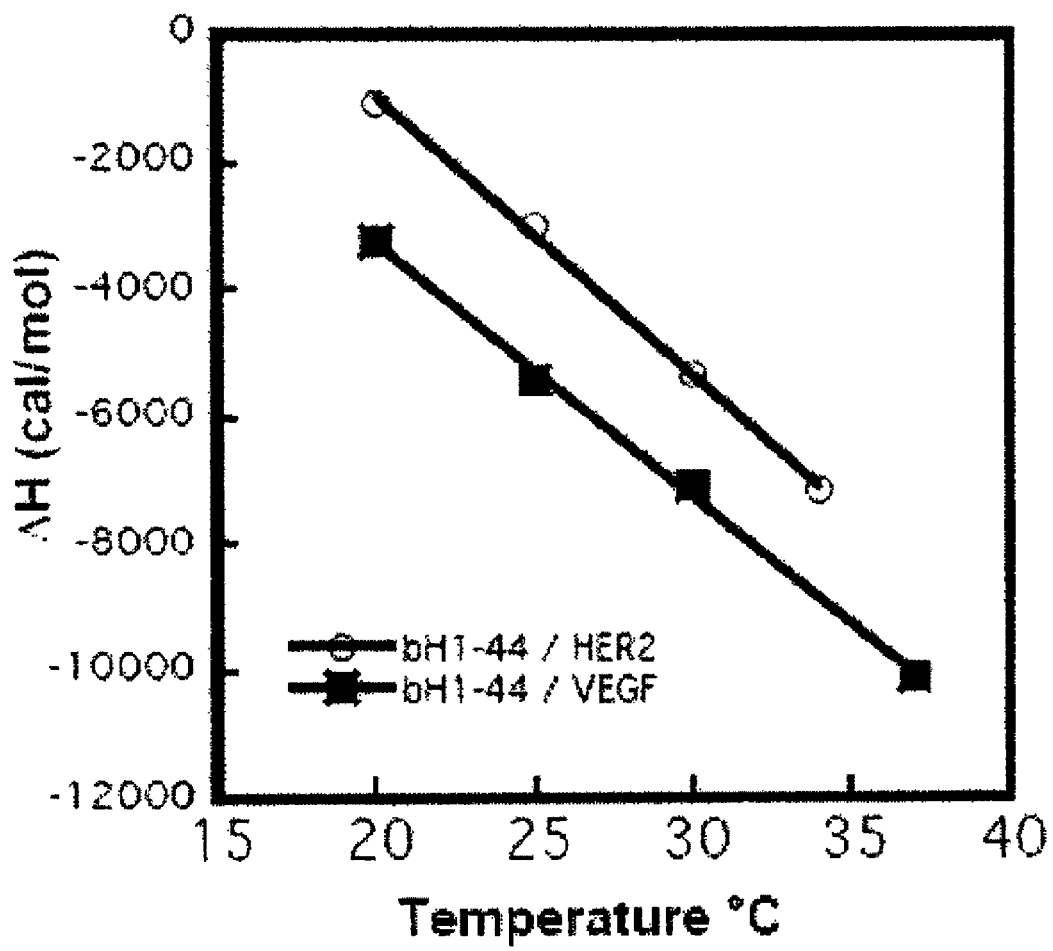

FIG. 62 shows the estimated heat capacity changes associated with bH1-44 Fab binding with VEGF or HER2. ΔCp was determined from the slope of the temperature dependence of ΔH between 20 and 37° C. Over this range, ΔCp appears to be independent of T, based on the linear relationship between ΔH and T (R=0.991 for bH1-44/HER2, R=0.9989 for bH1-44/VEGF). The ΔCp for Herceptin®/HER2 was previously determined by Kelley et al. (Biochemistry, 1992).

Figure 63:
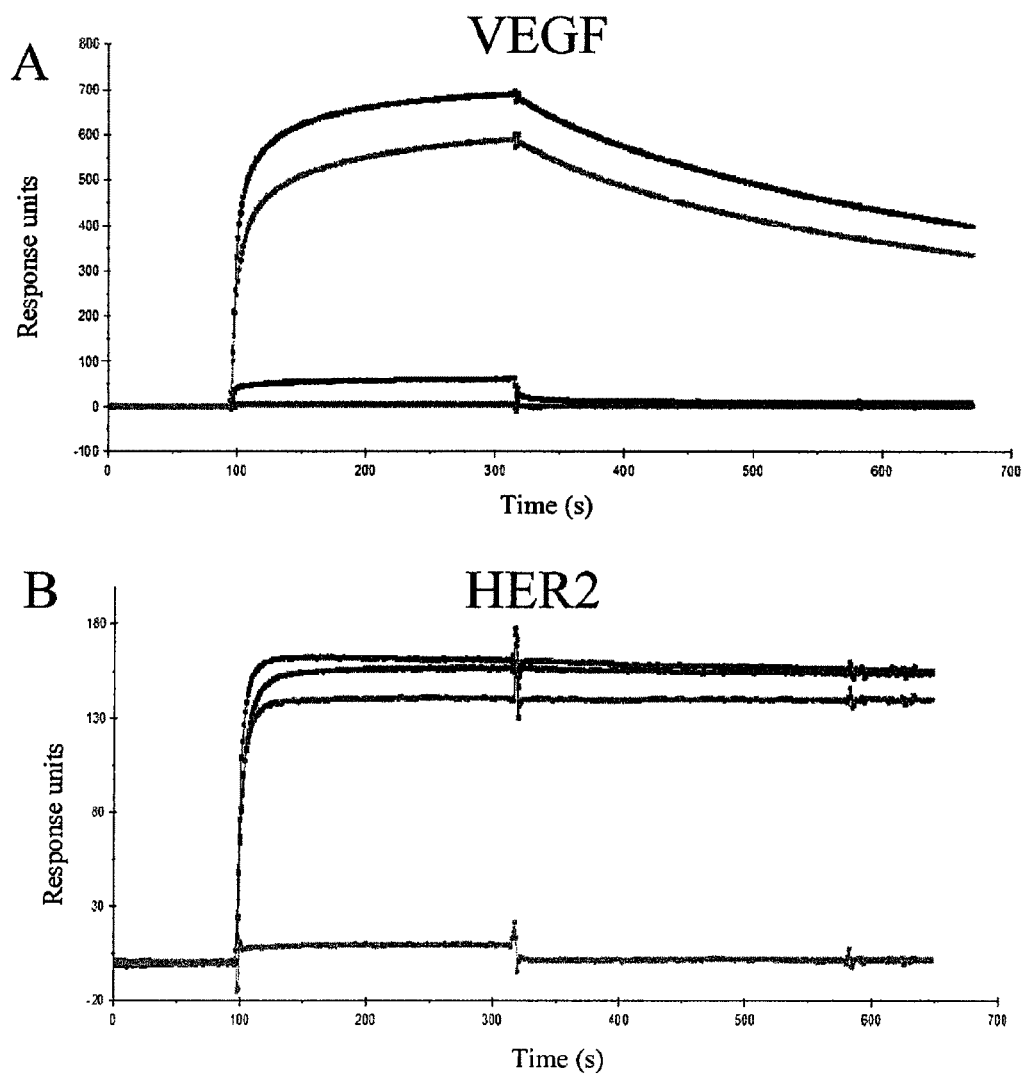

FIGS. 63A-B show the binding kinetics of bH1-44 variants measured by BIAcore. The figures show overlays of representative response versus time plots for the binding interactions between immobilized (A) $VEGF_{109}$ or (B) HER2-ECD and 0.5 μM solutions of bH1-44 Fab (A and B: top), bH1-44-LC-Y32 (A: second from bottom; B: second from top), bH1-44-LC-129A+Y32A (A: bottom; B: second from bottom), and bH1-44-HC-R50A+R58A (A: second from top; B: bottom). The traces represent binding to the same immobilized CM5 chip, which was regenerated after each Fab run. No binding was detected for bH1-44-LC-129A+Y32A to VEGF or for bH1-44-HC-R50A+R58A to HER2 at 0.5 μM. The variant bH1-44-Y32A displayed significantly weakened binding to VEGF compared to the wild type bH1-44.

FIGS. 64A-D show the mapping of the specificity determining residues of bH1-44 on the crystal structure of bH1. The residues that are important for VEGF binding (LC-129 and LC-Y32: A and B) and the residues that are important for HER binding (HC-R50 and HC-R58; C and D) are shown in dark grey as sticks on the bH1/VEGF (A and C, 2.6 Å resolution) or bH1/HER2 (B and D, 2.9 Å resolution) crystal structures. The residues 129 and Y32 appear to be involved in intra-chain interactions that serve to maintain the CDR-L1 loop conformation necessary for VEGF-binding. 129 is solvent exposed in the HER2 structure. Y32 packs against HER2, but does not engage in productive antigen contact. R50 and R58 pack against D560 and E558 on HER2, and appear to engage in charge-charge interactions. R50 and R58 are solvent exposed in the VEGF solvent structure.

Figure 65:
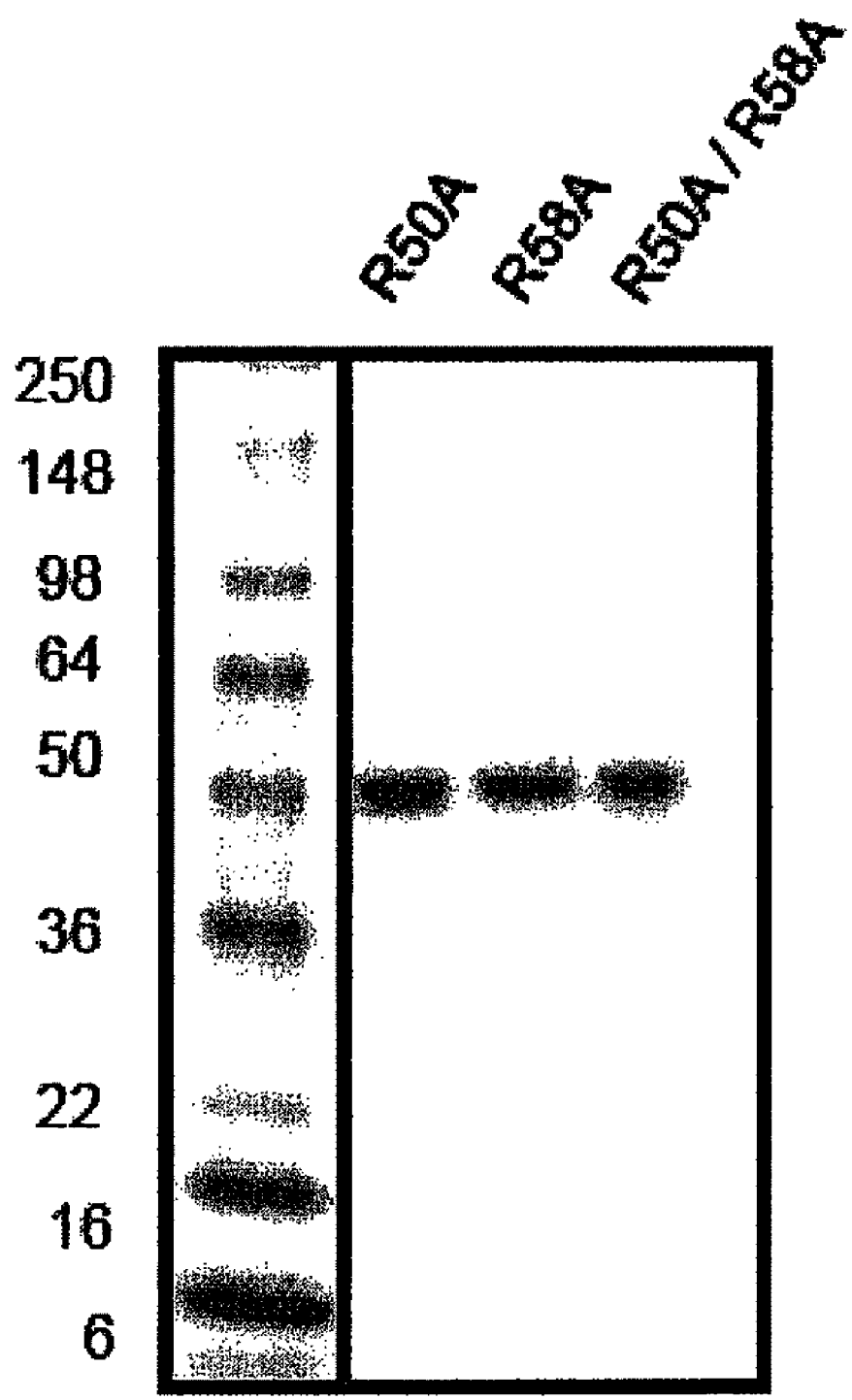

FIG. 65 shows the expression of the Herceptin® mutant Fabs (R50A, R58A, and R50A/R58A).

DETAILED DESCRIPTION OF THE INVENTION

The present invention provides methods of making multispecific antibodies and antibody fragments, as well as antibodies identified using these methods and their use. In general, the methods of the invention involve diversifying the light chain variable domain or the heavy chain variable domain of an antibody to generate variants that can be stably expressed in a library. Diversified antibodies that are capable of specifically binding two epitopes are then selected from this library and further characterized.

Exemplary antibodies identified using the methods of the invention include antibodies that bind both HER2 (human epidermal growth factor receptor 2) and VEGF (vascular endothelial growth factor). In particular, the data described herein, for instance, in the below Examples, show that mutations in the light chain complementarity determining regions (CDRs) of a HER2 antibody confer dual binding capabilities for unrelated protein antigens as well as HER2. One bi-specific high affinity HER2/VEGF antibody is extensively characterized. In addition, the crystal structures of this bi-specific Fab in complex with HER2 and VEGF are shown and the energetic contribution of the Fab residues by mutagenesis is evaluated. The binding sites for the two antigens overlap extensively; most of the CDR residues that contact HER2 also engage VEGF. Energetically, however, the residues of the heavy chain dominate the HER2 specificity while the light chain dominates VEGF specificity.

The HER2/VEGF bi-specific antibody inhibits both HER2 and VEGF-mediated cell proliferation in vitro and in vivo. These results demonstrate that altering the sequence of the light chain variable domain of an antibody can generate antibodies with dual specificity and function. For example, bH1-44 and bH1-81 have the potential to target two mechanisms of tumor progression: tumor cell proliferation mediated by HER2 and tumor angiogenesis mediated by VEGF. Co-targeting two antigens with a single antibody is an alternative to combination therapy.

I. Definitions

The term "multispecific antibody" is used in the broadest sense and specifically covers an antibody comprising a heavy chain variable domain ($V_H$) and a light chain variable domain ($V_L$), where the $V_H V_L$ unit has polyepitopic specificity (i.e., is capable of binding to two different epitopes on one biological molecule or each epitope on a different biological molecule). Such multispecific antibodies include, but are not limited to, full length antibodies, antibodies having two or more $V_L$ and $V_H$ domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM.

The basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four $C_H$ domains for µ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and µ, respectively. The γ and α classes are further divided into subclasses on the basis of relatively minor differences in $C_H$ sequence and function, e.g., humans express the following subclasses: IgG 1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., around residues 24-34 (L1), 50-56 (L2) and 89-97 (L3) in the $V_L$, and around about residues 26-35 (H1), 50-65 (H2) and 95-102 (H3) in the $V_H$ (in one embodiment, H1 is around about residues 31-35); Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2), and 91-96 (L3) in the $V_L$, and 26-32 (H1), 53-55 (H2), and 96-101 (H3) in the $V_H$; Chothia and Lesk, J. Mol. Biol. 196:901-917 (1987)).

"Framework regions" (FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In one embodiment, for the VL, the subgroup is subgroup kappa I as in Kabat. In one embodiment, for the VH, the subgroup is subgroup III as in Kabat.

The term "monoclonal antibody" as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5): 1073-1093 (2004); Fellouse, Proc. Nat. Acad. Sci. USA 101 (34):12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO/9634096, WO/9633735, and WO/91 10741, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; WO 97/17852, U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368:812-813 (1994); Fishwild et al., Nature Biotechnology, 14:845-851 (1996); Neuberger, Nature Biotechnology, 14: 826 (1996); and Lonberg and Huszar, Intern. Rev. Immunol., 13:65-93 (1995).

An "intact" antibody is one which comprises an antigen-binding site as well as a $C_L$ and at least heavy chain constant domains, $C_H1$, $C_H2$, and $C_H3$. The constant domains can be native sequence constant domains (e.g., human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 (1995)); single-chain antibody molecules; and multispecific antibodies formed from antibody fragments. The expression "linear antibodies" generally refers to the antibodies described in Zapata et al., Protein Eng., 8(10):1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region; this region is also the part recognized by Fc receptors (FcR) found on certain types of cells.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g., NNK, NNS, XYZ, DVK, and the like (e.g., NNK codon refers to N=A/T/G/C at positions 1 and 2 in the codon and K=G/T at equimolar ratio in position 3 to encode all 20 natural amino acids). A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al., J. Mol. Biol. 296:57-86, 1999); Garrard and Henner, Gene 128:103, 1993). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but do not necessarily, include restriction enzyme sites useful for, for example, cloning purposes.

An antibody of this invention "which binds" an antigen of interest is one that binds the antigen with sufficient affinity such-that the antibody is useful as a diagnostic and/or therapeutic agent in targeting a protein or a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA) or ELISA. With regard to the binding of an antibody to a target molecule, the term "specific binding" or "specifically binds to" or is "specific for" a particular polypeptide or an epitope on a particular polypeptide target means binding that is measurably different from a non-specific interaction (e.g., for bH1-44 or bH1-81, a non-specific interaction is binding to bovine serum albumin, casein, fetal bovine serum, or neuravidin). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater.

In one embodiment, the term "specific binding" refers to binding where a molecule binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value" according to this invention is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µL/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a polypeptide of this invention means having the ability to bind to a biological molecule, except where specified otherwise.

"Biological molecule" refers to a nucleic acid, a protein, a carbohydrate, a lipid, and combinations thereof. In one embodiment, the biologic molecule exists in nature.

"Isolated," when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The amino acid sequences described herein are contiguous amino acid sequences unless otherwise specified.

"Structurally unsimilar" biological molecules according to this invention refers to biological molecules that are not in the same class (protein, nucleic acid, lipid, carbohydrates, etc.) or, for example, when referring to proteins, having less than 60% amino acid identity, less than 50% amino acid identity, less than 40% amino acid identity, less than 30% amino acid identity, less than 20% amino acid identity or less than 10% amino acid identity compared to each other.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" can be identified as described by Sambrook et al., *Molecular Cloning: A Laboratory Manual*, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. Nos. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. (Proc. Natl. Acad. Sci. USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody or antibody fragment to treat a disease or disorder in a subject. In the case of tumor (e.g., a cancerous tumor), the therapeutically effective amount of the antibody or antibody fragment (e.g., a multispecific antibody or antibody fragment that specifically binds HER2 and VEGF) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth/proliferation. Included in this definition are benign and malignant cancers. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma, anal carcinoma, penile carcinoma, melanoma, and various types of head and neck cancer.

By "early stage cancer" is meant a cancer that is not invasive or metastatic or is classified as a Stage 0, I, or II cancer.

The term "precancerous" refers to a condition or a growth that typically precedes or develops into a cancer.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

A "non-malignant disease or disorder involving abnormal activation of HER2" is a condition which does not involve a cancer where abnormal activation of HER2 is occurring in cells or tissue of the subject having, or predisposed to, the disease or disorder. Examples of such diseases or disorders include autoimmune disease (e.g. psoriasis), see definition below; endometriosis; scleroderma; restenosis; polyps such as colon polyps, nasal polyps or gastrointestinal polyps; fibroadenoma; respiratory disease (e.g., chronic bronchitis, asthma including acute asthma and allergic asthma, cystic fibrosis, bronchiectasis, allergic or other rhinitis or sinusitis, al-anti-trypsin deficiency, coughs, pulmonary emphysema, pulmonary fibrosis or hyper-reactive airways, chronic obstructive pulmonary disease, and chronic obstructive lung disorder); cholecystitis; neurofibromatosis; polycystic kidney disease; inflammatory diseases; skin disorders including psoriasis and dermatitis; vascular disease; conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osler Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi, Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia;

ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a noncancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, apthhous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

An "anti-angiogenic agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF (e.g., bevacizumab (AVASTIN®), bH1, bH1-44, bH1-81), antibodies to VEGF receptors, small molecules that block VEGF receptor signaling (e.g., PTK787/ZK2284, SU6668, SUTENT/SU11248 (sunitinib malate), AMG706). Anti-angiogensis agents also include native angiogenesis inhibitors, e.g., angiostatin, endostatin, etc. See, e.g., Klagsbrun and D'Amore, *Annu. Rev. Physiol.,* 53:217-39 (1991); Streit and Detmar, *Oncogene,* 22:3172-3179 (2003) (e.g., Table 3 listing anti-angiogenic therapy in malignant melanoma); Ferrara & Alitalo, *Nature Medicine* 5(12):1359-1364 (1999); Tonini et al., *Oncogene,* 22:6549-6556 (2003) (e.g., Table 2 listing anti-angiogenic factors); and, Sato Int. *J. Clin. Oncol.,* 8:200-206 (2003) (e.g., Table 1 lists anti-angiogenic agents used in clinical trials). Dysregulation of angiogenesis can lead to many disorders that can be treated by compositions and methods of the invention. These disorders include both non-neoplastic and neoplastic conditions.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed herein. Other cytotoxic agents are described herein. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone (HGH), N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor (EGF); hepatic growth factor; fibroblast growth factor (FGF); prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

By "cytokine antagonist" is meant a molecule that partially or fully blocks, inhibits, or neutralizes a biological activity of at least one cytokine. For example, the cytokine antagonists may inhibit cytokine activity by inhibiting cytokine expression and/or secretion, or by binding to a cytokine or to a cytokine receptor. Cytokine antagonists include antibodies, synthetic or native-sequence peptides, immunoadhesins, and small-molecule antagonists that bind to a cytokine or cytokine receptor. The cytokine antagonist is optionally conjugated with or fused to a cytotoxic agent. Exemplary TNF antagonists are etanercept (ENBREL®), infliximab (REMICADE®), and adalimumab (HUMIRA™).

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665,077); mycophenolate mofetil such as CELLCEPT®; azathioprine (IMURAN®, AZASAN®/6-mercaptopurine; bromocriptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-γ, -β, or -α antibodies, anti-tumor necrosis factor-α antibodies (infliximab or adalimumab), anti-TNFα immunoadhesin (ENBREL®, etanercept), anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 1990/08187, published Jul. 26, 1990); streptokinase; TGF-13; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al. Science, 251: 430-432 (1991); WO 1990/11294; laneway, Nature, 341: 482 (1989); and WO 1991/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®), naproxen (NAPROSYN®), acetylsalicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, amitriptyline (ELAVIL®), carbamazepine (TEGRETOL®), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines desirably result in stimulating the immune system of the subject to produce antibodies to one or several specific antigens, and/or to produce killer T cells to attack cancer cells that have those antigens.

"Cytotoxic radiotherapy" as used herein refers to radiation therapy that inhibits or prevents the function of cells and/or causes destruction of cells. Radiation therapy may include, for example, external beam irradiation or therapy with a radioactive labeled agent, such as an antibody. The term is intended to include use of radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu).

An "anti-emetic" is a compound that reduces or prevents nausea in a subject. Anti-emetic compounds include, for example, neurokinin-1 receptor antagonists, 5HT3 receptor antagonists (such as ondansetron, granisetron, tropisetron, and zatisetron), GABAB receptor agonists, such as baclofen, a corticosteroid such as dexamethasone, KENALOG®, ARISTOCORT®, or NΔSALIDE®, an antidopaminergic, phenothiazines (for example prochlorperazine, fluphenazine, thioridazine and mesoridazine), dronabinol, metroclopramide, domperidone, haloperidol, cyclizine, lorazepam, prochlorperazine, and levomepromazine.

A "subject" is a vertebrate, preferably a mammal, more preferably a human. Mammals include, but are not limited to, farm animals (such as cows), sport animals, pets (such as cats, dogs and horses), primates, mice, and rats.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

Throughout this specification and claims, the word "comprise," or variations such as "comprises" or "comprising," will be understood to imply the inclusion of a stated integer or group of integers but not the exclusion of any other integer or group of integers.

II. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to ligate them to cistrons encoding the target light and heavy chains (Siebenlist et al., (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits (Proba and Pluckthun, Gene, 159:203 (1995)).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC 177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers.

Another method for transformation employs polyethylene glycol/DMSO. Yet another technique used is electroporation. Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), Proc. Natl. Acad. Sci. USA 95:2773-2777; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureus* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably termed "antibody-drug conjugates" or "ADC"), comprising any of the anti-Notch1 NRR antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et at (2000) Jour. of the Nat. Cancer Inst. 92(19):1573-1581; Mandler et al., (2000) Bioorganic & Med. Chem. Letters 10:1025-1028; Mandler et al., (2002) Bioconjugate Chem. 13:786-791), maytansinoids (EP 1391213; Liu et al., (1996) Proc. Natl. Acad. Sci. USA 93:8618-8623), and calicheamicin (Lode et al., (1998) Cancer Res. 58:2928; Hinman et al., (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al., (2000) Eur. Jour. Nucl. Med. 27(7):766-77; Wiseman et al., (2002) Blood 99(12):4336-42; Witzig et al., (2002) J. Clin. Oncol. 20(10):2453-63; Witzig et al., (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,6937,62; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al., (2003) Nature Biotechnology 21(7):778-784) and are under therapeutic development.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Immunoconjugates containing maytansinoids, methods of making same, and their therapeutic use are disclosed, for example, in U.S. Pat. Nos. 5,208,020, 5,416,064, and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolastatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al., (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., (1989) J. Am. Chem. Soc. 111:5463-5465; Pettit et al., (1998) Anti-Cancer Drug Design 13:243-277; Pettit, G. R., et al., Synthesis, 1996, 719-725; and Pettit et al., (1996) J. Chem. Soc. Perkin Trans. 1 5:859-863. See also Doronina (2003) Nat. Biotechnol. 21(7):778-784; "Monomethylvaline Compounds Capable of Conjugation to Ligands," US20050238649, published Oct. 27, 2005, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^1$, $\alpha_2^1$, $\alpha_3^1$, N-acetyl-$\gamma_1^1$, PSAG and $\theta_1^1$, (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or I$^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc$^{99m}$ or I$^{123}$, Re$^{186}$, Re$^{188}$ and In$^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production Ab-(L-D)$_p$     I of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations comprising an antibody of the invention are prepared for storage by mixing the antibody having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended. The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semi-permeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

III. Therapeutic Uses

The antibodies and antibody fragments described herein which bind both HER2 and VEGF (e.g., bH1-44 or bH1-88 or fragments thereof) can be used for the treatment of tumors, including pre-cancerous, non-metastatic, and cancerous tumors (e.g., early stage cancer), for the treatment of autoimmune disease, for the treatment of an angiogenesis disorder, for the treatment of a disease involving abnormal activation of HER2, or for the treatment of a subject at risk for developing cancer (for example, breast cancer, colorectal cancer, lung cancer, renal cell carcinoma, glioma, or ovarian cancer), an angiogenesis disorder, an autoimmune disease, or a disease involving abnormal activation of HER2.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific antibodies that bind both VEGF and HER2 (e.g., bH1-44 or bH1-88 or a fragment thereof) desirably are used to treat breast cancer, colorectal cancer, lung cancer, renal cell carcinoma, glioma, or ovarian cancer.

It is now well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., J. Biol. Chem., 267:10931-10934 (1992); Klagsbrun et al., Annu. Rev. Physiol. 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

Abnormal angiogenesis occurs when new blood vessels either grow excessively, insufficiently or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state, such as in cancer, especially vascularized solid tumors and metastatic tumors (including colon, lung cancer (especially small-cell lung cancer), or prostate cancer), diseases caused by ocular neovascularization, especially diabetic blindness, retinopathies, primarily diabetic retinopathy or age-related macular degeneration (AMD), diabetic macular edema, cerebral edema (e.g., associated with acute stroke/closed head injury/trauma), synovial inflammation, pannus formation in rheumatoid arthritis, myositis ossificans, hypertropic bone formation, refractory ascites, polycystic ovarian disease, 3rd spacing of fluid diseases (pancreatitis, compartment syndrome, burns, bowel disease), uterine fibroids, premature labor, neovascularization of the angle (rubeosis), malignant pulmonary effusions, vascular restenosis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis, various inflammatory diseases, such as arthritis, especially rheumatoid arthritis, inflammatory bowel disease, psoriasis, psoriatic arthritis, psoriatic plaques, sarcoidosis, arterial arteriosclerosis, and diseases occurring after transplants, renal allograft rejection, endometriosis or chronic asthma, and more than 70 other conditions. The new blood vessels can feed the diseased tissues, destroy normal tissues, and in the case of cancer, the new vessels can allow tumor cells to escape into the circulation and lodge in other organs (tumor metastases). Insufficient angiogenesis occurs when there is inadequate blood vessels growth that contributes to the worsening of a diseased state, e.g., in diseases such as coronary artery disease, stroke, and delayed wound healing. Further, ulcers, strokes, and heart attacks can result from the absence of angiogenesis that normally is required for natural healing. The present invention contemplates treating those patients that have or are at risk of developing the above-mentioned illnesses using an antibody that specifically binds both VEGF and HER2 (e.g., the bH1-81 or bH1-44 antibody).

Other patients that are candidates for receiving compositions of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus luteum formation, inhibition of implantation, and inhibition of embryo development in the uterus.

Anti-angiogenesis therapies are useful in the general treatment of graft rejection, lung inflammation, primary pulmonary hypertension, nephrotic syndrome, preeclampsia, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion (such as associated with pericarditis), permeability associated with cardiovascular diseases such as the condition following myocardial infarctions and strokes and the like, and sepsis.

Other angiogenesis-dependent diseases according to this invention include angiofibroma (abnormal blood of vessels which are prone to bleeding), neovascular glaucoma (growth of blood vessels in the eye), arteriovenous malformations (AVM; abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), meningioma, thyroid hyperplasias (including Grave's disease), trachoma (leading cause of blindness in the third world), hemophilic joints, synovitis, dermatitis, vascular adhesions, and hypertrophic scars (abnormal scar formation).

IV. Dosages and Formulations

The antibody (e.g., bH1-44 or bH1-81) or antibody fragment compositions will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the antibody or antibody fragment to be administered will be governed by such considerations, and is the minimum amount necessary to prevent, ameliorate, or treat a cancer or autoimmune disorder. The antibody or antibody fragment need not be, but is optionally, formulated with one or more agents currently used to prevent or treat cancer or an autoimmune disorder or a risk of developing cancer or an autoimmune disorder. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the antibody or antibody fragment is used to prevent the occurrence or reoccurrence of cancer or an autoimmune disorder in the subject.

In one embodiment, the present invention can be used for increasing the duration of survival of a human patient susceptible to or diagnosed with a cancer or autoimmune disorder. Duration of survival is defined as the time from first administration of the drug to death. Duration of survival can also be measured by stratified hazard ratio (HR) of the treatment group versus control group, which represents the risk of death for a patient during the treatment.

In yet another embodiment, the treatment of the present invention significantly increases response rate in a group of human patients susceptible to or diagnosed with a cancer who are treated with various anti-cancer therapies. Response rate is defined as the percentage of treated patients who responded to the treatment. In one aspect, the combination treatment of the invention using an antibody or antibody fragment and surgery, radiation therapy, or one or more chemotherapeutic agents significantly increases response rate in the treated patient group compared to the group treated with surgery, radiation therapy, or chemotherapy alone, the increase having a Chi-square p-value of less than 0.005.

Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies and antibody fragments described herein (e.g., bH1-44 or bH1-81 or fragments thereof) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with VEGF and/or HER2 antagonism. An ex vivo strategy can also be used for therapeutic applications. Ex vivo strategies involve transfecting or transducing cells obtained from the subject with a polynucleotide encoding an antibody or antibody fragment. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the antibody (e.g., bH1-44 or bH1-81) or antibody fragment is administered locally, e.g., by direct injections, when the disorder or location of the tumor permits, and the injections can be repeated periodically. The antibody or antibody fragment can also be delivered systemically to the subject or directly to the tumor cells, e.g., to a tumor or a tumor bed following surgical excision of the tumor, in order to prevent or reduce local recurrence or metastasis.

V. Articles of Manufacture and Kits

Another embodiment of the invention is an article of manufacture containing materials useful for the treatment of autoimmune diseases and cancers. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a multispecific antibody or antibody fragment antibody of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In other embodiments, the package insert indicates that the composition is used for treating breast cancer, colorectal cancer, lung cancer, renal cell carcinoma, glioma, or ovarian cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials from a commercial and user standpoint, including other buffers, diluents, filters, needles, and syringes.

Kits are also provided that are useful for various purposes, e.g., for purification or immunoprecipitation of VEGF or HER2 from cells. For isolation and purification of VEGF, or HER2, the kit can contain a VEGF/HER2 antibody (e.g., bH1-44 or bH1-81) coupled to beads (e.g., sepharose beads). Kits can be provided which contain the antibodies for detection and quantitation of VEGF or HER2 in vitro, e.g., in an ELISA or a Western blot. As with the article of manufacture, the kit comprises a container and a label or package insert on or associated with the container. The container holds a composition comprising at least one multispecific antibody or antibody fragment of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Library Design and Construction

The antigen-binding site of antibody is formed by the association of the variable domain ($V_H$, $V_L$) of heavy chain (HC) and light chain (LC), each containing three CDR loops for antigen recognition. In many cases one of the two variable domains, often $V_H$, determines the antigen specificity. Mice with transgenic FTC but intact LC repertoire generate neutralizing antibody titers (Senn et al., Eur. J. Immunol. 33:950-961, 2003). We set out to investigate how bi-specificity of an antibody can occur and whether different utilization of the $V_H$ and the $V_L$ domains can enable dual antigen binding specificity.

A semi-empirical approach was taken to find a design for diversifying the amino acid composition and CDR length of antibody light chain and a library template that enabled generation of a functional phage-displayed antibody library from which antibodies binding specifically to a protein antigen could be selected. The sequence and length diversity of the CDR regions of approximately 1500 human kappa light chain sequences, as represented in the Kabat database, served to guide the library design process. Solvent exposed residues were targeted for randomization. A subset of the randomized positions were tailored to represent amino acids which are part of the natural repertoire at these sites, whereas the remaining sites were randomized to include all 20 naturally occurring amino acids.

In particular, the light chain template (variable domain) set forth below was modified as described herein (underlined residues are randomized) (SEQ ID NO:10).

DIQMTQSPSSLSASVGDRVTITCRAS QD²⁸VNTAVAWYQQKPGKAPKLLI

YS⁵⁰ASFLYSGVPSRFSGSGSGTDFTLTISSLQPEDFATYYCQQH⁹¹YTT

PPTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

Four sets of libraries were generated based on 3 human Fab and scFv templates where distinct sets of positions were targeted for randomization (FIG. 1).

In all of the libraries the heavy chain was held constant with its sequence defined by the library template. The heavy chain template (variable domain) sequence is set forth below (SEQ ID NO:11).

EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTH

The library designs are summarized in FIG. 1 and FIG. 2. All library templates contained a stop codon (Sidhu et al., 2004) embedded in CDR L1 preventing the presence of template light chain among the phage-displayed antibody library members. The template CDR sequences are summarized in FIG. 3.

In one example, we introduced mutations in the LC variable domain of a HER2-specific antibody to identify variants that can bind a different protein antigen while retaining the original binding specificity. We took a conservative approach to randomize the LC CDRs in order to generate variants that can be stably expressed. Twelve solvent exposed LC CDR positions were selected for randomization: five in CDR1 (28, 29, 30, 31, 32), three in CDR2 (50, 51, 53) and four in CDR3 (91, 92, 93, 94). Further, to guide the design of amino acid diversity at elected sites, the natural diversity of these positions was examined by analysis of approximately 1500 human kappa LC CDR sequences (Johnson and Wu, Nucleic Acids Res. 28:214, 2000; Chothia and Lesk, J. Mol. Biol. 196:901, 1987) (FIG. 4). Some positions with relatively high natural diversity (30, 31, 50, 92, 93) were fully randomized while other positions were limited to as few as two amino acid types to mimic natural antibodies. The length variation of natural LC CDR1 and CDR3 was also reflected in the library (FIG. 4). In FIG. 4, X denotes the amino acid types designed at low frequencies as shown. Length diversity is constructed by inserting 1 to 5 residues between residues 30 and 31 and between residues 93 and 94.

The LC library is a productive naive repertoire (Table 1). Listed are results from the screening of 95 random clones at the end of four rounds of selection. In particular, selection for new binding specificity was performed as described on immobilized targets (VEGF, DR5, and human Fc) (Sidhu et al., J. Mol. Biol. 338:299, 2004). After four rounds of selection 95 phage clones were assayed using ELISA for binding to the target, HER2, and a non-target protein, BSA, to ensure specific binding. To enrich for target binding clones that maintained HER2 binding, a final round of selection on HER2 was performed. The positive clones were sequenced. To identify the highest affinity binders, the $IC_{50}$ for antigen binding was determined by competitive ELISA (Sidhu et al., J. Mol. Biol. 338:299, 2004). The number of unique clones as determined by sequence analysis and the number of unique clones that maintain HER2 binding (bispecific clones) are shown. These clones show minimum background binding signals to irrelevant antigens, such as BSA.

TABLE 1

Light chain library selection summary

| | Positive % | Unique Seq. | HER2 positive |
|---|---|---|---|
| Human Fc fusion | 63 | 31 out of 61 | 1 |
| hVEGF | 77 | 41 out of 74 | 30 out of 41 |
| DR5 long | 85 | 5 out of 82 | 2* out of 5 |

*= weak binding signal

| Target | Bi-Specific, Screen | Bi-Specific, Selection |
|---|---|---|
| Human Fc fusion | 1 out of 31 | Not determined |
| hVEGF | 30 out of 41 | 94 out of 94 |
| DR5 long | 2* out of 5 | 2 out of 7** |

*= weak binding signal Her2
**= weak binding signal DR5

Selection against three protein antigens: human vascular endothelial growth factor (hVEGF), death receptor 5 (DR5), and complement binding fragment of IgG (Fc) generated many binding clones (FIG. 5A). Some clones lost binding affinity for HER2, while others maintained HER2-binding and were thus bi-specific. Sequence analysis of the 131 unique Herceptin® antibody variants with new binding specificity identified the amino acid substitutions and insertions compared to the Herceptin® antibody (FIG. 5B).

The number of mutations ranged from 3-17. The clones that retained HER2 binding (the bi-specific clones) contained fewer mutations on average than those that lost HER2 binding. Retaining the Herceptin® antibody CDR-L3 sequence was preferred but not sufficient to conserve HER2 binding. This is consistent with the report that the Herceptin® antibody CDR-L3 is the most important LC CDR for HER2 binding (Kelley and O'Connell, Biochemistry 32:6828. 1993). Representative VEGF-binding clones were expressed as Fab and IgG proteins (Table 2).

TABLE 2

The representative antibodies isolated from the light chain library of the Herceptin ® antibody (SEQ ID NOS: 12-23).

| | CDR-L1 | | | | | | | | | | CDR-L2 | | | | CDR-L3 | | | | | | | |
|---|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 93b | 94 | Specificity | $K_D$ (nM) |
| Herceptin ® | D | V | N | — | — | — | — | T | A | V | S | A | S | F | H | Y | T | | | T | HER2 | 0.1 |
| 3-1[a] | N | V | W | | | | | D | W | V | P | A | S | S | G | W | Y | I | | A | VEGF | 15 |
| bH1 | D | I | P | R | S | I | S | G | Y | V | W | G | S | Y | H | Y | T | | | T | VEGF/ | 300/26 |

TABLE 2-continued The representative antibodies isolated from the light chain library of the Herceptin ® antibody (SEQ ID NOS: 12-23).

| | CDR-L1 | | | | | | | CDR-L2 | | | | | | | CDR-L3 | | | | | | Specificity | $K_D$ (nM) |
|---|---|---|---|---|---|---|---|---|---|---|---|---|---|---|---|---|---|---|---|---|---|---|
| | 28 | 29 | 30 | 30a | 30b | 30c | 30d | 31 | 32 | 33 | 50 | 51 | 52 | 53 | 91 | 92 | 93 | 93a | 93b | 94 | | |
| bH3 | D | I | G | L | | | | G | S | V | W | A | S | Y | H | Y | T | | | T | HER2 | 19,000/8 |
| bH4 | D | I | R | S | | | | G | S | V | W | G | S | Y | H | Y | T | | | T | | 3,500/11 |

[a]Differences from Herceptin ® antibody are shown in bold.

Figure 6:
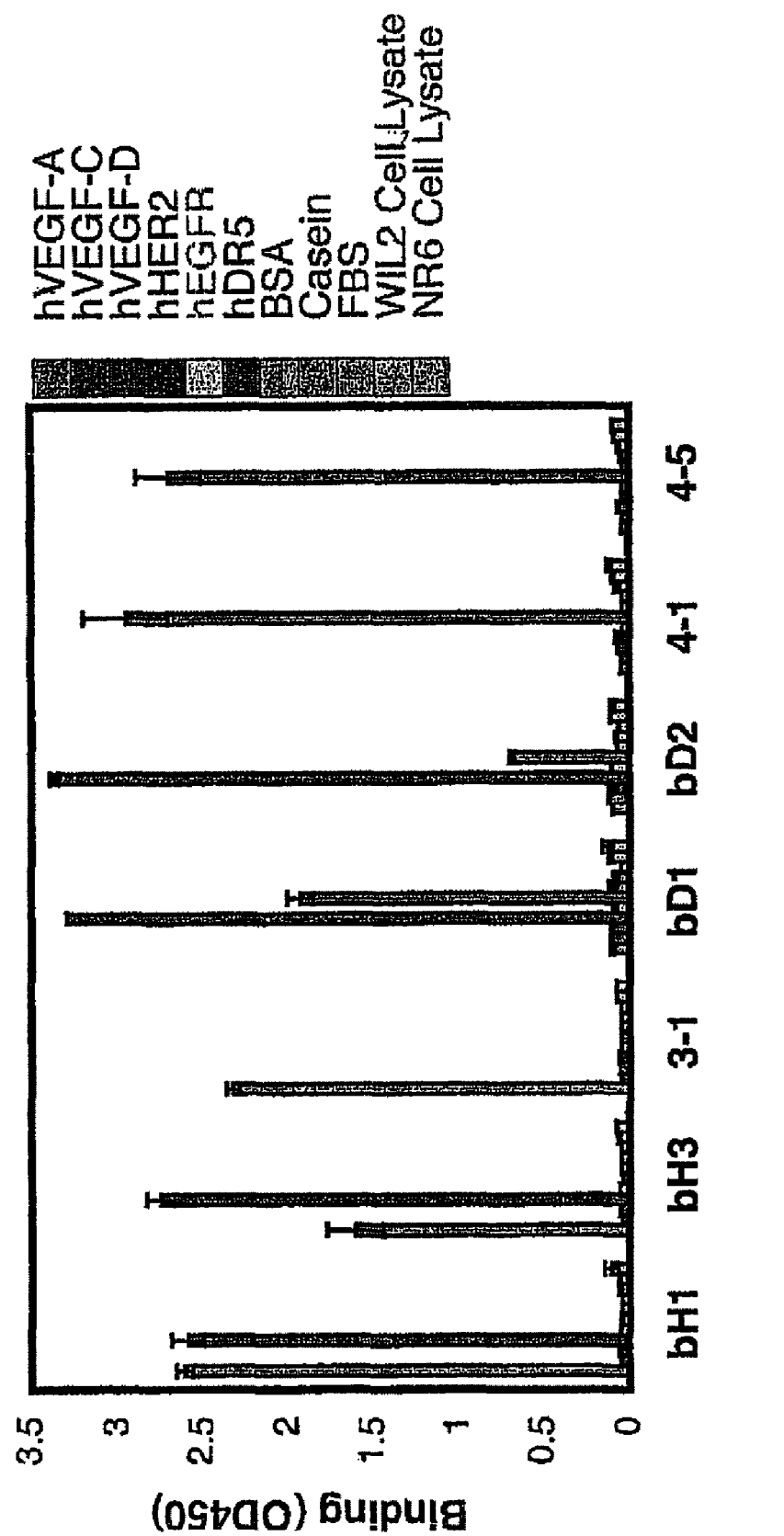
FIG. 6 is a graph showing binding specificity of the antibodies derived from the LC library. The results for antibodies bH1, bH3, 3-1, bD1, bD2, 4-1, and 4-5 are shown. Bound IgG antibodies were detected spectrophotometrically (optical density at 450 nm, y-axis). The proteins included in the assay were (left to right for each antibody) human vascular endothelial growth factor A (hVEGF-A), hVEGF-C, hVEGF-D, hHER2 extracellular domain (ECD), epidermal growth factor receptor extracellular domain (hEGFR), human death receptor 5 (hDR5), bovine serum albumin (BSA), casein, fetal bovine serum (FBS), WIL2 cell lysate, and NR6 cell lysate.

To demonstrate that these antibodies bound specifically to their cognate antigens and did not interact non-specifically with other proteins, we showed that there was no detectable binding to a panel of mammalian cell lysates and non-antigen proteins. The assay confirmed the mono- and bi-specificity of the purified IgGs or Fabs (FIG. 6).

Equilibrium binding affinities ($K_D$) of the LC library-derived mono-specific antibodies ranged from 15-150 nM. The bi-specific antibodies bound the new antigens (i.e., VEGF) with high nM to low μM affinity and HER2 with low nM affinity (Table 2). Of the antibodies shown in Table 2, the antibody bH1 displayed the highest bi-specific affinity for the two different protein antigens VEGF ($K_D$=300 nM) and HER2 ($K_D$=26 nM).

Materials

Enzymes and M13-KO7 helper phage were from New England Biolabs. *E. coli* XL1-Blue was from Stratagene. Bovine serum albumin (BSA), ovalbumin, and Tween 20 were from Sigma. Neutravidin, casein, and Superblock were from Pierce. Immobilized protein G and anti-M 13 conjugated horse-radish peroxidase (HRP) were from GE Healthcare (Piscataway, N.J.). Maxisorp immunoplates were from NUNC (Roskilde, Denmark). Tetramethylbenzidine (TMB) substrate was from Kirkegaard and Perry Laboratories (Gaithersburg, Md.). All protein antigens were generated by research groups at Genentech, Inc. DNA degeneracies were represented using the IUB code and represent equimolar mixtures unless indicated otherwise: N=A/C/G/T, D=A/G/T, V=A/C/G, B=C/G/T, H=A/C/T, K=G/T, M=A/C, R=A/G, S=G/C, W=A/T, Y=C/T.

For example, at certain randomized positions, the wild-type codon was replaced by a degenerate NNK codon (N=A/T/G/C, K=G/T in an equimolar ratio) that encodes all 20 natural amino acids. The XYZ codon refers to a codon with unequal nucleotide ratios at each position of the codon triplet. X contained 38% G, 19% A, 26% T and 17% C; Y contained 31% G, 34% A, 17% T and 18% C; and Z contained 24% G and 76% C.

Phagemid Vectors for Library Construction

Standard molecular biology techniques were used for vector construction. Three templates were constructed for library generation. All templates are derivatives of plasmid pV0354 used in heavy chain libraries based on modified humanized 4D5 (version 8) (Lee et al., 2004a).

The 2C4 Fab-C template phagemid pJB0290 was constructed by cloning the 2C4 heavy chain variable domain into a pV0354-Fab-C vector containing the alkaline phosphatase promoter (Lowman et al., 1991) and stII secretion signal for both light and heavy chain of Fab. It is engineered to contain a single cysteine at the C-terminus of the heavy chain variable domain 1 to allow bivalent M13 phage display of the 2C4 Fab as previously described (Lee et al., 2004b). The 2C4 light chain CDRs were incorporated into the Fab-C vector by site-directed mutagenesis using the method of Kunkel et al (Kunkel et al., 1987). An epitope tag (gD tag) (Lasky and Dowbenko, 1984) was added at the C-terminus of the light chain to enable determination of the level of display as described (Sidhu et al., 2004). The Fab12-G library template pV1283 was created by cloning a highly displayed heavy chain variable domain into pV0354-Fab-C, and the light chain variable domain was modified to contain CDR-L3 of Fab-12 (humanized A4.6.1, an anti-VEGF antibody). The highly-displayed $V_H$ was selected from a Fab library that randomized heavy chain CDR residues of G6 Fab using shotgun alanine scanning mutagenesis (Liang et al., 2006; Vajdos et al., 2002) with CDR-L3 converted to Fab-12 ($Y_{91}STVPW_{96}$; SEQ ID NO:24) by panning on immobilized anti-gD antibody. The design and construction of the phagemid pV1384, displaying 4d5 (LC-R66G) scFv bivalently on the surface of M13 phage particles was modified from the template pS2018 described previously (Sidhu et al., 2004). The scFv fragment contained a gD epitope tag in the linker region between light chain and heavy chain. LC framework residue Arg66 was mutated to Gly66, which is the prevalent residue in this position in over 95% of natural kappa light chains. The mutation R66G reduces Herceptin® antibody binding affinity to HER2 only slightly (<2 fold) as described in Kelley and Connell (Biochemistry 32:6828, 1993). The CDR sequences of the library templates are summarized in FIG. 3.

Library Construction

Phage-displayed libraries were created using oligonucleotide-directed mutagenesis as described (Sidhu et al., 2004). The library template vectors contained a stop codon (TAA) embedded in CDR-L1, which was repaired during the mutagenesis reaction using degenerate oligonucleotides that annealed over the sequences encoding CDR-L1, CDR-L3 (all libraries), CDR-L2 (L1/L2/L3-A, -B, -C, +L4-D) and the light chain framework 3 (L1/L4 and L1/L2/L3+L4-D). The library mutagenesis reactions were performed according to the method of Kunkel et al (Kunkel et al., 1987). The light chain CDR designs for the libraries are described in FIG. 1, which summarizes the degenerate codons used at each position for the different libraries. Three or four oligonucleotides were mixed at certain ratios for each CDR to encode the desired frequency of amino acid types at each position targeted for randomization (FIG. 4). The oligonucleotides were combined in different ratios to fine-tune the diversity to reflect the amino acid frequency in natural light chain kappa sequences at selected positions. For CDR1, three oligonucleotides containing codons for positions 91-94: CAT NNK NNK RST (SEQ ID NO:25), KMT XYZ XYZ RST (SEQ ID NO:26), or DGG XYZ XYZ RST (SEQ ID NO:27) were mixed at 1:3:1 ratios. XYZ is a variation of NNK that has equal proportions of the A/G/T/C for each site to reduce the coverage of aliphatic hydrophobic amino acids (Lee et al., J. Mol. Biol. 340:1073, 2004). For CDR2, four oligonucleotides containing codons for positions 50-53: NNK GST TCC NNK (SEQ ID NO:28), TGG GST TCC NNK (SEQ ID NO:29), KGG GST TCC TMT (SEQ ID NO:30), or NNK GST TCC TMT (SEQ ID NO:31) were mixed at 1:1:2:10 ratios. For CDR3, each length was a mixture of three oligonucleotides containing codons for position 28-33: $G_{70}A_{70}C_{70}$ RTT NNK NNK TAC STA (SEQ ID NO:32), $G_{70}A_{70}C_{70}$ RTT NNK NNK DGG STA (SEQ ID NO:33), or $G_{70}A_{70}C_{70}$ RTT NNK NNK NMT STA (SEQ ID NO:34) at 1:1:2 ratios. $G_{70}A_{70}C_{70}$ is a "soft" codon that allows 70% of the designated nucleotide and 10% each of the other three, encoding ~50% of Glu and ~50% of the other amino acids.

Structural analysis of a number of representative antibodies with kappa LCs shows that CDR1 has the widest range of conformations, which is likely a result of the variation in loop lengths (11-17 residues between position 24 and 34). Different CDR-L1 lengths (lengths 11-16) were thus included in the library. Natural CDR-L3 also varies in length (lengths 7-10 residues between position 89-96), which is reflected by the library design (lengths 8-10; FIG. 4).

FIG. 1 shows the comparison of the light chain natural diversity and the actual library designs. The mutagenesis products were pooled into one reaction per library and electroporated into E. Coli SS320 cells supplemented with KO7 helper phage and were grown overnight at 30° C. (Lee et al., J. Mol. Biol. 340:1073, 2004). ~$10^{11}$ cells and ~5-10 µg DNA were used in each electroporation reaction. The library phage were purified (Sidhu et al., J. Mol. Biol. 338:299, 2004). The number of transformants ranged from $10^9$-$10^{10}$. The display level of intact Fabs or scFv on the surface of phage was determined in an ELISA binding assay where 96 randomly selected clones from each library were tested for their ability to bind an anti-gD antibody. The display level ranged from 5-25% (FIG. 2). 25% of the clones displaying antibody retained HER2 binding. Approximately 150 displaying clones were sequenced to examine the actual library diversity as compared to the design diversity. A portion (~30%) of the functionally displayed library members retained the Herceptin® antibody CDR-L2 and/or CDR-L3 sequence due to incomplete mutagenesis (a template stop codon in CDR-1 ensured 100% mutation of this CDR in expressed scFvs). These were excluded from the sequence analysis of the actual library diversity. At the majority of the randomized positions, the diversity of the phage displayed library of the displaying clones did not deviate significantly ($p>0.05$, odds ratio test) from the designed diversity. Exceptions were position 29 of the CDR-L1 where Val was found to be slightly over-represented compared to Ile ($p=0.005$) and positions 51 and 53 of CDR-L2, where Gly and Ser were more prevalent than Ala and Tyr, respectively ($p<0.01$).

Example 2

Evaluation of Library Performance

Library Sorting and Screening

A library was considered functional when antibodies binding specifically to various protein antigens could be isolated after 4-5 rounds of sorting. Many protein targets were known to allow functional immobilization for library panning and specific antibodies have been generated from validated phage-displayed libraries (Fellouse et al., 2005) (Lee et al., 2004a). To evaluate each set of libraries, we chose a subset of these targets for selection (FIG. 2). The libraries were subjected to an initial round of binding selection with anti-gD antibody or protein L as the capture target to eliminate clones in which the Fab/scFv gene had been deleted, followed by 4-5 rounds of antigen selection. Alternatively, they were directly subjected to target binding selection without pre-selection with anti-gD or protein L. NUNC 96-well Maxisorp plates were coated overnight with antigen (5 µg/ml) and blocked for 1 hour with alternating blocking agents (FIG. 7). Phage solutions of $10^{13}$ phage/ml were added to the coated immunoplates in the first selection cycle. The phage concentration was decreased in each round of selection. Following incubation of the phage solutions on the immunoplates to allow binding to the immobilized antigen, the plates were washed with PBS, 0.5% Tween 20, repeatedly. To increase the stringency, the incubation time was decreased (4 hours for $1^{st}$ round, 3 hours $2^{nd}$, 3 hours $3^{d}$, 2 hours $4^{th}$, 1.75 hours $5^{th}$) and the number of washes was increased in each round of selection (FIG. 7). Bound phage was eluted with 0.1 M HCl for 30 minutes and the eluant was neutralized with 1.0 M Tris base. The recovery of phage per antigen-coated immunoplate well was calculated and compared to that of a blocked well without coated antigen to study the enrichment of phage clones displaying Fabs or scFvs that specifically bound the target antigen (FIG. 7). Eluted phage were amplified in E. coli and used for further rounds of selection. Random clones from rounds 4 and 5 were selected for screening and assayed using phage ELISA in which binding to target and anti-gD was compared to binding of a non-relevant protein (BSA) for checking non-specific binding. Clones that bound the anti-gD antibody and target but not the non-specific protein were considered specific positives. Libraries L1/L3, L1/L4, L1/L2/L3-A, L1/L2/L3-B_1 and L1/L2/L3-B_2 did not yield any specific positive clones whereas libraries L1/L2/L3-C and L1/L2/L3+L4-D enabled isolation of specific antibodies to the target antigens. For example, random clones from round four were assayed using phage ELISA where binding of individually amplified clones to the target and HER2 was compared to binding of a non-target protein (BSA) to test binding specificity. To enrich the phage clones that maintained HER2 binding, the eluted phage from the third and fourth round of VEGF or DR5 selection were amplified and subjected to another round of selection on HER2 coated wells. The $V_E$ and $V_A$ regions of the positive clones were amplified by PCR and sequenced.

The hit rate for hFC, hVEGF, and hDR5-1f, was 63, 77, and 85% respectively. The $V_L$ regions of the positive clones were amplified by PCR and sequenced as described (Sidhu et al., 2004). The DNA sequence analysis of the positive specific binders revealed a percentage of unique clones of 51% (hFC), 55% (hVEGF), and 6.1% (hDR5-1f). The sequences of unique hVEGF binding clones are summarized in FIG. 8.

Combined Plate and Solution Selection of hVEGF Binding Clones

High diversity of hVEGF binding clones after four rounds of sorting was observed. In order to identify high affinity hVEGF binding clones a solution based selection approach was taken following the $4^{th}$ plate based sort. 50 nM biotinylated hVEGF was incubated with the phage propagated from the $4^{th}$ round of selection on immobilized antigen. After 2 hours of incubation at room temperature with shaking, hVEGF-bound phage was captured on neutravidin-coated and blocked immunoplates followed by repeated washes. Phage clones were eluted, screened, and sequenced as previously described. Sequences of hVEGF binding clones from the last solution selection step are found in FIG. 9.

Isolation of Bi-specific Clones from Libraries L1/L2/L3-C and L1/L2/L3+L4-D

Figure 10A:
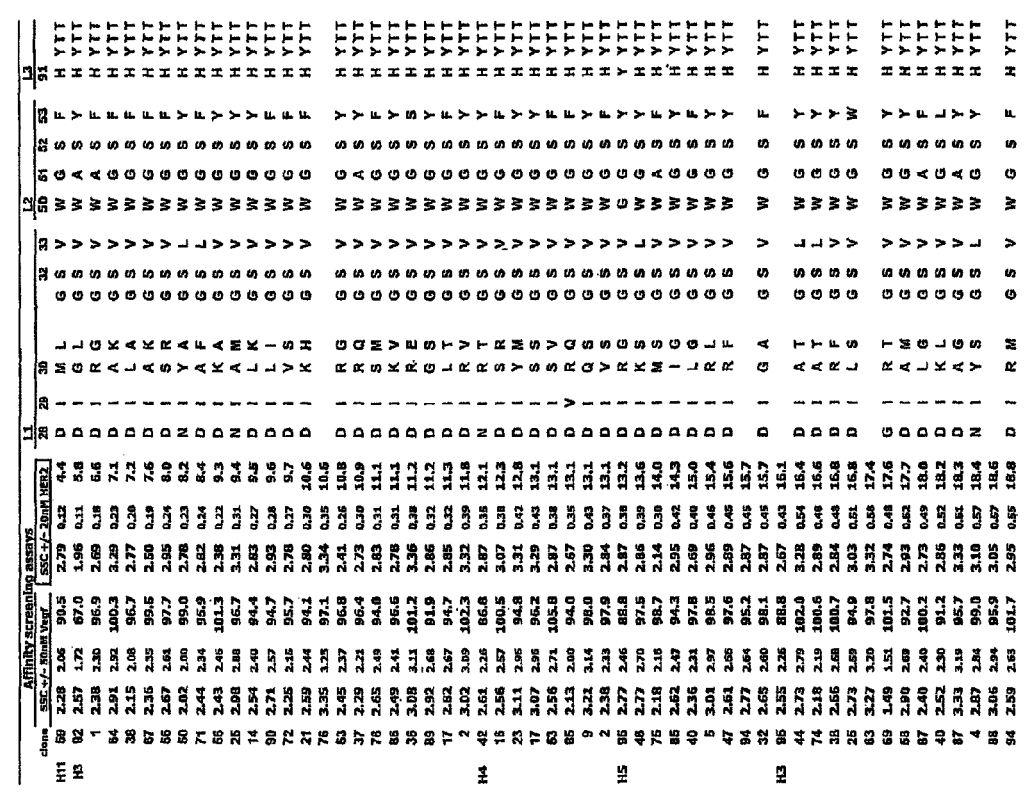
Figure 10B:
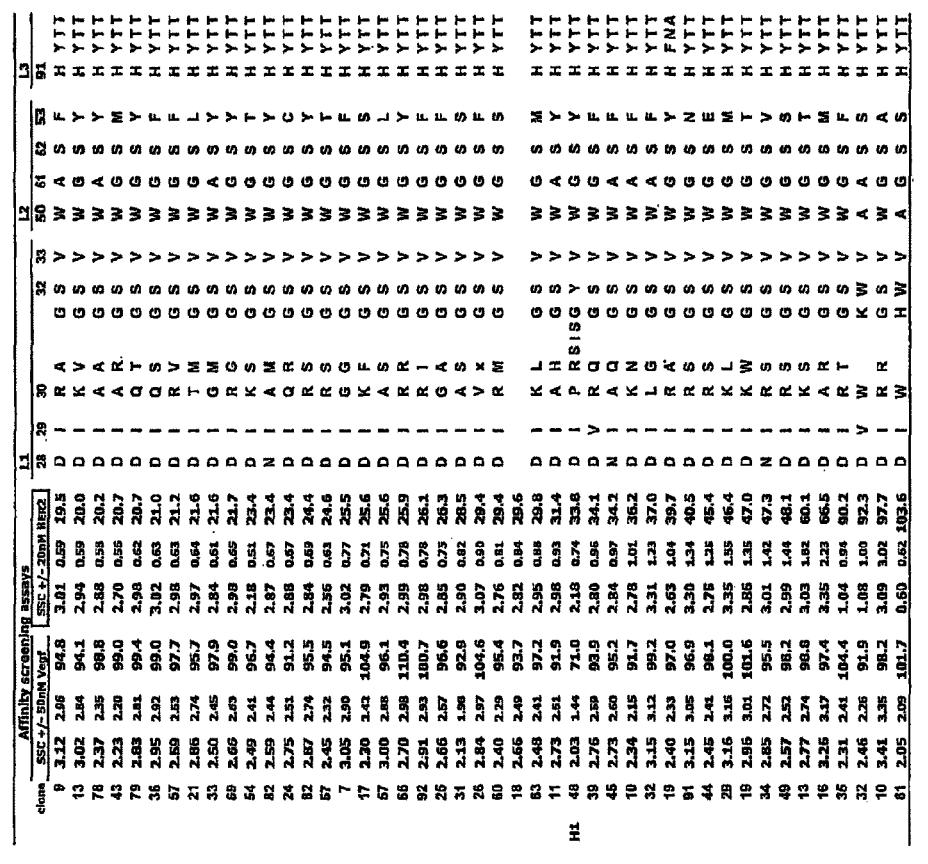

The library template for libraries L1/L2/L3-C and L1/L2/L3+L4-D was an scFv fragment modified from the hu4D5 antibody, which binds Her2 with high affinity. Mapping of the functional paratope of hu4D5-5 for Her2 binding by alanine-scan mutagenesis of the CDR regions showed that heavy chain residues contribute the majority of the free energy of binding, whereas individual light chain residues contribute to a lesser extent (Kelley and O'Connell, 1993). Analysis of the atomic structure of the Herceptin® antibody Fab in complex with human Her2-ECD demonstrates that while the light chain is involved in making antigen contact, the heavy chain provides most of the structural interface with the antigen (Cho et al., Nature 421:756, 2003). We observed that some members of the functional light chain libraries built upon Herceptin® antibody template retained Her2 binding ability. In an attempt to isolate bi-specific scFv fragments from the functional libraries L1/L2/L3-C and L1/L2/L3+L4-D, capable of binding Her2 as well as a second antigen, two strategies were applied. In one approach the positive clones from the previously described target antigen selection was screened by ELISA for ones that retained Her2 binding. The percentage of specific positive clones capable of binding Her2 varied depending on the second antigen specificity. Only 1 out of 61 unique hFc specific positive clones clone still bound Her2 (1.6%), 30 out of 41 unique hVEGF binding clones still bound Her2 (73%), and 2 out of 5 unique hDR5 binders still bound Her2 (40%). In addition, a selection-based approach was taken to isolate bi-specific antibodies by selecting Her2 binders from the pool of hVEGF and hDR5 binding antibodies. The elution from round 4 of target antigen sorting was subjected to an additional round of selection by incubating $2 \times 10^{13}$ phage/ml on Her2 coated (54 ml) and BSA-blocked Maxisorp immunoplates for 1 hour. The plates were washed 15 times with PBS, 0.5% Tween 20 and bound phage eluted as described previously. Random clones were selected and assayed for Her2, anti-gD and target binding and compared to non-specific binding to an un-relevant protein (BSA). All 192 clones tested were identified as specific positives and sequenced as described previously. Sequencing revealed 94 unique sequences. In summary, this method generated 94 Her2/hVEGF bi-specific clones out of the 94 unique clones tested (100%) (FIG. 8). The sequences of all isolated unique hVEGF/Her2 bi-specific antibodies from both isolation strategies are summarized in FIGS. 10A and 10B. The sequences of isolated clones that lost all detectable binding to Her2 are shown in FIG. 11. Of the clones that have dual specificity, nearly all retained the Herceptin® antibody CDR-L3, making it likely that maintaining CDR-L3 is important for maintaining HER2 binding. In the case of hDR5, 2 out of the 7 unique Her2-binding clones were bi-specific (29%, 12 clones sequenced). One of the dual specific clones had some homologous changes in CDR-L3.

High-throughput Characterization of hVEGF Binding Clones

A high-throughput single spot competitive ELISA in a 96-well format (Sidhu et al., 2004) was used to screen for high affinity clones for hVEGF and to study the VEGFR1-blocking profiles. Briefly, Maxisorp Immunoplates were coated with 2 µg/ml hVEGF$_{109}$, overnight at 4° C. and blocked with 1% (w/v) BSA for 1 hour. Phagemid clones in *E. coli* XL1-Blue were grown in 150 µl of 2YT broth supplemented with carbenicillin and M13-KO7 helper phage; the cultures were grown with shaking overnight at 37° C. in a 96-well format. Culture supernatants containing phage were diluted five-fold in PBST (PBS with 0.05% Tween 20 and 0.5% (w/v) BSA) with or without the addition of 100 nM hVEGF$_{109}$ for affinity screen. For receptor blocking screens, hVEGF coated wells were incubated with or without VEGFR1Domain 1-3 (D1-3) and VEGFR1Domain 2 (D2) before adding five-fold diluted phage supernatant (Liang et al., 2006; Wiesmann et al., 1997). After incubation for 1 hour at room temperature (RT), the mixtures were transferred to the coated plates with hVEGF$_{109}$ and incubated for 10 minutes. The plate was washed with PBT (PBS with 0.05% Tween 20) and incubated for 30 minutes with anti-M13 antibody horseradish peroxidase conjugate diluted 5000-fold to 1 nM in PBST. The plates were washed, developed with TMB substrate for approximately five minutes, quenched with 1.0 M H$_3$PO$_4$, and read spectrophotometrically at 450 nm. In the single-spot affinity assay, the ratio of the absorbance in the presence of solution-phase hVEGF$_{109}$ to that in the absence of solution-phase hVEGF$_{109}$ was used as an indication of the affinity. A low ratio would indicate that most of the Fab-phage were bound to solution-phase hVEGF$_{109}$ in the initial incubation stage and, therefore, were unavailable for capture by immobilized hVEGF$_{109}$. The high-throughput affinity assay results of the first 41 unique clones are summarized in FIG. 12. Similarly, for the blocking assay, a low ratio indicated that the binding of a clone to hVEGF$_{109}$ is blocked by the hVEGF$_{109}$-VEGFR1 interaction, indicating that some clones have an overlapping binding site (epitope) on VEGF with the respective VEGF receptor fragments (FIGS. 13A and 13B) and these clones are likely to be displaying the blocking antibodies.

High-throughput Characterization of Bi-specific hVEGF/Her2 Clones

Figure 14:
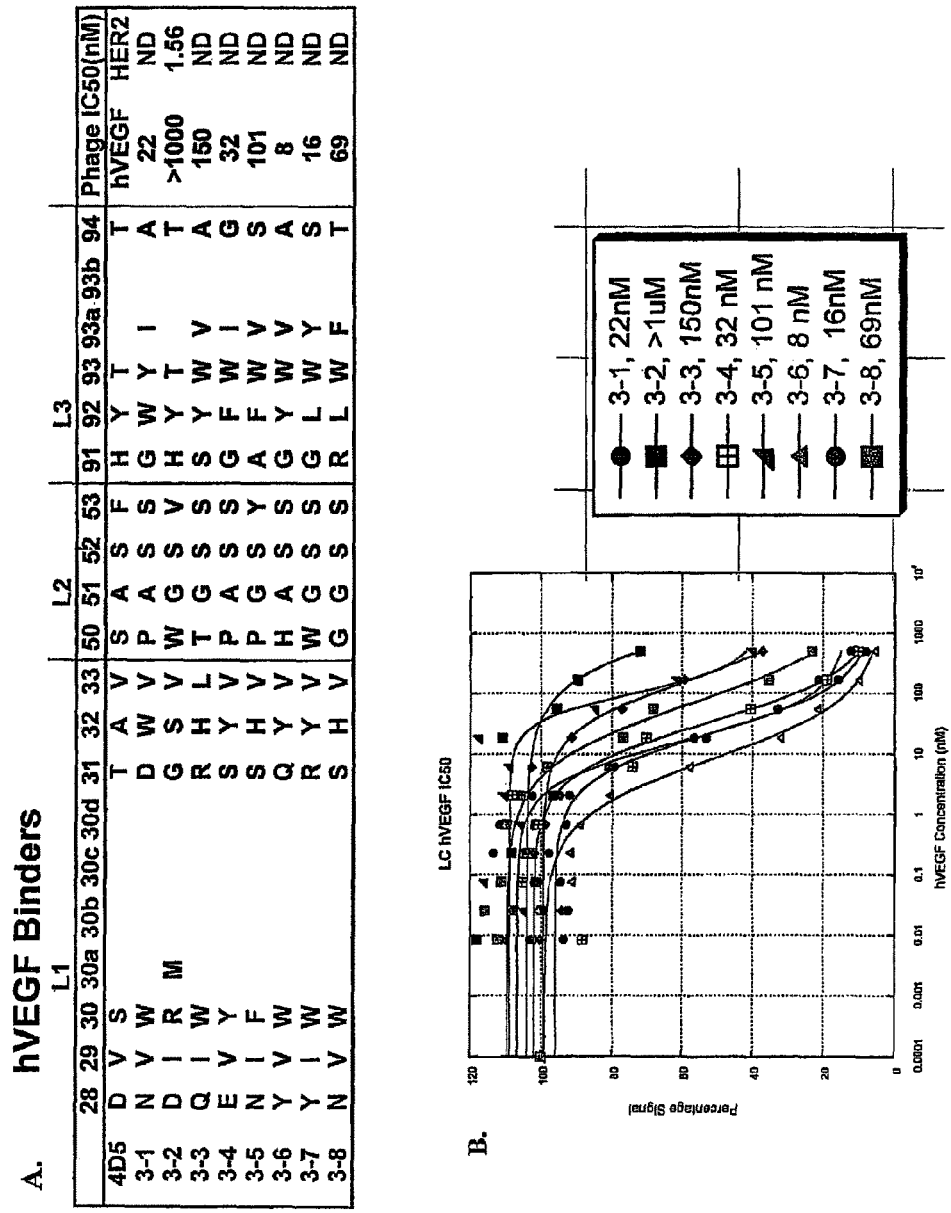
FIGS. 14A and 14B show VEGF binders and the affinities of VEGF binders from library L1/L2/L3-C,D.

The same principle as described in the previous section was applied to enable isolation of clones with high affinity for hVEGF and Her2 for further characterization (FIG. 14A). The high-throughput single point competitive ELISA was used to screen for high affinity clones for hVEGF and Her2 by coating Maxisorp Immunoplates with 2 µg/ml hVEGF$_{109}$, and Her2-ECD overnight at 4° C., followed by blocking with 1% (w/v) BSA for 1 hour. Phage clones that were identified as bi-specific in the previous single spot ELISA screen were grown as described previously and incubated with and without the addition of 20 nM Her2-ECD and 50 nM hVEGF. After incubation for 1 hour at room temperature, the solutions were applied to the coated immunoplates and the binding signals recorded and analyzed as described in the previous section. Clones with low ratio for both hVEGF and Her2 were selected for further characterization. hVEGF-specific and hVEGF/Her2 bi-specific phage clones that gave rise to the lowest signal ratios in the single spot competitive ELISA were selected for affinity measurement by competitive ELISA as well as the DR5-binding and DR5/Her2 bi-specific phage clones from the initial single spot ELISA screen and VEGF binding clones from the combined plate and solution selection. Phage clones were propagated from a single colony by growing in 25 ml of 2YT culture supplemented with carbenicillin and KO7 helper phage overnight at 30° C. Phage purified by precipitation in PEG/NaCl were first diluted serially in PBST and tested for binding to an antigen-coated plate. The dilution that gave 50-70% saturating signal was used in the solution binding assay in which phage were first incubated with increasing concentration of antigen for one to two hours and then transferred to antigen-coated plates for 10-15 minutes to capture the unbound phage. IC$_{50}$ was calculated as the concentration of antigen in solution-binding stage that inhibited 50% of the phage from binding to immobilized antigen (Lee et al., 2004a). FIG. 14B depicts the curves from which the IC$_{50}$ was calculated for the analyzed hVEGF binding clones from the plate sorting strategy. The IC$_{50}$ values ranged from 22 nM to >1 µM (FIG. 14B). The IC$_{50}$ values for the hVEGF binders isolated by combined plate and solution based selection ranged from 41 nM-226 nM (FIG. 9). IC$_{50}$ values of DR5-binding clones ranged from 20 nM to >I M. The IC$_{50}$ values for hVEGF/Her2 bi-specific clones are summarized in FIG. 15.

Example 3

Characterization of Antibodies from the Light Chain Library

Conversion of scFvs to Fabs

To test whether conversion of the scFvs'2 as displayed on phage to Fabs affected the affinity of the binding clones from the library, 2 clones (3-7 anti-hVEGF and 4-1 anti-hDR5) were chosen for conversion to Fab and displayed on phage. The $V_L$ region of phagemid DNA for selected hVEGF and DR5 scFv fragments was digested with restriction enzymes, which cleaved the DNA upstream of the region encoding for CDR-L1 (EcoRV) and downstream of the region encoding for CDR-L3 (KpnI). The digested DNA fragment was ligated into a similarly digested vector (pAP2009) designed for the phage display of Fab hu4D5 by fusion to the C-terminal domain of the M13 gene-3 minor coat protein (Lee et al., 2004b). The resulting bi-cistronic phagemid contains the light chain fused to an epitope (gD) tag at the C-terminus and heavy chain ($V_H$ and $C_H1$) fused to the gene for M13 minor coat protein (p3) C-terminally under the control of the alkaline phosphatase promoter. The first open reading frame encoded a polypeptide consisting of the stII secretion signal followed by the Fab4D5 light chain, with the CDRs replaced by those of 3-7 anti-hVEGF and 4-1 anti-hDR5 scFv'2, followed by a gD-tag epitope. The second open reading frame encoded a fusion polypeptide consisting of the following: the stII secretion signal, the Fab4D5 heavy chain, an amber (TAG) stop codon, a Gly/Ser linker sequence and c-terminal domain of g3 protein (cP3). Expression in E. coli XL-1 Blue co-infected with M13-KO7 resulted in the production of M13 bacteriophage displaying Fab versions of 3-7 and 4-1 scFv'2. Competitive phage ELISAs were used to estimate the affinities of the phage-displayed scFvs and Fabs for hVEGF and hDR5 as $IC_{50}$ values. The data from the two different formats were in good agreement (data not shown).

To enable display of bH1 Fab on the surface of M13 bacteriophage, plasmid pAP2009 was modified to encode bH1Fab. Versions of the bH1 Fab were used as library templates containing stop codons (TAA) in either the three LC CDRs or the three HC CDRs for the LC and HC library, respectively. Separate heavy chain and light chain alanine and homolog scanning libraries were constructed as previously described (Vajdos et al., J. Mol. Biol. 320:415, 2002). The degeneracy ranged from $1 \times 10^5$ to $1 \times 10^8$ and the actual library size from $6 \times 10^9$ to $4 \times 10^{10}$. The libraries were constructed as described above. Two to three rounds of selection were performed on immobilized targets (VEGF, HER2-ECD, protein L, or anti-gD mIgG) (Vajdos et al., J. Mol. Biol. 320:415, 2002). Target binding clones were screened by phage ELISA for target binding followed by DNA sequencing and sequence alignment to calculate the wild-type/mutation ratios at each position. The ratios from sequence analysis of approximately 100 unique sequences of VEGF and HER2 binding clones were corrected for display and protein folding effect by dividing with ratios calculated from the sequences of more than 100 anti-gD binding clones to yield the $F_{wt/mut}$ values. As only the Fab heavy chain is fused to the phage coat, the phage display of the gD tag, which is fused to the light chain, is indicative of proper folding and association of light chain and heavy chain. Consistently, protein L binding to a non-linear epitope on the light chain of the Fab also resulted in similar wild-type/mutation ratios as gD tag selections. $F_{wt/mut}$ values were converted to $\Delta\Delta G$ using the formula $\Delta\Delta G = RT \ln(K_{a,wt}/K_{a,mut}) = RT \ln(F_{wt/mut})$ as described in Vajdos et al. (J. Mol. Biol. 320:415, 2002).

Expression of Library Binders as Free Human Fab and IgG

To accurately determine the affinity, specificity and other properties of the antibodies, representative clones from each specificity group exhibiting the highest affinity in the competition ELISA experiments were selected for expression as free Fab and hIgG (FIG. 16). The variable domain of light chain and heavy chain was cloned into a vector previously designed for Fab expression in E. coli or transient human IgG expression in mammalian cells (Lee et al., 2004a). Fab protein was generated by growing the transformed 34B8 E. coli cells in complete C.R.A.P. medium at 30° C. for 26 hours as described (Presta et al., 1997). The hIgGs were expressed by transient transfection of 293 cells and hIgG was purified with protein A affinity chromatography (Fuh et al., J. Biol. Chem. 273:11197, 1998). The 1 L E. coli cultures were purified with protein G affinity chromatography. The columns were washed with PBS and Fab protein was eluted with 100 mM acetic acid and dialyzed against PBS. The 4 L E. coli cultures were purified on a protein A affinity column followed by cation exchange chromatography as previously described (Muller et al., 1998). Protein concentrations were determined spectrophotometrically. The final yield for Fab was typically 0.8-15 mg/l purified from a small-scale shake flask growth. IgG production yield was medium to high at 6.7-60 mg/l in small-scale culture (FIG. 17). The purified proteins were first characterized using size exclusion chromatography and light scattering to ensure that the proteins did not exhibit significant levels of protein aggregation (<5%).

Figure 18:
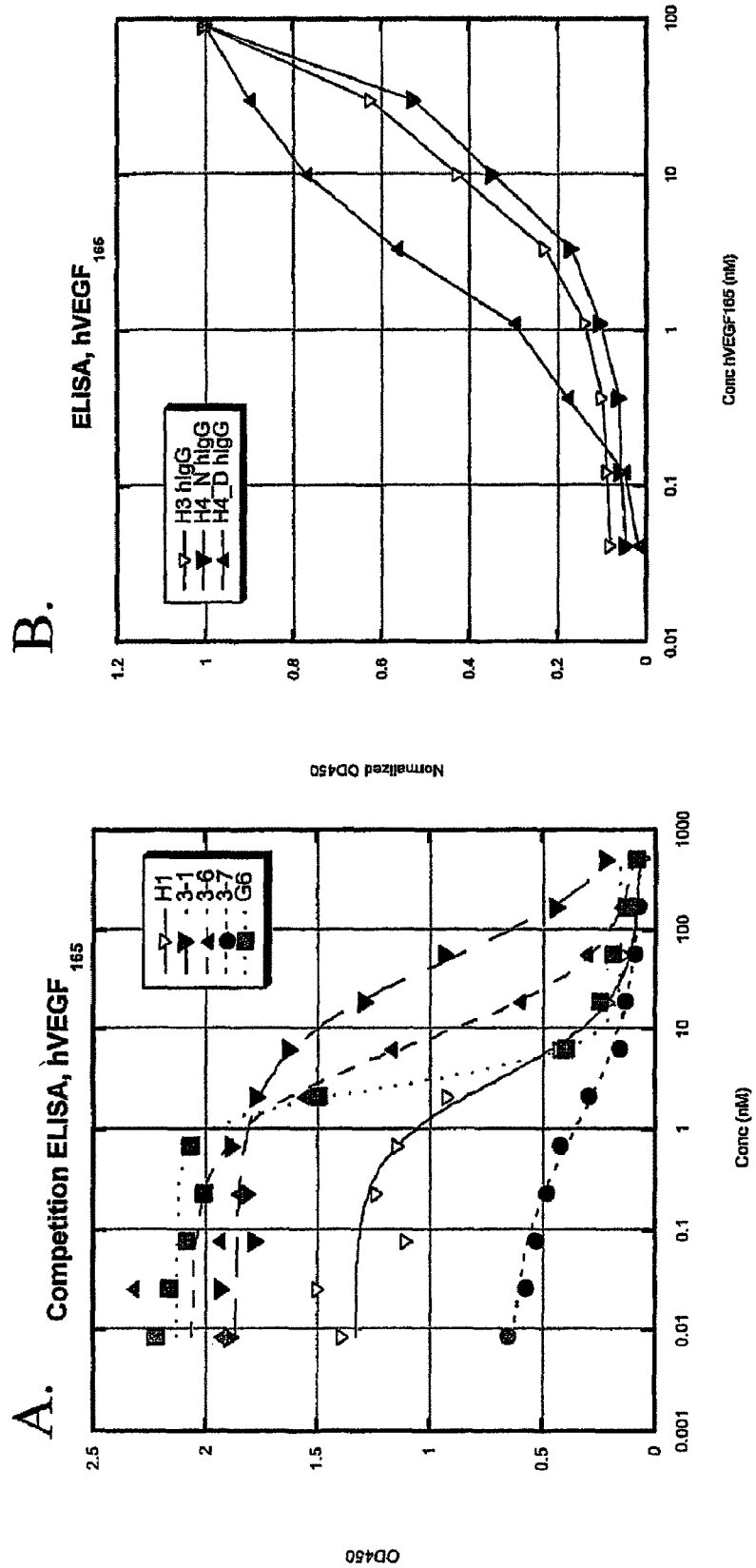
FIGS. 18A and 18B show ELISAs of clones in hIgG form binding to hVEGF165.

Briefly, the Fabs and hIgGs expressed were screened by ELISA for binding their respective antigen(s). All but one variant were found to bind their cognate antigen(s). Clone 4-6 lost hDR5 binding ability when converted to Fab and hIgG. Selected anti-VEGF clones, raised against the shorter form hVEGF$_{109}$, were tested for binding to hVEGF$_{165}$ using standard ELISA (H3, H4_N, H4_D hIgG), and competitive ELISA (bH1, 3-1, 3-6, 3-7 hIgG). G6 hIgG (Fuh et al., 2006) was used as a positive control (FIGS. 18A and 18B). As expected, all clones bound hVEGF$_{165}$.

To study the extent of protein aggregation selected clones were analyzed by Size-Exclusion chromatography (SEC) followed by Light Scattering (LS) Analysis as purified Fab and IgG. The samples were assayed in PBS at a concentration of 0.5 mg/ml (hIgG) and 1 mg/ml (Fab). A maximum of 5% aggregation was observed for all samples at the given concentration (FIG. 17), which is within range of what we have previously observed for other phage-display derived antibodies. Clones 3-6 and 3-7 did not come out at the expected time point, which suggested these reformatted IgG and Fab exhibit aggregation and or non-specific interaction with the resin (data not shown). These clones were taken out of the set of clones that underwent further analysis.

Figure 19:
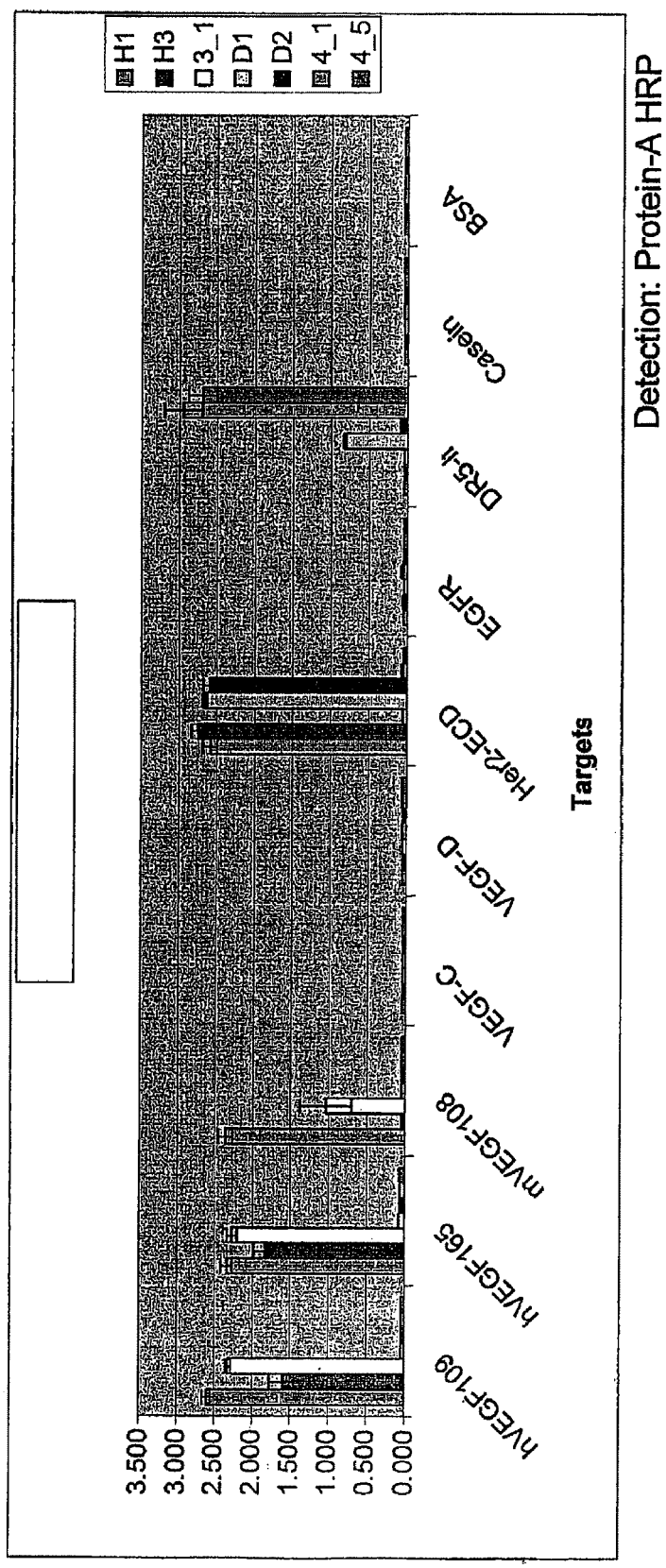
FIG. 19 shows ELISAs of clones in hIgG form binding to immobilized protein targets.

To rule out cross-reactivity and non-specific binding, we studied binding of selected hIgG at high concentration (100 nM) to a panel of immobilized a panel of protein targets including whole cell lysates, the cognate antigens, and homologues in a standard ELISA assay. In addition to antigen, we immobilized a murine version of hVEGF to test cross-species reactivity of the anti-hVEGF clones. In particular, the panel of proteins was immobilized on Maxisorp plates and blocked with 1% BSA in PBS for 1 hour. The hIgGs (or Fabs) were diluted in PBST to a concentration of 100 or 500 nM and transferred to the coated plates. After a 1-hour incubation, the plates were washed and incubated with HRP-conjugated protein A. The binding signals were developed by addition of TMB substrate for approximately 5 minutes, quenched with 1M $H_3PO_4$, and read spectrophotometrically at $A_{450}$. The hIgGs tested bound specifically to their antigen(s). Clones bH1 and 3-1 exhibited cross-reactivity to murine VEGF (mVEGF) (FIG. 19).

Figure 20:
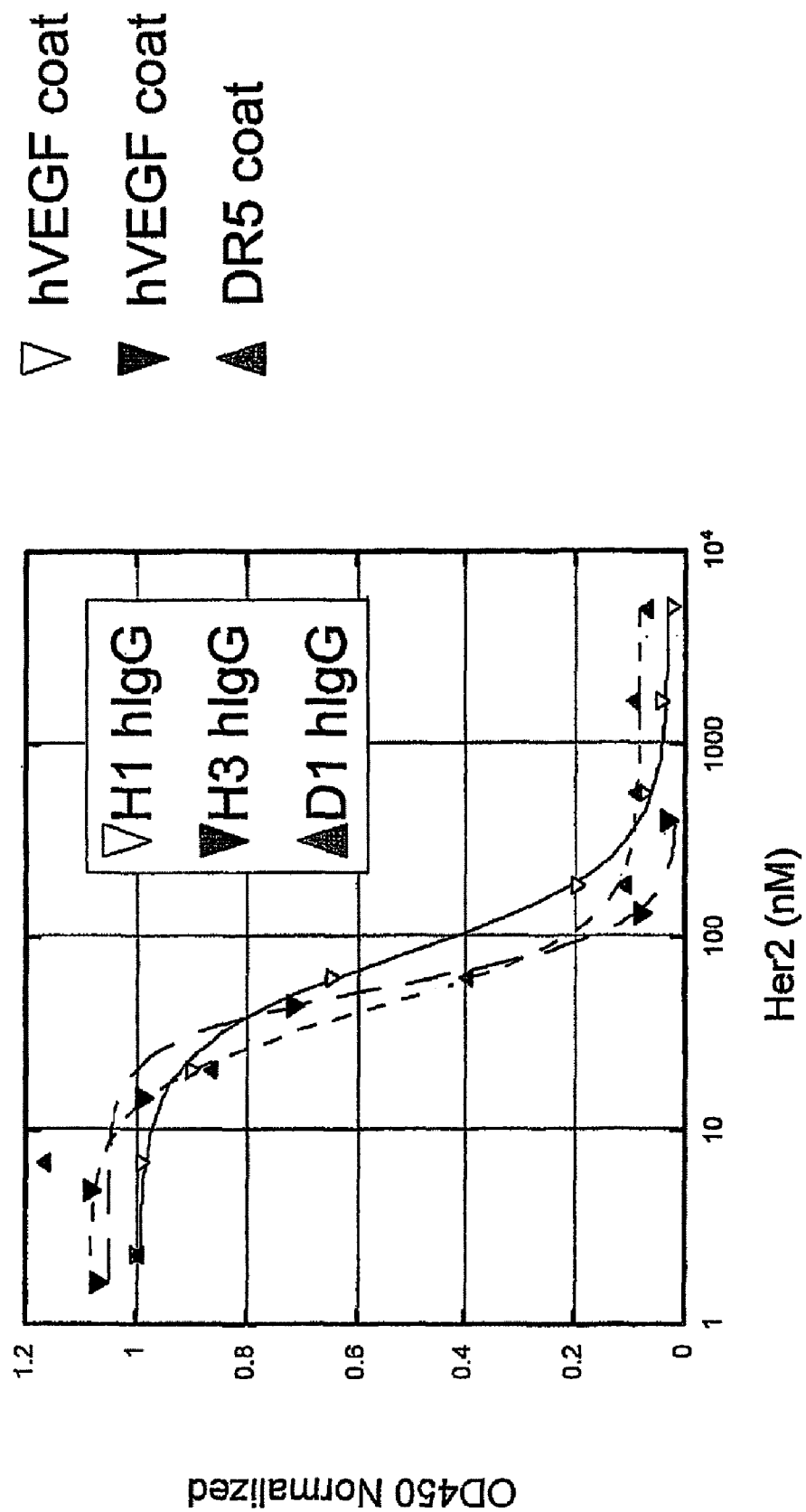
FIG. 20 shows competitive ELISAs of clones in hIgG form in the presence of Her2 and VEGF or DR5.

To test whether the bi-specific antibodies bH1, H3 (anti-hVEGF/Her2), and D1 (anti-hDR5/Her2) could simultaneously bind their cognate antigens or if the antigens compete for antibody binding, hVEGF and hDR5 were immobilized at a concentration of 2 ng/ml. A fixed concentration of hIgG was incubated with serial dilutions of Her2-ECD followed by capture of the hIgG on the immobilized antigen. In each case, Her2-ECD binding was found competitive with binding to the other antigens (FIG. 20).

To accurately determine the affinity of IgGs and Fabs (i.e., anti-hVEGF and anti-hVEGF/Her2 Fab and IgG isolated from the libraries) and to study the binding profiles in real time, we used surface plasmon resonance (SPR) assays on a BIAcore™-3000 (BIAcore, Uppsala, Sweden) machine with immobilized hVEGF, mVEGF, DR5, and Her2-ECD CM5 sensor chips at response units (RU) of 40-300 depending on the analyte studied. Immobilization was performed as described (Chen et al., 1999). To minimize avidity effects of the bivalent IgG analytes, a lower density of ligand was targeted on the sensor chip in these cases. Samples of increasing concentrations ranging from a concentration approximately 10-fold below to 10-fold above the estimated $K_D$ (based on competition ELISA experiments) were injected at 22-30 μl/minute, and binding responses were corrected by subtraction of RU from a reference flow-cell. In addition, the responses were double referenced to normalize for instrument drift by subtracting RU from ligand-conjugated flow-cell injected with sample buffer (PBS with 0.05% Tween 20). For kinetic analysis of the Fabs, a 1:1 Langmuir binding model of was used to calculate the $k_{on}$ and $k_{off}$. When necessary (at high analyte concentrations) a 1:1 Langmuir binding model with mass-transfer limitation was applied. For the IgG analytes, a bivalent analyte binding model with or without mass-transfer limitation was used (BIAcore Evaluation Software 3.2). In the case of H3 hIgG, H4_N Fab, and H4_D hIgG, the fit of responses to the kinetic binding models was not satisfactory. Therefore, steady state binding analysis was applied where the equilibrium response was plotted against analyte concentration. The $K_D$ was estimated as the $EC_{50}$. A summary of the BIAcore binding analysis can be found in FIG. 21. The affinity of the hVEGF binding antibodies 3-1, 3-6 and 3-7 was found to be in the nano molar range. The bi-specific antibodies analyzed (bH1, H3, H4_N, H4_D) showed low micromolar to micromolar affinities for hVEGF. In contrast, the affinities for Her2 ranged from 8-59 nM (Fab).

Figure 22:
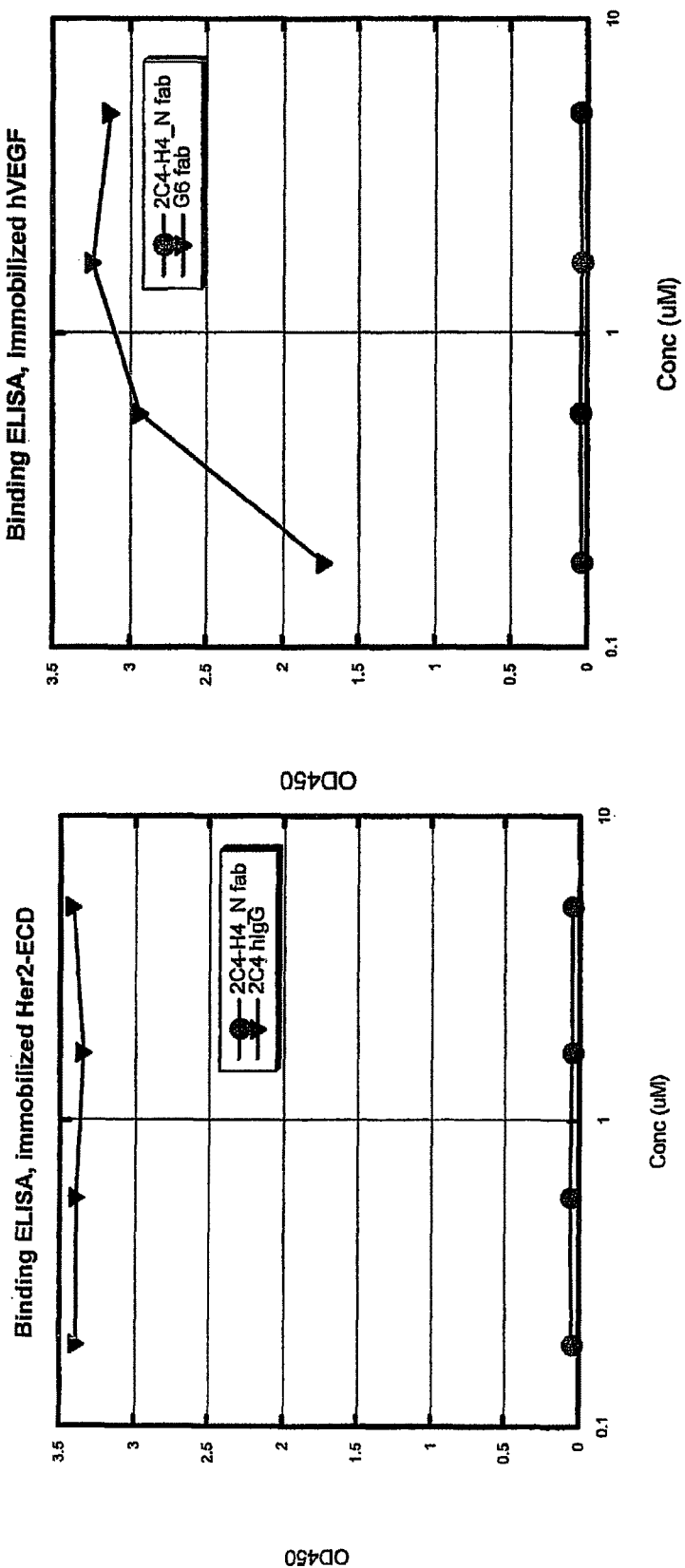
FIG. 22 shows binding to HER2-ECD or hVEGF with an IgG or Fab having a light chain obtained from a different binding clone.

To determine whether the light chain of anti-hVEGF binders bH1, H3, and H4_N could bind hVEGF independent of the sequence of the associated heavy chain, the light chain variable domains were grafted onto the anti-Her2 2C4 Fab by cloning the light chain variable domains into a 2C4 Fab expression vector pJB0524, thus replacing 2C4 light chain variable domain. The Fabs were expressed as previously described. The bH1/2C4 and H3/2C4 chimeric Fabs did not express at detectable levels. The H4_N/2C4 chimeric Fab protein was isolated and tested for binding to hVEGF (bH1 original specificity) and Her2 (bH1, 2C4 original specificity). No binding was detected to hVEGF and Her2 by a standard ELISA binding assay (FIG. 22). The results indicate that the heavy chain of bH1 is required for antigen binding.

Comparison of Anti-hVEGF Epitopes

Figure 23A:
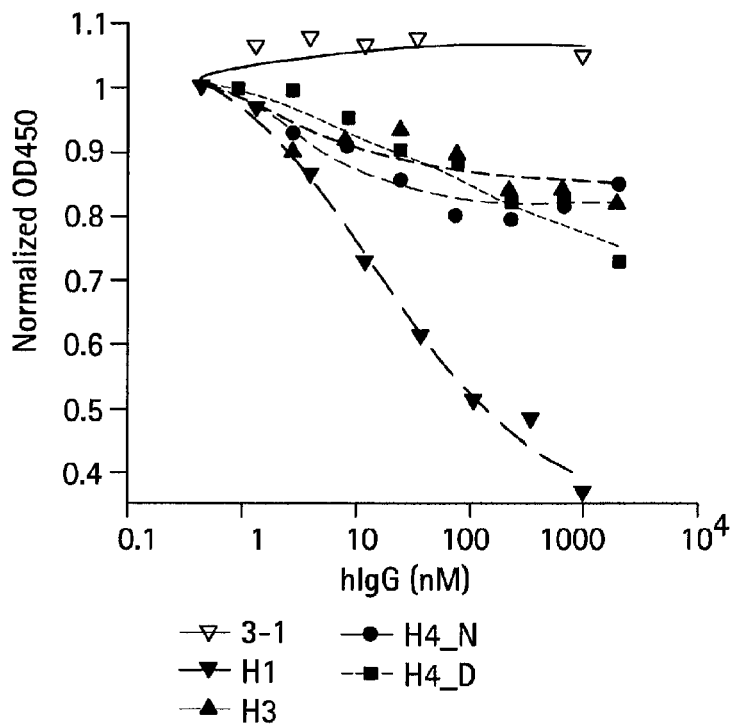
FIGS. 23A and 23B show an anti-VEGF antibody blocking VEGF interaction with VEGFR1D1-3 and KDR D1-7.
Figure 23B:
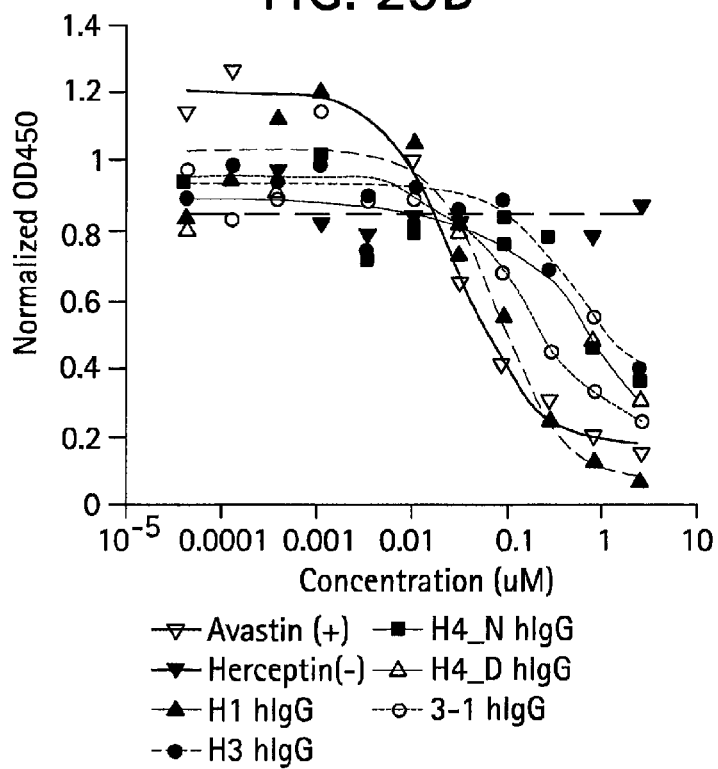

In an attempt to roughly map out the epitopes of the anti-hVEGF antibodies on hVEGF, we studied the ability of these newly isolated anti-VEGF antibody to compete with other hVEGF binding antibodies and VEGF receptors with known binding sites (Fuh et al., 2006; Muller et al., 1998; Wiesmann et al., 1997). The assays were done in a competitive ELISA format where the VEGFR1 (Flt) Domain 1-3 and anti-hVEGF antibodies Avastin® (IgG), B20-4.1 (IgG), G6 (Fab), and KDR Domain 1-7 Fc fusion protein were immobilized on Maxisorp immunoplates at 2 μg/ml. The solution competition binding assay used biotinylated VEGF equilibrated with serial dilutions of purified IgG proteins, and the unbound biotin-VEGF was captured with immobilized Fab or IgG coated on Maxisorb plates and was detected with streptavidin-conjugated HRP (Lee et al., J. Mol. Biol. 340:1073, 2004). Antibodies that block hVEGF from binding other hVEGF-binding antibodies or hVEGF-receptors are likely to share over-lapping epitopes. High concentrations (μM) of the bi-specific hVEGF/Her2-binding antibody, bH1, enabled complete blocking of hVEGF binding to its receptors, VEGFR1 and VEGFR2, suggesting bH1 epitope overlaps sufficiently with VEGFR1 (FIG. 23) and VEGFR2 (FIG. 23). In addition, bH1 blocks hVEGF binding to B20-4.1 (FIG. 24). H3, H4_N, and H4_D also block hVEGF-binding to both receptors, which points to similar epitopes as bH1 (FIG. 23). The incomplete blocking profiles are likely to be a consequence of their relatively low affinity for hVEGF (FIG. 21). 3-1, in contrast, does not block hVEGF from binding VEGFR1, even at the highest concentration (0.5 μM) (FIG. 23). Furthermore, we could not detect 3-1 hIgG blocking of the Avastin® antibody (FIG. 25). However, 3-1 hIgG block hVEGF binding to VEGFR2 (KDR) (FIG. 23) as well as to B20-4.1 (FIG. 24). These results indicate that 3-1 has a unique epitope compared to the other antibodies.

Example 4

Structure-Function Studies of bH1, Anti-hVEGF/Her2 Bi-specific Antibody

To elucidate the nature of the bH1 interaction with its two antigens, VEGF and HER2, structural and functional studies was performed. The Herceptin® antibody and bH1 differ in CDR-L1 ($V^{29}NTA^{32}$ vs. $I^{29}PRSISGY^{32}$; SEQ ID NOS:35 and 36) and CDR-L2 ($S^{50}\Delta SF^{53}$ vs. $W^{50}GSY^{53}$; SEQ ID NOS:37 and 38). The bH1 anti-VEGF/Her2 was chosen as representative for structural characterization based on its dual specific nature and its relatively high affinity for VEGF and Her2. In order to study the functional and structural epitopes on VEGF and Her2, we crystallized the bH1 Fab in complex with $VEGF_{109}$ and the extracellular domain of hHer2 and solved the structures of the two complexes by X-ray crystallography. In addition, we performed alanine and homolog shotgun scanning analysis using combinatorial phage displayed libraries as described (Vajdos et al., 2002).

bH1 Fab Expression, Purification, Crystallization and Data Collection

The receptor-binding portion of human VEGF, consisting of residues 8-109, was expressed, refolded and purified as described previously (Christinger et al., 1996). Residue 1-624 of the extra cellular domain of Her2 was expressed and purified as previously described (Franklin et al., 2004; Hudziak and Ullrich, 1991).

For large-scale bH1 Fab preparation, whole cell pellet was obtained from a ten liter *E. coli* fermentation. 220 gams of cell paste was thawed into 1 L PBS, 25 mM EDTA, 1 mM PMSF. The mixture was homogenized and then passed twice through a microfluidizer. The suspension was then centrifuged at 12 k in 250 ml aliquots for 90 minutes. The protein was then loaded onto a Protein G column (25 ml) equilibrated with PBS at 5 ml/minute. The column was washed with equilibration buffer and then eluted with 0.58% acetic acid. The fractions were assayed by SDS PAGE (data not shown). Fractions containing bH1 Fab were pooled and then loaded onto a 50 ml Cation Exchange SP Sepharose column (Pharmacia) equilibrated with 20 mM MES pH 5.5. The Fab was eluted with a sodium chloride gradient in the equilibration buffer. The gradient was linear to 0.5 M NaCl, 20 mM MES pH 5.5. Fractions containing the Fab were identified by SDS-PAGE (data not shown), and pooled. bH1 Fab eluted at a NaCl concentration of approximately 0.5 M. The Fab concentration was determined by measuring the $A_{280}$. The final yield for bH1 Fab was 67 mg/l fermenter growth.

Complexes were obtained by mixing the purified bH1 Fab and VEGF or Her2 ECD in 2:1 molar ratio and purified by size-exclusion chromatography (SP-200, Pharmacia) in 25 mM Tris-HCl, pH 7.5 and 0.3 M sodium chloride for VEGF-Fab complex and with 25 mM Tris-HCl, pH 8 and 0.15 M sodium chloride for the Her2 ECD-Fab complex. The composition of the resulting complexes was verified by SDS PAGE (data not shown). The protein complex was concentrated and used in crystallization trials. Initial hanging-drop experiments using the vapor-diffusion method at 19° C. resulted in small isomorphous crystals from 14 different conditions within 1 week in the case of the bH1-VEGF complex. Crystals of the bH1-Her2 complex appeared in 4 conditions within a week. Crystals from one condition was chosen for further optimization in each case.

For crystallization of bH1 Fab-VEGF (8-109), equal volumes of protein complex solution (10.6 mg/ml protein, 300 mM NaCl, 25 mM Tris-HCl pH 7.5) and crystallization buffer containing 0.15 M D, L Malic Acid pH 7.0, 20% $PEG_{3350}$ was mixed and equilibrated at 19° C. Large crystals appeared after 24 hours which belonged to space group $C222_1$ with cell dimensions of a=100.6, b=198.0, c=77.7. The crystal forms contained 1 Fab and 1 VEGF monomer in the asymmetric unit. Prior to data collection the crystals were cryo-protected by transfer between drops containing 5%, 10%, and 15% glycerol in artificial mother liquor, followed by a flash freeze in liquid nitrogen. Data was collected to 2.6 Å at the beam line 5.0.1 of the Advanced Light Source (Berkeley).

Crystals of bH1 Fab-Her2(1-624) was obtained by mixing protein solution (11 mg/ml, 25 mM Tris pH 8 and 150 mM sodium chloride) with crystallization buffer containing 25% w/v $PEG_{2000}$, 0.1 M MES pH 6.5. Crystals appeared after 12 hours that belonged to space group $P2_12_12_1$ with cell dimensions of a=62.3, b=115.1, c=208.2. The crystals contained one Her2-Fab complex in the asymmetric unit. Before data collection the crystals were flash frozen in liquid nitrogen with 20% Ethylene Glycol as cryo-protectant. Data was collected to 2.9 Å at the beam line 5.0.1 of the Advanced Light Source (Berkeley).

Data Processing, Structure Determination, and Refinement

The data was processed using Denzo and Scalepack (Otwinowski, 1997). The structures of bH1 Fab complexes was solved by Phaser (L. C. Storoni, 2004; Read, 2001). The bH1-Fab-VEGF(8-109) complex was solved using coordinates of VEGF from a previously described VEGF-Fab complex (2FJG) and Fab fragments containing either the variable domains $V_L/V_H$ or the constant domains $C_{H1}/C_L$ of the Herceptin® antibody Fab-Her2 complex (1N8Z). Fragments of Her2 and the variable domain of the Herceptin® antibody Fab from the Her2-Fab complex 1 N8Z were used as search models when solving bH1-Her2 structure. The constant domain of the bH1 Fab could not be found using the Herceptin® antibody Fab constant portion as a search model (1N8Z) and had to be docked manually guided by the Herceptin® antibody Fab-Her2 complex structure. Model building and refinement were performed using the programs Refmac (Collaborative Computational Project, 1994) and Coot (Emsley and Cowtan, 2004), respectively. Stereochemical parameters were analyzed using MolProbity (Lovell et al., Proteins 50:437 (2003)). The structures were refined to $R_{value}$=0.22 and $R_{free}$=0.27 for the Fab-VEGF-complex and $R_{value}$0.25 and $R_{free}$=0.31 for the Fab-Her2-complex. A crystal structure of bH1 Fab in complex with VEGF as well as Her2-ECD was modeled. Some bH1 Fab residues were within 4.5, 4.0, and 3.5 Å of the antigens. The two paratopes (the area on the antibody that makes contact with the antigen) for the two antigens on the same antibody overlap significantly and residues from both light chain and heavy chain are involved with the binding with both antigens. bH1 binds a similar epitope on VEGF as the Avastin® antibody, and bH1 binds Her2 on an essentially identical epitope as the Herceptin® antibody.

The crystal structures of bH1 Fab bound to the extracellular domain (ECD) of HER2 (residue 1-624) and to the VEGF receptor-binding domain (residue 8-109) were determined at 2.9 Å and 2.6 Å resolutions, respectively (FIG. 26 and Table 3). FIG. 26 shows the bH1 Fab/HER2 crystal structure superimposed with the Herceptin® antibody/HER2 complex, and the crystal structure of the bH1 Fab/VEGF complex.

Figure 27:
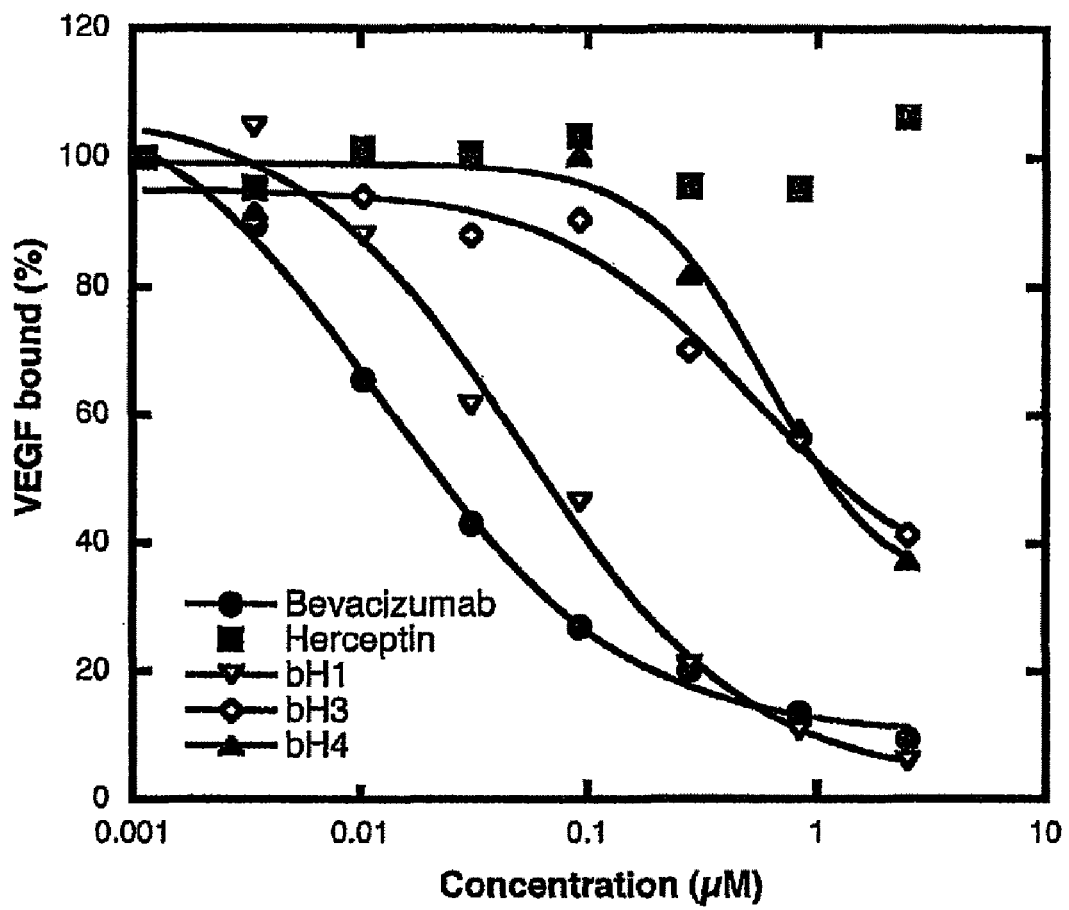
FIG. 27 is a graph showing that anti-VEGF antibodies block hVEGF binding to VEGF receptor 2 (VEGFR2).

In the bH1/HER2 complex, the Fab binds to domain IV of HER2 in a manner similar to the Herceptin® antibody (Cho et al., Nature 421:756, 2003); the two complexes superimpose with a root mean square deviation (r.m.s.d.) of Cα positions of 2.3 Å. In the VEGF complex, bH1 recognizes an epitope that overlaps with the binding sites of the VEGF receptors VEGFR1 and VEGFR2 and of other VEGF antibodies (Wiesmann et al., Cell 91:695, 1997; Muller et al., Proc. Natl. Acad. Sci. USA 94:7192, 1997). Consistently, the bH1 blocking of VEGF binding to its receptors was observed (FIG. 27). For the data shown in FIG. 27, biotinylated human $VEGF_{65}$ was equilibrated with increasing concentrations of IgG (x-axis). Unbound $hVEGF_{165}$ was captured on immobilized VEGFR2-ECD Fc fusion and detected spectrophotometrically (optical density at 450 nm, y-axis).

Figure 29:
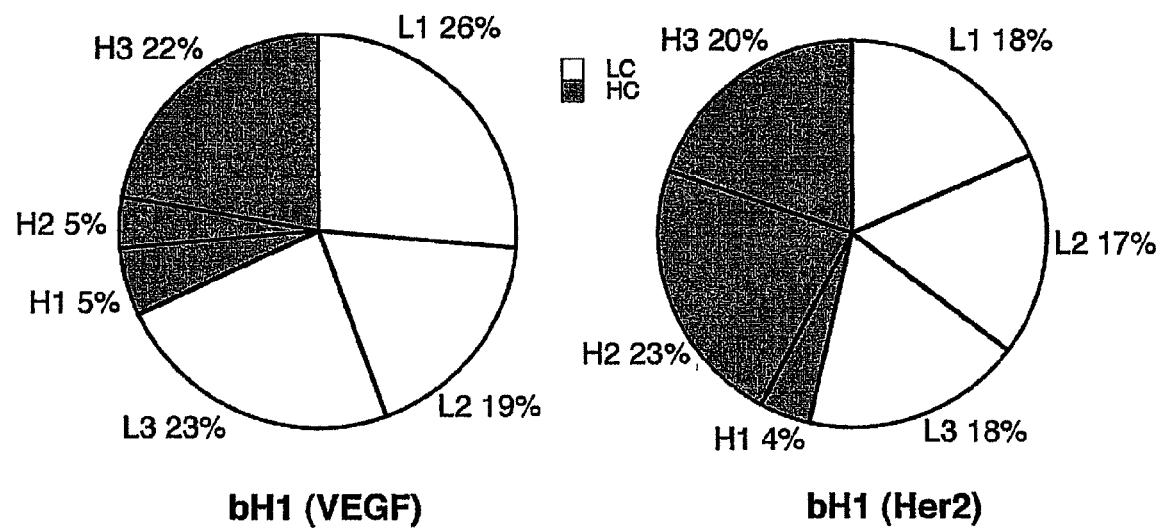
FIG. 29 is a series of pie charts showing the individual CDR contributions to the structural paratope for bH1. The paratope size for VEGF is 730 Å$^2$ and for HER2 is 690 Å$^2$. The heavy chain CDRs are indicated in gray and the light chain CDRs in white.

As shown in FIG. 28, the binding sites for VEGF and HER2 on bH1 overlap extensively. Twelve out of the fourteen residues that engage HER2 also contact VEGF. Both binding sites include CDR residues from the HC as well as LC. In the HER2 complex, the LC and HC CDRs contribute approximately equal antigen contact area (53% and 47% respectively) while in the VEGF complex, the LC CDRs constitute nearly 70% of the buried surface (FIG. 29). The HER2 binding site on the Herceptin® antibody and bH1 are similar and differ only in the CDR-L1 and -L2 regions where the Herceptin® antibody sequence is not conserved in bH1 (FIG. 28). In FIG. 28, residues on the bH1 or the Herceptin® antibody Fab surface are shaded according to the extent buried by VEGF or HER2 (dark shading and white lettering >75% buried, intermediate shading and white lettering 50-75% buried, light shading and black lettering 25-49% buried). The underlined residues differ between bH1 and the Herceptin® antibody. The white dotted line depicts the divide of light and heavy chain.

TABLE 3

Crystallographic Studies

|  | bH1 Fab/hVEGF complex | bH1 Fab/HER2-ECD complex |
|---|---|---|
| Data Collection Statistics |  |  |
| Space group | C222$_1$ | P2$_1$2$_1$2$_1$ |
| Unit Cell (Å) | a = 100.6, b = 198.0, c = 77.7 | a = 62.3, b = 115.1, c = 208.2 |
| Beamline, wavelength | ALS 5.0.1 | ALS 5.0.1 |
| Resolution (Å) | 50.0-2.6 | 50.0-2.9 |
| Rsym$^a$ | 0.090 (0.66) | 0.095 (0.66) |
| Number of Observations | 151689 | 192951 |
| Unique Reflections | 24705 | 34149 |
| Completeness (%)* | 99.8 (100) | 100 (100) |
| 1/σ (1)* | 16.0 (3.0) | 18.5 (2.6) |
| Refinement Statistics |  |  |
| Content of assymmetric unit | ½ VEGF dimer, 1 Fab | 1 Her2-ECD monomer, 1 Fab |
| Resolution (Å) | 30.0-2.6 | 30.0-2.9 |
| Reflection used | 22977 | 32277 |
| R Factor$^b$, Rfree | 0.19, 0.25 | 0.22, 0.28 |
| RMS Deviation Bonds (Å) | 0.011 | 0.010 |
| RMS Deviation Angles (°) | 1.3 | 1.3 |
| Ramachandran Statistics |  |  |
| Favoured Regions (%) | 96.5% | 89.9% |
| Allowed Regions (%) | 99.4% | 97.9% |
| Outliers (%) | 0.6% | 2.1% |
| Number of Residues | 528 | 1017 |
| Numbers of waters | 49 | 0 |
| Number of Sugars | 0 | 2 |
| Number of Ligands/Ions | 1 (Glycerol) | 1 (MES) |

Rsym$^a$ = Σ I − <I> ΣI. <I> is the average intensity of symmetry-related observations of a unique reflection.
R Factor$^b$ = ΣF0 − Fc ΣIF0. Rfree is calculated as R except for 5% of the reflections excluded from all refinements.
*Values in parenthesis denote values of the highest resolution shell.

Figure 30:
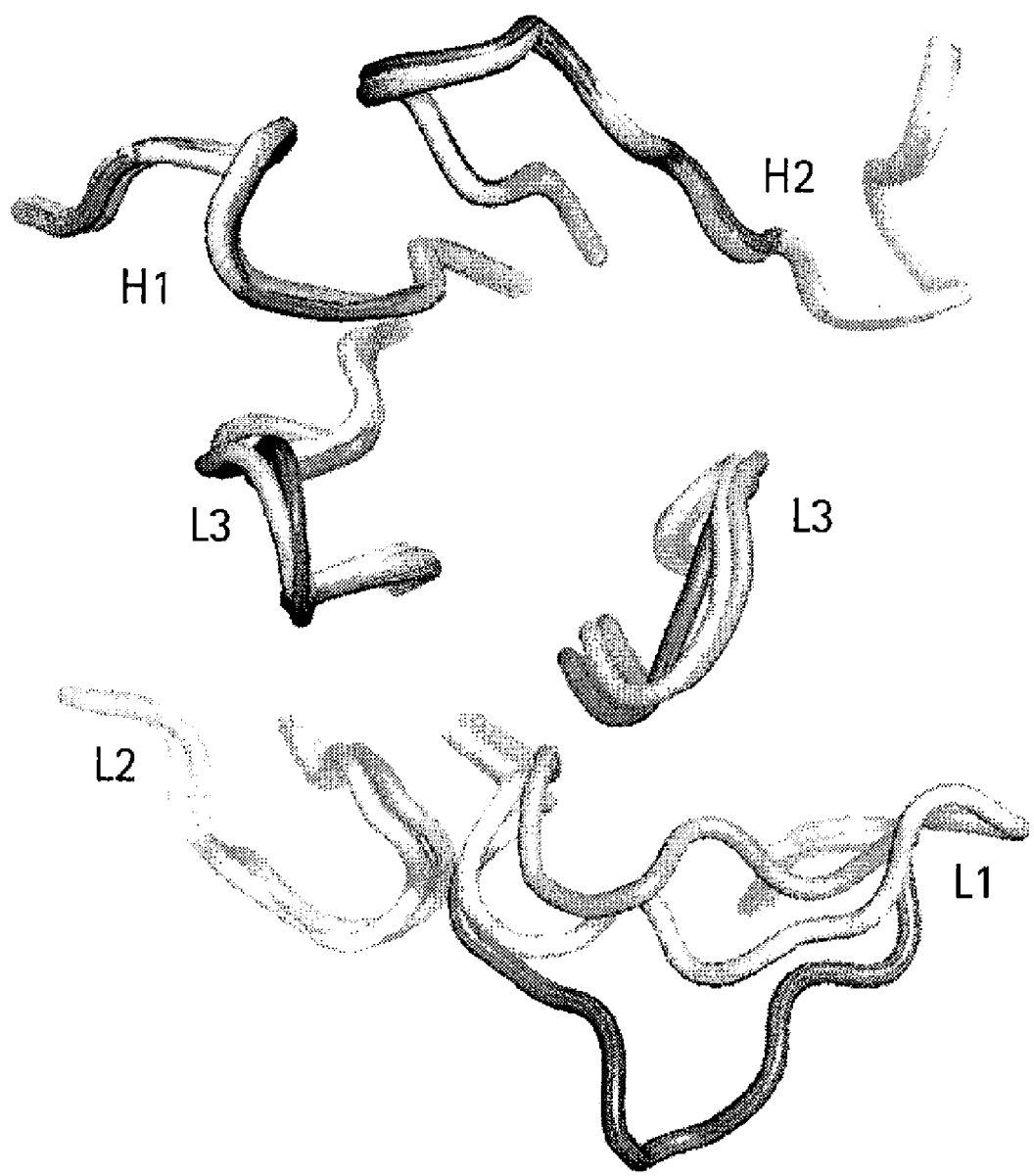
FIG. 30 shows the superposition of the CDR loops of VEGF/HER2-bound bH1 or HER2-bound Herceptin® antibody in the same orientation as FIG. 28.
Figure 31:
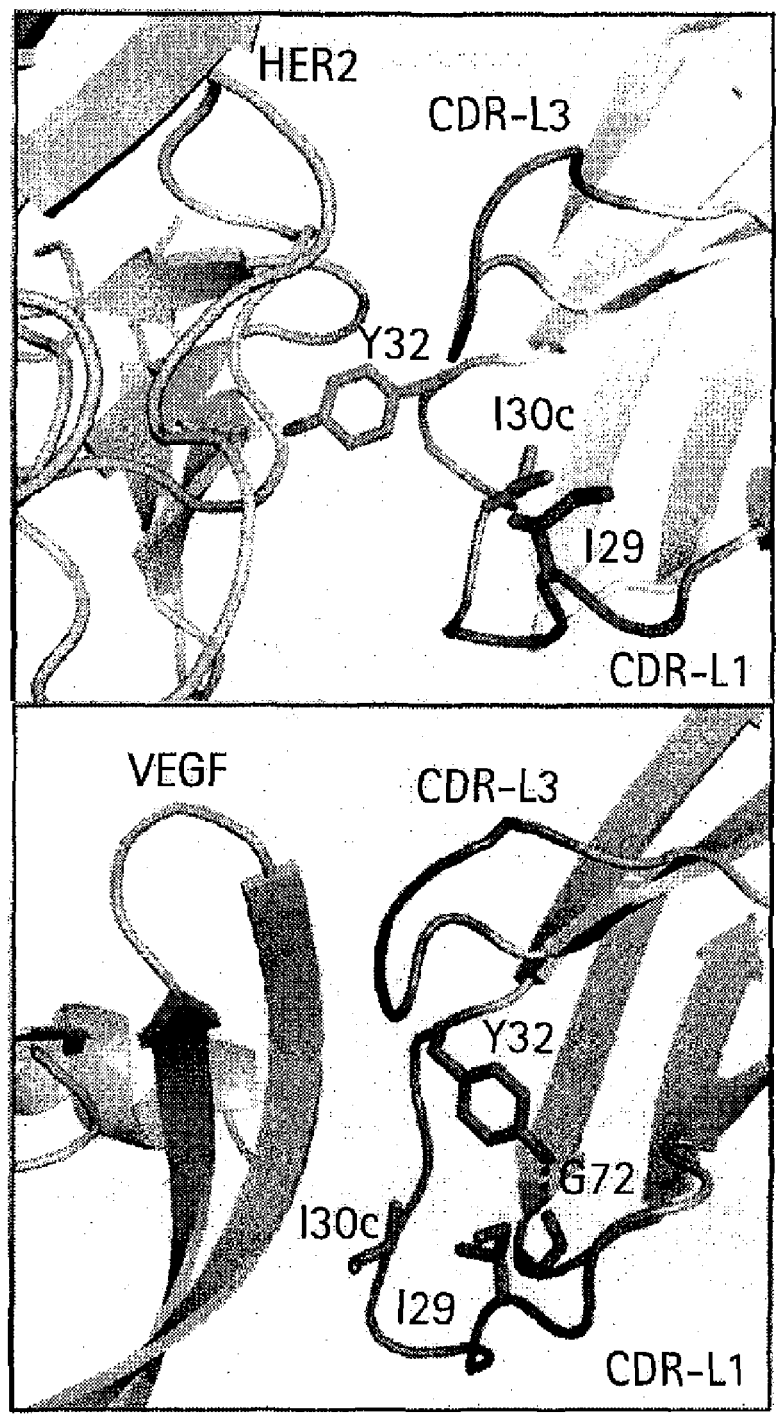
FIG. 31 shows crystal structures of the bispecific bH1 Fab bound to HER2 or VEGF. CDR-L1 of the two bH1 complexes are shown in the same orientation.
Figure 37:
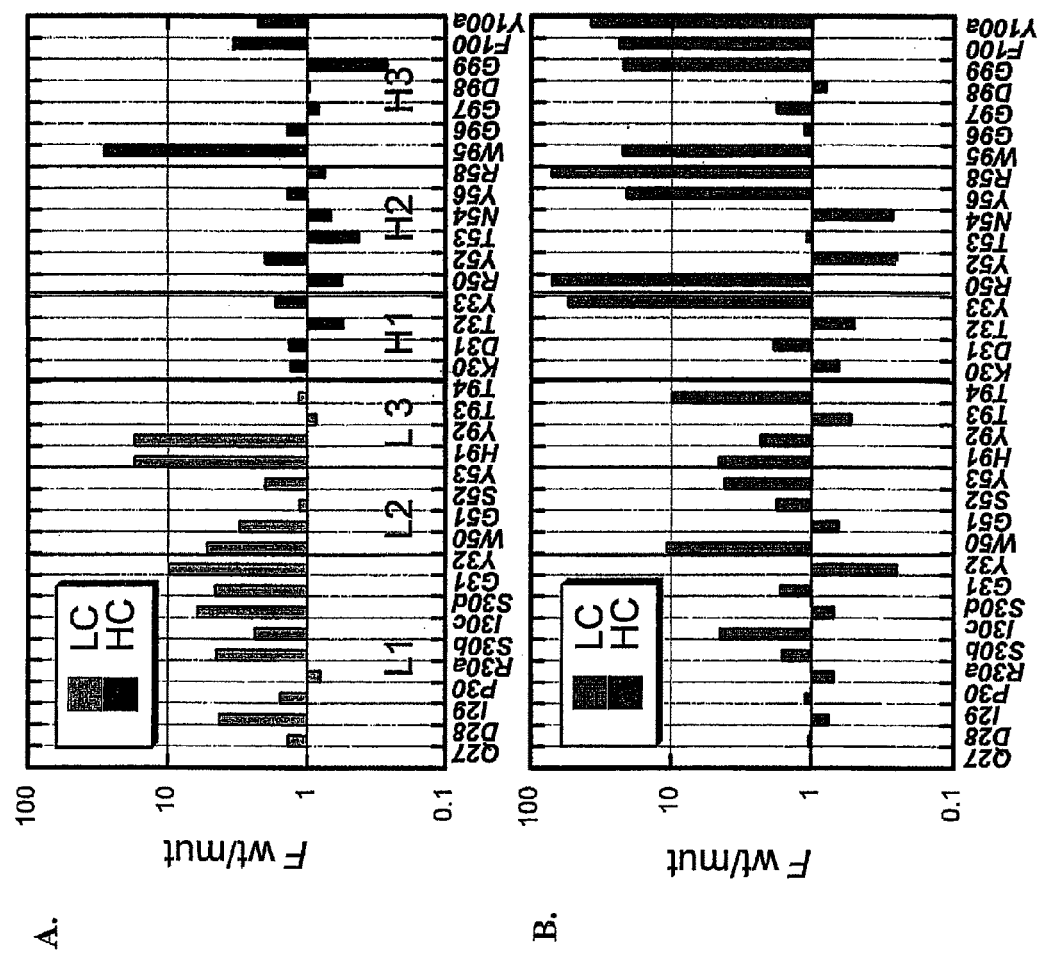
FIGS. 37A-37D show alanine scanning results.
Figure 37:
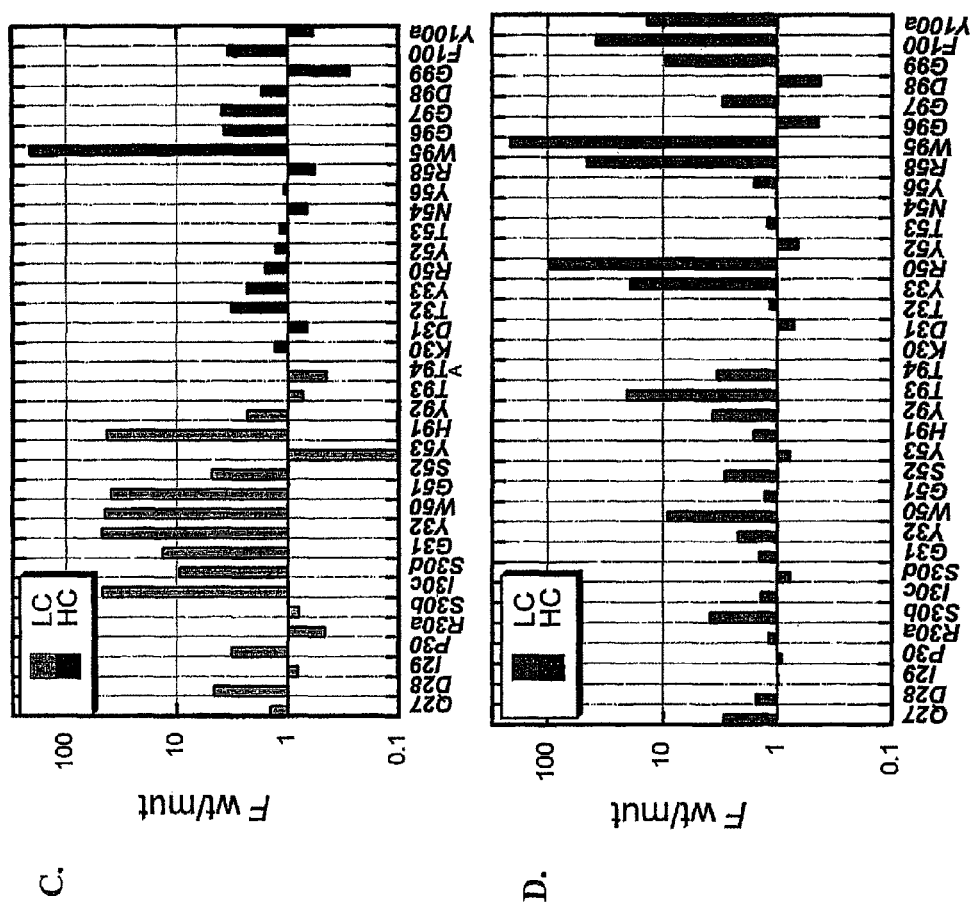

The conformation of bH1 Fab in complex with HER2 is markedly similar to that of the VEGF-bound Fab (r.m.s.d.=0.7 Å, Cα). The CDRs of both bH1 Fab structures superimpose well with each other and with the parent Herceptin® antibody Fv and bH1 Fv (HER2) r.m.s.d.=0.6 Å, the Herceptin® antibody Fv and bH1 Fv (VEGF) r.m.s.d.=1.2 Å. The CDR-L1 is an exception and differs significantly in the two complex structures; the deviation is 4.6 Å (Cα of residues 27-32). FIG. 30 shows that the CDR conformations of bH1 Fab bound to VEGF are markedly similar to HER2-bound bH1 and to the Herceptin® antibody, with exception of the CDR-L1. FIG. 30 is a superposition of the CDR loops as tubes of VEGF-bound bH1 (dark shading), HER2-bound bH1 (white) and HER2-bound the Herceptin® antibody (light shading). The CDR-L1 loop exhibits significantly different conformations in the two bH1 structures (r.m.s.d.$_{Cα}$=4.6 for bH1 residues 27-32) (FIG. 31). In the HER2 complex, the CDR-L1 is minimally involved in antigen interaction and part of the loop (residues 28-30b) appears flexible. For VEGF binding, the entire loop is well structured and contributes 26% of surface area buried by VEGF.

Two residues in CDR-L1, 11e30c and Tyr32, have different conformations and play different roles in bH1 binding to HER2 or VEGF. In the HER2 complex, the side chain of Ile30c is buried in the hydrophobic core formed by CDR-L1 and CDR-L3 residues. In the VEGF complex, this side chain forms hydrophobic contacts with VEGF. The Cα of Tyr32 is in the same position in the two structures, but its side chain is rotated ~130 degrees. In the HER2 complex Tyr32 packs against the receptor, while in the VEGF complex the side chain, together with Ile29, form the hydrophobic core and support the conformation of CDR-L1 and CDR-L3. The CDR-L1 conformation is further stabilized by hydrogen bonds between Tyr32 and the LC framework residue Gly72. The structural analysis confirms that Tyr32 is critical for VEGF binding as mutation to either alanine or phenylalanine is not tolerated. Contrary to VEGF binding, mutation of Tyr32 to alanine (back to the Herceptin antibody residue) is preferred for HER2 binding. Superposition of the two complexes reveals that VEGF would clash with Tyr32 of CDR-L1 in its HER2 bound state (FIG. 31). In FIG. 31 the side chains of residues Tyr32, Ile30c, Ile29, and Gly72 are shown as sticks. Residues with temperature factors higher than average are shown in darker shading (residues 28-30b). Hydrogen bonding between Tyr32 and Gly72 is illustrated by a dotted line.

The above results indicate that the capability to rearrange CDR-L1 is necessary for the bi-specificity of bH1. Similar conformational flexibility of CDR-L1 has been shown to play a role in antigen recognition of natural antibodies (Jimenez et al., Proc. Natl. Acad. Sci. USA 100:92, 2003; Mylvaganam et al., J. Mol. Biol. 281:301, 1998). FIGS. 26, 28, 30, 31, and 32 are generated from the crystal structure coordinates (PDB codes, 3BDY, 3BE1, 1N8Z) using PYMOL (DeLano Scientfic, San Carlos, Calif.).

bH1 Shotgun Scanning

To study the antigen-binding sites of bH1 Fab, shotgun scanning combinatorial mutagenesis using phage-displayed Fab libraries was performed (Vajdos et al., J. Mol. Biol. 320:415, 2002; Weiss et al., Proc. Natl. Acad. Sci. USA 97:8950, 2000). Binding selections on the antigens (hVEGF and Her2-ECD) to isolate functional clones followed by DNA sequencing enabled calculations of wild-type/mutant ratios at each varied position (Vajdos et al., 2002). These ratios were then used to determine the contribution of each scanned side-chain to VEGF and Her2 binding. The results enabled mapping of the functional paratope for binding VEGF and Her2.

bH1 Shotgun Library Design

Solvent exposed residues in the CDRs were scanned using phage-displayed libraries in which the wild type residues were allowed to vary as either alanine or wild type (Alanine Scan) or as a homolog residue or wild type (Homolog Scan). The nature of the genetic code required some other substitutions to be included in the library in addition to Wt/Alanine or Wt/Homlog residues (FIG. 33). Separate heavy chain and light chain alanine and homolog scanning libraries were constructed. The libraries are described in FIG. 34. The degeneracy ranged from 1.3×10$^5$ to 1.3×10$^8$ and the actual library size from 6×10$^9$ to 4×10$^{10}$.

Construction of Shotgun Scanning Libraries

As noted above, to enable display of bH1 Fab on the surface of M13 bacteriophage, a previously described plasmid AP2009 designed to display hu4D5Fab on phage fused to the C-terminal domain of the M13 gene-3 minor coat protein, was modified to encode bH1Fab using standard molecular biology techniques. The C-terminus of the light chain contained an epitope (gD) tag. "Stop template" versions of the bH1 Fab was used as library template (Sidhu et al., 2004). The light chain alanine and homolog scanning library had stop codons in CDR-L1, CDR-L2 and CDR-L3 and the heavy chain alanine and homolog libraries contained stop codons in each heavy chain CDR. The libraries were constructed by previously described methods (Sidhu et al., 2004) using Kunkel mutagenesis (Kunkel et al., 1987) on the respective stop templates.

Library Selection

NUNC 96-well Maxisorp immunoplates were coated with 5 μg/ml capture target (hVEGF$_{109}$, Her2-ECD or anti-gD mIgG) and blocked with 1% BSA (w/v) in PBS. Phage from the above-described libraries were propagated with KO7 helper phage (NEB) as described (Lee et al., 2004a). The library phage solutions were added to the coated plates at a concentration of $10^{13}$ phage particles/ml and incubated for 1-2 hours at RT. The plates were washed 8 times with PBST and followed by elution of bound phage with 0.1 M HCl for 30 minutes. Enrichment after each round of selection was determined as described previously. After 2 rounds of target selection, 50-1000-fold enrichment was observed for all libraries except LC-Ala and LC-Hom sorted on hVEGF, which showed 5-10-fold enrichment. A number of random clones from each library exhibiting 50-1000-fold enrichment was selected for sequencing as described (Sidhu et al., 2004). Library LC-Ala was screened for hVEGF binding in phage ELISA (Sidhu et al., 2000). Clones that exhibited hVEGF ELISA signals at least two-fold over signals on a control plates coated with BSA were selected for sequencing. The LC-Hom library was subjected to 1 additional round of selection on hVEGF followed by phage ELISA screening and sequencing of VEGF-binding clones.

DNA Sequence Analysis

The high quality sequences from each library from the different target selections were translated and aligned (Data not shown). The number of sequences from each library subject to analysis is summarized in Table 4 below.

TABLE 4

Number of Sequences Analyzed

| Library | Total Sequences |
|---|---|
| LCA-V2b | 51 |
| LCH-V3 | 79 |
| LCA-H2 | 97 |
| LCH-H2 | 50 |
| LCA-gD | 112 |
| LCH-gD | 120 |
| LCA-pL | 60 |
| LCH-pL | 65 |
| HCA-V2 | 100 |
| HCH-V2 | 96 |
| HCA-H2 | 81 |
| HCH-H2 | 96 |
| HCA-gD | 105 |
| HCH-gD | 105 |
| HCA-pl | 102 |
| HCH-pl | 99 |

Figure 38:
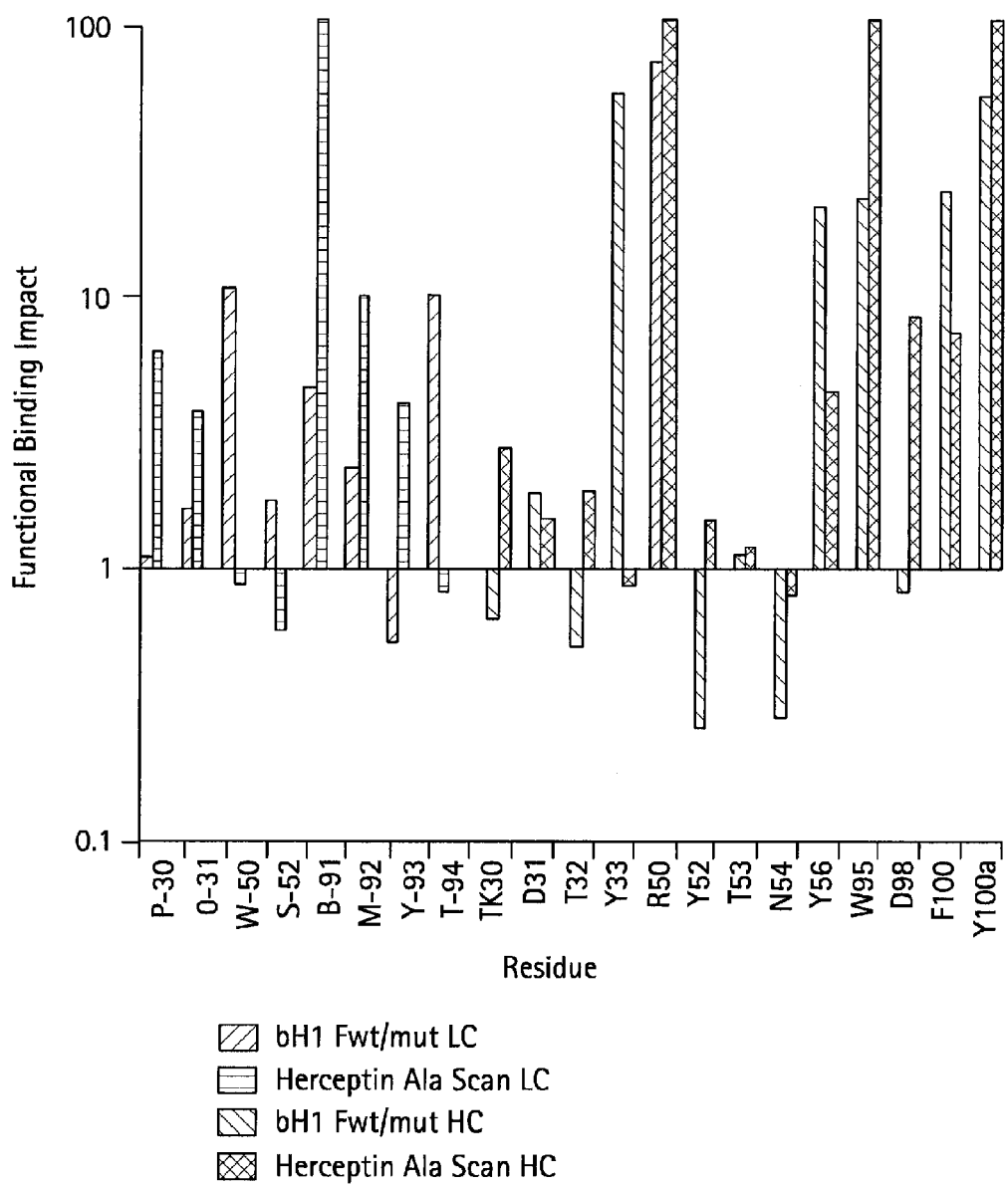
FIG. 38 shows alanine scanning results of bH1 or the Herceptin® antibody mutants.

The Wt/Mut ratios were calculated at each varied position (FIG. 35 and FIG. 36) thus allowing calculation of the $F_{wt/mut}$ values as listed (FIG. 35 and FIG. 36) which are corrected for display by division of the ratios from target selection by those from the display selection as described (Vajdos et al., 2002). A $F_{wt/mut}$ value greater than 1 indicates that Wt is preferred at this position and $F_{wt/mut}$ smaller than 1 indicates the mutation is preferred. $F_{wt/mut}$>5 indicate its important role in antigen binding. The importance of each scanned CDR residue is illustrated in FIGS. 37A-37D. The result demonstrates that residues from both heavy chain and light chain contribute energetically to the binding of both antigen (Her2 and hVEGF) binding. The impact of bH1 light chain and heavy chain residues on Her2 binding was compared to that of its parent antibody hu4D5 (Kelley and O'Connell, 1993) (FIG. 38).

FIG. 39A and FIG. 39B show shotgun alanine- and homolog scanning of bH1 Fab for binding to VEGF and HER2. The effects of mutation of alanine (m1), or additional mutations (m2, m3; due to limitations of shotgun-alanine codons), or to a homologous amino acid (m4) are calculated as the ratio of occurrence of wild-type and mutants (wt/mut) among the clones binding to human VEGF (FIG. 39A) or HER2 (FIG. 39B). In cases where only the wild-type residue appeared, the ratios are shown as larger than ">" the wild-type count. The identity of the amino acid substitutions (m1-m4) is shown as superscripts on the F values. When the wild-type residue is alanine, it was substituted by glycine (ml). The "*" indicates the extent of the bH1 residues that are buried upon VEGF or HER2 complex formation (*25-49% of accessible area buried, 50-75% of accessible area buried, *greater than or equal to 75% of accessible area buried).

Figure 40:
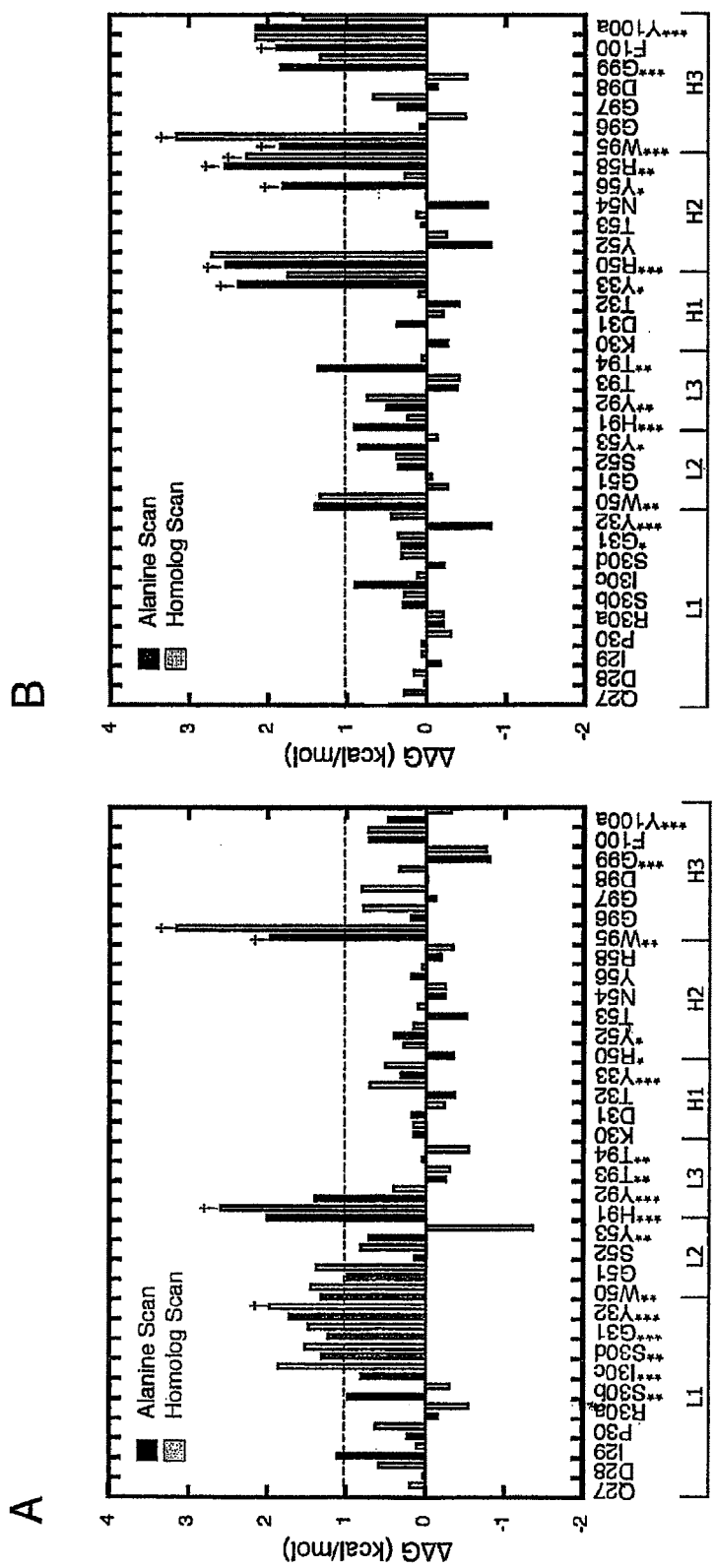
FIGS. 40A-40B show the energetically important binding sites of bH1 for VEGF and HER2 binding.

The residues that contribute significantly to the energetic interactions make up the functional paratopes, which constitute a subset of the structural binding sites. In contrast to the extensive overlap between the sites of antigen contact the two functional paratopes show limited overlap (FIGS. 32 and 40). In particular, based on shotgun scanning mutagenesis, the ΔΔG values (y-axis, kcal/mol) are plotted for each mutation to alanine (black bar) or a homologous amino acid (white bar) for VEGF (FIG. 40A) or HER2 (FIG. 40B) binding. The "†" represents a lower limit, as mutations were not observed at this position. The "*" indicates the extent of the bH1 residue surface area buried upon VEGF or HER2 complex formation. (*25-49% buried, 50-75%, *>75%). The VEGF binding interaction is mediated primarily by the LC CDRs with Tyr32 of CDR-L1 and His91 of CDR-L3 as the core hot spot (ΔΔG$_{wt/ala}$>1.5 kcal/mol). HER2 binding is mainly contributed by HC CDRs. FIG. 32 shows crystal structures where the bH1 and the Herceptin® antibody residues are shaded on the Fab surface based on their functional importance (dark shading and white lettering, ΔΔG≧1.5 kcal/mol; intermediate shading and black lettering, 1≦ΔΔG<1.5 kcal/mol; light shading and black lettering, 0.5≦ΔΔG<1 kcal/mol of alanine mutation). The black dotted line outlines the contact area as in FIG. 28. The white dotted line depicts the divide of light and heavy chain.

For VEGF binding and HER2 binding, the functional paratope residues are distributed across HC and LC signifying the synergy of the two chains. Trp95 of CDR-H3 is the only common hot spot residue for the two interactions (ΔΔG$_{wt/ala}$>1.5 kcal/mol). As noted above, the VEGF binding interaction is mediated primarily by the LC CDRs while HER2 binding is dominated by HC CDRs. Compared to the Herceptin® antibody, bH1 with weaker HER2 binding affinity (300 fold) maintains the same core hot spot residues for HER2 binding (Arg50, Trp95, and Tyr100a) while the importance of peripheral residues is redistributed (FIG. 32). Overall, most of the important side chains in heavy chain contributing hu4D5/Her2 binding are still important for bH1/Her2 binding ($\Delta\Delta G$>1.5 kcal/mol). There are some changes. Light chain residues have more shuffling in contributions—some residues became less important and some more important. Overall, the functional sites are part of the structural interface from the crystal structure of the bH1-VEGF and bH1-Her2 complexes.

In short, the interaction of bH1 with the two structurally unrelated large proteins is characterized by the engagement of a distinct set of bH1 residues in the energetic interaction with each antigen: While most of the two extensively overlapping binding sites for the two different antigens exhibit a single conformation, the flexibility of one CDR loop (L1) facilitates the accommodation of both HER2 and VEGF. The mechanism is reminiscent of the molecular versatility observed in multi-specific antibodies binding unrelated small haptens or peptides. Previous studies describe multi-specificity mediated either by differential positioning of the small ligands at spatially distinct regions of a single antibody conformation (Sethi et al., Immunity 24:429, 2006) or by multiple pre-existing conformations of the antigen binding site (James et al., Science 299:1362, 2003). The versatility of antibody molecules in antigen recognition is further highlighted by how limited LC mutations can give rise to antibodies that bind two unrelated protein antigens.

bH1 Affinity Maturation

Figure 41:
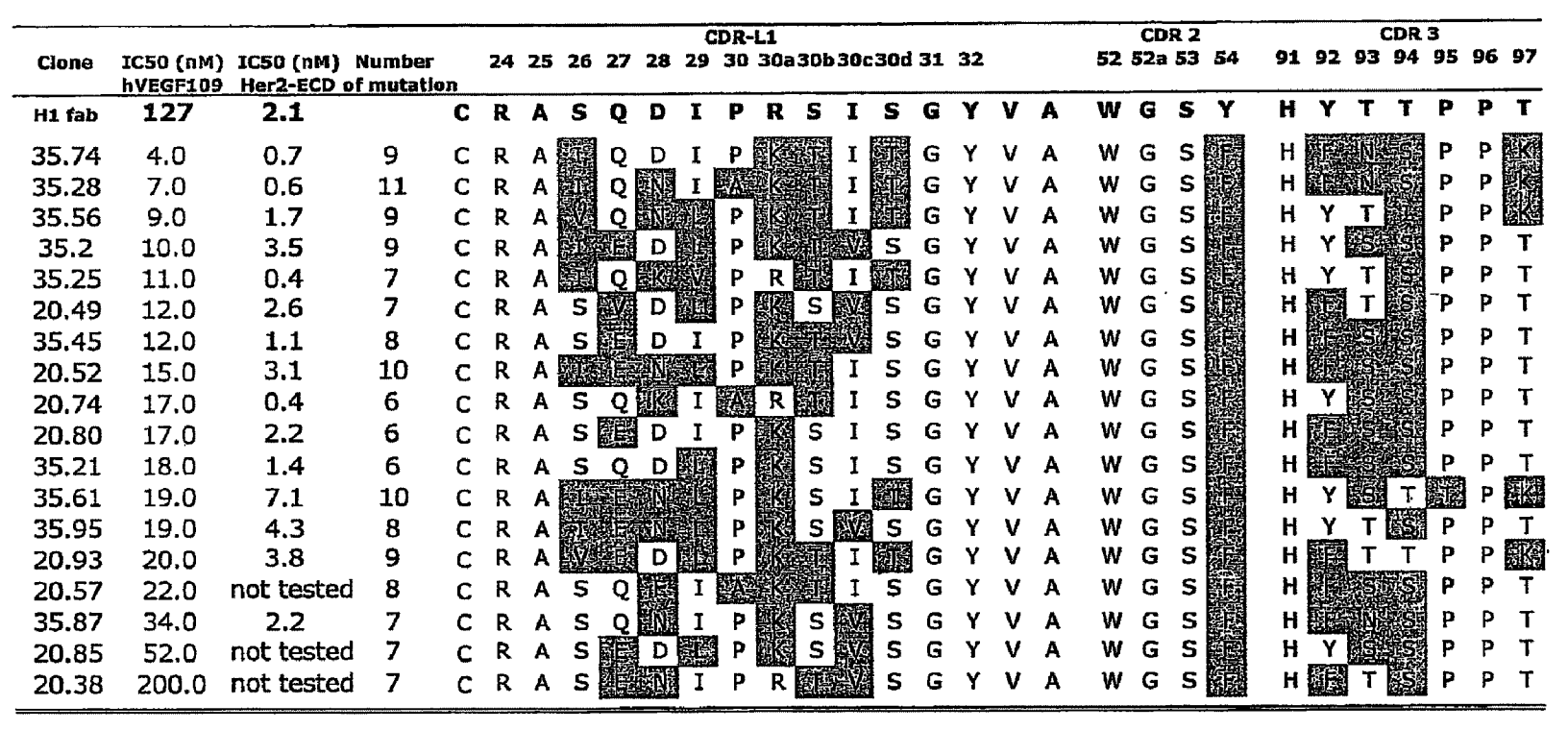

In an attempt to investigate whether the VEGF-binding affinity of bH1 could be increased by optimization of the light chain sequence before the structural and functional results became available, a library was constructed where the CDR residues at highly solvent-accessible positions based on the crystal structure of h4D5[42] Fab (Eigenbrot et al., 2001), which is assumed to closely resemble bH1 Fab, were diversified. Targeted residues were allowed to vary as either wild type or a few homologous residues (FIG. 34). The library was constructed as described in section "Construction of shotgun scanning libraries." A solution-based selection method was used to select for higher affinity VEGF-binders as described. Two rounds of solution-based selection were performed. The stringency was increased in each round of selection by decreasing the concentration of biotinylated VEGF from 50 nM in the first round to 20 nM in the second round. 138 clones were sequenced from the last round of selection. Most clones were found to be unique. A high-throughput ELISA assay with immobilized VEGF (8-109), anti-gD antibody, and Her2-ECD was used to identify clones that bound to VEGF, Her2-ECD, and anti-gD mIgG but not to BSA. The VEGF-ELISA binding signals were normalized by the anti-gD ELISA signals to estimate the relative affinity of the VEGF binding clones. Clones with high VEGF/anti-gD ratios were selected for further characterization. The affinity of the selected clones for VEGF and Her2 was estimated by competition ELISA as phage-displayed Fabs as previously described. The bH1 variants show improved VEGF binding-affinity compared to the parent bH1 clone. Interestingly, some clones have slightly improved $IC_{50}$ values for Her2 binding even though that affinity-based selection for Her2 was not performed. This shows that it is possible to affinity mature the bH1 clone for VEGF binding without affecting Her2 binding ability significantly. There are some VEGF-affinity improved clones that showed reduced Her2 binding affinity compared to the parent bH1 clone. This result indicates that the light chain actively contributes to the binding ability of bH1 to Her2 despite the fact that heavy chain is the main contributor to the binding energy based on the bH1-Her2 complex structure and shotgun alanine scanning analysis. The sequences and $IC_{50}$ values of the characterized clones are summarized in FIG. 41. The finding that most sequences were unique suggests that the light chain sequence of these variants is not yet fully optimized for VEGF binding and that it is possible to further affinity-improve bH1 clone by additional rounds of selection.

As shown in Table 5, significant affinity improvement of a single Fab for two antigens is achievable and generally applicable. For instance, the $K_D$ for human VEGF was increased from 250 (bH1; IgG) to 41 (bH1-81; IgG) or 16 nM (bH1-44; IgG) and the $K_D$ for HER2 was increased from 21 (bH1; IgG) to 7 (bH1-81; IgG) or 1 nM (bH1-44; IgG).

The affinity was improved by introducing mutations in the HC and LC CDRs of bH1. The positions were selected based on the information about the functional paratopes for VEGF and HER2 described herein. The bH1 variants were isolated in two steps by selection and screening of phage display libraries as described herein. The improved clone bh1-81 was isolated by affinity-based selections of the described light chain homolog shotgun scan library. In the second step, the highest affinity clone (bH1-44) was isolated from a library by randomizing residues of bH1-81. In particular, oligonucleotides were designed that randomized sites in the HC and the LC of bH1-81 (Table 5) to encode ~50% wild-type and 50% of all other 19 amino acids at each position (Gallop et al., Journal of Medicinal Chimistry 37:1233, 1994).

The $K_D$s of bH1 affinity-improved variants (Table 5) were measured for Fab fragments and IgG antibodies. Fab fragments and IgG antibodies were expressed in *E. Coli* and 293 cells respectively, and purified as described herein. Surface plasmon resonance (SPR) measurements with BIAcore3000 were used to determine the binding affinities of Fab fragments and IgG antibodies as described in Lee et al. (J. Mol. Biol. 340:1073, 2004). To study the affinity of the antibody as monovalent Fab fragments, the antigens (hVEGF$_{109}$, murine VEGF$_{102}$, and HER2ECD) were immobilized at low density on a BIAcore CM5 chip. Serial dilutions of Fab fragments were contacted with the immobilized antigens and the binding responses measured by SPR. A 1:1 Langmuir binding model was used to calculate the $k_{on}$, $k_{off}$, and $K_D$. To determine the $K_D$ of the IgG antibodies, the IgG was captured on a BIAcore CM5 chip by immobilized anti-Fc antibody and exposed to serial dilutions of hVEGF$_{109}$, murine VEGF$_{102}$, and HER2-ECD. For HER2 a simple 1;1 Langmuir binding model was used to determine the $K_D$, while VEGF required a bivalent analyte model. All the experiments were performed at 30° C.

Table 5 shows the randomized positions in bold and summarizes the CDR sequences (SEQ ID NOS:1-9 and 39-41) of bH1, bH1-81, and bH1-44 and their affinities (as determined by surface plasmon resonance).

TABLE 5

Variants of bH1 with improved dual affinity

| | Light Chain | | | | | | | | | | | | | | |
|---|---|---|---|---|---|---|---|---|---|---|---|---|---|---|---|
| | CDR-L1 | | | | | | | | | CDR-L2 | | | | | |
| Antibody | 28 | 29 | 30 | 30a | 30b | 30c | 30d | 31 | 32 | 50 | 51 | 52 | 53 | 54 | 55 |
| bH1 | D | I | P | R | S | I | | S | G | Y | W | G | S | Y | L | Y |
| bH1-81 | N | | A | K | T | | | | | | | | | F | | |
| bH-44 | N | | A | K | T | | | | | | | | | F | | |

| | Light Chain | | | | | | Kd (nM) | | | | | |
|---|---|---|---|---|---|---|---|---|---|---|---|---|
| | CDR-L3 | | | | | | hVEGF | | mVEGF | | HER2 | |
| Antibody | 91 | 92 | 93 | 94 | 95 | 96 | Fab | IgG | Fab | IgG | Fab | IgG |
| bH1 | H | Y | T | T | P | P | 300 | 250 | >1000 | >1000 | 26 | 21 |
| bH1-81 | | | S | S | | | 58 | 41 | ND | 150 | 6 | 7 |
| bH-44 | | | S | S | | | 9 | 16 | 33 | 36 | 0.7 | 1 |

| | Heavy Chain | | | | | | | | | | | | | | | |
|---|---|---|---|---|---|---|---|---|---|---|---|---|---|---|---|---|
| | CDR-H1 | | | | | | CDR-H2 | | | | | | | | | |
| Antibody | 28 | 29 | 30 | 31 | 32 | 33 | 50 | 51 | 52 | 52a | 53 | 54 | 55 | 56 | 57 | 58 |
| bH1 | N | I | K | D | T | Y | R | I | Y | P | T | N | G | Y | T | R |
| bH1-81 | | | | | | | | | | | | | | | | |
| bH-44 | | | S | G | | | | | | | S | E | | | | |

| | CDR-H3 | | | | | | | | | |
|---|---|---|---|---|---|---|---|---|---|---|
| Anitbody | 95 | 96 | 97 | 98 | 99 | 100 | 100a | 100b | 101 | 102 |
| bH1 | W | G | G | D | G | F | Y | A | M | D |
| bH1-81 | | | | | | | | | | |
| bH-44 | | | V | | V | | | | | |

ND = not determined.

The monovalent affinity of the antibodies for human $VEGF_{109}$, murine $VEGF_{102}$, and HER2ECD was measured by BIAcore. Table 5 shows representative dissociation constants ($K_d$) for each binding interaction. The receptor-binding fragment of VEGF ($VEGF_{109}$) was used in the BIAcore experiment because the bH1 variants bind the full-length protein ($VEGF_{165}$) and $VEGF_{109}$ with similar affinity in solution competition experiments (data not shown). Different assay formats and evaluation models were used to calculate the $K_d$ for Fab fragments/IgG antibodies as described herein. The different assay/evaluation formats yielded consistent dissociation constants for the individual interactions.

Example 5

Analysis of IgG Activity in Cell Assays

Figure 42:
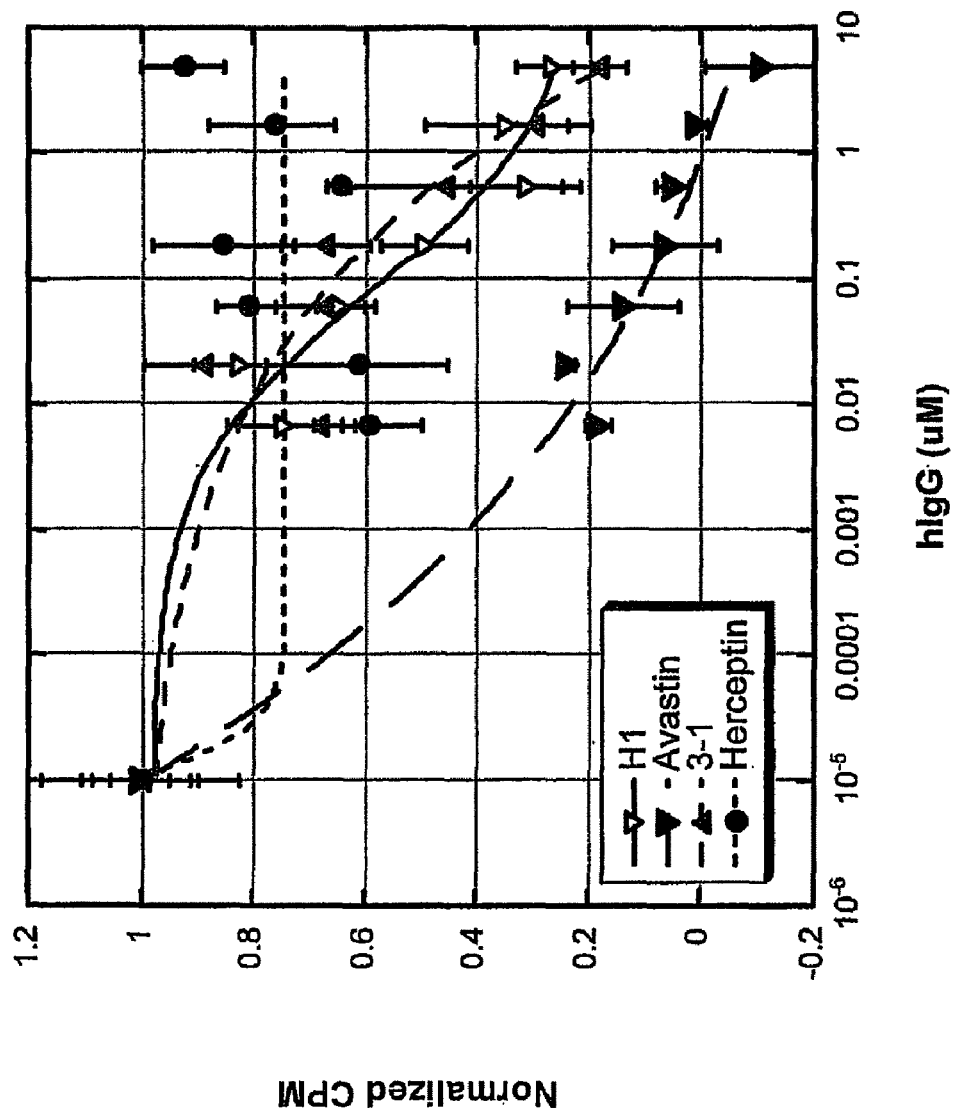
FIG. 42 shows the inhibition of VEGF induced HUVEC cell proliferation with anti-VEGF antibodies.

To determine whether the bH1 and 3-1 antibodies could inhibit $hVEGF_{165}$ induced proliferation of human umbilical vein endothelial (HUVEC) cells, they were tested in a proliferation assay. Human umbilical vein endothelial cells (HUVEC) (Cambrex, East Rutherford, N.J.) were grown and assayed as described (Fuh et al., J. Biol. Chem. 273:11197, 1998). Approximately 4000 HUVECs were plated in each well of the 96-well cell culture plate and incubated in Dulbecco's modified Eagle's/F-12 medium (1:1) supplemented with 1.0% (v/v) fetal bovine serum (assay medium) for 18 hours. Fresh assay medium with fixed amounts of VEGF (0.2 nM final concentration), which was first titrated as a level of VEGF that can stimulate submaximal DNA synthesis, and increasing concentrations of anti-VEGF antibodies (e.g., bH1) were then added to the cells. After incubation at 37° C. for 18 hours, cells were pulsed with 0.5 μCi/well of [$^3$H] Thymidine for 24 hours and harvested for counting with TopCount Microplate Scintillation counter. The results demonstrate that both 3-1 and bH1 can inhibit VEGF-induced growth of HUVEC cells by preventing hVEGF induced signaling and subsequent proliferation. The Avastin® antibody (anti-VEGF) was used as a positive control and the Herceptin® antibody as a negative control (FIG. 42).

Figure 43:
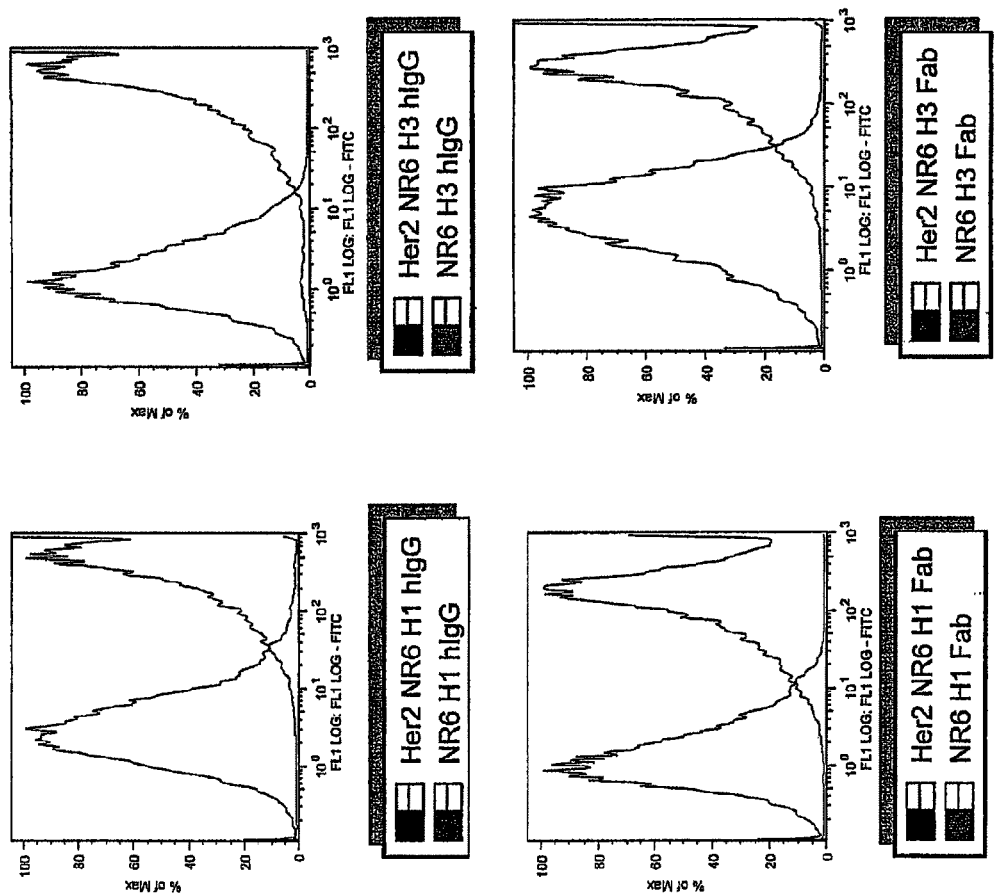
FIG. 43 shows binding of bispecific antibodies to HER2 expressed on NR6 cells.

To study binding of bi-specific anti-Her2/VEGF antibodies to Her2 expressed on mammalian cells, the binding of bH1 and bH3 antibodies to NR6 fibroblast cells over-expressing Her2 (NR6-Her2) was studied by Flow Cytometry. One million NR6-Her2 cells were incubated with 100 μg/ml Fab and IgG for 1 hour, followed by incubation with an Alexa488-conjugated murine anti-human IgG antibody for 1 hour. As negative controls, Fab and IgG binding to non-expressing NR6 cells was studied. As demonstrated in FIG. 43, bH1 and bH3 bind specifically to Her2 on NR6 cells as Fab and as IgG.

Figure 44:
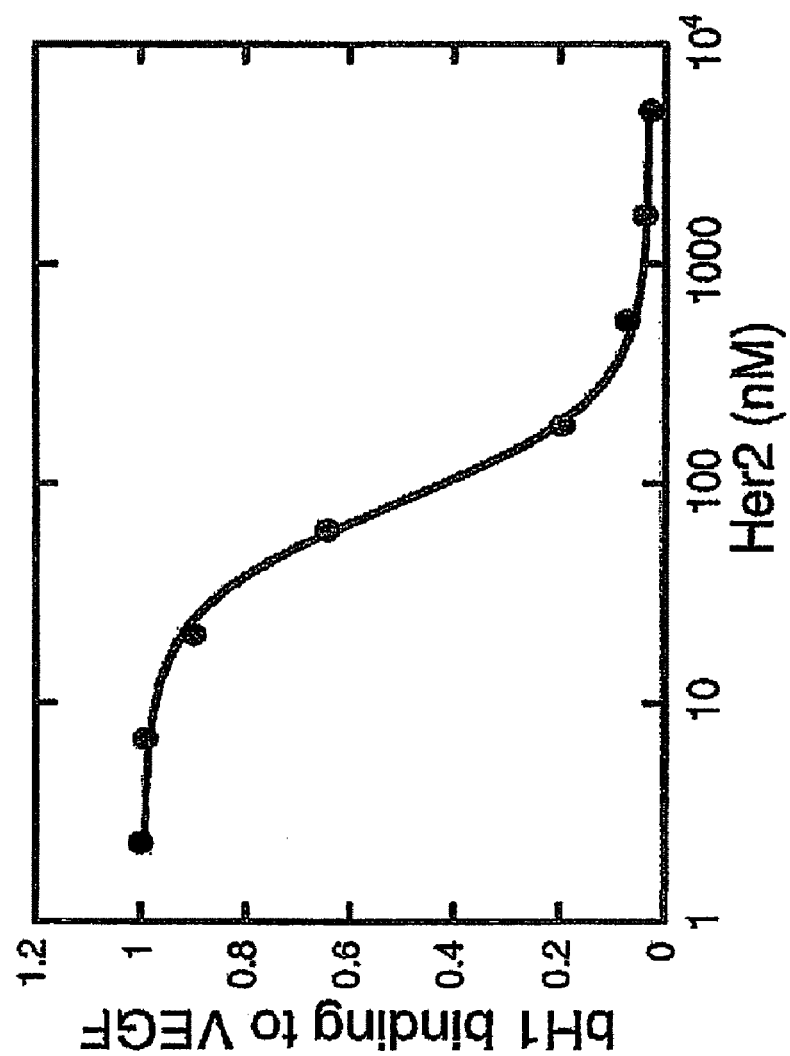
FIG. 44 shows the results of competitive binding experiments for bH1 to VEGF or HER2.
Figure 45:
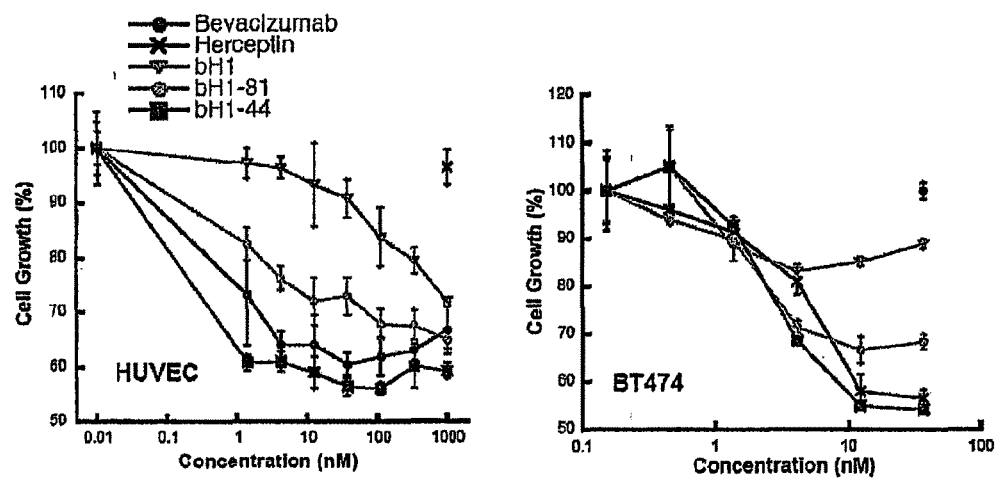
FIG. 45 shows that bH1 and affinity improved variants bH1-44 and bH1-81 IgG inhibit HER2 and VEGF-mediated cell proliferation in vitro.

FIG. 44 shows the results of competitive binding experiments for bH1 to VEGF or HER2. bH1 inhibited VEGF induced proliferation of human umbilical vein endothelial cells (HUVEC) with an $IC_{50}$ of 200 nM, which is consistent with its affinity of 300 nM, and the proliferation of HER2-expressing breast cancer cell line BT474 after 5-day incubation, albeit with lower efficiency than the Herceptin® antibody due to its reduced affinity (FIG. 45). The Herceptin® IgG antibody and bevacizumab (anti-VEGF) served as controls. As shown in FIG. 45, bH1-81 and bH1-44 antibodies inhibit VEGF-induced proliferation of HUVEC cells and growth of BT474 cells to a greater extent than bH1. The increased potencies of the bH1 variants correlate with their relative affinities. The highest affinity variant, bH1-44, inhibits growth of HUVEC and BT474 cells with a potency similar to bevacizumab or Herceptin® antibody, respectively.

To carry out these experiments, VEGF-stimulated HUVECs were treated with increasing concentrations of human IgG and the proliferation inhibition after 2-days of incubation was measured as described in Liang et al. (J. Biol. Chem. 281:951, 2006). Breast cancer cells BT474 were cultured in RPMI media supplemented with 10% FBS. For the assays, $10^4$ cells were plated per well in a 96-well plate and incubated overnight (18 hours) at 37° C. Increasing concentrations of human IgG were added to the cells. The cells were then incubated at 37° C. for five days, followed by addition of 10% AlamarBlue (Biosource International, Camarillo, Calif.) according to the manufacturer's instructions. The antibody-dependent inhibition of proliferation of the HER2 expressing cells was determined by measuring the fluorescent signal after 6 hours.

Example 6

Analysis of Binding Specificity

Figure 46:
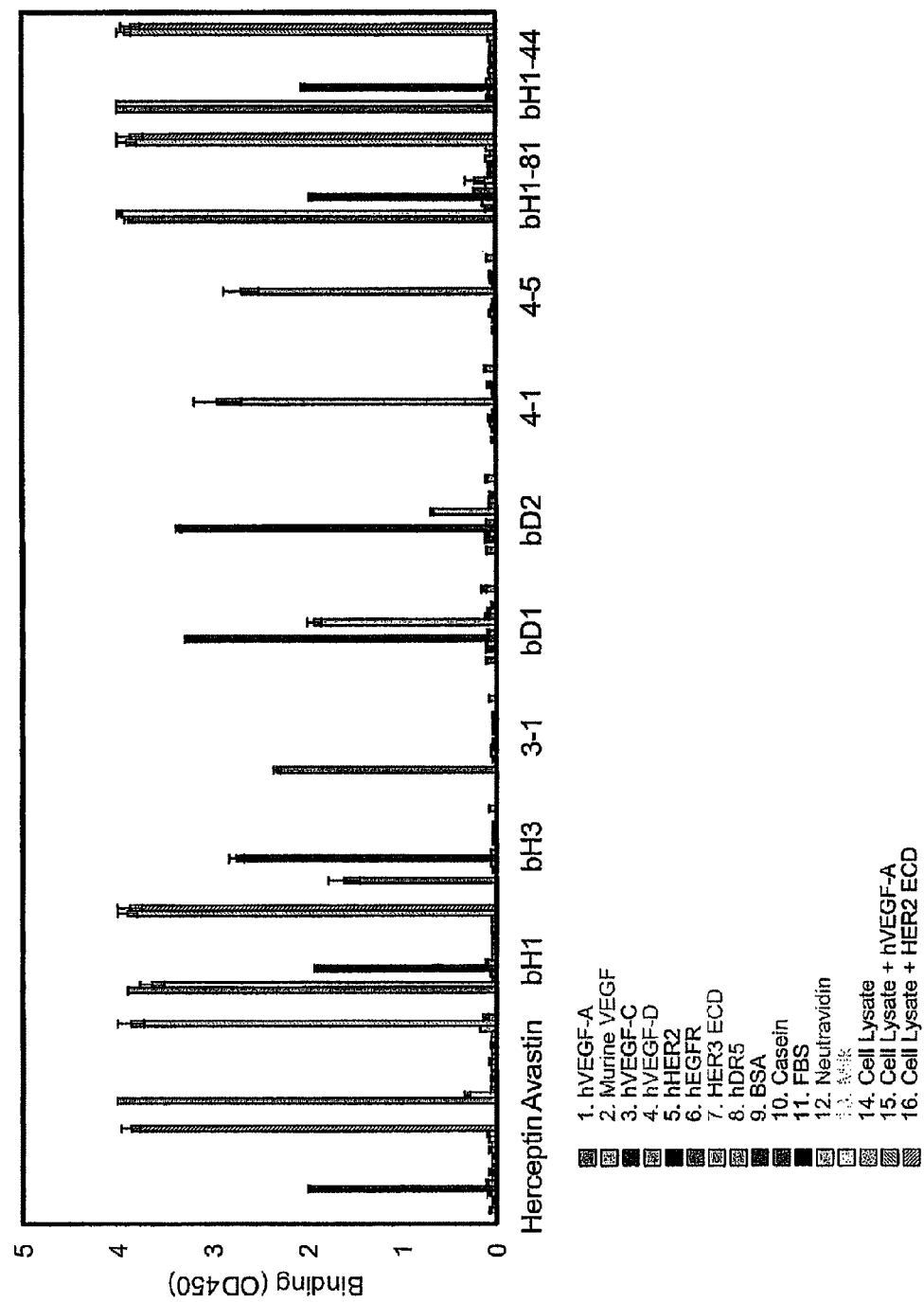
FIG. 46 shows the binding specificity of bispecific antibodies derived from the LC library.

The binding specificity of the antibodies derived from the LC library was determined. IgGs binding to various immobilized purified proteins or cell lysates including the cognate antigens was assayed by ELISA. The antigens were immobilized and incubated with hIgG at a concentration of 15 μg/mL for an hour. Bound IgG were detected spectrophotometrically (optical density at 450 nm; y-axis; FIG. 46). The proteins included in the assay were (left to right in FIG. 46): vascular endothelial growth factor A (VEGF), murine vascular endothelial growth factor (murine VEGF), vascular endothelial growth factor C, (hVEGF-C), vascular endothelial growth factor D, (hVEGF-D), HER2 extracellular domain (HER2ECD), epidermal growth factor receptor extracellular domain (hEGFR), ErbB3/HER3 extracellular domain (HER3ECD), human death receptor 5 (hDR5), bovine serum albumin (BSA), Casein, Fetal Bovine Serum (FBS), Neutravidin, 5% milk, mouse fibroblast cell lysate, and mouse fibroblast cell lysate spiked with hVEGF-A or HER2ECD. In FIG. 46, error bars represent the standard error means (SEM) of duplicates. The antibodies bH3, 3-1, bD1, bD2, 4-1, and 4-5 were not tested for binding to murine VEGF, HER3ECD, Neutravidin, 5% milk, cell lysate spiked with hVEGF-A, and cell lysate spiked with HER2ECD.

Figure 47:
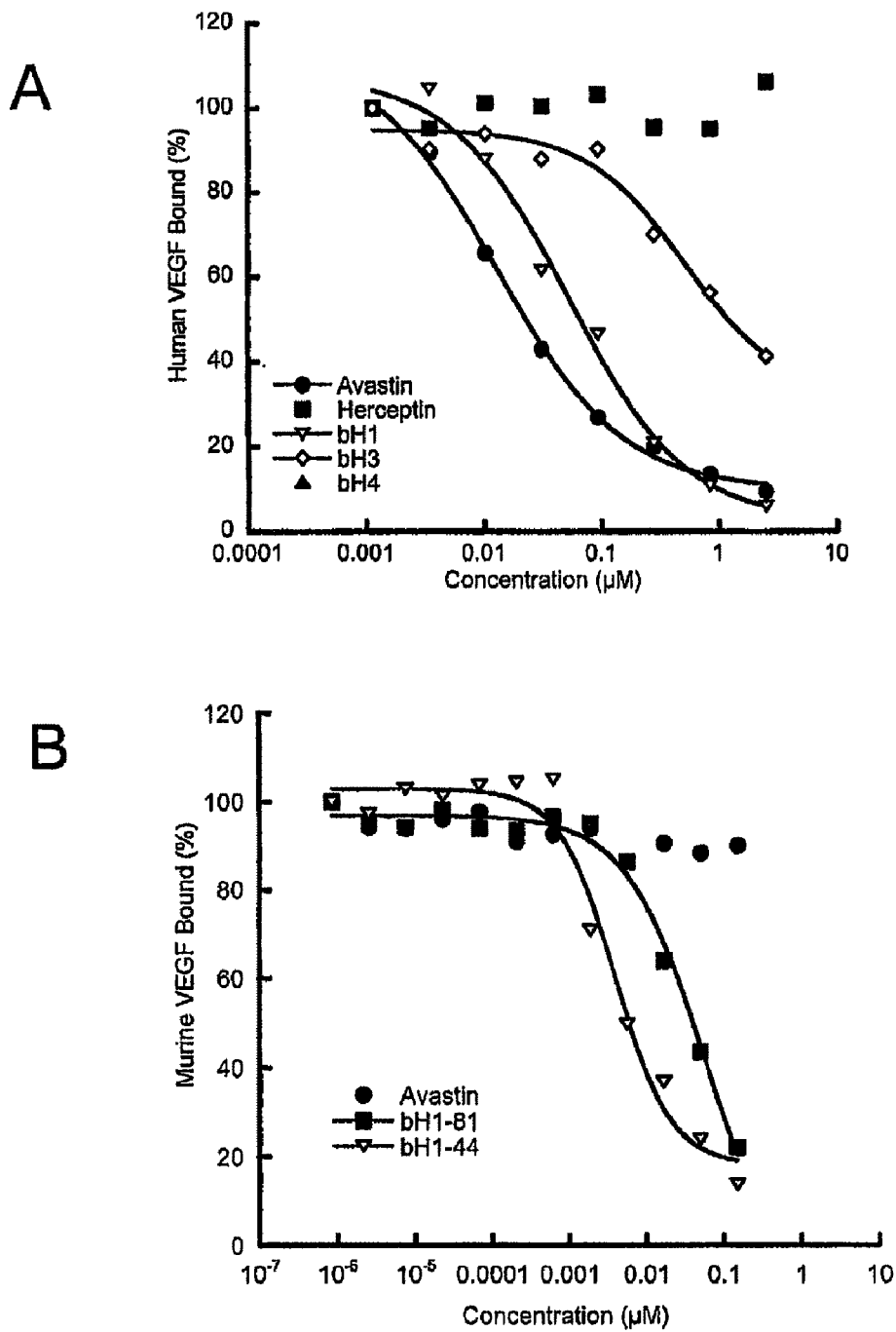
FIG. 47 shows that anti-VEGF antibodies block VEGF binding to VEGFR2 receptors.

The ability of various antibodies (Avastin® antibody, Herceptin® antibody, bH1, bH3, bH4, bH1-81, and bH1-44) to block VEGF binding to VEGF receptors was also determined (FIG. 47). Biotinylated human $VEGF_{165}$ (FIG. 47A) or murine $VEGF_{164}$ (FIG. 47B) were equilibrated with increasing concentrations of IgG α-axis). Unbound VEGF was captured on immobilized human VEGFR2-ECD Fc fusion protein and detected spectrophotometrically (optical density at 450 nm, y-axis). Similar inhibition was also observed with VEGFR1. The anti-VEGF antibodies block VEGF binding to VEGF receptors.

Figure 48:
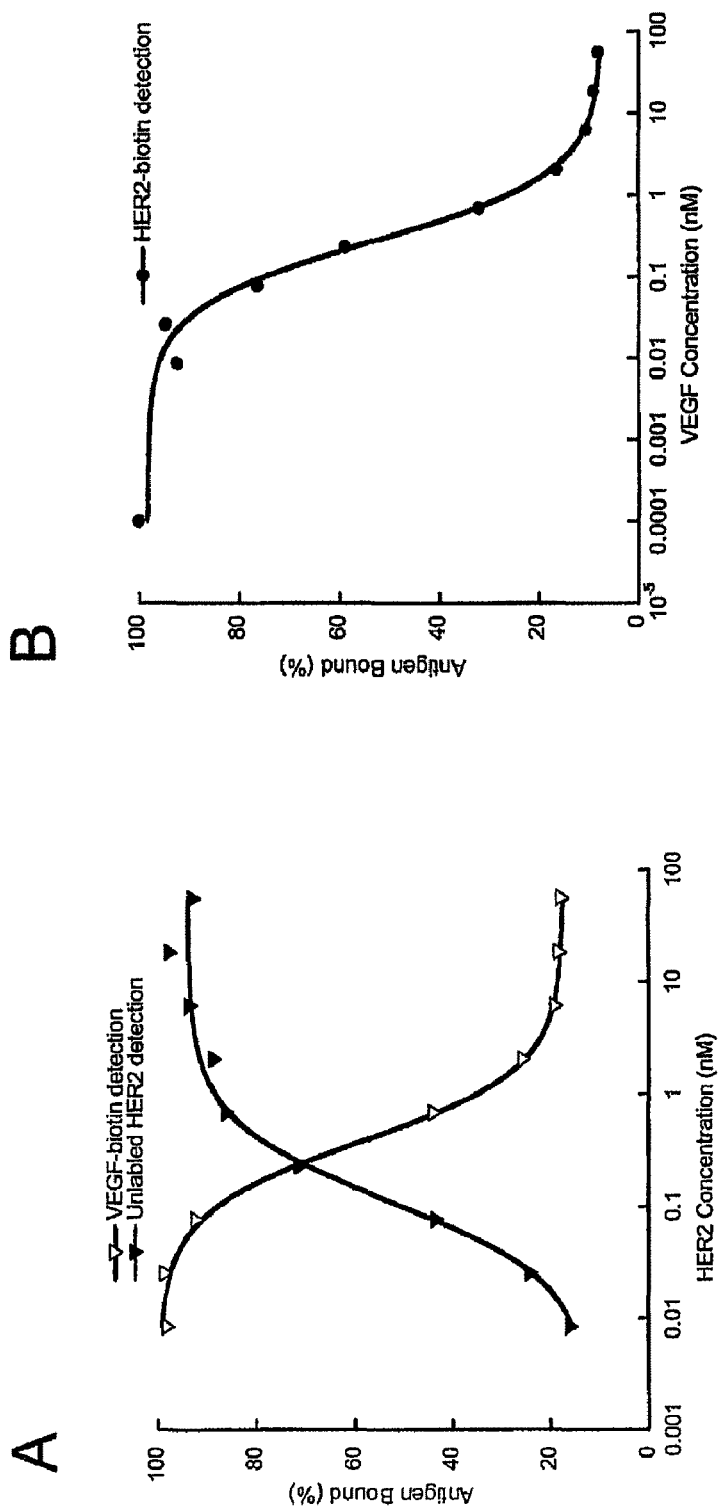
FIGS. 48A and 48B show that VEGF and HER2 compete for binding to bH1-44 bispecific IgG in solution.

The antigens VEGF and HER2 were shown to compete for binding to bH1-44 bispecific IgG antibody in solution (FIG. 48). Human bH1-44 IgG antibody at a concentration of 0.1 nM was incubated with 0.1 nM biotinylated human $VEGF_{165}$ in the presence of increasing concentrations of HER2ECD. bH1-44 was captured by immobilized anti-human Fc and bH1-44-bound biotin-VEGF detected with streptavidin-HRP. HER2ECD bound to captured bH1-44 was detected using a murine anti-HER2 antibody binding a non-overlapping epitope on HER2 followed by an HRP-conjugated goat anti-mouse IgG (FIG. 48A). Human bH1-44 IgG at a concentration of 0.2 nM was incubated with 0.6 nM biotinylated HER2 in the presence of increasing concentrations of human $VEGF_{165}$. bH1-44 was captured by immobilized anti-human Fc and bH1-44-bound biotin-HER2 detected with streptavidin-HRP (FIG. 48B).

Figure 49:
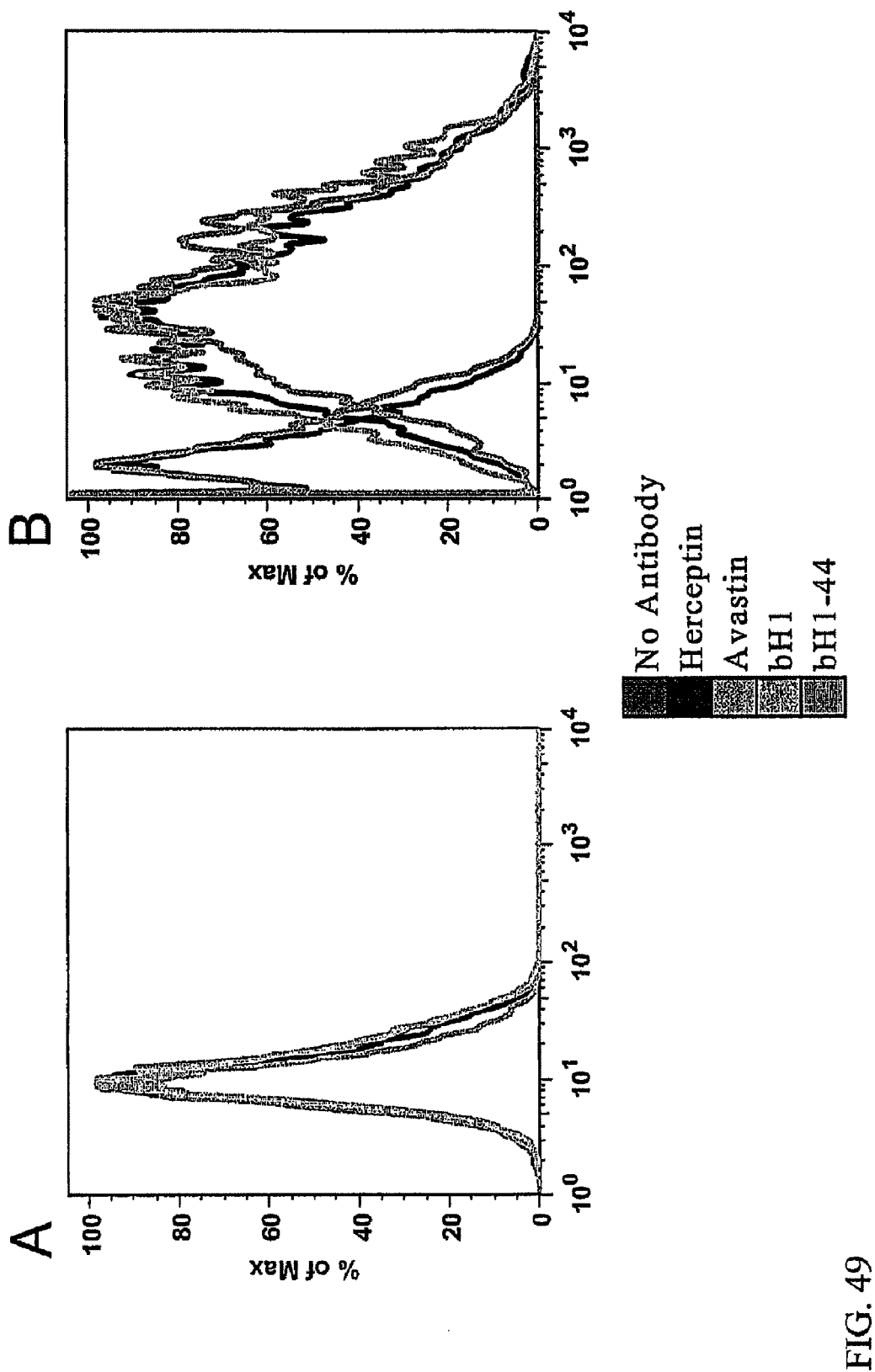
FIGS. 49A and 49B show that the bispecific antibodies bH1 and bH1-44 bind to HER2 expressing mouse fibroblast cells (NR6.

The specific binding of bH1 and bH1-44 to cells as also detected by using FACS (Fluorescence Activated Cell Sorting; FIG. 49). The bispecific antibodies (bH1 and bH1-44) bind to HER2 expressing mouse fibroblast (NR6) cells (FIG. 49B) but not to HER2 negative NR6 cells (FIG. 49A). 0.5-1 million cells were incubated with 15 μg/mL hIgG on ice for an hour. Primary antibodies bound to cells were detected using a secondary fluorescent PE conjugated goat-anti-human IgG. The cells were analyzed using a FACS Calibur flow cytometer. bH1 and bH1-44 do not cross react with the rat ortholog of HER2, as no binding was detected to mouse fibroblast cells transfected with rat neu (rat ortholog of HER2).

Figure 50:
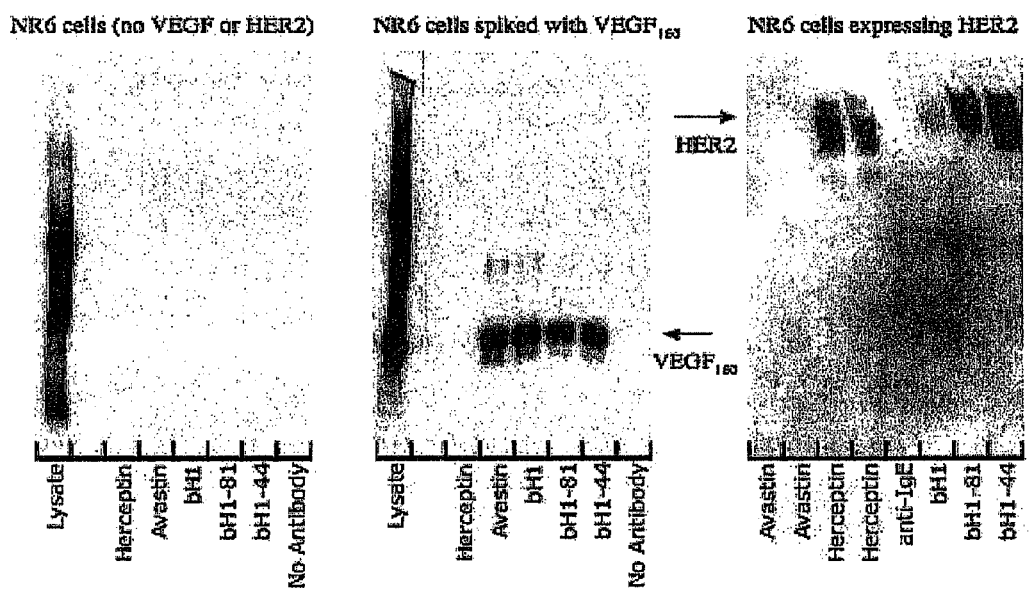
FIG. 50 shows that the bispecific bH1 antibody specifically immunoprecipitates VEGF or HER2 from mouse fibroblast (NR6) lysates, but not other proteins.

To further characterize the specificity of the bH1 antibody variants bH1-81 and bH1-44, immunoprecipitation experiments were conducted and the bH1 antibody variants were shown to specifically immunoprecipitate VEGF or HER2 from mouse fibroblast (NR6) lysates, but not other proteins (FIG. 50). NR6 cells were non-specifically biotinylated, lysed, and cell membrane proteins detergent solubilized. Cell lysates corresponding to 5-10 million cells/mL of NR6 cells, NR6 cells spiked with 0.1 μg/mL biotinylated $VEGF_{165}$, or HER2 over expressing NR6 cells were incubated with 15 μg/mL antibody. The antibody was captured using proteinA-coated sepharose beads and bound proteins eluted. The eluted proteins were separated by SDS-PAGE. Cell lysates corresponding to approximately 25-50,000 cells and immunoprecipate from approximately 0.12-0.25 million cells were loaded onto the gel. Captured biotinylated proteins were detected by Western blotting using streptavidin-HRP.

Example 7

Analysis of IgG Activity in in vivo Assays

To assess whether the dual activity of these antibodies in vitro translates to a corresponding activity in vivo, we employed mouse engraft tumor models known to be responsive to treatment by anti-VEGF antibody (Colo205, a colorectal cancer cell line) or Herceptin® antibody (BT474M1, breast cancer cell line). In particular, Colo205 xenografts were used in nu/nu mice and BT474M1 xenografts were used in beige nude XID mice. All animal studies were in accordance with the guidelines of the American Association for Accreditation of Laboratory Animal Care and the Genentech Institutional Animal Care and Use Committee.

In particular, the BT474M1 (in-house) and Colo205 (ATCC, Manassas, Va.) cells were cultured in RPMI media/ 10% fetal bovine serum. $5\times10^6$ BT474M1 cells suspended in Hank's Buffered Salt Solution (HBSS) and matrigel (1:1) mixture were injected into the mammary fat pad of Harlan beige nude XID mice (Indianapolis, Ind.) implanted with an estradiol pellet subcutaneously. For Colo205 xenografts, $5\times10^6$ Colo205 cells in HBSS were subcutaneously injected into Charles River nu/nu mice (Hollister, Calif.). When the mean tumor size reached ~200 mm$^3$, the mice were randomly grouped into 7 groups of 8 mice (BT474M1) or 10 mice (Colo205). Antibodies were administered intraperitoneally once a week. The tumor sizes were measured twice a week.

Volumes were calculated as V=0.5ab$^3$ (a is the longest dimension of the tumor and b perpendicular to a). The statistical evaluation used one-way analysis followed by two-tailed student t tests. Adjustment of the alpha level due to multiple comparisons (Bonferroni) did not alter the significance of our conclusions. Partial responses (PR) were defined as a response of 50-99% reduction in tumor volume compared to V0, Serum samples were collected 7 days after the first and third treatment. The concentration of human antibody was determined using ELISA. Donkey anti-human IgG Fc was immobilized on an immuno plate. Dilutions of serum and an antibody standard were incubated on the plate for 2 hours. Bound antibody was detected by Horseradish Peroxidase conjugated goat anti-human IgG Fc followed by TMB Substrate/1 M Phosphoric Acid. The plates were read at 450/620 nm. Sample concentrations were determined using a 4-parameter algorithm.

The bH1-44 treated groups were compared with groups treated with anti-VEGF (B20-4.1) (Liang et al., J. Biol. Chem. 281:951, 2006), Herceptin® antibody, or the combination (Herceptin® antibody+anti-VEGF) to further establish that bH1-44 antibody was capable of inhibiting VEGF and HER2 mediated tumor growth. In all groups, antibody was present in serum from Colo205 xenografts at high levels (estimated by ELISA) 7 days after the start of treatment, indicating normal pharmacokinetics (Table 6).

TABLE 6

Antibody serum levels

| Group | Antibody Concentration (µg/ml) | |
|---|---|---|
| | Mean | SD |
| Control IgG 10 mg/kg | 65 | 14 |
| Herceptin ® 10 mg/kg | 83 | 47 |
| Anti-VEGF 10 mg/kg | 20 | 8 |
| Anti-VEGF + Herceptin ® 10 + 10 mg/kg | 41 | 25 |
| bH1-44 10 mg/kg | 30 | 12 |
| bH1-44 20 mg/kg | 37 | 9 |

Figure 51:
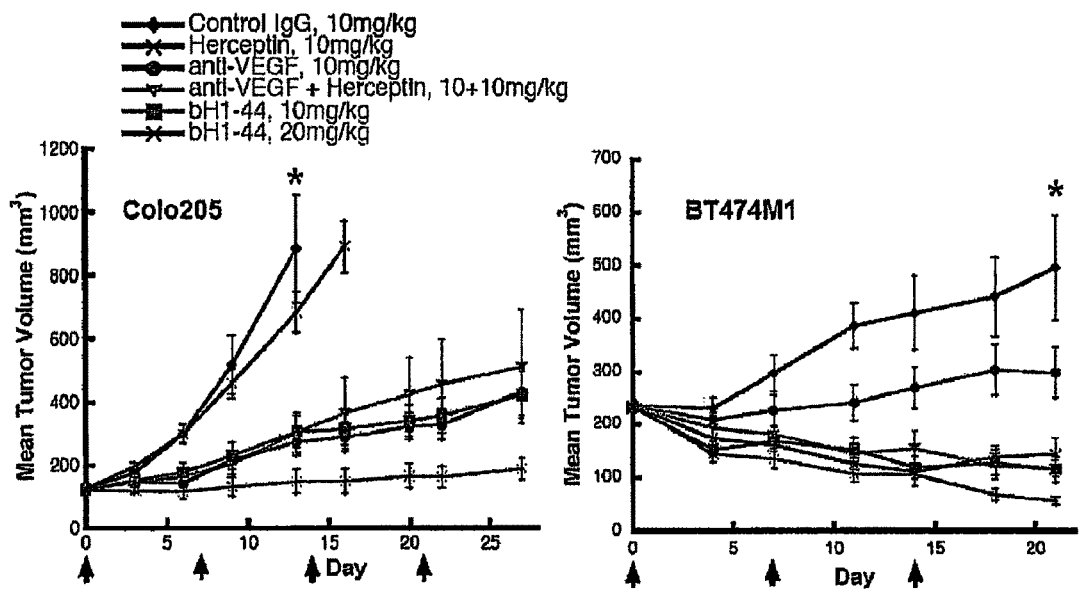
FIG. 51 shows tumor inhibition of bH1-44 in Colo205 and BT474M1 xenografts in immuno-compromised mice.

For each group, n = 5;
SD = Standard Deviation bH1-44 dosed weekly at 10 mg/kg inhibited Colo205 tumor growth compared to control antibody (p<0.0001, n=10), with similar efficacy as anti-VEGF (10 mg/kg/week), while Herceptin® antibody had no effect on Colo205 growth (p=0.12, n=10). As expected, the combination treatment showed similar efficacy as anti-VEGF alone. bH1-44 antibody administered at 10 and 20 mg/kg/week yielded dose-dependent responses. In the BT474M1 model, significant tumor growth inhibition was observed in the group of mice treated with bH1-44 antibody (10 mg/kg/week, p=0.0005, n=8 and 20 mg/kg/week, p=0.0001, n=7). Like the groups dosed with Herceptin® antibody or Herceptin®/antiVEGF combination, more than half of the tumors treated with bH1-44 antibody showed regression of more than 50% from the initial volume (i.e., partial response, FIG. 51). Anti-VEGF alone, on the other hand, only exhibited modest growth inhibitory effects on BT474M1 compared to control (p=0.06, n=7) and exhibited no partial response. The bispecific bH1-44 antibody was thus shown to inhibit two distinct mechanisms important for tumor growth in vivo.

The above results indicate the potential of the affinity-improved variants of bH1 antibody (e.g., bH1-44 and bH1-81) to inhibit two mechanisms that are important for tumor growth in vivo.

Example 8

Characterization of VEGF and HER2 Binding Interfaces with bH1 and bH1-44

To further compare the structural characteristics of bH1 and bH1-44, the VEGF and HER2 binding interfaces with these antibodies were identified. The structural contacts listed in Table 7 were identified based on the crystal structure coordinates 3BDY (bH1/VEGF) and 3BE1 (bH1/HER2). The binding interface was calculated using the program XSAE. This program defined the interface as polar, hydrophobic, and mixed. Table 7 lists the bH1 residues with >25% of the total surface area buried upon HER2 or VEGF binding. Table 7 also lists the VEGF and HER2 residues within 4.5 Å of the bH1 residues. The surface area of each residue that is buried upon complex formation was calculated using IMOL based on the coordinates of the crystal structures 3BDY, 3BE1, and 1N8Z (PDB). The polar and hydrophobic interface areas reported in Table 11 reflect the polar interface area and half of the mixed. The hydrophobic interface area reported consists of the hydrophobic areas and half of the mixed.

The crystal structure and alanine scanning showed that bH1 retains the same binding epitope on HER2 as the Herceptin® antibody (Bostrom et al., 2009). The crystal structure of Herceptin® Fab in complex with HER2 superimposes well onto the bH1/HER2 complex (r.m.s.d of 0.8 Å) (Bostrom et al., 2009; Cho et al., 2003). Further, the Herceptin® antibody residues that contribute more than 10% of the total binding energy based on alanine scanning mutagenesis are conserved, and many of them are also part of the binding hotspots of bH1 and bH1-44 (Bostrom et al., 2009; Kelley and O'Connell, 1993) (Table 14, FIG. 62). The interfaces between bH1/VEGF and bH1/HER2 bury 1506 Å$^2$ and 1579 Å$^2$, respectively, and are mainly hydrophobic (60% and 63%, respectively). The Herceptin®/HER2 binding interface has similar size and composition as the bH1/HER2 interface (1524 Å$^2$, 60% hydrophobic, Table 11), and is also characterized by high shape complementarity (Table 8) (Bostrom et al., 2009).

TABLE 7

List of structural contacts of the complex of bH1 Fab/HER2 ECD and bH1/Fab/VEGF$_{109}$. The table lists residues with >25% of the total surface area buried upon HER2 and VEGF binding. The VEGF and HER2 residues within 4.5 Å of the bH1 residues are listed. The surface area of each residue that is buried upon complex formation was calculated using IMOL based on the coordinates of the crystal structures 3BDY, 3BE1, and 1N8Z (PDB).

| bH1 residue | | Area buried by HER2 (%) | HER2 residues contacting bH1 | Area buried by VEGF (%) | VEGF residues contacting bH1 |
|---|---|---|---|---|---|
| Heavy Chain | Y33 | 48 | E558 F573 | 87 | H86 |
| | R50 | 97 | E558 D560 F573 | 35 | H86 |
| | Y52 | | | 30 | H86 |
| | Y56 | 42 | P557 E558 | | |
| | R58 | 50 | E558 Q561 | | |

TABLE 7-continued

List of structural contacts of the complex of bH1 Fab/HER2 ECD and bH1/Fab/VEGF$_{109}$. The table lists residues with >25% of the total surface area buried upon HER2 and VEGF binding. The VEGF and HER2 residues within 4.5 Å of the bH1 residues are listed. The surface area of each residue that is buried upon complex formation was calculated using IMOL based on the coordinates of the crystal structures 3BDY, 3BE1, and 1N8Z (PDB).

| bH1 residue | | Area buried by HER2 (%) | HER2 residues contacting bH1 | Area buried by VEGF (%) | VEGF residues contacting bH1 |
|---|---|---|---|---|---|
| | W95 | 100 | P572 F573 | 61 | H86 Q87 |
| | G99 | 93 | D570 P579 K593 | 75 | K48 I83 Q89 |
| | Y100a | 80 | D570 P571 P572 F573 | 88 | I83 K84 P85 H86 Q87 G88 Q89 |
| Light Chain | S28 | | | 59 | I91 G92 E93 |
| | I29 | | | 77 | R82 H90 I91 G92 |
| | S30 | | | 69 | H90 I91 |
| | G31 | | | 85 | G88 Q89 H90 I91 |
| | Y32 | 97 | D570 P571 A600 C601 Q602 | 89 | Q89 H90 |
| | W50 | 62 | K593 P603 | 59 | F17 M81 Q89 |
| | Y53 | 44 | P603 C604 P605 | 74 | F17 M18 I91 |
| | H91 | 90 | P571 P572 | 81 | G88 Q89 |
| | Y92 | 55 | K569 P571 P572 | 76 | Y45 K84 G88 Q89 H90 |
| | T93 | | | 61 | K84 Q87 G88 |
| | T94 | 68 | D560 P572 | 55 | H86 Q87 |

The shape complementarity (represented as Sc in Table 8) between the antibody and the antigen was determined as described (Lawrence et al., 1993). The high shape complementarity in the bH1/VEGF and bH1/HER2 complexes, similar to the complementarity between the Herceptin® antibody and HER2, are in the range of reported antibody-antigen complexes (Sc ~0.64-0.68; Lawrence et al., 1993). Superposition of HER2 with bH1 in its VEGF-bound conformation or VEGF with bH1 in its HER2-bound form reveals little shape complementarity observed when juxtaposing an antibody with an unrelated antigen. (Sc 0.35; Lawrence et al., 1993). The results demonstrate the extent to which bH1 rearranges to accommodate the two different antigens.

TABLE 8

Different surface conformations of bH1 for binding HER2 and VEGF. Shape complementarity in antibody/antigen complexes

| Antibody | Antigen | Sc* |
|---|---|---|
| Herceptin | HER2 | 0.75 |
| bH1 | HER2 | 0.72 |
| bH1 | VEGF | 0.68 |
| bH1 (VEGF-bound conformation) | HER2 | 0.40 |
| bH1 (HER2-bound conformation) | VEGF | 0.44 |

*Sc = Median Shape Complementarity Statistic

The affinity of bH1 was improved by selecting the high affinity variant bH1-44 from phage-displayed antibody libraries of bH1. Shotgun alanine scanning mutagensis demonstrated that bH1-44 conserved the hotspot for antigen binding of bH1 (Tables 9A-B, 10, and 14). Shotgun alanine scanning mutagensis of bH1-44 was performed using the techniques described above for the shotgun alanine scanning mutagenesis of bH1.

In Tables 9A-B the effects of mutation to alanine (m1), or additional mutations (m2, m3; due to limitations of shotgun codons), or to a homologous amino acid (m4) are calculated as the ratio of occurrence of wild type (wt) or wt/mut for VEGF (Table 9A) or HER2 (Table 9B) binding clones. When the wt was alanine, it was substituted by glycine (m1). The wt/mut ratios are corrected for protein folding/expression effects by division with wt/mut ratios from display selection to obtain the F values. Display selection was performed independently by selecting clones binding to protein L, which binds a non-linear epitope of the antibody light chain. As only the Fab heavy chain is fused to the phage coat protein (p3), protein L binding indicates proper folding and association of light chain and heavy chain.

In Table 10, the antibody residues of bH1 and bH1-44 that contact VEGF and/or HER2 in the crystal structure are listed. The energetic hotspots for binding are defined by the antibody residues that result in $\Delta\Delta G_{wt/ala}$ greater than approximately 10% of the total binding energy of the interaction.

The data in Table 11 indicate that the polarity and size of the binding interfaces are similar between bH1/VEGF, bH1/HER2, and the Herceptin®/HER2 complex. The polarity of each interface was analyzed using XSAE. All the numbers depicted in Table 11 represent the area in Å$^2$, unless otherwise indicated.

TABLE 9A

Shotgun alanine- and homolog-scanning of bH1-44 Fab for binding to VEGF.

| | Antigen selection (VEGF) | | | | Display Selection (Protein L) | | | | Fwt/mut values | |
|---|---|---|---|---|---|---|---|---|---|---|
| | wt/m1 | wt/m2 | wt/m3 | wt/m4 | wt/m1 | wt/m2 | wt/m3 | wt/m4 | Fwt/m1 | Fwt/m2 |
| CDR-L1 | | | | | | | | | | |
| Q27 | 0.3 | 1.0 | 9.0 | 1.2 | 0.8 | 0.9 | 0.4 | 2.8 | 0.4 | 1.1 |
| N28 | 1.8 | 0.6 | 3.5 | 1.2 | 0.6 | 0.9 | 1.0 | 8.4 | 2.8 | 0.7 |
| I29 | 39.0 | 39.0 | 3.9 | 36.0 | 0.8 | 0.7 | 0.4 | 0.8 | 46.8 | 59.8 |
| A30 | 2.8 | NA | NA | 1.7 | 0.4 | NA | NA | 0.2 | 6.5 | |
| K30a | 3.0 | 2.7 | 9.0 | 1.6 | 1.4 | 3.1 | 1.1 | 0.2 | 2.1 | 0.9 |
| T30b | 7.0 | NA | NA | 1.4 | 0.9 | NA | NA | 0.5 | 7.7 | |

TABLE 9A-continued

Shotgun alanine- and homolog-scanning of bH1-44 Fab for binding to VEGF.

| | | | | | | | | | | |
|---|---|---|---|---|---|---|---|---|---|---|
| I30c | 16.0 | 5.3 | 0.5 | 0.9 | 2.3 | 2.1 | 0.7 | 1.0 | 7.1 | 2.6 |
| S30d | 15.7 | NA | NA | 74.0 | 1.7 | NA | NA | 0.5 | 9.1 | |
| G31 | 24.0 | NA | NA | 74.0 | 2.6 | NA | NA | 3.0 | 9.4 | |
| Y32 | 46.0 | 23.0 | 46.0 | 74.0 | 0.5 | 1.9 | 0.3 | 1.6 | 99.1 | 12.4 |
| CDR-L2 | | | | | | | | | | |
| W50 | 46.0 | 15.3 | 46.0 | 74.0 | 2.3 | 1.5 | 2.4 | 1.1 | 20.4 | 10.2 |
| G51 | 24.0 | NA | NA | 74.0 | 7.3 | NA | NA | 7.5 | 3.3 | |
| S52 | 15.7 | NA | NA | 36.0 | 4.1 | NA | NA | 7.5 | 3.9 | |
| F53 | 22.0 | 44.0 | 14.7 | 5.7 | 1.9 | 2.4 | 1.4 | 0.4 | 11.6 | 18.1 |
| CDR-L3 | | | | | | | | | | |
| H91 | 7.3 | 44.0 | 44.0 | 73.0 | 0.0 | 0.1 | 0.3 | 2.6 | 150.3 | 880.0 |
| Y92 | 48.0 | 48.0 | 48.0 | 13.8 | 3.8 | 6.3 | 1.0 | 2.8 | 12.6 | 7.6 |
| S93 | 1.0 | NA | NA | 1.7 | 3.0 | NA | NA | 2.5 | 0.4 | |
| S94 | 15.7 | NA | NA | 3.4 | 1.0 | NA | NA | 0.9 | 15.3 | |
| CDR-H1 | | | | | | | | | | |
| S30 | 1.2 | NA | NA | 1.7 | 1.2 | NA | NA | 1.3 | 1.0 | |
| G31 | 2.4 | NA | NA | 5.6 | 1.2 | NA | NA | 5.0 | 2.0 | |
| T32 | 0.5 | NA | NA | 0.5 | 0.9 | NA | NA | 0.6 | 0.5 | |
| Y33 | 10.2 | 1.0 | 2.2 | 12.5 | 1.4 | 2.0 | 0.8 | 2.3 | 7.1 | 0.5 |
| CDR-H2 | | | | | | | | | | |
| R50 | 0.6 | 0.9 | 20.5 | 0.4 | 2.1 | 1.3 | 70.0 | 1.3 | 0.3 | 0.7 |
| Y52 | 1.8 | 30.0 | 7.5 | 1.4 | 2.0 | 2.5 | 1.8 | 2.7 | 0.9 | 11.9 |
| S53 | 1.4 | NA | NA | 1.0 | 1.2 | NA | NA | 1.1 | 1.2 | |
| E54 | 1.2 | NA | NA | 0.7 | 0.4 | NA | NA | 1.0 | 3.4 | |
| Y56 | 9.2 | 6.5 | 6.9 | 0.7 | 1.6 | 2.3 | 1.3 | 1.2 | 5.8 | 2.8 |
| R58 | 1.5 | 1.8 | 8.1 | 1.3 | 2.1 | 2.3 | 4.9 | 2.7 | 0.7 | 0.8 |
| CDR-H3 | | | | | | | | | | |
| W95 | 139.0 | 139.0 | 8.7 | 243.0 | 0.8 | 0.2 | 0.3 | 4.5 | 185.3 | 685.7 |
| V96 | 0.5 | NA | NA | 1.4 | 2.1 | NA | NA | 1.5 | 0.2 | |
| G97 | 0.8 | NA | NA | 2.9 | 0.9 | NA | NA | 5.7 | 0.9 | |
| V98 | 2.3 | NA | NA | 1.2 | 1.5 | NA | NA | 0.8 | 1.6 | |
| G99 | 2.1 | NA | NA | 3.0 | 1.2 | NA | NA | 1.8 | 1.7 | |
| F100 | 6.2 | 9.5 | 5.0 | 2.2 | 2.0 | 2.0 | 0.9 | 1.8 | 3.0 | 4.7 |
| Y100a | 27.2 | 27.2 | 15.1 | 2.2 | 1.5 | 1.5 | 0.6 | 0.9 | 17.9 | 18.6 |

| | Fwt/mut values | | $\Delta\Delta G_{wt/mut}$ (kcal/mol) | | | |
|---|---|---|---|---|---|---|
| | Fwt/m3 | Fwt/m4 | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L1 | | | | | | |
| Q27 | 20.3 | 0.5 | — | 0.04 | 1.8 | −0.5 |
| N28 | 3.5 | 0.1 | 0.6 | −0.2 | 0.7 | −1.1 |
| I29 | 8.8 | 42.7 | 2.3 | 2.4 | 1.3 | 2.2 |
| A30 | | 9.9 | 1.1 | | | 1.4 |
| K30a | 7.8 | 8.7 | 0.4 | −0.1 | 1.2 | 1.3 |
| T30b | | 2.7 | 1.2 | | | 0.6 |
| I30c | 0.7 | 0.9 | 1.2 | 0.6 | −0.2 | −0.1 |
| S30d | | 150.4 | 1.3 | | | 3.0 |
| G31 | | 24.3 | 1.3 | | | 1.9 |
| Y32 | 152.2 | 45.9 | 2.7 | 1.5 | 3.0 | 2.3 |
| CDR-L2 | | | | | | |
| W50 | 19.2 | 65.1 | 1.8 | 1.4 | 1.7 | 2.5 |
| G51 | | 9.8 | 0.7 | | | 1.4 |
| S52 | | 4.8 | 0.8 | | | 0.9 |
| F53 | 10.8 | 13.5 | 1.5 | 1.7 | 1.4 | 1.5 |
| CDR-L3 | | | | | | |
| H91 | 154.0 | 27.9 | 3.0 | 4.0 | 3.0 | 2.0 |
| Y92 | 46.7 | 5.0 | 1.5 | 1.2 | 2.3 | 1.0 |
| S93 | | 0.7 | −0.6 | | | −0.2 |
| S94 | | 3.7 | 1.6 | | | 0.8 |
| CDR-H1 | | | | | | |
| S30 | | 1.3 | 0.0 | | | 0.2 |
| G31 | | 1.1 | 0.4 | | | 0.1 |
| T32 | | 0.9 | −0.4 | | | −0.1 |
| Y33 | 2.6 | 5.5 | 1.2 | −0.4 | 0.6 | 1.0 |

TABLE 9A-continued

Shotgun alanine- and homolog-scanning of bH1-44 Fab for binding to VEGF.

| | | | | | | |
|---|---|---|---|---|---|---|
| CDR-H2 | | | | | | |
| R50 | 0.3 | 0.3 | −0.7 | −0.2 | −0.7 | −0.8 |
| Y52 | 4.3 | 0.5 | −0.1 | 1.5 | 0.9 | −0.4 |
| S53 | | 0.9 | 0.1 | | | 0.0 |
| E54 | | 0.7 | 0.7 | | | −0.3 |
| Y56 | 5.3 | 0.6 | 1.0 | 0.6 | 1.0 | −0.3 |
| R58 | 1.6 | 0.5 | −0.2 | −0.2 | 0.3 | −0.4 |
| CDR-H3 | | | | | | |
| W95 | 27.2 | 53.7 | 3.1 | 3.9 | 2.0 | 2.4 |
| V96 | | 1.0 | −0.9 | | | 0.0 |
| G97 | | 0.5 | −0.1 | | | −0.4 |
| V98 | | 1.4 | 0.3 | | | 0.2 |
| G99 | | 1.7 | 0.3 | | | 0.3 |
| F100 | 5.4 | 1.2 | 0.7 | 0.9 | 1.0 | 0.1 |
| Y100a | 26.6 | 2.5 | 1.7 | 1.7 | 1.9 | 0.5 |

NA = Mutation not included.

TABLE 9B

Shotgun alanine- and homolog-scanning of bH1-44 Fab for binding to HER2.

| | Antigen Selection (HER2) | | | | Display Selection (Protein L) | | | | Fwt/mut values | |
|---|---|---|---|---|---|---|---|---|---|---|
| | wt/m1 | wt/m2 | wt/m3 | wt/m4 | wt/m1 | wt/m2 | wt/m3 | wt/m4 | Fwt/m1 | Fwt/m2 |
| CDR-L1 | | | | | | | | | | |
| Q27 | 0.9 | 1.0 | 0.6 | 1.4 | 0.8 | 0.9 | 0.4 | 2.8 | 1.2 | 1.0 |
| N28 | 1.3 | 0.9 | 1.2 | 1.1 | 0.6 | 0.9 | 1.0 | 8.4 | 2.0 | 1.0 |
| I29 | 1.5 | 1.9 | 0.8 | 0.8 | 0.8 | 0.7 | 0.4 | 0.8 | 1.8 | 3.0 |
| A30 | 0.3 | NA | NA | 1.1 | 0.4 | NA | NA | 0.2 | 0.8 | |
| K30a | 1.5 | 2.6 | 1.8 | 1.1 | 1.4 | 3.1 | 1.1 | 0.2 | 1.1 | 0.8 |
| T30b | 1.0 | NA | NA | 0.3 | 0.9 | NA | NA | 0.5 | 1.1 | |
| I30c | 4.4 | 5.3 | 1.8 | 1.5 | 2.3 | 2.1 | 0.7 | 1.0 | 1.9 | 2.6 |
| S30d | 0.9 | NA | NA | 1.0 | 1.7 | NA | NA | 0.5 | 0.5 | |
| G31 | 2.0 | NA | NA | 2.2 | 2.6 | NA | NA | 3.0 | 0.8 | |
| Y32 | 0.0 | 1.0 | 0.02 | 1.9 | 0.5 | 1.9 | 0.3 | 1.6 | 0.1 | 0.5 |
| CDR-L2 | | | | | | | | | | |
| W50 | 8.1 | 24.3 | 8.1 | 91.0 | 2.3 | 1.5 | 2.4 | 1.1 | 3.6 | 16.2 |
| G51 | 8.4 | NA | NA | 44.5 | 7.3 | NA | NA | 7.5 | 1.2 | |
| S52 | 8.4 | NA | NA | 6.6 | 4.1 | NA | NA | 7.5 | 2.1 | |
| F53 | 3.1 | 9.8 | 2.0 | 0.4 | 1.9 | 2.4 | 1.4 | 0.4 | 1.6 | 4.0 |
| CDR-L3 | | | | | | | | | | |
| H91 | 1.7 | 58.0 | 58.0 | 5.5 | 0.05 | 0.1 | 0.3 | 2.6 | 34.0 | 1160.0 |
| Y92 | 22.5 | 90.0 | 90.0 | 4.1 | 3.8 | 6.3 | 1.0 | 2.8 | 5.9 | 14.2 |
| S93 | 1.5 | NA | NA | 2.8 | 3.0 | NA | NA | 2.5 | 0.5 | |
| S94 | 30.3 | NA | NA | 7.3 | 1.0 | NA | NA | 0.9 | 29.7 | |
| CDR-H1 | | | | | | | | | | |
| S30 | 1.3 | NA | NA | 1.0 | 1.2 | NA | NA | 1.3 | 1.0 | |
| G31 | 1.5 | NA | NA | 3.3 | 1.2 | NA | NA | 5.0 | 1.3 | |
| T32 | 0.6 | NA | NA | 1.5 | 0.9 | NA | NA | 0.6 | 0.7 | |
| Y33 | 150.0 | 150.0 | 150.0 | 5.7 | 1.4 | 2.0 | 0.8 | 2.3 | 104.3 | 75.0 |
| CDR-H2 | | | | | | | | | | |
| R50 | 150.0 | 150.0 | 150.0 | 134.0 | 2.1 | 1.3 | 70.0 | 1.3 | 70.7 | 113.6 |
| Y52 | 1.0 | 1.5 | 0.9 | 1.2 | 2.0 | 2.5 | 1.8 | 2.7 | 0.5 | 0.6 |
| S53 | 1.0 | NA | NA | 1.1 | 1.2 | NA | NA | 1.1 | 0.9 | |
| E54 | 1.2 | NA | NA | 2.2 | 0.4 | NA | NA | 1.0 | 3.4 | |
| Y56 | 49.0 | 147.0 | 147.0 | 0.9 | 1.6 | 2.3 | 1.3 | 1.2 | 31.2 | 64.1 |
| R58 | 23.7 | 142.0 | 142.0 | 66.0 | 2.1 | 2.3 | 4.9 | 2.7 | 11.2 | 61.4 |
| CDR-H3 | | | | | | | | | | |
| W95 | 150.0 | 150.0 | 150.0 | 134.0 | 0.8 | 0.2 | 0.3 | 4.5 | 200.0 | 740.0 |
| V96 | 0.9 | NA | NA | 1.2 | 2.1 | NA | NA | 1.5 | 0.4 | |
| G97 | 1.8 | NA | NA | 6.9 | 0.9 | NA | NA | 5.7 | 2.0 | |
| V98 | 0.6 | NA | NA | 1.5 | 1.5 | NA | NA | 0.8 | 0.4 | |
| G99 | 6.5 | NA | NA | 21.3 | 1.2 | NA | NA | 1.8 | 5.2 | |

TABLE 9B-continued

Shotgun alanine- and homolog-scanning of bH1-44 Fab for binding to HER2.

| | | | | | | | | | | |
|---|---|---|---|---|---|---|---|---|---|---|
| F100 | 145.0 | 145.0 | 29.0 | 133.0 | 2.0 | 2.0 | 0.9 | 1.8 | 71.1 | 71.1 |
| Y100a | 149.0 | 149.0 | 149.0 | 6.9 | 1.5 | 1.5 | 0.6 | 0.9 | 98.0 | 101.9 |

| | Fwt/mut values | | $\Delta\Delta G_{wt/mut}$ (kcal/mol) | | | |
|---|---|---|---|---|---|---|
| | Fwt/m3 | Fwt/m4 | $\Delta\Delta G_{wt/m1}$ | $\Delta\Delta G_{wt/m2}$ | $\Delta\Delta G_{wt/m3}$ | $\Delta\Delta G_{wt/m4}$ |
| CDR-L1 | | | | | | |
| Q27 | 1.3 | 0.5 | 0.1 | 0.0 | 0.1 | −0.4 |
| N28 | 1.2 | 0.1 | 0.4 | 0.0 | 0.1 | −1.2 |
| I29 | 1.7 | 1.0 | 0.3 | 0.6 | 0.3 | 0.0 |
| A30 | | 6.5 | −0.2 | | | 1.1 |
| K30a | 1.6 | 6.0 | 0.0 | −0.1 | 0.3 | 1.1 |
| T30b | | 0.6 | 0.1 | | | −0.3 |
| I30c | 2.6 | 1.6 | 0.4 | 0.6 | 0.6 | 0.3 |
| S30d | | 2.1 | −0.4 | | | 0.4 |
| G31 | | 0.7 | −0.1 | | | −0.2 |
| Y32 | 0.1 | 1.2 | −1.8 | −0.4 | −1.6 | 0.1 |
| CDR-L2 | | | | | | |
| W50 | 3.4 | 80.1 | 0.8 | 1.7 | 0.7 | 2.6 |
| G51 | | 5.9 | 0.1 | | | 1.1 |
| S52 | | 0.9 | 0.4 | | | −0.1 |
| F53 | 1.5 | 1.0 | 0.3 | 0.8 | 0.2 | 0.0 |
| CDR-L3 | | | | | | |
| H91 | 203.0 | 2.1 | 2.1 | 4.2 | 3.1 | 0.4 |
| Y92 | 87.6 | 1.5 | 1.1 | 1.6 | 2.7 | 0.2 |
| S93 | | 1.1 | −0.4 | | | 0.1 |
| S94 | | 8.1 | 2.0 | | | 1.2 |
| CDR-H1 | | | | | | |
| S30 | | 0.8 | 0.0 | | | −0.1 |
| G31 | | 0.7 | 0.1 | | | −0.2 |
| T32 | | 2.6 | −0.2 | | | 0.6 |
| Y33 | 179.3 | 2.5 | 2.8 | 2.6 | 3.1 | 0.5 |
| CDR-H2 | | | | | | |
| R50 | 2.1 | 100.5 | 2.5 | 2.8 | 0.5 | 2.7 |
| Y52 | 0.5 | 0.4 | −0.4 | −0.3 | −0.4 | −0.5 |
| S53 | | 1.0 | −0.1 | | | 0.0 |
| E54 | | 2.2 | 0.7 | | | 0.5 |
| Y56 | 112.3 | 0.7 | 2.0 | 2.5 | 2.8 | −0.2 |
| R58 | 28.8 | 24.8 | 1.4 | 2.4 | 2.0 | 1.9 |
| CDR-H3 | | | | | | |
| W95 | 470.0 | 29.6 | 3.1 | 3.9 | 3.6 | 2.0 |
| V96 | | 0.8 | −0.5 | | | −0.1 |
| G97 | | 1.2 | 0.4 | | | 0.1 |
| V98 | | 1.8 | −0.5 | | | 0.3 |
| G99 | | 12.0 | 1.0 | | | 1.5 |
| F100 | 31.3 | 73.0 | 2.5 | 2.5 | 2.0 | 2.5 |
| Y100a | 262.7 | 7.8 | 2.7 | 2.7 | 3.3 | 1.2 |

NA = Mutation not included.

TABLE 10

The structural and functional paratopes for VEGF and HER2.

| | VEGF only | HER2 only | Shared |
|---|---|---|---|
| Structural contacts (bH1) | LC-S30b | HC-Y56 | LC-Y32 |
| | LC-I30c | HC-R58 | LC-W50 |
| | LC-S30d | | LC-Y53 |
| | LC-G31 | | LC-H91 |
| | LC-T93 | | LC-Y92 |
| | | | LC-T94 |
| | | | HC-Y33 |
| | | | HC-R50 |
| | | | HC-W95 |
| | | | HC-G99 |
| | | | HC-Y100a |
| Hotspot residues (bH1) | LC-I29 | LC-T94 | LC-W50 |
| | LC-S30b | HC-Y33 | HC-W95 |
| | LC-S30d | HC-R50 | |
| | LC-G31 | HC-Y56 | |
| | LC-Y32 | HC-R58 | |
| | LC-G51 | HC-G99 | |
| | LC-H91 | HC-F100 | |
| | LC-Y92 | HC-Y100a | |
| Hotspot residues (bH1-44) | LC-I29 | HC-Y33 | LC-H91 |
| | LC-T30b | HC-R50 | LC-S94 |
| | LC-S30d | HC-Y56 | HC-W95 |
| | LC-G31 | HC-R58 | |

TABLE 10-continued

The structural and functional paratopes for VEGF and HER2.

| VEGF only | HER2 only | Shared |
|---|---|---|
|  | LC-Y32 | HC-F100 |
|  | LC-W50 | HC-Y100a |
|  | LC-F53 |  |
|  | LC-Y92 |  |
|  | HC-Y100a |  | estimate the $k_a$ (onrate) and $k_d$ (offrate). The $K_D$ values were determined from the ratios of $k_a$ and $k_d$.

The bH1 Fab/VEGF interaction is characterized by a relatively high on-rate ($k_{on}$=3.7×10$^4$) and a fast off-rate ($k_{off}$=0.013), which results in a moderate $K_D$ of 300 nM. The affinity of the bH1/HER2 interaction ($K_D$=26 nM, $k_{on}$=9.6× 10$^4$, $k_{off}$=2.4×10$^{-3}$) is 52-fold lower than the Herceptin®/HER2 interaction ($K_D$=0.5 nM, $k_{on}$=7.1×10$^5$, $k_{off}$=3.5×10$^{-4}$) with a slower on-rate and faster off-rate. The affinity improved bH1 variants, bH1-81 and bH1-44, displayed improvements in both the on-rates and off-rates of the VEGF

TABLE 11

The polarity and size of the binding interfaces of bH1/VEGF, bH1/HER2, and Herceptin ®/HER2 complexes.

| | bH1 Fab/VEGF binding interface | | | | bH1 Fab/HER1 binding interface | | | | Hercepin Fab/HER2 binding interface | | | |
|---|---|---|---|---|---|---|---|---|---|---|---|---|
| | bH1 | VEGF | Combined | Percent (%) | bH1 | HER2 | Combined | Percent (%) | Herceptin | HER2 | Combined | Percent (%) |
| Polar | 311 | 295 | 607 | 40% | 308 | 282 | 591 | 37% | 307 | 308 | 614 | 40% |
| Hydrophobic | 438 | 462 | 900 | 60% | 470 | 518 | 988 | 63% | 441 | 469 | 910 | 60% |
| Total | 749 | 757 | 1506 | | 779 | 800 | 1579 | | 747 | 777 | 1524 | |

HER2/VEGF Dual Specific bH1-44 Antibody Maintains the HER2 Binding Kinetics of the Herceptin® Antibody Surface plasmon resonance was performed to study the binding kinetics of bH1 and its Fab variants to immobilized VEGF or HER2 (Table 12). An SPR-based assay was performed using a BIAcore 3000. VEGF$_{109}$ and HER2 extracellular domains were immobilized on CM5 chips at a density that allowed for an Rmax in the range of 50-150 RU. Serial dilutions of Fabs in PBS with 0.05% Tween20 were injected at 30 μl/min. The binding responses were corrected by subtracting responses from a blank flow cell and by normalizing for buffer effects. A 1:1 Langmuir fitting model was used to and HER2 interactions. The high affinity clone bH1-44 binds HER2 with an affinity similar to Herceptin® ($K_D$=0.2 nM, Table 12).

Table 12 depicts the kinetic profiles of the bH1 variants and the Herceptin® antibody determined by surface plasmon resonance measurement using BIAcore at 30° C. In these experiments, Fabs were bound to immobilized VEGF or HER2, and the on-rate ($k_a$), off-rate ($k_d$), and dissociation constant ($K_D$) were determined using a 1:1 Langmuir binding fitting model. The bH1-44 antibody has a similar kinetic profile and affinity for HER2 as the Herceptin® antibody. The two double mutants (bH1-44 129A+Y32A and bH1-44 R50A+R58A) that lost binding to VEGF or HER2 retained the kinetic profile and affinity for the other antigen.

TABLE 12

Kinetic profiles of the bH1 variants and the Herceptin ® antibody.

| | VEGF$_{109}$ | | | HER2 ECD | | |
|---|---|---|---|---|---|---|
| | ka (1/Ms) | kd (1/s) | $K_D$ (nM) | ka (1/Ms) | kd (1/s) | $K_D$ (nM) |
| Herceptin ® Fab | — | — | NB | 7.1E+05 | 3.5E−04 | 0.5 +/− 0.06 |
| Herceptin ® (R50A) Fab | — | — | NB | 2.7E+04 | 2.0E−03 | 74 |
| Herceptin ® (R58A) Fab | — | — | NB | 5.9E+04 | 7.3E−04 | 12 |
| Herceptin ® (R50A + R58A) Fab | — | — | NB | — | — | NB |
| bH1 Fab | 3.7E+04 | 0.013 | 300 +/− 87 | 9.6E+04 | 2.4E−03 | 26 +/− 28 |
| bH1-81 | 1.2E+05 | 0.007 | 58 +/− 12 | 2.2E+05 | 1.4E−03 | 6 +/− 0.6 |
| BH1-44 Fab | 4.0E+05 | 0.001 | 3 +/− 0.3 | 3.7E+05 | 8.0E−05 | 0.2 +/− 0.07 |
| bH1-44 (Y32A) Fab | — | — | weak | 6.2E+05 | 3.5E−05 | 0.1 |
| bH1-44 (I29A + Y32A) Fab | — | — | NB | 4.2E+05 | 8.3E−05 | 0.2 +/− 0.07 |
| bH1-44 (R50A + R58A) Fab | 3.5E+05 | 0.001 | 3 +/− 0.7 | — | — | NB |

NB = No binding detectable.

Dual Specific Antibodies Interact with HER2 and VEGF with Similar Thermodynamic Properties The enthalpy (ΔH) and entropy (ΔS) changes for the interactions between the bH1 Fab variants and the two antigens, VEGF (the receptor binding domain of VEGF, $VEGF_{8-109}$) and HER2 extracellular domain (ECD) were also determined (FIG. 59A-F, FIG. 60, Table 13), using isothermal titration calorimetry (ITC).

Microcalorimetric measurements of the interactions between Fabs and human $VEGF_{109}$ and the extracellular domain of HER2 were performed on a VP-ITC titration calorimeter (Microcal Inc.) as described (Starovasnik et al., 1999). Protein solutions were extensively dialyzed into phosphate-buffered saline. The antigen and Fabs were dialyzed in the same vessel to minimize mixing heat effects due to differences in buffer composition. Fabs at a concentration of 100-220 µM were titrated into antigen solutions (HER2-ECD or $VEGF_{109}$) at a concentration of 10-22 µM. This concentration of antigen was required for precise enthalpy measurements, but precludes determination of the $K_D$ in cases where the binding affinity is high. Fifteen or twenty injections were performed to obtain a 2-fold excess of antibody. The heats of reaction were determined, heats of Fab dilution were subtracted, and the ΔH was calculated.

The dissociation constants ($K_D$) determined by surface plasmon resonance (Table 12) were used to calculate the binding free energy (ΔG) according to:

$$\Delta G = RT \ln(K_D)$$

The entropy change upon association (ΔS) was calculated according to:

$$\Delta S = (\Delta H - \Delta G)/T, \text{ where T is the temperature (K)}.$$

To determine the ΔCp, microcalorimetric measurements were performed as described above at different temperatures ranging from 20 to 37° C. The ΔCp was determined by linear regression by plotting ΔH as a function of the temperature (FIG. 62).

The interactions of the dual specific antibody, bH1, with either of its two antigens, VEGF and HER2 were first characterized. The binding of bH1 with VEGF and HER2 exhibited similar thermodynamic properties (Table 13). Both interactions, measured at 30° C. in PBS at pH 7.4, are exothermic (ΔH=−2.4 and −2.4 kcal/mol for VEGF and HER2, respectively, Table 13, FIG. 60) with a highly favorable entropy change contributing to the binding energy (−TΔS=−6.6 and −7.9 kcal/mol for VEGF and HER2, respectively, Table 13, FIG. 60).

Table 13 depicts the ΔG (binding free energy), ΔS (entropy change), and ΔH (enthalpy change) in kcal/mol. The affinities shown were measured in at least two independent experiments using kinetic analysis by BIAcore at 30° C. The ΔH was measured using ITC and represents the average of two or three independent measurements followed by the standard deviations. The ΔG and ΔS were calculated as described above.

The high affinity variants bH1-81 and bH1-44 displayed similar thermodynamic profiles as bH1. Their interactions with VEGF and HER2 were also characterized by favorable enthalpy and entropy (Table 13, FIG. 60). For the VEGF interaction, the affinity improvement was associated with a significantly more favorable enthalpy change (ΔH=−7.1 for bH1-44 versus −2.4 kcal/mol for bH1 at 30° C.) and a slightly less positive entropy change (−TΔS=−6.6 for bH1-44 versus −4.7 for bH1 at 30° C., Table 13, FIG. 60). The improved affinity for HER2 was also associated with a more favorable enthalpy change (ΔH=−5.3 versus −2.4 kcal/mol, 30° C., Table 13, FIG. 60).

TABLE 13

Antigen binding affinities and thermodynamics for the bH1 variants and the Herceptin ® antibody.

| | $VEGF_{109}$ | | | | HER2-ECD | | | |
|---|---|---|---|---|---|---|---|---|
| | $K_D$ (nM) | ΔG | ΔH | −TΔS | $K_D$ (nM) | ΔG | ΔH | −TΔS |
| Herceptin ® | — | — | — | — | 0.5 | −12.9 +/− 0.06 | −13.6 +/− 0.2 | −0.3 +/− 0.2 |
| bH1 | 300 | −9.0 +/− 0.2 | −2.4 +/− 0.7 | −6.6 +/− 0.7 | 26 | −10.5 +/− 0.4 | −2.4 +/− 0.5 | −7.9 +/− 0.6 |
| bH1-81 | 58 | −10 +/− 0.1 | −6.2 +/− 0.1 | −3.8 +/− 0.2 | 6 | −11.4 +/− 0.05 | −3.8 | −7.6 |
| bH1-44 | 3 | −11.8 +/− 0.07 | −7.1 +/− 0.3 | −4.7 +/− 0.3 | 0.2 | −13.5 +/− 0.3 | −5.3 + 0.4 | −8.1 +/− 0.5 |
| bH1-44 (LC-I29A/Y32A) | — | — | — | — | 0.2 | −13.5 +/− 0.3 | −6.4 +/− 0.5 | −7.6 +/− 0.6 |
| bH1-44 (HCR50A/R58A) | 4 | −11.6 +/− 0.1 | −7.7 | −3.9 | — | — | — | — | bH1-44 and Herceptin® Interact with HER2 with Distinct Thermodynamics

In contrast to the dual specific antibodies, the HER2/Herceptin® interaction is characterized by a large favorable enthalpy change (ΔH=−13.6 kcal/mol) without any significant entropy change (−TΔS=−0.3 kcal/mol, FIG. 60, Table 13) (Kelley et al., 1992). Although bH1-44 interacts with HER2 with similar affinity as Herceptin®, the binding free energy is made up of a greater entropy component (−TΔS=−8.1 kcal/mol, 30° C.) and a smaller enthalpy component (ΔH=−5.3 kcal/mol, 30° C.). The distinct thermodynamic properties contrast the many similarities in HER2 binding characteristics between Herceptin® and bH1-44, which include affinity, kinetics, and many of the residues of the energetic hotspots. Although the hot spot residues of Herceptin® that contribute more than 10% of the total binding energy for HER2 are similar to those of bH1 and bH1-44, there are some clear differences.

Table 14 shows the bH1, bH1-44, and the Herceptin® antibody hotspots for HER2 binding determined by alanine scanning mutagenesis. The mutagenesis was performed as described in Kelley et al., 1993. The numbers in Table 14 represent the change in binding free energy ($\Delta\Delta G_{wt-mut}$) when the residue is mutated to alanine. The hotspot residues in Table 14 are shaded and are defined as ΔΔG greater than or equal to 10% of the total binding free energy (ΔG).

Residues LC-Thr94, HC-Tyr33, HC-Asp98 are conserved in sequence in bH1 but have different functions in HER2 binding (Table 14, FIG. 61). Hence, the mutations in the antigen-binding site of Herceptin® that recruited VEGF binding appear to have made some fundamental changes to the antigen-binding site that affect the interaction with HER2. The dual specific antibodies accommodate the introduced mutations by utilizing a different HER2 recognition strategy that results in equally high affinity for HER2 as Herceptin®. It is interesting to note that except for LC-Ser94 of bH1-44 the mutations that improved the affinity for HER2 more than 100-fold compared to bH1 are not parts of the binding hotspot, but appear to optimize the existing interactions.

Large Negative Heat Capacities in the Dual Specific Interactions

To further understand the common energetics driving the dual specific interactions and how they are distinguished from that of the monospecific parent Herceptin®, a series of experiments were performed to study following three Fab/antigen interactions: bH1-44 with VEGF or HER2, and Herceptin® with HER2. The heat capacities of the dual specific interactions was measured by determining the enthalpy of binding ($\Delta H$) at multiple temperatures ranging from 20° C. to 37° C. ($\Delta T=17°$ C., FIG. 62, Table 15). The heat capacity ($\Delta Cp$) is a function of $\Delta H$ and Temperature (T) and can be described by the equation:

$$\Delta Cp = \delta(\Delta H)/\delta T$$

$\Delta Cp$ was estimated from the slope of the temperature dependence of $\Delta H$ by linear regression (FIG. 62, Table 15). $\Delta Cp$ of bH1-44 was determined to −400 cal/molK for the interaction with VEGF, and −440 cal/molK for the interaction with HER2. The large negative heat capacities indicate the importance of the hydrophobic effect as previously described (Kauzmann, 1959), which is consistent with the hydrophobic nature of the structural interfaces in the two complexes (Table 11). The $\Delta Cp$ for Herceptin®/HER2, which was previously determined to −370 cal/molK in a similar temperature interval (Kelley et al., 1992), is smaller than the $\Delta Cp$ of bH1-44/HER2, but still indicates the important role of the hydrophobic effect in HER2 binding.

The total entropy change ($\Delta S$) of binding free energy is a sum of entropy changes from three sources (Murphy et al., 1994): entropy changes associated with desolvation of the binding surfaces ($\Delta S_{SOLV}$), entropy changes from the loss of rotational and translational degree of freedom ($\Delta S_{RT}$), and entropy changes due to the changes in configurational and conformational dynamics of the interacting molecules ($\Delta S_{CONF}$).

$$\Delta S_{TOT} = \Delta S_{SOLV} + \Delta S_{RT} + \Delta S_{CONF} \quad (1)$$

Typically, only $\Delta S_{SOLV}$ is positive while $\Delta S_{RT}$ and $\Delta S_{CONF}$ are both negative. The cratic entropy term, $\Delta S_{RT}$, for the association of two molecules can be estimated to −8 cal/Kmol as described (Murphy et al., 1994). $\Delta S_{SOLV}$ can be assumed to be dominated by the hydrophobic effect due to the burial of apolar surface area and can be described as a function of $\Delta Cp$:

$$\Delta S_{SOLV} = \Delta Cp \ln(T/T^*), T^*=385 K \quad (2)$$

$\Delta S_{CONF}$ can thus be estimated as:

$$\Delta S_{CONF} = \Delta S_{TOT} - \Delta S_{RT} - \Delta S_{SOLV} \quad (3)$$

According to equation (3), $\Delta S_{SOLV}$ is estimated to 96 cal·mol$^{-1}$K$^{-1}$ for bH1-44/VEGF, 105 cal·mol$^{-1}$K$^{-1}$ for bH1-44/HER2, and 89 cal·mol$^{-1}$K$^{-1}$ for Herceptin®/HER2 (Table 15). This translates to $\Delta S_{CONF}$ of −72 cal·mol$^{-1}$K$^{-1}$ for bH1-44/VEGF, −70 cal·mol$^{-1}$K$^{-1}$ for bH1-44/HER2, and −80 cal·mol$^{-1}$K$^{-1}$ for Herceptin®/HER2 (Table 15).

To examine the overall structural stability of the dual specific Fabs compared to its parent Herceptin®, thermal denaturation experiments using differential scanning calorimetry (DSC) were performed. Thermal denaturation experiments were performed on a differential scanning calorimeter from Microcal Inc. Fabs were dialyzed against 10 mM sodium acetate pH 5, 150 mM sodium chloride. The solutions were adjusted to a concentration of 0.5 mg/ml and heated to 95° C. at a rate of 1° C./min. The melting profiles were baseline corrected and normalized. The melting temperature ($T_M$) was determined using the software supplied by the manufacturer. As expected, none of the Fabs displayed reversible thermal denaturation profiles (Kelley et al., 1992) (data not shown). The $T_M$ of the dual specific variants (77.2° C., 75.6° C., 74.3° C. for bH1, bH1-81, and bH1-44, respectively, Table 16) are slightly lower than that of Herceptin® (82.5° C.), but high and within the range of what has been reported for other therapeutic antibodies (Garber and Demarest, 2007).

The Binding Kinetics and Thermodynamics of bH1 Variants with High Affinity for Only VEGF or HER2

Interestingly, the dual specific antibodies derive the majority of their binding energy from entirely distinct regions of the shared VEGF/HER2 binding site. These data show that the VEGF or HER2 binding function of the dual specific antibodies can be selectively disrupted without affecting the remaining binding specificity. Structural studies indicated that the structural paratopes on bH1 for VEGF and HER2 overlap significantly, but shotgun alanine mutagenesis of bH1 and bH1-44 demonstrated that the VEGF and HER2 interactions are mediated by two unique sets of CDR residues with little overlap (FIGS. 54 and 57, Tables 9A, 9B, and 10). The shotgun alanine scanning of bH1 and bH1-44 indicated that some CDR residues are exclusively important for binding either VEGF or HER2 (FIGS. 54 and 57, Tables 9A, 9B, and 10), including LC-11e29, LC-Tyr32, which are important for VEGF binding, and HC-Arg50, HC-Arg58 for HER2 binding (FIGS. 54 and 57, Tables 9 and 10). To confirm the unique importance of the side chains of these residues in each interaction, each residue was mutated to alanine in the bH1-44 (LC-Ile29, LC-Tyr32, HC-Arg50, HC-Arg58) or the Herceptin® (HC-Arg50, HC-Arg58) scaffolds, individually or in combination, and expressed the mutants as Fabs and IgGs.

Vectors that encoded bH1-44 or Herceptin® Fabs fused to the N-terminus of geneIII via the heavy chain was used as the templates for Kunkel mutagenesis (Kunkel et al., 1987). Oligonucleotides were designed to introduce the desired alanine mutations at selected positions. The Fab alanine mutants were expressed as phage, and the binding verified by competition ELISA (FIG. 58). The heavy chain and the light chain variable domains were then cloned into Fab and IgG expression vectors, and Fabs and IgGs expressed and purified as described (Bostrom et al., 2009). SDS-PAGE verified the correct protein size (FIG. 65). Size exclusion chromatography showed aggregation levels of less than 5%.

Binding to the two antigens was examined by competition ELISA and/or BIAcore, All single alanine mutations in the bH1-44 scaffold impaired binding to varying degrees (data not shown). The most striking single mutation was LC-Y32A, which significantly disrupted VEGF binding while maintaining HER2 binding affinity and kinetics (Table 12, FIG. 58, and FIG. 63). The double mutations 129A+Y32A (LC) or R50A+R58A (HC) almost completely disrupted binding to VEGF or HER2, respectively, while maintaining the binding affinity and kinetics for the other antigen (Table 12, FIG. 58, and FIG. 63). The alanine mutations HC-R50A, HC-R58A in the Herceptin® scaffold also disrupted binding to HER2 to various extents, while the double mutant HC R50A+R58A showed no detectable HER2 binding (Table 12).

The thermodynamic parameters of the double mutants were next analyzed and compared to the values for bH1-44. The binding free energy of bH1-44 mutants LC-129A+Y32A and HC-R50A+R58A with HER2 or VEGF, respectively, result from favorable contributions of enthalpy and entropy ($\Delta H=-7.7$ and $-T\Delta S=-3.9$ for VEGF, $\Delta H=-6.4$ and $-T\Delta S=-7.6$ for HER2, Table 13, FIG. 60), which is approximately equivalent to bH1-44 measured at 30° C. (Table 13, FIG. 60). Hence, the double mutants displayed the same thermodynamic and kinetic profiles as bH1-44.

Structural Basis for the Functions of the Specificity-altering Residues

Figure 64:
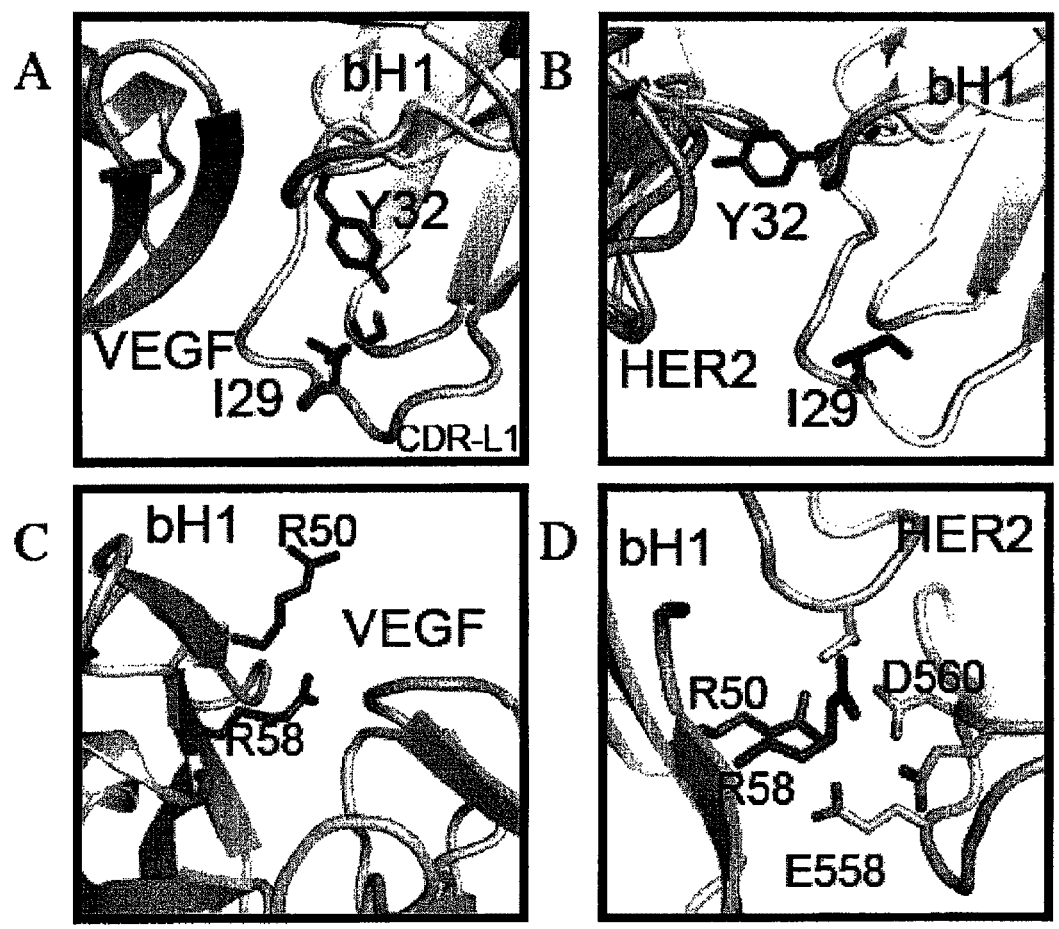

Next, the crystal structures of bH1 in complex with VEGF or HER2 were analyzed (Bostrom et al., 2009) to reveal the specific interactions of the binding determinants in each antigen complex (FIG. 64). The resulting analyses explained how mutations of the two specificity-determining residues disrupt binding capability for one antigen without affecting the affinity, kinetics, and binding thermodynamics for the other. The CDR-L1 of bH1 contains the majority of the changes in sequence from Herceptin® and is important for VEGF binding. The conformations of CDR-L1 of bH1 differ significantly in the two complex structures; the average deviation is 4.6 Å ($C_\alpha$ of residues 27-32). In contrast, the overall conformation of bH1 Fab in complex with VEGF is markedly similar to that of the HER2-bound Fab (r.m.s.d.=0.7 Å, for 398 backbone atoms, $C_\alpha$). The CDR-L1 loop constitutes 26% of the surface area buried by VEGF while this loop is situated at the periphery of the HER2 paratope and minimally involved in HER2 contact.

Superposition of the two complexes indicated that VEGF would clash with Tyr32 and the adjacent residues of CDR-L1 in its HER2-bound conformation. The main chain $C_\alpha$ atom of Tyr32 resides in the same position in the two structures, but its side chain is rotated by ~130°. In the VEGF complex, Tyr32 and 11e29 appear to play structural roles in enabling the conformation of CDR-L1 required for VEGF binding. Mutation of Tyr32 to either Ala or Phe is not tolerated for VEGF binding (Bostrom et al., 2009). Although the side chain of Tyr32 points toward HER2, it does not appear to be involved in productive antigen contacts. 11e29 is far away from HER2, with its side chain exposed to solvent and mutation of 11e29 and Tyr32 to Ala, is well tolerated for HER2 binding.

TABLE 14

Comparison of bH1, bH1-44, and Herceptin® hotspots for HER2 binding determined by alanine scanning mutagenesis

| | | | $\Delta\Delta G$ (kcal/mol) | | |
|---|---|---|---|---|---|
| Residue | bH1/ VEGF | bH1-44/ VEGF | bH1/ HER2 | bH1-44/ HER2 | Herceptin |
| Light Chain | | | | | |
| 27 | | -0.6 | | 0.1 | |
| 28 | 0.05 | 0.6 | 0.03 | 0.4$^a$ | -0.3 |
| 29 | 1.1 | 2.3 | -0.2$^a$ | 0.3$^a$ | |
| 30 | 0.2 | 1.1 | 0.1$^a$ | -0.2$^a$ | 1.1 |
| 30a | -0.2 | 0.4 | -0.2$^a$ | 0.04$^a$ | — |
| 30b | 1$^c$ | 1.2 | 0.3$^a$ | 0.05$^a$ | — |
| 30c | 0.8$^c$ | 1.1 | 0.9$^a$ | 0.4$^a$ | — |
| 30d | 1.3$^c$ | 1.3 | -0.2$^a$ | -0.4$^a$ | — |
| 31 | 1.2$^c$ | 1.3 | 0.3$^a$ | -0.1$^a$ | 0.8 |
| 32 | 1.7$^c$ | 2.7 | -0.8$^{ac}$ | -1.8$^a$ | |
| 50 | 1.3$^c$ | 1.8 | 1.4$^{ac}$ | 0.8$^a$ | -0.1 |
| 51 | 1 | 0.7 | -0.3$^a$ | -0.09$^a$ | |
| 52 | 0.1 | 0.8 | 0.3 | 0.4 | -0.3 |
| 53 | 0.7$^c$ | 1.5 | 0.9$^{ac}$ | 0.3 | |
| 91 | 2$^c$ | 3.0 | 0.9$^c$ | 2.1 | 3.2 |
| 92 | 1.4$^c$ | 1.5 | 0.5$^c$ | 1.1 | 1.4 |
| 93 | -0.3$^c$ | -0.6 | -0.4 | -0.4$^a$ | 0.8 |
| 94 | 0.05$^c$ | 1.6 | 1.4$^c$ | 2.0$^a$ | -0.1 |
| Heavy Chain | | | | | |
| 30 | 0.2 | 0.0 | -0.3 | 0.01$^a$ | 0.6 |
| 31 | 0.2 | 0.4 | 0.4 | 0.1$^a$ | 0.2 |
| 32 | -0.4 | -0.4 | -0.4 | -0.2 | 0.4 |
| 33 | 0.3$^c$ | 1.2 | 2.4$^c$ | 2.8 | -0.1 |
| 50 | -0.3$^c$ | -0.7 | 2.5$^c$ | 2.5 | 3.3 |
| 52 | 0.4 | -0.1 | -0.8 | -0.4 | 0.2 |
| 53 | -0.5 | 0.1 | 0.06 | -0.07$^a$ | 0.1 |
| 54 | -0.2 | 0.7 | -0.8 | 0.7$^a$ | -0.1 |
| 56 | 0.2 | 1.0 | 1.8$^c$ | 2.0 | 0.9 |
| 58 | -0.2 | -0.2 | 2.5$^c$ | 1.4 | 1.9 |
| 95 | 2$^c$ | 3.1 | 1.8$^c$ | 3.1 | 5.8 |
| 96 | 0.2 | -0.9 | 0.08 | -0.5$^a$ | |
| 97 | -0.1 | -0.1 | 0.3 | 0.4 | |
| 98 | 0 | 0.3 | -0.1 | -0.5$^a$ | 1.2 |
| 100 | 0.7 | 0.7 | 1.9 | 2.5 | 1.2 |
| 100a | 0.5$^c$ | 1.7 | 2.2 | 2.7 | 5.6 |

$^a$bH1/bH1-44 residues that differ from the Herceptin® antibody.
$^c$Indicates a contact residue in the bH1/VEGF or bH1/HER2 complex structures.
(—) Indicates that the Herceptin® antibody has no residue at this position.

TABLE 15

Thermodynamic parameters of the VEGF and HER2 interactions.

| | $\Delta Cp$ (cal/Kmol) | $\Delta$Stot (cal/Kmol) | $\Delta$Sconf (cal/Kmo) | $\Delta$Sdesolv (cal/Kmol) | $\Delta$Srt (cal/Kmol) |
|---|---|---|---|---|---|
| bH1-44/VEGF | -400 | 16 | -72 | 96 | -8 |
| bH1-44/HER2 | -440 | 27 | -70 | 105 | -8 |
| Herceptin®/HER2 | -370 | 0.8 | -80 | 89 | -8 |

$\Delta S_{CONF} = \Delta S_{TOT} - \Delta S_{SOLV} - \Delta S_{RT}$ as described by Murphy et. al., Proteins, 1994. $\Delta S_{RT}$ was estimated to -8 cal/molK for a simple binding reaction. $\Delta S_{SOLV} = \Delta S^* + \Delta Cpln(T/Ts^*)$, where T = 303.15, Ts* = 385.15 and $\Delta S^* \sim 0$.

TABLE 16

Melting Temperatures ($T_M$) of the dual specific Fabs and the Herceptin ® antibody

| Fab | $T_M$ (° C.) |
| --- | --- |
| Herceptin | 82.5 |
| bH1 | 77.2 |
| bH1-81 | 75.6 |
| bH1-44 | 74.3 |

The structure of the uniquely important residues for HER2 binding in the bH1/HER2 complex were also examined. The side chains of Arg50 and Arg58 pack against acidic residues on HER2 (Glu558 and Asp560) in the bH1-HER2 structure (FIG. 64). The interactions appear to be highly side chain-specific, as mutations to Lys as well as Ala are disruptive (Bostrom et al., 2009). In the VEGF structure, however, Arg50 and Arg58 are solvent exposed and far away from VEGF, and mutations to Ala or Lys are well tolerated (Bostrom et al., 2009).

References Cited

Baselga, J., L. Norton, J. Albanell, et al., 1998, Cancer Res. V. 58, p. 2825.
Bostrom, J., S. F. Yu, D. Kan, B. A. Appleton, C. V. Lee, K. Billeci, W. Man, F. Peale, S. Ross, C. Wiesmann, and G. Fuh, 2009, Science, v. 323, p. 1610-4.
Chen Y., C. Wiesmann, G. Fuh, B. L1, H. W. Christinger, P. McKay, A. M. de Vos, and H. B. Lowman, 1999, J Mol Biol, v. 293, p. 865-81.
Cho, H. S., K. Mason, K. X. Ramyar, A. M. Stanley, S. B. Gabelli, D. W. Denney, Jr., and D. J. Leahy, 2003, Nature, v. 421, p. 756-60.
Chothia, C., A. M. Lesk, 1987, J. Mol. Biol., v. 196, p. 901.
Christinger, H. W., Y. A. Muller, L. T. Berleau, B. A. Keyt, B. C. Cunningham, N. Ferrara, and A. M. de Vos, 1996, Proteins, v. 26, p. 353-7.
Collaborative Computational Project, N., 1994: Acta Crystallogr. Section D. Biol. Crystallogr., v. 50, p. 760-763.
Dall'Acqua, W., E. R. Goldman, E. Eisenstein, et al., 1996, Biochemistry, v. 35, p. 1967.
Emsley, P., and K. Cowtan, 2004, Acta Crystallogr D Biol Crystallogr, v. 60, p. 2126-32.
Fellouse, F. A., B. Li, D. M. Compaan, A. A. Peden, S. G. Hymowitz, and S. S. Sidhu, 2005, Mol Biol, v. 348, p. 1153-62.
Fields, B. A., F. A. Goldbaum, X. Ysern, et al., 1995, Nature, v. 374, p. 739.
Franklin, M. C., K. D. Carey, F. F. Vajdos, D. J. Leahy, A. M. de Vos, and M. X.
Sliwkowski, 2004, Cancer Cell, v. 5, p. 317-28.
Fuh, G., B. Li, C. Crowley, B. Cunningham, and J. A. Wells, 1998, J Biol Chem, v. 273, p. 11197-204.
Fuh, G., P. Wu, W. C. Liang, M. Ultsch, C. V. Lee, B. Moffat, and C. Wiesmann, 2006, J Biol Chem, v. 281, p. 6625-31.
Gallop, M. A., R. W. Barrett, W. J. Dower, et al., 1994, Journal of Medicinal Chemistry, V. 37, p. 1233.
Garber, E., and S. J. Demarest, 2007, Biochem Biophys Res Commun, v. 355, p. 751-7.
Hudziak, R. M., and A. Ullrich, 1991, J Biol Chem, v. 266, p. 24109-15.
James, L. C., Roversi, P., Tawfik, D. S., 2003, Science, v. 299, p. 1362.
Jimenez, R., G. Salazar, K. K. Baldridge, et al., 2003, Proc. Natl. Acad. Sci. USA, v. 100, p. 92.
Johnson, G., T. T. Wu, 2000, Nucleic Acids Res., v. 28, p. 214.
Kauzmann, W., 1959, Adv Protein Chem, v. 14, p. 1-63.
Kelley, R. F., and M. P. O'Connell, 1993, v. 32, p. 6828-35.
Kelley, R. F., M. P. O'Connell, P. Carter, L. Presta, C. Eigenbrot, M. Covarrubias, B. Snedecor, J. H. Bourell, and D. Vetterlein, 1992, Biochemistry, v. 31, p. 5434-41.
Kunkel, T. A., J. D. Roberts, and R. A. Zakour, 1987, Methods Enzymol, v. 154, p. 367-82.
L. C. Storoni, A. J. M. a. R. J. R., 2004, Acta Cryst., p. 432-438.
Lasky, L. A., and D. J. Dowbenko, 1984, DNA, v. 3, p. 23-9.
Lawrence, M. C., Colman, P. M. et al., 1993, J Mol Biol, v. 234, pp. 946-950.
Lee, C. V., W. C. Liang, M. S. Dennis, C. Eigenbrot, S. S. Sidhu, and G. Fuh, 2004a, J Mol Biol, v. 340, p. 1073-93.
Lee, C. V., S. S. Sidhu, and G. Fuh, 2004b, J Immunol Methods, v. 284, p. 119-32.
Lee, C. V., S. G. Hymowitz, H. J. Wallweber, et al.
Liang, W. C., X. Wu, F. V. Peale, C. V. Lee, Y. G. Meng, J. Gutierrez, L. Fu, A. K. Malik, H. P. Gerber, N. Ferrara, and G. Fuh, 2006, J Biol Chem, v. 281, p. 951-61.
Lovell, S. C., I. W. Davis, W. B. Arendall, et al., 2003, Proteins, v. 50, p. 437.
Lowman, H. B., S. H. Bass, N. Simpson, and J. A. Wells, 1991, Biochemistry, v. 30, p. 10832-8.
McCoy, Y. A. J., R. J. Read, and L. C. Storoni, 2004, Acta Cryst., 432.
Muller, Y. A., Y. Chen, H. W. Christinger, B. Li, B. C. Cunningham, H. B. Lowman, and A. M. de Vos, 1998, Structure, v. 6, p. 1153-67.
Muller, B., H. Li, W. Christinger, et al., 1997, Proc. Natl. Acad. Sci. USA, v. 94, p. 7192.
Murphy, K. P., D. Xie, K. S. Thompson, L. M. Amzel, and E. Freire, 1994, Proteins, v. 18, p. 63-7.
Mylvaganam, S. E., Y. Paterson, and E. D. Getzoff, 1998, J. Mol. Biol., v. 281, p. 301.
Nemazee, D., 2006, Nat. Rev. Immunol., v. 6, p. 728.
Otwinowski, Z., and Minor, W., 1997, Methods Enzymol., v. 276, p. 307-326.
Pauling, L., 1940, J. Am. Chem. Soc., v. 62, p. 2643.
Presta, L. G., H. Chen, S. J. O'Connor, V. Chisholm, Y. G. Meng, L. Krummen, M. Winkler, and N. Ferrara, 1997, Cancer Res, v. 57, p. 4593-9.
Read, R. J., 2001, Acta Cryst., v. D57, p. 1373-1382.
Reichert, J. M., Rosenzweig, C. J., Faden, L. B., et al., 2005, Nat. Biotechnol., v. 23, p. 1703.
Senn, B. M., Lopez-Macias, C., Kalinke, U., et al., 2006, Eur. J. Immunol., v. 33, p. 950.
Sethi, D. K., Agarwal, A., Manivel, V., et al., 2006, Immunity, v. 24, p. 429.
Sidhu, S. S., B. Li, Y. Chen, F. A. Fellouse, C. Eigenbrot, and G. Fuh, 2004, J Mol Biol, v. 338, p. 299-310.
Sidhu, S. S., H. B. Lowman, B. C. Cunningham, and J. A. Wells, 2000, Methods Enzymol, v. 328, p. 333-63.
Starovasnik, M. A., M. P. O'Connell, W. J. Fairbrother, and R. F. Kelley, 1999, Protein Sci, v. 8, p. 1423-31.
Vajdos, F. F., C. W. Adams, T. N. Breece, L. G. Presta, A. M. de Vos, and S. S. Sidhu, 2002, Mol Biol, v. 320, p. 415-28.
Weiss, G. A., C. K. Watanabe, A. Zhong, et al., 2000, Proc. Natl. Acad. Sci. USA, v. 97, p. 8950.
Wiesmann, C., G. Fuh, H. W. Christinger, C. Eigenbrot, J. A. Wells, and A. M. de Vos, 1997, Cell, v. 91, p. 695-704.
Winn, M. D., M. N. Isupov, and G. N. Murshudov, 2001, Acta Crystallogr. D. Biol. Crystallogr., v. 57, p. 122.

All patents, patent applications, patent application publications, and other publications cited or referred to in this specification are herein incorporated by reference to the same extent as if each independent patent, patent application, patent application publication or publication was specifically and individually indicated to be incorporated by reference.

What is claimed is:

1. An isolated antibody, wherein said antibody comprises HVR-L1, HVR-L2, HVR-L3, HVR-H1, HVR-H2, and HVR-H3, wherein each, in order, comprises the sequence of SEQ ID NO:1, 2, 3, 4, 5, and 6, and wherein said antibody specifically binds HER2 and VEGF.

2. An isolated antibody, wherein said antibody comprises HVR-L1, HVR-L2, HVR-L3, HVR-H1, HVR-H2, and HVR-H3, wherein each, in order, comprises the sequence of SEQ ID NO:1, 2, 3, 7, 8, and 9, and wherein said antibody specifically binds HER2 and VEGF.

3. The antibody of claim 1 or 2, wherein said antibody is a monoclonal antibody.

4. The antibody of claim 1 or 2, wherein said antibody is an IgG antibody.

5. The antibody of claim 1 or 2, wherein at least a portion of the framework sequence is a human consensus framework sequence.

6. The antibody of claim 1 or 2, wherein said antibody binds human or murine VEGF with a nanomolar affinity.

7. The antibody of claim 6, wherein said antibody binds human and murine VEGF with a nanomolar affinity.

8. The antibody of claim 1 or 2, wherein said antibody binds HER2 with a nanomolar affinity.

9. The antibody of claim 1 or 2, wherein said antibody inhibits VEGF-induced cell proliferation and proliferation of a HER2 expressing cell relative to a control.

10. The antibody of claim 1 or 2, wherein said antibody inhibits VEGF binding to VEGF receptor 2 (VEGFR2).

11. A fragment of the antibody of claim 1 or 2, wherein said fragment specifically binds HER2 and VEGF.

12. The fragment of claim 11, wherein said fragment is a Fab fragment or a single chain variable fragment (scFv).

13. The antibody fragment of claim 11, wherein said fragment binds human or murine VEGF with a nanomolar affinity.

14. The antibody fragment of claim 13, wherein said fragment binds human and murine VEGF with a nanomolar affinity.

15. The antibody fragment of claim 11, wherein said fragment binds HER2 with a nanomolar affinity.

16. The antibody fragment of claim 11, wherein said fragment inhibits VEGF-induced cell proliferation and proliferation of a HER2 expressing cell relative to a control.

17. The antibody fragment of claim 11, wherein said fragment inhibits VEGF binding to VEGF receptor 2 (VEGFR2).

\* \* \* \* \*

UNITED STATES PATENT AND TRADEMARK OFFICE
CERTIFICATE OF CORRECTION

PATENT NO.       : 8,193,321 B2
APPLICATION NO.  : 12/552177
DATED            : June 5, 2012
INVENTOR(S)      : Jenny M. Bostrom et al.

It is certified that error appears in the above-identified patent and that said Letters Patent is hereby corrected as shown below:

Column 2, Line 20, replace "glycine at $X_5$" with --glycine at $X_8$--.

Column 9, Line 6, replace "HVR-1-12" with --HVR-H2--.

Column 13, Line 24, replace "VEGFR1D1-3" with --VEGFR1 D1-3--.

Column 15, Line 25, replace "HER2-bound bill" with --HER2-bound bH1--;

Line 39, replace "α-axis)" with --(x-axis)--;

Line 49, replace "values of bill" with --values of bH1--;

Line 52, replace "129A" with --I29A--;

Line 57, replace "129A" with --I29A--;

Line 66, replace "129A" with --I29A--.

Column 16, Line 12, replace "129A" with --I29A--;

Line 51, replace "129A" with --I29A--;

Line 55, replace "129A" with --I29A--;

Line 61, replace "129" with --I29--;

Line 66, replace "129" with --I29--.

Column 17, Line 1, replace "129" with --I29--.

Column 18, Line 38, replace "IgG 1" with --IgG1--.

Column 21, Line 26, replace "Rosenburg" with --Rosenberg--.

Column 23, Line 54, replace "spectrophometer" with --spectrophotometer--;

Line 55, replace "(ThermoSpectronic)" with --(Thermo Spectronic)--.

Column 24, Line 22, replace "spectrophometer" with --spectrophotometer--;

Line 23-24, replace "(ThermoSpectronic)" with --(Thermo Spectronic)--.

Column 26, Line 55, replace "a animal model" with --an animal model--.

Column 27, Line 4, replace "Daeron" with --Daëron--.

Signed and Sealed this
Eighth Day of January, 2013

David J. Kappos
*Director of the United States Patent and Trademark Office*

CERTIFICATE OF CORRECTION (continued)
U.S. Pat. No. 8,193,321 B2

Column 28, Line 29, replace "a1-anti-trypsin" with --α1-anti-trypsin--;

Line 50, replace "Guillain-Barre" with --Guillain-Barré--.

Column 29, Line 4, replace "Hasimoto's thyroiditis" with --Hashimoto's thyroiditis--.

Column 31, Line 16, replace "opthalmopathy" with --ophthalmopathy--;

Line 21, replace "alopecia greata" with --alopecia areata--;

Line 23, replace "sclerodactyl" with --sclerodactyly--.

Column 33, Line 44, replace "nitrosureas" with --nitrosoureas--;

Line 53, replace "caminomycin" with --carminomycin--.

Column 34, Lines 7-8, replace "elformithine" with --elfornithine--;

Line 14, replace "sizofuran" with --sizofiran--.

Column 35, Line 4, replace "abherant cell" with --aberrant cell--.

Column 38, Line 2, replace "NΔSALIDE®" with --NASALIDE®--.

Column 40, Line 29-30, replace "*Serratia marcescans*" with --*Serratia marcescens*--;

Line 51, replace "pACYC 177" with --pACYC177--.

Column 43, Line 66, replace "alleukaryotic" with --all eukaryotic--.

Column 44, Line 24-25, replace "papilloma virus" with --papillomavirus--.

Column 46, Line 55, replace "(Mandler et at" with --(Mandler et al.--.

Column 55, Line 60, replace "hypertropic" with --hypertrophic--.

Column 56, Line 44, replace "Sogren's syndrome" with --Sjögren's syndrome--;

Line 45, replace "Stargart's disease" with --Stargardt's disease--.

Column 67, Line 27, replace "(54 ml)" with --5 μg/ml--.

Column 71, Line 8, replace "2 ng/ml" with --2 μg/ml--;

Line 49, replace "anti-h VEGF" with --anti-hVEGF--.

Column 72, Line 64, replace "220 gams" with --220 grams--.

Column 75, Line 60, replace "11e30c" with --Ile30c--.

Column 80, Line 39, replace "Chimistry" with --Chemistry--;

Line 50, replace "HER2ECD" with --HER2 ECD--.

Column 81, Line 38, replace "HER2ECD" with --HER2 ECD--.

Column 83, Line 39, replace "HER2ECD" with --HER2 ECD--;

Line 41, replace "HER3ECD" with --HER3 ECD--;

Line 44, replace "HER2ECD" with --HER2 ECD--;

Line 47, replace "HER3ECD" with --HER3 ECD--;

Line 49, replace "HER2ECD" with --HER2 ECD--;

Line 55, replace "α-axis)" with --(x-axis)--;

Line 65, replace "HER2ECD" with --HER2 ECD--.

CERTIFICATE OF CORRECTION (continued)
U.S. Pat. No. 8,193,321 B2

Column 84, Line 1, replace "HER2ECD" with --HER2 ECD--;
      Line 46, replace "engraft tumor" with --xenograft tumor--.

Column 87, Line 51, replace "mutagensis" with --mutagenesis--.

Column 88, Line 25, replace "mutagensis" with --mutagenesis--.

Column 100, Line 46, replace "11e29" with --Ile29--.

Column 101, Line 7, replace "129A" with --I29A--.

SEQUENCE LISTING

<160> NUMBER OF SEQ ID NOS: 85

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Asn Ile Ala Lys Thr Ile Ser Gly Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Trp Gly Ser Phe Leu Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: Syntheitc Peptide

<400> SEQUENCE: 3

His Tyr Ser Ser Pro Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Asn Ile Lys Asp Thr Tyr
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Arg Ile Tyr Pro Thr Asn Gly Tyr Thr Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Trp Gly Gly Asp Gly Phe Tyr Ala Met Asp

```
<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Asn Ile Ser Gly Thr Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Arg Ile Tyr Pro Ser Glu Gly Tyr Thr Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Trp Val Gly Val Gly Phe Tyr Ala Met Asp
1               5                   10

<210> SEQ ID NO 10
<211> LENGTH: 214
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                            165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 11
<211> LENGTH: 227
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His
225

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Asp Val Asn Thr Ala Val
1               5

<210> SEQ ID NO 13
<211> LENGTH: 4
```

```
<212> TYPE: PRT
<213> ORGANISM: Artificial Sequence
<220> FEATURE:
<223> OTHER INFORMATION: Synthetic peptide

<400> SEQUENCE: 13

Ser Ala Ser Phe
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

His Tyr Thr Thr
1

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Asn Val Trp Asp Trp Val
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Pro Ala Ser Ser
1

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Gly Trp Tyr Ile Ala
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Asp Ile Pro Arg Ser Ile Ser Gly Tyr Val
1               5                   10

<210> SEQ ID NO 19
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 19

Trp Gly Ser Tyr
1

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide

<400> SEQUENCE: 20

His Tyr Thr Thr
1

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Asp Ile Gly Leu Gly Ser Val
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Trp Ala Ser Tyr
1

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Asp Ile Arg Ser Gly Ser Val
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Tyr Ser Thr Val Pro Trp
1               5

<210> SEQ ID NO 25
<211> LENGTH: 12
<212> TYPE: DNA
<213> ORGANISM: Artificial Sequence
<220> FEATURE:
<223> OTHER INFORMATION: Synthetic formula sequence
```

```
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: g and t present in equimolar ratios
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: g and t present in equimolar ratios

<400> SEQUENCE: 25
catnnknnkr st                                                             12

<210> SEQ ID NO 26
<211> LENGTH: 12
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (4)..(9)
<223> OTHER INFORMATION: a, g, c, and t present in equimolar ratios

<400> SEQUENCE: 26
kmtnnnnnnr st                                                             12

<210> SEQ ID NO 27
<211> LENGTH: 12
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (4)..(9)
<223> OTHER INFORMATION: a, g, c, and t present in equimolar ratios

<400> SEQUENCE: 27
dggnnnnnnr st                                                             12

<210> SEQ ID NO 28
<211> LENGTH: 12
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: g and t present in equimolar ratios
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: g and t present in equimolar ratios

<400> SEQUENCE: 28
nnkgsttccn nk                                                             12
```

```
<210> SEQ ID NO 29
<211> LENGTH: 12
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: g and t present in equimolar ratios

<400> SEQUENCE: 29
tgggsttccn nk                                                             12

<210> SEQ ID NO 30
<211> LENGTH: 12
<212> TYPE: DNA
<213> ORGANISM: Artificial Sequence
<220> FEATURE:
<223> OTHER INFORMATION: Synthetic formula sequence

<400> SEQUENCE: 30
kgggsttcct mt                                                             12

<210> SEQ ID NO 31
<211> LENGTH: 12
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: g and t present in equimolar ratios

<400> SEQUENCE: 31
nnkgsttcct mt                                                             12

<210> SEQ ID NO 32
<211> LENGTH: 18
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (1)..(1)
<223> OTHER INFORMATION: g present at 70%, t present at 10%, a present
      at 10%, and c present at 10%
<220> FEATURE:
<221> NAME/KEY: misc_feature
<222> LOCATION: (2)..(2)
<223> OTHER INFORMATION: g present at 10%, t present at 10%, a present
      at 70%, and c present at 10%
<220> FEATURE:
<221> NAME/KEY: misc_feature
<222> LOCATION: (3)..(3)
<223> OTHER INFORMATION: g present at 10%, t present at 10%, a present
      at 10%, and c present at 70%
<220> FEATURE:
<221> NAME/KEY: misc_feature
<222> LOCATION: (7)..(8)
<223> OTHER INFORMATION: n is a, c, g, or t
<220> FEATURE:
```

```
<221> NAME/KEY: misc_feature
<222> LOCATION: (9)..(9)
<223> OTHER INFORMATION: g and t present in equimolar ratios
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: g and t present in equimolar ratios

<400> SEQUENCE: 32
nnnrttnnkn nktacsta                                                       18

<210> SEQ ID NO 33
<211> LENGTH: 18
<212> TYPE: DNA
<213> ORGANISM: Artificial Sequence
<220> FEATURE:
<223> OTHER INFORMATION: Synthetic Formula Sequence
<220> FEATURE:
<221> NAME/KEY: misc_feature
<222> LOCATION: (1)..(1)
<223> OTHER INFORMATION: g present at 70%, t present at 10%, a present
      at 10%, and c present at 10%
<220> FEATURE:
<221> NAME/KEY: misc_feature
<222> LOCATION: (2)..(2)
<223> OTHER INFORMATION: g present at 10%, t present at 10%, a present
      at 70%, and c present at 10%
<220> FEATURE:
<221> NAME/KEY: misc_feature
<222> LOCATION: (3)..(3)
<223> OTHER INFORMATION: g present at 10%, t present at 10%, a present
      at 10%, and c present at 70%
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: g and t present in equimolar ratios
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: g and t present in equimolar ratios

<400> SEQUENCE: 33
nnnrttnnkn nkdggsta                                                       18

<210> SEQ ID NO 34
<211> LENGTH: 18
<212> TYPE: DNA
<213> ORGANISM: Artificial Sequence
<220> FEATURE:
<223> OTHER INFORMATION: Synthetic formula sequence
<220> FEATURE:
<221> NAME/KEY: misc_feature
<222> LOCATION: (1)..(1)
<223> OTHER INFORMATION: g present at 70%, t present at 10%, a present
      at 10%, and c present at 10%
<220> FEATURE:
<221> NAME/KEY: misc_feature
<222> LOCATION: (2)..(2)
<223> OTHER INFORMATION: g present at 10%, t present at 10%, a present
      at 70%, and c present at 10%
<220> FEATURE:
<221> NAME/KEY: misc_feature
<222> LOCATION: (3)..(3)
<223> OTHER INFORMATION: g present at 10%, t present at 10%, a present
```

-continued

```
        at 10%, and c present at 70%
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: g and t present in equimolar ratios
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: g and t present in equimolar ratios
<220> FEATURE:
<221> NAME/KEY: misc_feature
<222> LOCATION: (13)..(13)
<223> OTHER INFORMATION: n is a, c, g, or t

<400> SEQUENCE: 34
nnnrttnnkn nknmtsta                                               18

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Val Asn Thr Ala
1

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Ile Pro Arg Ser Ile Ser Gly Tyr
1               5

<210> SEQ ID NO 37
<211> LENGTH: 4
<212> TYPE: PRT
<213> ORGANISM: Artificial Sequence
<220> FEATURE:
<223> OTHER INFORMATION: Syntheitc peptide

<400> SEQUENCE: 37

Ser Ala Ser Phe
1

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide

<400> SEQUENCE: 38

Trp Gly Ser Tyr
1

<210> SEQ ID NO 39
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Asp Ile Pro Arg Ser Ile Ser Gly Tyr
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Trp Gly Ser Tyr Leu Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide

<400> SEQUENCE: 41

His Tyr Thr Thr Pro Pro
1               5

<210> SEQ ID NO 42
<211> LENGTH: 30
<212> TYPE: PRT
<213> ORGANISM: Artificial Sequence
<220> FEATURE:
<223> OTHER INFORMATION: Synthetic peptide

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 43
<211> LENGTH: 14
<212> TYPE: PRT
<213> ORGANISM: Artificial Sequence
<220> FEATURE:
<223> OTHER INFORMATION: Synthetic peptide

<400> SEQUENCE: 43

Trp Val Arg Gln Ala Pro Gly Gln Gly Leu Glu Trp Met Gly
1               5                   10

<210> SEQ ID NO 44
<211> LENGTH: 32
<212> TYPE: PRT
<213> ORGANISM: Artificial Sequence
<220> FEATURE:
<223> OTHER INFORMATION: Synthetic peptide

<400> SEQUENCE: 44

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
```

```
                    20                  25                  30

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide

<400> SEQUENCE: 45

Trp Gly Gln Gly Thr Leu Val Thr Val Ser Ser
1               5                   10

<210> SEQ ID NO 46
<211> LENGTH: 25
<212> TYPE: PRT
<213> ORGANISM: Artificial Sequence
<220> FEATURE:
<223> OTHER INFORMATION: Synthetic peptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 47
<211> LENGTH: 13
<212> TYPE: PRT
<213> ORGANISM: Artificial Sequence
<220> FEATURE:
<223> OTHER INFORMATION: Synthetic peptide

<400> SEQUENCE: 47

Trp Val Arg Gln Ala Pro Gly Gln Gly Leu Glu Trp Met
1               5                   10

<210> SEQ ID NO 48
<211> LENGTH: 31
<212> TYPE: PRT
<213> ORGANISM: Artificial Sequence
<220> FEATURE:
<223> OTHER INFORMATION: Synthetic peptide

<400> SEQUENCE: 48

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic peptide

<400> SEQUENCE: 49

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 50
<211> LENGTH: 30
<212> TYPE: PRT
```

<213> ORGANISM: Artificial Sequence
<220> FEATURE:
<223> OTHER INFORMATION: Synthetic peptide

<400> SEQUENCE: 50

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 51
<211> LENGTH: 14
<212> TYPE: PRT
<213> ORGANISM: Artificial Sequence
<220> FEATURE:
<223> OTHER INFORMATION: Synthetic peptide

<400> SEQUENCE: 51

Trp Ile Arg Gln Pro Pro Gly Lys Gly Leu Glu Trp Ile Gly
1               5                   10

<210> SEQ ID NO 52
<211> LENGTH: 32
<212> TYPE: PRT
<213> ORGANISM: Artificial Sequence
<220> FEATURE:
<223> OTHER INFORMATION: Synthetic peptide

<400> SEQUENCE: 52

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 53
<211> LENGTH: 25
<212> TYPE: PRT
<213> ORGANISM: Artificial Sequence
<220> FEATURE:
<223> OTHER INFORMATION: Synthetic peptide

<400> SEQUENCE: 53

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 54
<211> LENGTH: 13
<212> TYPE: PRT
<213> ORGANISM: Artificial Sequence
<220> FEATURE:
<223> OTHER INFORMATION: Synthetic peptide

<400> SEQUENCE: 54

Trp Ile Arg Gln Pro Pro Gly Lys Gly Leu Glu Trp Ile
1               5                   10

<210> SEQ ID NO 55
<211> LENGTH: 31
<212> TYPE: PRT
<213> ORGANISM: Artificial Sequence
<220> FEATURE:
<223> OTHER INFORMATION: Syntheitic peptide

<400> SEQUENCE: 55

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 56
<211> LENGTH: 30
<212> TYPE: PRT
<213> ORGANISM: Artificial sequence
<220> FEATURE:
<223> OTHER INFORMATION: Synthetic peptide

<400> SEQUENCE: 56

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Syntheitc peptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 58
<211> LENGTH: 14
<212> TYPE: PRT
<213> ORGANISM: Artificial Sequence
<220> FEATURE:
<223> OTHER INFORMATION: Synthetic peptide

<400> SEQUENCE: 58

Trp Val Arg Gln Ala Pro Gly Lys Gly Leu Glu Trp Val Ser
1               5                   10

<210> SEQ ID NO 59
<211> LENGTH: 32
<212> TYPE: PRT
<213> ORGANISM: Artificial Sequence
<220> FEATURE:
<223> OTHER INFORMATION: Synthetic peptide

<400> SEQUENCE: 59

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 60
<211> LENGTH: 25
<212> TYPE: PRT
<213> ORGANISM: Artificial Sequence
<220> FEATURE:
<223> OTHER INFORMATION: Synthetic peptide

<400> SEQUENCE: 60

Glu Val Gln Leu Val Glu Ser Gly Gly Gly Leu Val Gln Pro Gly Gly
1               5                   10                  15

```
Ser Leu Arg Leu Ser Cys Ala Ala Ser
            20                  25

<210> SEQ ID NO 61
<211> LENGTH: 13
<212> TYPE: PRT
<213> ORGANISM: Artificial Sequence
<220> FEATURE:
<223> OTHER INFORMATION: Synthetic peptide

<400> SEQUENCE: 61

Trp Val Arg Gln Ala Pro Gly Lys Gly Leu Glu Trp Val
1               5                   10

<210> SEQ ID NO 62
<211> LENGTH: 31
<212> TYPE: PRT
<213> ORGANISM: Artificial Sequence
<220> FEATURE:
<223> OTHER INFORMATION: Synthetic peptide

<400> SEQUENCE: 62

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Synthetic peptide

<400> SEQUENCE: 63

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Synthetic peptide

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 65
<211> LENGTH: 32
<212> TYPE: PRT
<213> ORGANISM: Artificial sequence
<220> FEATURE:
<223> OTHER INFORMATION: Synthetic peptide

<400> SEQUENCE: 65

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30
```

<210> SEQ ID NO 66
<211> LENGTH: 31
<212> TYPE: PRT
<213> ORGANISM: Artificial Sequence
<220> FEATURE:
<223> OTHER INFORMATION: Synthetic peptide

<400> SEQUENCE: 66

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Synthetic peptide

<400> SEQUENCE: 67

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 68
<211> LENGTH: 31
<212> TYPE: PRT
<213> ORGANISM: Artificial Sequence
<220> FEATURE:
<223> OTHER INFORMATION: Synthetic peptide

<400> SEQUENCE: 68

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Synthetic peptide

<400> SEQUENCE: 69

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 70
<211> LENGTH: 23
<212> TYPE: PRT
<213> ORGANISM: Artificial Sequence
<220> FEATURE:
<223> OTHER INFORMATION: Synthetic peptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 71
<211> LENGTH: 15
<212> TYPE: PRT
<213> ORGANISM: Artificial Sequence
<220> FEATURE:
<223> OTHER INFORMATION: Synthetic peptide

<400> SEQUENCE: 71

Trp Tyr Gln Gln Lys Pro Gly Lys Ala Pro Lys Leu Leu Ile Tyr
1               5                   10                  15

<210> SEQ ID NO 72
<211> LENGTH: 32
<212> TYPE: PRT
<213> ORGANISM: Artificial Sequence
<220> FEATURE:
<223> OTHER INFORMATION: Synthetic peptide

<400> SEQUENCE: 72

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73

Phe Gly Gln Gly Thr Lys Val Glu Ile Lys
1               5                   10

<210> SEQ ID NO 74
<211> LENGTH: 23
<212> TYPE: PRT
<213> ORGANISM: Artificial Sequence
<220> FEATURE:
<223> OTHER INFORMATION: Synthetic peptide

<400> SEQUENCE: 74

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide

<400> SEQUENCE: 75

Trp Tyr Leu Gln Lys Pro Gly Gln Ser Pro Gln Leu Leu Ile Tyr
1               5                   10                  15

<210> SEQ ID NO 76
<211> LENGTH: 32
<212> TYPE: PRT
<213> ORGANISM: Artificial Sequence
<220> FEATURE:
<223> OTHER INFORMATION: Synthetic peptide

<400> SEQUENCE: 76

-continued

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 77
<211> LENGTH: 23
<212> TYPE: PRT
<213> ORGANISM: Artificial Sequence
<220> FEATURE:
<223> OTHER INFORMATION: Synthetic peptide

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide

<400> SEQUENCE: 78

Trp Tyr Gln Gln Lys Pro Gly Gln Ala Pro Arg Leu Leu Ile Tyr
1               5                   10                  15

<210> SEQ ID NO 79
<211> LENGTH: 32
<212> TYPE: PRT
<213> ORGANISM: Artificial Sequence
<220> FEATURE:
<223> OTHER INFORMATION: Synthetic peptide

<400> SEQUENCE: 79

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 80
<211> LENGTH: 23
<212> TYPE: PRT
<213> ORGANISM: Artificial Sequence
<220> FEATURE:
<223> OTHER INFORMATION: Synthetic peptide

<400> SEQUENCE: 80

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 81
<211> LENGTH: 15
<212> TYPE: PRT
<213> ORGANISM: Artificial Sequence
<220> FEATURE:
<223> OTHER INFORMATION: Synthetic construct

<400> SEQUENCE: 81

Trp Tyr Gln Gln Lys Pro Gly Gln Pro Pro Lys Leu Leu Ile Tyr
1               5                   10                  15

```
<210> SEQ ID NO 82
<211> LENGTH: 32
<212> TYPE: PRT
<213> ORGANISM: Artificial Sequence
<220> FEATURE:
<223> OTHER INFORMATION: Synthetic peptide

<400> SEQUENCE: 82

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 83
<211> LENGTH: 10
<212> TYPE: PRT
<213> ORGANISM: Artificial Sequence
<220> FEATURE:
<223> OTHER INFORMATION: Synthetic formula sequence
<220> FEATURE:
<221> NAME/KEY: MISC_FEATURE
<222> LOCATION: (1)..(1)
<223> OTHER INFORMATION: Xaa is any amino acid except Asp
<220> FEATURE:
<221> NAME/KEY: MISC_FEATURE
<222> LOCATION: (3)..(3)
<223> OTHER INFORMATION: Xaa is any amino acid except Pro
<220> FEATURE:
<221> NAME/KEY: MISC_FEATURE
<222> LOCATION: (4)..(4)
<223> OTHER INFORMATION: Xaa is any amino acid except Arg
<220> FEATURE:
<221> NAME/KEY: MISC_FEATURE
<222> LOCATION: (5)..(5)
<223> OTHER INFORMATION: Xaa is any amino acid except Ser
<220> FEATURE:
<221> NAME/KEY: MISC_FEATURE
<222> LOCATION: (6)..(9)
<223> OTHER INFORMATION: Xaa is any amino acid

<400> SEQUENCE: 83

Xaa Ile Xaa Xaa Xaa Xaa Xaa Xaa Xaa Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic formula sequence
<220> FEATURE:
<221> NAME/KEY: MISC_FEATURE
<222> LOCATION: (2)..(9)
<223> OTHER INFORMATION: Xaa is any amino acid

<400> SEQUENCE: 84

Arg Xaa Xaa Xaa Xaa Xaa Xaa Xaa Xaa Arg
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic Formula sequence
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
```

```
<222> LOCATION: (5)..(5)
<223> OTHER INFORMATION: Xaa is any amino acid except Thr
<220> FEATURE:
<221> NAME/KEY: MISC_FEATURE
<222> LOCATION: (6)..(6)
<223> OTHER INFORMATION: Xaa is any amino acid except Asn
<220> FEATURE:
<221> NAME/KEY: MISC_FEATURE
<222> LOCATION: (7)..(9)
<223> OTHER INFORMATION: Xaa is any amino acid

<400> SEQUENCE: 85

Arg Xaa Xaa Xaa Xaa Xaa Xaa Xaa Xaa Arg
1               5                   10
```